(12) United States Patent
Cho et al.

(10) Patent No.: US 8,735,401 B2
(45) Date of Patent: May 27, 2014

(54) THIENOPYRIMIDINE COMPOUNDS AND USE THEREOF

(75) Inventors: Nobuo Cho, Osaka (JP); Takashi Imada, Osaka (JP); Takenori Hitaka, Osaka (JP); Kazuhiro Miwa, Osaka (JP); Masami Kusuka, Osaka (JP); Nobuhiro Suzuki, Tsukuba (JP)

(73) Assignee: Takeda Pharmaceutical Company Limited, Osaka-shi (JP)

( * ) Notice: Subject to any disclaimer, the term of this patent is extended or adjusted under 35 U.S.C. 154(b) by 7 days.

(21) Appl. No.: 13/242,541

(22) Filed: Sep. 23, 2011

(65) Prior Publication Data

US 2012/0071486 A1 Mar. 22, 2012

Related U.S. Application Data

(62) Division of application No. 11/848,939, filed on Aug. 31, 2007, now Pat. No. 8,058,280, which is a division of application No. 10/544,069, filed as application No. PCT/JP2004/000741 on Jan. 28, 2004, now Pat. No. 7,300,935.

(30) Foreign Application Priority Data

Jan. 29, 2003 (JP) ................................. 2003-020854

(51) Int. Cl.
*A61K 31/519* (2006.01)
*A61P 35/04* (2006.01)
*C07D 495/04* (2006.01)

(52) U.S. Cl.
USPC ....................................... 514/260.1; 544/278

(58) Field of Classification Search
USPC ....................................... 544/278; 514/260.1
See application file for complete search history.

(56) References Cited

U.S. PATENT DOCUMENTS

| | | | |
|---|---|---|---|
| 6,048,863 | A | 4/2000 | Furuya et al. |
| 6,297,379 | B1 | 10/2001 | Furuya et al. |
| 6,340,686 | B1 | 1/2002 | Furuya et al. |
| 2003/0004172 | A1 | 1/2003 | Harter et al. |
| 2003/0055269 | A1 | 3/2003 | Fukuoka et al. |
| 2003/0134863 | A1 | 7/2003 | Furuya et al. |
| 2004/0023987 | A1 | 2/2004 | Hata et al. |
| 2004/0034039 | A1 | 2/2004 | Nakano et al. |

FOREIGN PATENT DOCUMENTS

| | | |
|---|---|---|
| EP | 1297850 | 4/2003 |
| JP | 2001-278884 | 10/2001 |
| JP | 2001-316391 | 11/2001 |
| JP | 2001-354588 | 12/2001 |
| JP | 2002-68982 | 3/2002 |
| JP | 2002-80397 | 3/2002 |
| JP | 2002-167327 | 6/2002 |
| JP | 2003-292492 | 10/2003 |
| JP | 2004-2321 | 1/2004 |
| JP | 2004-2377 | 1/2004 |
| WO | 96/24597 | 8/1996 |
| WO | 00/56739 | 9/2000 |
| WO | 02/43766 | 6/2002 |
| WO | 02/47722 | 6/2002 |
| WO | 02/64598 | 8/2002 |
| WO | 03/064429 | 8/2003 |
| WO | 03/075958 | 9/2003 |
| WO | 03/086464 | 10/2003 |

OTHER PUBLICATIONS

Guo, Z. et al.; "Synthesis and structure-activity relationships of thieno (2, 3-d) pyrimidine-2, 4-dione derivatives as potent GnRH receptor agnagonists"; Bioorg. Med. Chem. Lett., Oct. 20, 2003; vol. 13; No. 20; pp. 3617 to 3622 full test; p. 3619,. compound 18.

Hara, T. et al.; "Suppression of a pituitary-ovarian axis by chronic oral administration of a novel nonpeptide gonadotrop in-releasing hormone antagonist, TAK-013, in cynomolgus monkesy"; J. Clin. Endocrinol. Metab.; (Apr. 2003); vol. 88; No. 4; pp. 1697 to 1704; full text.

Sasaki, S. et al.; "Discovery of a thieno (2, 3-d) pyrimidine-2, 4-dione bearing a p-methoxyureido phenyl moiety at the 6-poswition; a highlypotent and orally bioavailable non-peptide antagonist for the human luteinizing hormone-releasing hormone receptor:"; J. Med. Chem.; Jan. 2, 2003; vol. 46; No. 1; pp. 113 to 124; full text; p. 115, compound 9k-9m, p. 117, table 2.

(Continued)

*Primary Examiner* — Susanna Moore
(74) *Attorney, Agent, or Firm* — Edwards Wildman Palmer LLP; David G. Conlin; Edmund J. Koundakjian

(57) ABSTRACT

The present invention provides a compound represented by the formula:

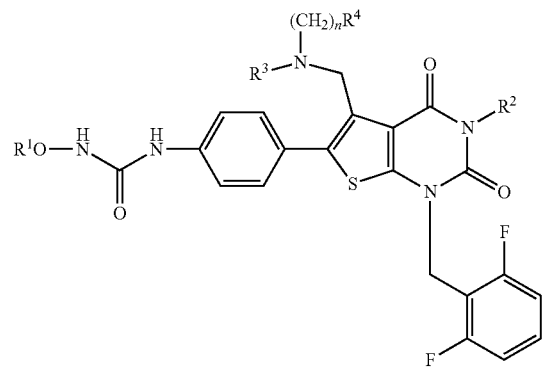

wherein $R^1$ is a $C_{1-4}$ alkyl; $R^2$ is (1) a 5- to 7-membered nitrogen-containing heterocyclic group which may have a substituent selected from the group consisting of (1') a halogen, (2') a hydroxy group, (3') a $C_{1-4}$ alkyl and (4') a $C_{1-4}$ alkoxy, (2) a phenyl which may have a substituent selected from the group consisting of (1') a halogen, (2') a $C_{1-4}$ alkoxy-$C_{1-4}$ alkyl, (3') a mono-$C_{1-4}$ alkyl-carbamoyl-$C_{1-4}$ alkyl, (4') a $C_{1-4}$ alkoxy and (5') a mono-$C_{1-4}$ alkylcarbamoyl-$C_{1-4}$ alkoxy, or the like; $R^3$ is a $C_{1-4}$ alkyl; $R^4$ is a $C_{1-4}$ alkoxy, or the like; n is an integer of 1 to 4; or a salt thereof, as a thienopyrimidine compound having gonadotropin-releasing hormone antagonistic activity.

3 Claims, No Drawings

(56) References Cited

OTHER PUBLICATIONS

Wolff, Manfred E. "Burger's Medicinal Chemistry, 5ed, Part I," John Wiley & Sons, 1995, pp. 975-977.

Banker, G.S. et al, "Modern Pharmaceuticals, 3ed.," Marcel Dekker, New York, 1996, pp. 451 and 596.

Banker, G.S. et al., Modern Pharmaceutics, 3rd Ed., pp. 596, (1980).

Jones, J. et al., "British Society of Gastroenterology guidelines for the management of the irritable bowel syndrome," downloaded from gut.bmj.com on Nov. 16, 2006.

Wolff, M. Burger's Medicinal Chemistry and Drug Discovery, 5th Ed., vol. 1, pp. 975-977, (1995).

THIENOPYRIMIDINE COMPOUNDS AND USE THEREOF

CROSS-REFERENCE TO RELATED APPLICATIONS

This application is a divisional of U.S. Pat. No. 11/848,939, which was filed Aug. 31, 2007 and was issued as U.S. Pat. No. 8,058,280 on Nov. 15, 2011. U.S. Pat. No. 11/848,939 is a divisional of U.S. Pat. No. 10/544,069, which was filed Jul. 29, 2005 and was issued as U.S. Pat. No. 7,300,935 on Nov. 27, 2007. U.S. Pat. No. 10/544,069 is the U.S. national phase filing of PCT/JP2004/000741 which was filed Jan. 28, 2004 and published as WO 2004/067535 on Aug. 12, 2004. PCT/JP2004/000741 claims the benefit of Japanese Application No. 2003-020854 filed Jan. 29, 2003. The entire contents of each of the above are incorporated herein by reference.

TECHNICAL FIELD

The present invention relates to thieno[2,3-d]pyrimidine compounds exhibiting gonadotropin releasing hormone (GnRH) antagonizing activity, their production and use.

BACKGROUND ART

Secretion of anterior pituitary hormones undergoes feedback control by peripheral hormones secreted from target organs of the respective hormones and by secretion-regulating hormones from the hypothalamus, which is the upper central organ of the anterior lobe of the pituitary (hereinafter, these hormones are collectively called "hypothalamic hormones" in this specification). Presently, as hypothalamic hormones, the existence of nine kinds of hormones including, for example, thyrotropin releasing hormone (TRH), and gonadotropin releasing hormone [GnRH, sometimes called as LH-RH (luteinizing hormone releasing hormone)] has been confirmed. These hypothalamic hormones are believed to show their actions via the receptors which are considered to exist in the anterior lobe of the pituitary, and efforts to find the receptor-gene expression specific to these hormones, including cases of human, have been made. Accordingly, antagonists or agonists specifically and selectively acting on these receptors should control the action of the hypothalamic hormone and the secretion of anterior pituitary hormone. As a result, such antagonists or agonists are expected to prevent or treat anterior pituitary hormone dependent diseases.

Known compounds possessing GnRH-antagonizing activity include GnRH-derived linear peptides (U.S. Pat. No. 5,140,009 and U.S. Pat. No. 5,171,835), a cyclic hexapeptide derivative (JP-A-61-191698), a bicyclic peptide derivative (Journal of Medicinal Chemistry, Vol. 36, pp. 3265-3273 (1993)), and so forth. Non-peptide compounds possessing GnRH-antagonizing activity include compounds described in JP-A-8-295693 (WO 95/28405), JP-A-9-169768 (WO 96/24597), JP-A-9-169735 (WO 97/14682), JP-A-9-169767 (WO 97/14697), JP-A-11-315079 (WO 99/33831), JP-A-2000-219691 (WO 00/00493), JP-A-2001-278884 (WO 00/56739) and JP-A-2002-30087.

Peptide compounds pose a large number of problems to be resolved with respect to oral absorbability, dosage form, dose volume, drug stability, sustained action, metabolic stability etc. There is strong demand for an oral GnRH antagonist, especially one based on a non-peptide compound, that has excellent therapeutic effect on hormone-dependent cancers, e.g., prostatic cancer, endometriosis, precocious puberty etc., that does not show transient hypophysial-gonadotropic action (acute action) and that has excellent oral absorbability.

SUMMARY OF THE DISCLOSURE

We, the present inventors, have conducted various investigations, and as a result, have synthesized the following novel compound represented by the formula [hereinafter sometimes referred to briefly as Compound (I)]:

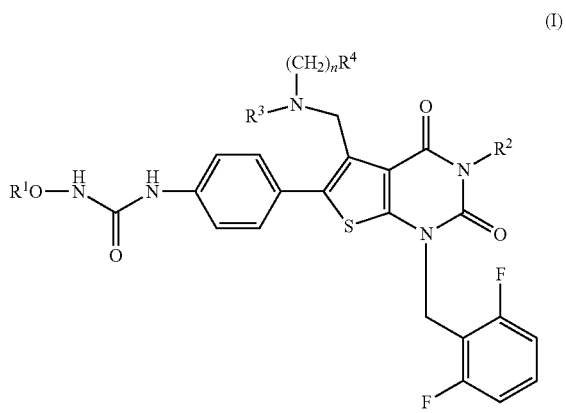

(I)

wherein
$R^1$ is a $C_{1-4}$ alkyl; $R^2$ is (1) a $C_{1-6}$ alkyl which may have a substituent selected from the group consisting of (1') a hydroxy group, (2') a $C_{1-4}$ alkoxy, (3') a $C_{1-4}$ alkoxy-carbonyl, (4') a di-$C_{1-4}$ alkyl-carbamoyl, (5') a 5- to 7-membered nitrogen-containing heterocyclic group, (6') a $C_{1-4}$ alkyl-carbonyl and (7') a halogen, (2) a $C_{3-8}$ cycloalkyl which may have (1') a hydroxy group or (2') a mono-$C_{1-4}$ alkyl-carbonylamino, (3) a 5- to 7-membered nitrogen-containing heterocyclic group which may have a substituent selected from the group consisting of (1') a halogen, (2') a hydroxy group, (3') a $C_{1-4}$ alkyl and (4') a $C_{1-4}$ alkoxy, (4) a phenyl which may have a substituent selected from the group consisting of (1') a halogen, (2') a $C_{1-4}$ alkoxy-$C_{1-4}$ alkyl, (3') a mono-$C_{1-4}$ alkyl-carbamoyl-$C_{1-4}$ alkyl, (4') a $C_{1-4}$ alkoxy and (5') a mono-$C_{1-4}$ alkylcarbamoyl-$C_{1-4}$ alkoxy or (5) a $C_{1-4}$ alkoxy; $R^3$ is a $C_{1-4}$ alkyl; $R^4$ is (1) a hydrogen atom, (2) a $C_{1-4}$ alkoxy, (3) a $C_{6-10}$ aryl, (4) a N—$C_{1-4}$ alkyl-N—$C_{1-4}$ alkylsulfonylamino, (5) a hydroxy group or (6) a 5- to 7-membered nitrogen-containing heterocyclic group which may have a substituent selected from the group consisting of (1') oxo, (2') a $C_{1-4}$ alkyl, (3') a hydroxy-$C_{1-4}$ alkyl, (4') a $C_{1-4}$ alkoxy-carbonyl, (5') a mono-$C_{1-4}$ alkyl-carbamoyl and (6') a $C_{1-4}$ alkyl-sulfonyl; n is an integer of 1 to 4; provided that when $R^2$ is a phenyl which may have a substituent, $R^4$ is a 5- to 7-membered nitrogen-containing heterocyclic group which may have a substituent selected from the group consisting of (1) oxo, (2) a hydroxy-$C_{1-4}$ alkyl, (3) a $C_{1-4}$ alkoxy-carbonyl, (4) a mono-$C_{1-4}$ alkyl-carbamoyl and (5) a $C_{1-4}$ alkylsulfonyl; or a salt thereof; which is characterized by having 3-$C_{1-4}$ alkoxyureido on the para-position of its phenyl group at the six position of the thieno[2,3-d]pyrimidine skeleton. And we also have found that Compound (1) has an unexpected, excellent GnRH-antagonizing activity, especially strong antagonistic activity, based upon the above specific chemical structure, and extremely low toxicity and is therefore satisfactory as a medicine having GnRH-antagonizing activity, and developed the present invention based on these findings.

DETAILED DESCRIPTION OF THE DISCLOSURE

Accordingly, the present invention relates to:
[1] A compound of the formula:

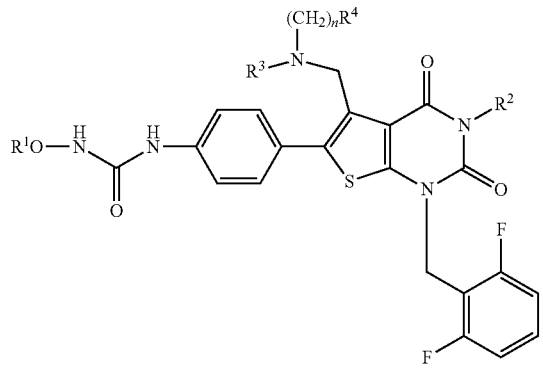

wherein
$R^1$ is a $C_{1-4}$ alkyl;
$R^2$ is
(1) a $C_{1-6}$ alkyl which may have a substituent selected from the group consisting of (1') a hydroxy group, (2') a $C_{1-4}$ alkoxy, (3') a $C_{1-4}$ alkoxy-carbonyl, (4') a di-$C_{1-4}$ alkyl-carbamoyl, (5') a 5- to 7-membered nitrogen-containing heterocyclic group, (6') a $C_{1-4}$ alkyl-carbonyl and (7') a halogen,
(2) a $C_{3-8}$ cycloalkyl which may have (1') a hydroxy group or (2') a mono-$C_{1-4}$ alkyl-carbonylamino,
(3) a 5- to 7-membered nitrogen-containing heterocyclic group which may have a substituent selected from the group consisting of (1') a halogen, (2') a hydroxy group, (3') a $C_{1-4}$ alkyl and (4') a $C_{1-4}$ alkoxy,
(4) a phenyl which may have a substituent selected from the group consisting of (1') a halogen, (2') a $C_{1-4}$ alkoxy-$C_{1-4}$ alkyl, (3') a mono-$C_{1-4}$ alkyl-carbamoyl-$C_{1-4}$ alkyl, (4') a $C_{1-4}$ alkoxy and (5') a mono-$C_{1-4}$ alkylcarbamoyl-$C_{1-4}$ alkoxy, or
(5) a $C_{1-4}$ alkoxy;
$R^3$ is a $C_{1-4}$ alkyl;
$R^4$ is
(1) a hydrogen atom,
(2) a $C_{1-4}$ alkoxy,
(3) a $C_{6-10}$ aryl,
(4) a N—$C_{1-4}$ alkyl-N—$C_{1-4}$ alkylsulfonylamino,
(5) a hydroxyl group, or
(6) a 5- to 7-membered nitrogen-containing heterocyclic group which may have a substituent selected from the group consisting of (1') oxo, (2') a $C_{1-4}$ alkyl, (3') a hydroxy-$C_{1-4}$ alkyl, (4') a $C_{1-4}$ alkoxy-carbonyl, (5') a mono-$C_{1-4}$ alkyl-carbamoyl and (6') a $C_{1-4}$ alkylsulfonyl;
n is an integer of 1 to 4;
provided that when $R^2$ is a phenyl which may have a substituent, $R^4$ is a 5- to 7-membered nitrogen-containing heterocyclic group which may have a substituent selected from the group consisting of (1) oxo, (2) a hydroxy-$C_{1-4}$ alkyl, (3) a $C_{1-4}$ alkoxy-carbonyl, (4) a mono-$C_{1-4}$ alkyl-carbamoyl and (5) a $C_{1-4}$ alkylsulfonyl; or a salt thereof;
[2] A compound as defined in [1] above, wherein $R^2$ is
(1) a $C_{1-4}$ alkyl which may have a substituent selected from the group consisting of (1') a hydroxy group, (2') a $C_{1-4}$ alkoxy, (3') a $C_{1-4}$ alkoxy-carbonyl, (4') a di-$C_{1-4}$ alkyl-carbamoyl and (5') a 5 to 7-membered nitrogen-containing heterocyclic group,
(2) a $C_{3-8}$ cycloalkyl which may have (1') a hydroxy group or (2') a mono-$C_{1-4}$ alkyl-carbonylamino,
(3) a 5- to 7-membered nitrogen-containing heterocyclic group which may have a substituent selected from the group consisting of (1') a halogen, (2') a hydroxy group, (3') a $C_{1-4}$ alkyl and (4') a $C_{1-4}$ alkoxy,
(4) a phenyl which may have a substituent selected from the group consisting of (1') a halogen, (2') a $C_{1-4}$ alkoxy-$C_{1-4}$ alkyl, (3') a mono-$C_{1-4}$ alkyl-carbamoyl-$C_{1-4}$ alkyl and (4') a mono-$C_{1-4}$ alkyl-carbamoyl-$C_{1-4}$ alkoxy, or
(5) a $C_{1-4}$ alkoxy;
$R^4$ is
(1) a $C_{1-4}$ alkoxy,
(2) a $C_{6-10}$ aryl,
(3) a N—$C_{1-4}$ alkyl-N—$C_{1-4}$ alkylsulfonylamino or
(4) a 5- to 7-membered nitrogen-containing heterocyclic group which may have a substituent selected from the group consisting of (1') oxo, (2') a hydroxy-$C_{1-4}$ alkyl, (3') a $C_{1-4}$ alkoxy-carbonyl, (4') a mono-$C_{1-4}$ alkyl-carbamoyl and (5') a $C_{1-4}$ alkylsulfonyl;
[3] A compound as defined in [1] above, wherein $R^1$ is methyl;
[4] A compound as defined in [1] above, wherein $R^2$ is a 5- to 7-membered nitrogen-containing heterocyclic group which may have a substituent selected from the group consisting of (1) a halogen, (2) a hydroxy group, (3) a $C_{1-4}$ alkyl and (4) a $C_{1-4}$ alkoxy;
[5] A compound as defined in [1] above, wherein $R^3$ is methyl;
[6] A compound as defined in [1] above, wherein $R^4$ is a $C_{1-4}$ alkoxy;
[7] A compound as defined in [1] above, wherein n is 2;
[8] A compound as defined in [1] above, wherein $R^3$ is methyl, $R^4$ is a hydrogen atom and n is 1;
[9] N-(4-(1-(2,6-difluorobenzyl)-5-(((2-methoxyethyl)(methyl)amino)methyl)-2,4-dioxo-3-(2-pyridinyl)-1,2,3,4-tetrahydrothieno[2,3-d]pyrimidin-6-yl)phenyl)-N'-methoxyurea, N-(4-(1-(2,6-difluorobenzyl)-5-(((2-ethoxyethyl)(methyl)amino)methyl)-2,4-dioxo-3-(2-pyridinyl)-1,2,3,4-tetrahydrothieno[2,3-d]pyrimidin-6-yl)phenyl)-N'-methoxyurea, N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or
N-(4-(1-(2,6-difluorobenzyl)-5-((dimethylamino)methyl)-3-(6-methoxypyridin-3-yl)-2,4-dioxo-1,2,3,4-tetrahydrothieno[2,3-d]pyrimidin-6-yl)phenyl)-N'-methoxyurea, or a salt thereof;
[10] N-(4-(5-(((2-methoxyethyl)methylamino)methyl)-1-(2,6-difluorobenzyl)-1,2,3,4-tetrahydro-2,4-dioxo-3-(4-methoxyphenyl)thieno[2,3-d]pyrimidin-6-yl)phenyl)-N'-methoxyurea or N-(4-(1-(2,6-difluorobenzyl)-5-((dimethylamino)methyl)-3-(4-methoxyphenyl)-2,4-dioxo-1,2,3,4-tetrahydrothieno[2,3-d]pyrimidin-6-yl)phenyl)-N'-methoxyurea, or a salt thereof;
[11] A prodrug of the compound as defined in [1] above;
[12] A pharmaceutical which comprises the compound as defined in [1] above or a prodrug thereof;
[13] A pharmaceutical as defined in [12] above, which is a gonadotropin-releasing hormone antagonist;
[14] A pharmaceutical as defined in [12] above, which is for preventing or treating a sex hormone dependent disease;
[15] A pharmaceutical as defined in [12] above, which is for preventing or treating sex hormone-dependent cancer, bone metastasis of sex hormone-dependent cancer, prostatic hypertrophy, hysteromyoma, endometriosis, metrofibroma, precocious puberty, amenorrhea, premenstrual syndrome, dysmenorrhea, multilocular ovary syndrome, polycystic ovary syndrome, acne, alopecia, Alzheimer's disease, infertility, irritable bowel syndrome, benign or malignant tumor which is hormone independent and LH-RH sensitive or hot flash; reproduction regulator; contraceptive agent; ovulation inducer; or for prevention of postoperative recurrence of sex hormone-dependent cancer;

[16] A method for antagonizing gonadotropin-releasing hormone, which comprises administering an effective amount of the compound as defined in [1] above to a mammal;

[17] Use of the compound as defined in [1] above for manufacturing a pharmaceutical composition for antagonizing gonadotropin-releasing hormone;

[18] A compound of the formula:

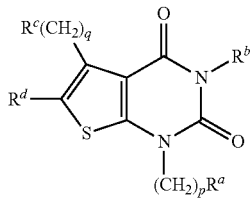

wherein
$R^a$ is (1) a hydrogen atom, (2) an aryl group which may have 1 to 5 substituents selected from the group consisting of (i) a halogen, (ii) nitro, (iii) cyano, (iv) amino, (v) a carboxyl group which may be esterified or amidated, (vi) an alkylenedioxy, (vii) an alkyl, (viii) an alkoxy, (ix) an alkylthio, (x) an alkylsulfinyl and (xi) an alkylsulfonyl, (3) a cycloalkyl group which may have a substituent or (4) a heterocyclic group which may have a substituent; $R^b$ is a nitrogen-containing heterocyclic group which may have a substituent; $R^c$ is an amino group which may have a substituent; $R^d$ is an aryl group which may have a substituent; p is an integer of 0 to 3; q is an integer of 0 to 3; or a salt thereof; and so forth.

The definition of each term is described in the following paragraphs.

Examples of the "$C_{1-4}$ alkyl" include a linear $C_{1-4}$ alkyl (e.g. methyl, ethyl, propyl, butyl, and the like), a branched $C_{3-4}$ alkyl (e.g., isopropyl, isobutyl, sec-butyl, tert-butyl, and the like), and the like.

Examples of the "$C_{1-6}$ alkyl" include a linear $C_{1-6}$ alkyl (e.g. methyl, ethyl, propyl, butyl, pentyl, hexyl and the like), a branched $C_{3-6}$ alkyl (e.g., isopropyl, isobutyl, sec-butyl, tert-butyl, isopentyl and the like), and the like.

Examples of the "$C_{1-4}$ alkoxy" include a linear $C_{1-4}$ alkoxy (e.g. methoxy, ethoxy, propoxy, butoxy, and the like), a branched $C_{3-4}$ alkoxy (e.g., isopropoxy, isobutoxy, sec-butoxy, tert-butoxy, and the like), and the like.

Examples of the "$C_{1-4}$ alkoxy-carbonyl" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, and the like.

Examples of the "di-$C_{1-4}$ alkyl-carbamoyl" include dimethylcarbamoyl, diethylcarbamoyl, dipropylcarbamoyl, diisopropylcarbamoyl, N-ethyl-N-methylcarbamoyl, and the like.

Examples of the "5- to 7-membered nitrogen-containing heterocyclic group" include pyrrolidin-1-yl, pyrrolidin-2-yl, pyrrolidin-3-yl, oxazolidin-3-yl, thiazolidin-3-yl, isoxazolidin-2-yl, isothiazolidin-2-yl, imidazolidin-1-yl, imidazolidin-2-yl, imidazolidin-4-yl, pyrazolidin-1-yl, pyrazolidin-3-yl, pyrazolidin-4-yl, pyrrol-1-yl, pyrrol-2-yl, pyrrol-3-yl, imidazol-1-yl, imidazol-2-yl, imidazol-4-yl, pyrazol-1-yl, pyrazol-3-yl, pyrazol-4-yl, 1,2,3-triazol-1-yl, 1,2,5-triazol-1-yl, tetrazol-1-yl, tetrazol-2-yl, tetrazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, piperidin-1-yl, piperidin-2-yl, piperidin-3-yl, piperidin-4-yl, piperazin-1-yl, piperazin-2-yl, morpholin-2-yl, morpholin-3-yl, morpholin-4-yl, pyridin-2-yl, pyridin-3-yl, pyridin-4-yl, pyrazin-2-yl, pyrimidin-2-yl, pyrimidin-4-yl, pyrimidin-5-yl, pyridazin-3-yl, pyridadin-4-yl, and the like. Among them, preferable examples are pyrrolidin-1-yl, pyrrolidin-2-yl, imidazol-1-yl, imidazol-2-yl, 1,2,3-triazol-1-yl, 1,2,5-triazol-1-yl, tetrazol-1-yl, tetrazol-2-yl, pyridin-2-yl, pyridin-4-yl, and the like.

Examples of the "$C_{1-4}$ alkyl-carbonyl" include methylcarbonyl, ethyl-carbonyl, propyl-carbonyl, isopropyl-carbonyl, butyl-carbonyl, isobutyl-carbonyl, sec-butyl-carbonyl, tert-butyl-carbonyl, and the like.

The "halogen" include fluorine, chlorine, bromine and iodine.

Examples of the "mono-$C_{1-4}$ alkyl-carbonylamino" include methylcarbonylamino, ethylcarbonylamino, propylcarbonylamino, isopropylcarbonylamino, butylcarbonylamino, isobutylcarbonylamino, sec-butylcarbonylamino, tert-butylcarbonylamino, and the like.

Examples of the "$C_{3-8}$ cycloalkyl" include cyclopropyl, cyclobutyl, cyclopentyl, cyclohexyl, cycloheptyl, cyclooctyl, and the like.

The "$C_{1-4}$ alkoxy-$C_{1-4}$ alkyl" include methoxymethyl, 1-methoxyethyl, 2-methoxyethyl, 1-methoxypropyl, 2-methoxypropyl, 3-methoxypropyl, 1-methoxybutyl, 2-methoxybutyl, 3-methoxybutyl, 4-methoxybutyl, 1-methoxy-1-methylethyl, 2-methoxy-1-methylethyl, 1-methoxy-1-methylpropyl, 2-methoxy-1-methylpropyl, 3-methoxy-1-methylpropyl, 1-(methoxymethyl)propyl, 1-methoxy-2-methylpropyl, 2-methoxy-2-methylpropyl, 3-methoxy-2-methylpropyl, 2-methoxy-1,1-dimethylethyl, ethoxymethyl, 2-ethoxyethyl, 3-ethoxypropyl, 4-ethoxybutyl, and the like.

Examples of the "mono-$C_{1-4}$ alkyl-carbamoyl-$C_{1-4}$ alkyl" include methylaminocarbonylmethyl, ethylaminocarbonylmethyl, 2-methylaminocarbonylethyl, 2-ethylaminocarbonylethyl, and the like.

Examples of the "mono-$C_{1-4}$ alkyl-carbamoyl-$C_{1-4}$ alkoxy" include methylaminocarbonylmethoxy, ethylaminocarbonylmethoxy, 2-methylaminocarbonylethoxy, 2-ethylaminocarbonylethoxy, and the like.

Examples of the "$C_{6-10}$ aryl" include phenyl, 1-naphthyl, 2-naphthyl, and the like.

Examples of the "N—$C_{1-4}$ alkyl-N—$C_{1-4}$ alkylsulfonylamino" include N-methyl-N-methylsulfonylamino, N-ethyl-N-methylsulfonylamino, N-ethylsulfonyl-N-methylamino, N-ethyl-N-ethylsulfonylamino, and the like.

Examples of the "hydroxy-$C_{1-4}$ alkyl" include hydroxymethyl, 1-hydroxyethyl, 2-hydroxyethyl, 1-hydroxypropyl, 2-hydroxypropyl, 3-hydroxypropyl, 1-hydroxybutyl, 2-hydroxybutyl, 3-hydroxybutyl, 4-hydroxybutyl, 1-hydroxy-1-methylethyl, 2-hydroxy-1-methylethyl, 1-hydroxy-1-methylpropyl, 2-hydroxy-1-methylpropyl, 3-hydroxy-1-methylpropyl, 1-(hydroxymethyl)propyl, 1-hydroxy-2-methylpropyl, 2-hydroxy-2-methylpropyl, 3-hydroxy-2-methylpropyl, 2-hydroxy-1,1-dimethylethyl, and the like.

Examples of the "mono-$C_{1-4}$ alkyl-carbamoyl" include methylcarbamoyl, ethylcarbamoyl, propylcarbamoyl, isopropylcarbamoyl, butylcarbamoyl, isobutylcarbamoyl, sec-butylcarbamoyl, tert-butylcarbamoyl, and the like.

Examples of the "$C_{1-4}$ alkylsulfonyl" include methylsulfonyl, ethylsulfonyl, propylsulfonyl, isopropylsulfonyl, butylsulfonyl, isobutylsulfonyl, sec-butylsulfonyl, tert-butylsulfonyl, and the like.

As $R^1$, methyl and ethyl are preferable, and especially methyl is preferable.

As $R^2$, 5- to 7-membered nitrogen-containing heterocyclic group which may have a substituent selected from the group consisting of (1) a halogen, (2) a hydroxy group, (3) a $C_{1-4}$ alkyl and (4) a $C_{1-4}$ alkoxy is preferable. Among them, pyridyl (pyridin-2-yl, pyridin-3-yl, pyridin-4-yl), which may have a substituent selected from the group consisting of (1) a halogen, (2) a hydroxy group, (3) a $C_{1-4}$ alkyl and (4) a $C_{1-4}$ alkoxy is more preferable. Especially, unsubstituted pyridin-2-yl is preferable.

As $R^3$, methyl and ethyl are preferable. Especially, methyl is preferable.

As $R^4$, a $C_{1-4}$ alkoxy is preferable. Especially, methoxy and ethoxy are preferable.

As n, 1 or 2 is preferable. Especially, 2 is preferable.

Preferable examples of the combination of $R^3$, $R^4$ and n, includes the case that $R^3$ is methyl, $R^4$ is a hydrogen atom and n is 1.

Preferable examples of Compound (I) include N-(4-(1-(2,6-difluorobenzyl)-5-(((2-methoxyethyl)(methyl)amino)methyl)-2,4-dioxo-3-(2-pyridinyl)-1,2,3,4-tetrahydrothieno[2,3-d]pyrimidin-6-yl)phenyl)-N'-methoxyurea, N-(4-(1-(2,6-difluorobenzyl)-5-(((2-ethoxyethyl)(methyl)amino)methyl)-2,4-dioxo-3-(2-pyridinyl)-1,2,3,4-tetrahydrothieno[2,3-d]pyrimidin-6-yl)phenyl)-N'-methoxyurea, N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or N-(4-(1-(2,6-difluorobenzyl)-5-((dimethylamino)methyl)-3-(6-methoxypyridin-3-yl)-2,4-dioxo-1,2,3,4-tetrahydrothieno[2,3-d]pyrimidin-6-yl)phenyl)-N'-methoxyurea.

Salts of Compound (I) are preferably physiologically acceptable acid addition salts. Such salts include, for example, salts with inorganic acids (e.g., hydrochloric acid, hydrobromic acid, nitric acid, sulfuric acid, phosphoric acid, etc.), salts with organic acids (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.), and the like. When Compound (I) has an acidic group, it may be formed into a physiologically acceptable salt with an inorganic base (e.g., alkali metals and alkaline earth metals such as sodium, potassium, calcium, magnesium, etc.; ammonia, and the like) or an organic base (e.g., trimethylamine, triethylamine, pyridine, picoline, ethanolamine, diethanolamine, triethanolamine, dicyclohexylamine, N,N'-dibenzylethylenediamine, and the like).

For example, Compound (I) can be produced according to the following production methods. Compounds illustrated in the following reaction schemes include their salts. Examples of the salts include the same salts as the salts of Compound (I), etc. Compounds (I)-(IV) illustrated in the following reaction schemes may be formed into the acceptable salts depending on the reaction conditions.

(Production Method 1)

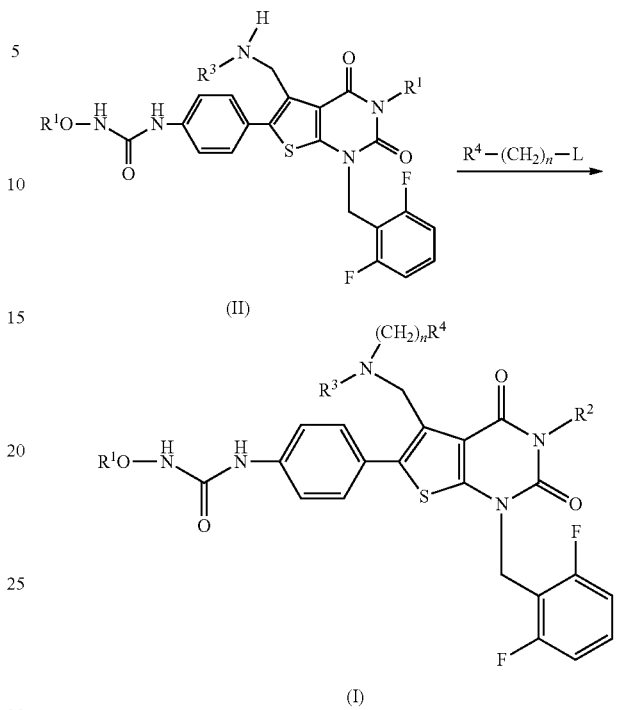

In the above formula, L is a leaving group, and other symbols are the same as defined above.

Examples of "leaving group" represented by L are a halogen atom, $C_{1-4}$ alkylsulfonyloxy which may have a halogen atom, and the like. Examples of "$C_{1-4}$ alkylsulfonyloxy which may have a halogen atom" are methanesulfonyloxy, ethanesulfonyloxy, trifluoromethanesulfonyloxy, and the like.

Compound (II) can be produced in any per se known manner, for example, according to the methods disclosed in JP-A-2001-278884, WO 00/56739 or analogous methods thereto.

For example, Compound (I) can be produced by reacting Compound (II) and a compound represented by the formula: $R^4$—$(CH_2)_n$-L. This reaction is preferably carried out in the presence of a base.

Examples of "base" are inorganic bases such as sodium carbonate, sodium hydrogen carbonate, potassium carbonate, potassium hydrogen carbonate, sodium hydroxide, potassium hydroxide, thallium hydroxide, and the like; and organic bases such as triethylamine, diisopropylethylamine, pyridine, and the like. The amount of the compound represented by the formula: $R^4$—$(CH_2)_n$-L in the reaction of Compound (II) and the compound represented by the formula: $R^4$—$(CH_2)_n$-L is about 1 to about 3 moles per 1 mole of Compound (II). The amount of a base is about 1 to about 3 moles per 1 mole of Compound (II).

This reaction is usually carried out in a solvent inert to the reaction. Examples of "solvent" are an ether (e.g., diethyl ether, dioxane, dimethoxyethane, tetrahydrofuran, and the like), an aromatic hydrocarbon (e.g., benzene, toluene, and the like), an amide (e.g., dimethylformamide, dimethylacetamide, and the like), a halogenated hydrocarbon (e.g., chloroform, dichloromethane, and the like), and the like.

The reaction temperature is usually about 0 to about 150° C., preferably about 50 to about 80° C. The reaction time is usually about 1 to about 24 hours.

(Production Method 2)

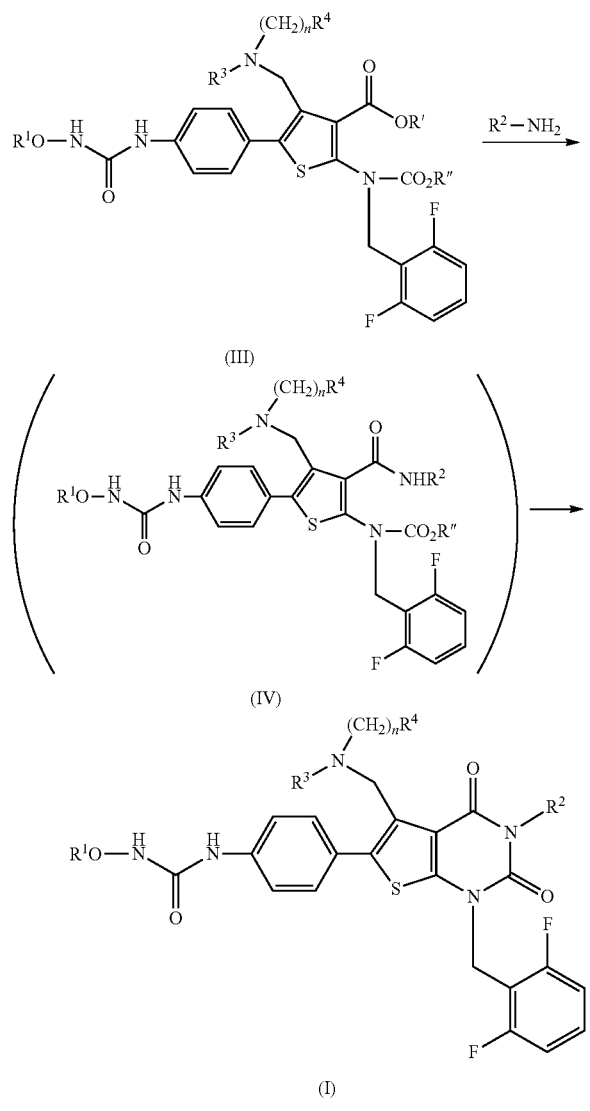

In the above formula, R' is a hydrogen atom or a $C_{1-4}$ alkyl; R" is a $C_{1-4}$ alkyl; and the other symbols are as defined above.

Examples of the $C_{1-4}$ alkyl represented by R' and R" are a linear $C_{1-4}$ alkyl (e.g., methyl, ethyl, propyl, butyl, and the like), a branched $C_{3-4}$ alkyl (e.g., isopropyl, isobutyl, sec-butyl, tert-butyl, and the like), and the like.

Compound (III) can be produced in any per se known manner, for example, by reacting p-nitrophenylacetone with a cyanoacetic ester compound and sulphur [e.g., Chem. Ber., 99, 94-100 (1966)] followed by subjecting the obtained 2-amino-4-methyl-5-(4-nitrophenyl)thiophene to the methods disclosed in JP-A-9-169768, WO 96/24597 or analogous methods thereto.

1) When R' is hydrogen atom, Compound (I) can be produced by reacting Compound (III) with a compound represented by the formula: $R^2$—$NH_2$ or a salt thereof in the presence of a condensing agent, to obtain Compound (IV), following by subjecting to cyclization.

Examples of "condensing agent" are WSC (1-ethyl-3-(3-dimethylaminopropyl)carbodiimide hydrochloride), DCC (dicyclohexylcarbodiimide), diethyl cyanophosphate, benzotriazol-1-yloxytripyrrolidinophosphonium hexafluorophosphate: PyBOP), and the like.

The amount of "condensing agent" is about 1 to about 3 moles per 1 mole of Compound (III).

This reaction is advantageously carried out in a solvent inert to the reaction.

Examples of the solvent are an alcohol (e.g., ethanol, methanol, and the like), an aromatic hydrocarbon (e.g., benzene, toluene, and the like), an amide (e.g., dimethylformamide, dimethylacetamide, and the like), a halogenated hydrocarbon (e.g., chloroform, dichloromethane, and the like), and so the like.

The reaction temperature is usually about 0 to about 150° C., preferably about 0 to 25° C. The reaction time is usually about 1 to about 36 hours.

The product as produced in the manner mentioned above may be applied to the next reaction while it is still crude in the reaction mixture, or may be isolated from the reaction mixture in any ordinary manner.

Compound (IV) is subjected to cyclization in the presence of a base.

Examples of "base" are inorganic bases such as sodium methoxide, sodium carbonate, sodium hydrogen carbonate, potassium carbonate, potassium hydrogen carbonate, sodium hydroxide, potassium hydroxide, thallium hydroxide; and organic bases such as triethylamine, pyridine, and the like; and the like.

The amount of "base" is about 2 to about 20 moles, preferably about 5 to about 12 mole per 1 mole of Compound (IV).

This reaction is usually carried out in a solvent inert to the reaction.

Examples of the solvent are an alcohol (e.g., ethanol, methanol, and the like), an aromatic hydrocarbon (e.g., benzene, toluene, and the like), an amide (e.g., dimethylformamide, dimethylacetamide, and the like), a halogenated hydrocarbon (e.g., chloroform, dichloromethane, and the like), and the like.

The reaction temperature is usually about 0 to 150° C., preferably room temperature (about 15 to 25° C.). The reaction time is usually about 1 to 36 hours.

2) When R' is an alkyl group, Compound (I) can be produced by reacting Compound (III) with an activated $R^2$—$NH_2$.

The activated $R^2$—$NH_2$ can be produced in any per se known manner, for example, by reacting an organo-aluminum reagent with $R^2$—$NH_2$ in a solvent inert to the reaction.

Examples of "organo-aluminum reagent" are trimethyl aluminum, dimethyl aluminum chloride, and the like; and a solution including them, and the like.

The amount of "organo-aluminum reagent" is about 1 to about 5 moles, preferably about 1 mole per 1 mole of $R^2$—$NH_2$.

Examples of the solvent are a halogenated hydrocarbon (e.g., chloroform, dichloromethane, and the like).

The reaction temperature is usually about 0 to about 150° C., preferably about 0 to 25° C. The reaction time is usually about 1 to about 6 hours.

The cyclization can be carried out by reacting Compound (III) with an activated $R^2$—$NH_2$ to obtain Compound (I).

The amount of "Compound (III)" is about ⅕ volume of a mixture of $R^2$—$NH_2$ and the organo-aluminum reagent.

This reaction is usually carried out in a solvent inert to the reaction.

Such solvent is the same as those used in the reaction to obtain an activated $R^2$—$NH_2$.

The reaction temperature is usually about 0 to about 150° C., preferably about 0 to 25° C. The reaction time is usually about 1 to about 48 hours.

Compound (I) can also be produced by a known hydrolysis reaction, deprotection reaction, acylation reaction, alkylation reaction, oxidation reaction, cyclization reaction, carbon bond expanding reaction, substituent exchanging reaction, or a combination thereof.

Compound (I) may be isolated and purified by per se known means of separation such as recrystallization, distillation and chromatography, and the like.

When Compound (I) is obtained in free form, it can be converted to a salt by per se known methods or methods analogous thereto. When Compound (I) is obtained in salt form, it can be converted to the free form or another salt by per se known methods or methods analogous thereto.

Compound (I) may be a hydrate or a non-hydrate. The hydrate is exemplified by monohydrate, sesquihydrate and dihydrate.

When Compound (I) is obtained as a mixture of optically active configurations, it can be resolved into the (R)- and (S)-forms by the conventional optical resolution techniques.

Compound (I) can be used as a prodrug. The prodrug of Compound (I) or a salt thereof means a compound which is converted to Compound (I) of the present invention under physiological conditions or with a reaction due to an enzyme, a gastric acid, and the like in the living body, that is, a compound which is converted to Compound (I) of the present invention with oxidation, reduction, hydrolysis, and the like according to an enzyme; a compound which is converted to Compound (I) of the present invention with gastric acid, etc. The prodrug for Compound (I) may for example be a compound obtained by subjecting an amino group in Compound (I) to an acylation, alkylation or phosphorylation (e.g., a compound obtained by subjecting an amino group in Compound (I) or to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in Compound (I) to an acylation, alkylation, phosphorylation or boration (e.g., a compound obtained by subjecting an hydroxy in Compound (I) to an acetylation, palmitoylation, propanoylation, pivaloylation, succinylation, fumarylation, alanylation, dimethylaminomethylcarbonylation, etc.). Any of these compounds can be produced from Compound (I) by a method known per se.

A prodrug of Compound (I) may also be one which is converted into Compound (I) under a physiological condition, such as those described in "IYAKUHIN no KAIHATSU (Development of Pharmaceuticals)", Vol. 7, Design of Molecules, p. 163-198, Published by HIROKAWA SHOTEN (1990).

Compound (I) may be labeled with an isotope (e.g., $^3$H, $^{14}$C, $^{35}$S) and the like.

In the reaction described above, a starting compound having an amino group, a carboxy group or a hydroxy group as its substituent may be present as a compound in which a protective group employed ordinarily in a peptide chemistry has been introduced into such a substituent, and an intended compound can be obtained by deprotection if necessary after the reaction.

A protective group for an amino group may for example be an optionally substituted $C_{1-6}$ alkyl-carbonyl (e.g., acetyl, propionyl, and the like), formyl, phenylcarbonyl, a $C_{1-6}$ alkyloxycarbonyl (e.g., methoxycarbonyl, ethoxycarbonyl, tert-butoxycarbonyl, and the like), phenyloxycarbonyl, a $C_{7-14}$ aralkyloxy-carbonyl (e.g., benzyloxycarbonyl, 9-fluorenylmethoxycarbonyl, and the like), trityl, phthaloyl and the like. Its substituent may for example be a halogen atom (e.g., fluorine, chlorine, bromine and iodine), a $C_{1-6}$ alkylcarbonyl (e.g., acetyl, propionyl, butyryl, and the like), nitro and the like, and the number of the substituents may be 1 to 3.

A protective group for a carboxy may for example be an optionally substituted $C_{1-6}$ alkyl (e.g., methyl, ethyl, propyl, isopropyl, butyl, tert-butyl, and the like), phenyl, trityl, silyl and the like. Its substituent may for example be a halogen atom (e.g., fluorine, chlorine, bromine and iodine), a $C_{1-6}$ alkylcarbonyl (e.g., acetyl, propionyl, butyryl, and the like), formyl, nitro, and the number of the substituents may be 1 to 3.

A protective group for a hydroxy group may for example be an optionally substituted $C_{1-6}$ alkyl (e.g., methyl, ethyl, propyl, isopropyl, butyl, tert-butyl, and the like), phenyl, a $C_{7-10}$ aralkyl (e.g., benzyl, and the like), a $C_{1-6}$ alkylcarbonyl (e.g., acetyl, propionyl, and the like), formyl, phenyloxycarbonyl, a $C_{7-10}$ aralkyloxycarbonyl (e.g., benzyloxycarbonyl, and the like), tetrahydropyranyl, tetrahydrofuranyl, silyl and the like. Its substituent may for example be a halogen atom (e.g., fluorine, chlorine, bromine and iodine), a $C_{1-6}$ alkyl, phenyl, a $C_{7-11}$ aralkyl, nitro, and the like, and the number of the substituents may be 1 to 4.

The method for introducing and removing the protective group is demonstrated in accordance with a known method or analogous method thereof (e.g., the method described in Protective Groups in Organic Chemistry (J. F. W. McOmie et al, Plenum Press)). A deprotection method may be a treatment with an acid, base, reduction, UV, hydrazine, phenylhydrazine, sodium N-methyldithiocarbamate, tetrabutylammonium fluoride, palladium acetate and the like.

Compound (I) of the present invention or a salt thereof (hereinafter also referred to as "the compound of the present invention") possesses excellent GnRH-antagonizing activity and low toxicity (for example, acute toxicity, chronic toxicity, genetic toxicity, reproduction toxicity, cardiotoxicity, drug interaction, carcinogenicity). In addition, it is excellent in oral absorbability, action sustainability, stability and pharmacokinetics. Also, it is scarcely influenced by plasma ingredients. The compound of the present invention can therefore be safely used in a mammal (e.g., human, monkey, bovine, horse, dog, cat, rabbit, rat, mouse, etc.) for the preventing and/or treating diseases depending on male or female hormones, diseases due to excess of these hormones, etc., by suppressing gonadotropin secretion with its GnRH receptor-antagonizing action to control plasma sex hormone concentrations.

For example, the compound of the present invention is useful for preventing and/or treating sex hormone-dependent cancers (e.g., prostatic cancer, uterine cancer, breast cancer, pituitary tumor, etc.), bone metastasis of sex hormone-dependent cancer, prostatic hypertrophy, hysteromyoma, endometriosis, metrofibroma, precocious puberty, amenorrhea, premenstrual syndrome, dysmenorrhea, multilocular ovary syndrome, polycystic ovary syndrome, acne, alopecia, Alzheimer's disease (Alzheimer's disease, senile dementia of Alzheimer type and a mixed type thereof), and the like. The compound of the present invention is also useful for the regulation of reproduction in males and females (e.g., pregnancy regulators, menstruation cycle regulators, etc.). The compound of the present invention can be also used as a male or female contraceptive, or as a female ovulation inducer. Based on its rebound effect after withdrawal, the compound of the present invention can be used to treat infertility. And the compound of this invention can be used as an agent for preventing and/or treating benign or malignant tumor which is hormone independent and LH-RH sensitive. And the compound of the present invention can be used as an agent for preventing and/or treating irritable bowel syndrome and for preventing postoperative recurrence of sex hormone-dependent cancer (an agent for preventing postoperative recurrence of prostatic cancer; an agent for preventing postoperative recurrence of breast cancer or ovarian cancer in the condition before or after menopause; especially, an agent for preventing postoperative recurrence of breast cancer or ovarian cancer in the condition before menopause).

In addition, the compound of the present invention is useful for regulation of animal estrus, improvement of meat quality and promotion of animal growth in the field of animal husbandry. The compound of the present invention is also useful as a fish spawning promoter.

The compound of the present invention can be also used to suppress the transient rise in plasma testosterone concentration (flare phenomenon) observed in administration of a GnRH super-agonist such as leuprorelin acetate. The compound of the present invention can be used in combination with a GnRH super-agonist such as leuprorelin acetate, gonadorelin, buserelin, triptorelin, goserelin, nafarelin, histrelin, deslorelin, meterelin, lecirelin, and the like. Among others, preferred is leuprorelin acetate.

It is also beneficial to use the compound of the present invention in conjunction with at least one member selected from the steroidal or nonsteroidal antiandrogen agent or antiestrogen agent, chemotherapeutic agent, GnRH antagonistic peptide, α-reductase inhibitor, α-receptor inhibitor, aromatase inhibitor, 17β-hydroxysteroid dehydrogenase inhibitor, adrenal androgen production inhibitor, kinase inhibitor, drug for hormone therapy, and drug inhibiting cell growth factor or its receptor, among others.

The "chemotherapeutic agent" mentioned above includes ifosfamide, adriamycin, peplomycin, cisplatin, cyclophosphamide, 5-FU, UFT, methotrexate, mitomycin C, mitoxantrone, etc.

The "GnRH antagonistic peptide" mentioned above includes non-oral GnRH antagonistic peptides such as cetrorelix, ganirelix, abarelix, etc.

The "adrenal androgen production inhibitor" mentioned above includes lyase ($C_{17, 20}$-lyase) inhibitors, etc.

The "kinase inhibitor" mentioned above includes tyrosine kinase inhibitor, etc.

The "drugs for hormone therapy" includes antiestrogens, progesterons (e.g., MPA, etc.), androgens, estrogens and androgen antagonists, among others.

The "cell growth factor" may be any substance that promotes proliferation of cells and generally includes peptides with molecular weights not over 20,000 which express the action at low concentrations through binding to receptors. Specifically, there can be mentioned (1) EGF (epidermal growth factor) or substances having substantially the same activity (e.g., EGF, heregulin (HER2 ligand), etc.), (2) insulin or substances having substantially the same activity (e.g., insulin, IGF (insulin-like growth factor)-1, IGF-2, etc.), (3) FGF (fibroblast growth factor) or substances having substantially the same activity (aFGF, bFGF, KGF (keratinocyte growth factor), HGF (hepatocyte growth factor), FGF-10, etc.), and (4) other growth factors (e.g., CSF (colony stimulating factor), EPO (erythropoietin), IL-2 (interleukin-2), NGF (nerve growth factor), PDGF (platelet-derived growth factor) and TGFβ (transforming growth factor β), etc.), among others.

The "cell growth factor receptor" may be any receptor capable of binding said cell growth factor, including EGF receptor, heregulin receptor (HER2), insulin receptor-1, insulin receptor-2, IGF receptor, FGF receptor-1, FGF receptor-2, etc.

The drug inhibiting the cell growth factor mentioned above includes herceptin (anti-HER2 receptor antibody), among others.

The drug inhibiting the growth factor mentioned above or its receptor includes herbimycin, PD153035 [e.g., Science, 265 (5175) p 1093, (1994)], etc.

As a further class of drugs inhibiting the cell growth factor or its receptor includes HER2 inhibitors. The HER2 inhibitor may be any substance that inhibits the activity of HER2 (e.g., phosphorylating activity), thus including an antibody, a low-molecular weight compound (synthetic or natural product), an antisense, an HER2 ligand, heregulin, and any of them as partially modified or mutated in structure. Moreover, it may be a substance which inhibits HER2 activity by inhibiting HER2 receptor (e.g. HER2 receptor antibody). The low molecular weight compound having HER2 inhibiting activity includes, for example, the compounds described in WO 98/03505, namely 1-[3-[4-[2-((E)-2-phenylethenyl)-4-oxazolylmethoxy]phenyl]propyl]-1,2,4-triazole and the like.

For prostatic hypertrophy, examples of such combination includes the compound of the present invention in combination with the GnRH super-agonist, androgen antagonist, antiestrogen, GnRH antagonistic peptide, α-reductase inhibitor, α-receptor inhibitor, aromatase inhibitor, 17β-hydroxysteroiddehydrogenase inhibitor, adrenal androgen production inhibitor, kinase inhibitor, or the like.

For prostatic cancer, examples of such combination includes the compound of the present invention in combination with the GnRH super-agonist, androgen antagonist, antiestrogen, chemotherapeutic agent (e.g., ifosfamide, UFT, adriamycin, peplomycin, cisplatin, etc.), GnRH antagonistic peptide, aromatase inhibitor, 17β-hydroxysteroid dehydrogenase inhibitor, adrenal androgen production inhibitor, kinase inhibitor, drug for hormone therapy such as estrogens (e.g., DSB, EMP, etc.), androgen antagonist (e.g., CMA. etc.), drug antagonizing growth factor or its receptor, and so forth.

For breast cancer, examples of such combination includes the compound of the present invention in combination with the GnRH super-agonist, antiestrogen, chemotherapeutic agent (e.g., cyclophosphamide, 5-FU, UFT, methotrexate, adriamycin, mitomycin C, mitoxantrone, etc.), GnRH antagonistic peptide, aromatase inhibitor, adrenal androgen production inhibitor, kinase inhibitor, drug for hormone therapy such as antiestrogen (e.g., tamoxifen, etc.), progesterons (e.g., MPA, etc.), androgens, estrogens, etc., drug antagonizing growth factor or its receptor, or the like.

The administration mode of the compound of the present invention and a concomitant medicament are not particularly limited, provided that the compound of the present invention and the concomitant medicament are combined upon administration. Such an administration mode may for example be (1) an administration of a single formulation obtained by formulating the compound of the present invention and a concomitant medicament simultaneously, (2) a simultaneous administration via an identical route of two formulations obtained by formulating the compound of the present invention and a concomitant medicament separately, (3) a sequential and intermittent administration via an identical route of two formulations obtained by formulating the compound of the present invention and a concomitant medicament separately, (4) a simultaneous administration via different routes of two formulations obtained by formulating the compound of the present invention and a concomitant medicament separately, (5) a sequential and intermittent administration via different routes of two formulations obtained by formulating the compound of the present invention and a concomitant medicament separately (for example, the compound of the present invention followed by concomitant medicament, or inverse order) and the like.

When the compound of the present invention is used as a preventing and/or treating agent for the above-mentioned diseases or used in the field of animal husbandry or fishery, it can be administered orally or non-orally, as formulated with a pharmaceutically acceptable carrier, normally in the form of solid preparations such as tablets, capsules, granules and powders for oral administration, or in the form of intravenous, subcutaneous, intramuscular or other injections, suppositories or sublingual tablets for non-oral administration. It may also be sublingually, subcutaneously, intramuscularly or otherwise administered in the form of sustained-release preparations of sublingual tablets, microcapsules, etc. Depending on symptom severity; subject age, sex, weight and sensitivity; duration and intervals of administration; property, dispensing and kind of pharmaceutical preparation; kind of active ingredient etc., daily dose is not subject to limitation. For use in the treatment of the above-described sex hormone-dependent cancers (e.g., prostatic cancer, uterine cancer, breast cancer, pituitary tumor, etc.), prostatic hypertrophy, hysteromyoma, endometriosis, precocious puberty etc., daily dose is normally about 0.01 to 30 mg, preferably about 0.02 to 10 mg, and more preferably 0.1 to 10 mg, especially preferably 0.1 to 5 mg per kg weight of mammal, normally in 1 to 4 divided dosages.

The above doses of the active ingredient (the compound of the present invention) for oral administration are applicable to the use of the compound of the present invention in the field of animal husbandry or fishery. Daily dose is about 0.01 to 30 mg, preferably about 0.1 to 10 mg, per kg weight of subject organism, normally in 1 to 3 divided dosages.

In the pharmaceutical composition of the present invention, the amount of Compound (I) is 0.01 to 100% by weight or so of the total weight of the composition.

The above pharmaceutically acceptable carriers are various organic or inorganic carrier substances in common use as pharmaceutical materials, including excipients, lubricants, binders and disintegrants for solid preparations; solvents, dissolution aids, suspending agents, isotonizing agents, buffers and soothing agents for liquid preparations; and the like. Other pharmaceutical additives such as preservatives, antioxidants, coloring agents and sweetening agents may be used as necessary.

Preferable examples of excipients include, for example, lactose, sucrose, D-mannitol, starch, crystalline cellulose, light silicic anhydride, and the like. Preferable examples of lubricants include, for example, magnesium stearate, calcium stearate, talc, colloidal silica, and the like. Preferable examples of binders include, for example, crystalline cellulose, sucrose, D-mannitol, dextrin, hydroxypropyl cellulose, hydroxypropylmethyl cellulose, polyvinylpyrrolidone, and the like. Preferable examples of disintegrants include, for example, starch, carboxymethyl cellulose, carboxymethyl cellulose calcium, crosslinked carmellose sodium, carboxymethyl starch sodium, and the like. Preferable examples of solvents include, for example, water for injection, alcohol, propylene glycol, macrogol, sesame oil, corn oil, and the like. Preferable examples of dissolution aids include polyethylene glycol, propylene glycol, D-mannitol, benzyl benzoate, ethanol, trisaminomethane, cholesterol, triethanolamine, sodium carbonate, sodium citrate, and the like. Preferable examples of suspending agents include surfactants such as stearyltriethanolamine, sodium lauryl sulfate, laurylaminopropionic acid, lecithin, benzalkonium chloride, benzethonium chloride, monostearic glycerol, and the like; and hydrophilic polymers such as polyvinyl alcohol, polyvinylpyrrolidone, carboxymethyl cellulose sodium, methyl cellulose, hydroxymethyl cellulose, hydroxyethyl cellulose, hydroxypropyl cellulose, and the like. Preferable examples of isotonizing agents include, for example, sodium chloride, glycerol, D-mannitol, and the like. Preferable examples of buffers include buffer solutions of phosphates, acetates, carbonates, citrates, and the like. Preferable examples of soothing agents include benzyl alcohol, and the like. Preferable examples of preservatives include paraoxybenzoic acid esters, chlorobutanol, benzyl alcohol, phenethyl alcohol, dehydroacetic acid, sorbic acid, and the like. Preferable examples of antioxidants include sulfites, ascorbic acid, and the like.

By adding suspending agents, dissolution aids, stabilizers, isotonizing agents, preservatives, and the like, the compound of the present invention can be prepared as an intravenous, subcutaneous or intramuscular injection by a commonly known method. In such cases, the compound of the present invention can be freeze-dried as necessary by a commonly known method. In administration to humans, for example, the compound of the present invention can be safely administered orally or non-orally as such or as a pharmaceutical composition prepared by mixing it with a pharmacologically acceptable carrier, excipient and diluent selected as appropriate.

Such pharmaceutical compositions include oral preparations (e.g., powders, granules, capsules, tablets), parenteral preparations [e.g., injections, drip infusions, external preparations (e.g., nasal preparations, transdermal preparations, and the like), suppositories (e.g., rectal suppositories, vaginal suppositories, and the like), and the like].

These preparations can be produced by commonly known methods in common use for pharmaceutical making processes.

An injection can be produced by, for example, preparing the compound of the present invention as an aqueous injection along with a dispersing agent (e.g., Tween 80 (produced by Atlas Powder Company, USA), HCO 60 (produced by Nikko Chemicals Co., Ltd.), polyethylene glycol, carboxymethyl cellulose, sodium alginate, and the like), a preservative (e.g., methyl paraben, propyl paraben, benzyl alcohol, and the like), an isotonizing agent (e.g., sodium chloride, mannitol, sorbitol, glucose, and the like), and the like, or as an oily injection in solution, suspension or emulsion in a vegetable oil such as olive oil, sesame oil, cottonseed oil or corn oil; propylene glycol and the like.

An oral preparation can be produced by formulating the compound of the present invention by a compression molding after addition of an excipient (e.g., lactose, sucrose, starch, and the like), a disintegrant (e.g., starch, calcium carbonate, and the like), a binder (e.g., starch, gum arabic, carboxymethyl cellulose, polyvinylpyrrolidone, hydroxypropyl cellulose, and the like), a lubricant (e.g., talc, magnesium stearate, polyethylene glycol 6000, and the like) and other additives, and, where necessary, coating the formulated product for the purpose of taste masking, enteric dissolution or sustained release by a commonly known method. Coating agents for this purpose include, for example, hydroxypropylmethyl cellulose, ethyl cellulose, hydroxymethyl cellulose, hydroxypropyl cellulose, polyoxyethylene glycol, Tween 80, Prulonic F68, cellulose acetate phthalate, hydroxypropylmethyl cellulose phthalate, hydroxymethyl cellulose acetate succinate, Eudragit (produced by Rohm Company, Germany; methacrylic acid/acrylic acid copolymer), dyes (e.g., iron oxide, titanium dioxide), and the like. For an enteric preparation, an intermediate phase may be provided between the enteric phase and the drug-containing phase for the purpose of separation of the two phases by a commonly known method.

An external preparation can be produced by converting the compound of the present invention as a solid, semi-solid or liquid composition by a commonly known method. Such a solid composition is produced by, for example, powdering the compound of the present invention as such or in mixture with an excipient (e.g., glycol, mannitol, starch, microcrystalline cellulose, and the like), a thickening agent (e.g., natural rubber, cellulose derivative, acrylic acid polymer, and the like) and other additives. Such a liquid composition is produced by preparing the compound of the present invention as an oily or aqueous suspension in almost the same manner as the injection. The semi-solid composition is preferably an aqueous or oily gel, or an ointment. All these compositions may contain pH regulators (e.g., carbonic acid, phosphoric acid, citric acid, hydrochloric acid, sodium hydroxide, and the like), preservatives (e.g., paraoxybenzoic acid esters, chlorobutanol, benzalkonium chloride, and the like) and other additives.

A suppository is produced by preparing the compound of the present invention as an oily or aqueous solid, semi-solid or liquid composition by a commonly known method. Useful oily bases for such compositions include glycerides of higher fatty acids (e.g., cacao fat, witepsols (produced by Dynamite Nobel Company, Germany) and the like; medium fatty acids (e.g., MIGLIOL, produced by Dynamite Nobel Company, Germany); and vegetable oils (e.g., sesame oil, soybean oil, cottonseed oil, and the like). Aqueous bases include, for example, polyethylene glycols and propylene glycol. Bases for aqueous gels include, for example, natural rubbers, cellulose derivatives, vinyl polymers and acrylic acid polymers.

A compound of the formula:

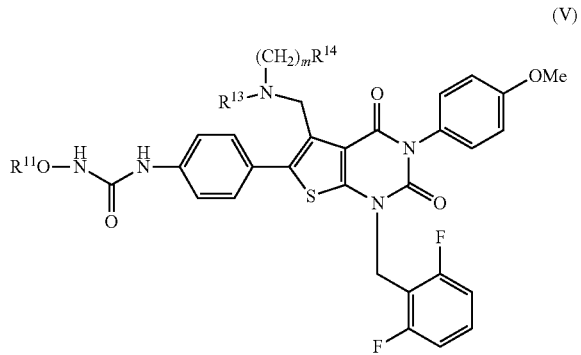

(V)

wherein $R^{11}$ and $R^{13}$ each is a $C_{1-4}$ alkyl, $R^{14}$ is a hydrogen atom or a $C_{1-4}$ alkoxy and m is an integer of 1 to 4 (hereinafter briefly referred to as Compound (V)) or a salt thereof also has an excellent GnRH antagonizing activity, especially a strong antagonistic activity though the compound falls outside the scope of Compound (I).

Examples of the "$C_{1-4}$ alkyl" represented by $R^{11}$ or $R^{13}$ include methyl, ethyl, propyl, isopropyl, butyl, isobutyl, sec-butyl, tert-butyl, etc.

Examples of the "$C_{1-4}$ alkoxy" represented by $R^{14}$ include methoxy, ethoxy, propoxy, isopropoxy, butoxy, isobutoxy, sec-butoxy, tert-butoxy, etc.

As $R^{11}$, methyl is preferable.
As $R^{13}$, methyl is preferable.
As $R^{14}$, a hydrogen atom and methoxy are preferable.
Preferable examples of m are 1 and 2.

Preferable examples of Compound (V) are N-(4-(5-(((2-methoxyethyl)methylamino)methyl)-1-(2,6-difluorobenzyl)-1,2,3,4-tetrahydro-2,4-dioxo-3-(4-methoxyphenyl)thieno[2,3-d]pyrimidin-6-yl)phenyl)-N'-methoxyurea or N-(4-(1-(2,6-difluorobenzyl)-5-((dimethylamino)methyl)-3-(4-methoxyphenyl)-2,4-dioxo-1,2,3,4-tetrahydrothieno[2,3-d]pyrimidin-6-yl)phenyl)-N'-methoxyurea and a salt thereof.

Salts of Compound (V) are preferably physiologically acceptable acid addition salts. Such salts include, for example, salts with inorganic acids (e.g., hydrochloric acid, hydrobromic acid, nitric acid, sulfuric acid, phosphoric acid), salts with organic acids (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.), and the like. When Compound (V) has an acidic group, it may form a physiologically acceptable salt with an inorganic base (e.g., alkali metals and alkaline earth metals such as sodium, potassium, calcium and magnesium, ammonia, and the like) or an organic base (e.g., trimethylamine, triethylamine, pyridine, picoline, ethanolamine, diethanolamine, triethanolamine, dicyclohexylamine, N,N'-dibenzylethylenediamine, and the like).

Compound (V) can be produced by the method described in JP-A-9-169768 (WO 96/24597) and JP-A-2001-278884 (WO 00/56739) and its analogous method.

Compound (V) may be a hydrate or a non-hydrate. The hydrate is exemplified by monohydrate, sesquihydrate and dihydrate.

Compound (V) can be used as a prodrug. The prodrug means a compound which is converted to Compound (V) by a reaction due to an enzyme, a gastric acid, or the like under physiological conditions in the living body, that is, a compound which is converted to Compound (V) with oxidation, reduction, hydrolysis, or the like according to an enzyme, or a compound which is converted to Compound (V) with gastric acid, etc. The prodrug for Compound (V) may for example be a compound obtained by subjecting an amino group in Compound (V) to an acylation, alkylation or phosphorylation (e.g., a compound obtained by subjecting an amino group in Compound (V) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.). These compounds can be produced from the compound of the present invention.

A prodrug of Compound (V) may also be one which is converted into Compound (V) under a physiological condition, such as those described in "IYAKUHIN no KAIHATSU (Development of Pharmaceuticals)", Vol. 7, Design of Molecules, p. 163-198, Published by HIROKAWA SHOTEN (1990).

Compound (V) may be labeled with an isotope (e.g., $^3$H, $^{14}$C, $^{35}$S) and the like.

And the compound represented by the formula:

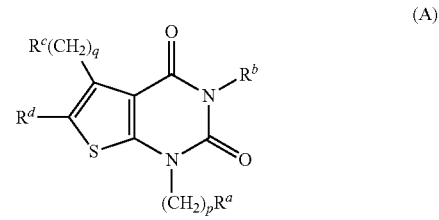

(A)

wherein $R^a$ is (1) a hydrogen atom, (2) an aryl group which may have 1 to 5 substituent(s) selected from the group consisting of (i) a halogen, (ii) a nitro, (iii) a cyano, (iv) an amino, (v) a carboxyl group which may be esterified or amidated, (vi) an alkylenedioxy, (vii) an alkyl, (viii) an alkoxy, (ix) an alkylthio, (x) an alkylsulfinyl and (xi) an alkylsulfonyl, (3) a cycloalkyl group which may have a substituent or (4) a heterocyclic group which may have a substituent; $R^b$ is a nitrogen-containing heterocyclic group which may have a substituent; $R^c$ is an amino group which may have a substituent; $R^d$ is an aryl group which may have a substituent; p is an integer of 0 to 3; and q is an integer of 0 to 3 (hereinafter as abbreviated as Compound (A)) or a salt thereof, which contains a part of the Compound (I) of the present invention, has an excellent GnRH antagonizing activity, especially strong antagonistic activity similar to Compound (I).

The definitions of the substituents of Compound (A) are shown below.

Examples of "aryl" of "aryl group which may have 1 to 5 substituent(s) selected from the group consisting of (i) a halogen, (ii) a nitro, (iii) a cyano, (iv) an amino, (v) a carboxyl group which may be esterified or amidated, (vi) an alkylenedioxy, (vii) an alkyl, (viii) an alkoxy, (ix) an alkylthio, (x) an alkylsulfinyl and (xi) an alkylsulfonyl" represented by $R^a$ are $C_{6-14}$ aryl such as phenyl, 1-naphthyl, 2-naphthyl, anthryl, phenanthryl, acenaphthylenyl, and the like.

Examples of "halogen" of "aryl group which may have 1 to 5 substituent(s) selected from the group consisting of (i) a halogen, (ii) a nitro, (iii) a cyano, (iv) an amino, (v) a carboxyl group which may be esterified or amidated, (vi) an alkylenedioxy, (vii) an alkyl, (viii) an alkoxy, (ix) an alkylthio, (x) an alkylsulfinyl and (xi) an alkylsulfonyl" represented by $R^a$ are fluorine, chlorine, bromine and iodine.

Examples of "carboxyl group which may be esterified or amidated" of "aryl group which may have 1 to 5 substituent(s) selected from the group consisting of (i) a halogen, (ii) a nitro, (iii) a cyano, (iv) an amino, (v) a carboxyl group which may be esterified or amidated, (vi) an alkylenedioxy, (vii) an alkyl, (viii) an alkoxy, (ix) an alkylthio, (x) an alkylsulfinyl and (xi) an alkylsulfonyl" represented by $R^a$ are carboxyl, a $C_{1-6}$ alkoxy-carbonyl (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl, and the like), a $C_{3-6}$ cycloalkyloxy-carbonyl (e.g., cyclopropyloxycarbonyl, cyclobutyloxycarbonyl, cyclopentyloxycarbonyl, cyclohexyloxycarbonyl, and the like), a $C_{6-14}$ aryloxy-carbonyl (e.g., phenoxycarbonyl, 1-naphthyloxycarbonyl, 2-naphthyloxycarbonyl, anthryloxycarbonyl, phenanthryloxycarbonyl, acenaphthylenyloxycarbonyl, and the like), a $C_{7-10}$ aralkyloxy-carbonyl (e.g., benzyloxycarbonyl, and the like), carbamoyl, a N-mono-$C_{1-6}$ alkyl-carbamoyl (e.g., methylcarbamoyl, ethylcarbamoyl, propylcarbamoyl, isopropylcarbamoyl, butylcarbamoyl, isobutylcarbamoyl, sec-butylcarbamoyl, tert-butylcarbamoyl, pentylcarbamoyl, hexylcarbamoyl, and the like), a N-mono-$C_{3-6}$ cycloalkyl-carbamoyl (e.g., cyclopropylcarbamoyl, cyclobutylcarbamoyl, cyclopentylcarbamoyl, cyclohexylcarbamoyl, and the like), a N-mono-$C_{6-14}$ aryl-carbamoyl (e.g., phenylcarbamoyl, 1-naphthylcarbamoyl, 2-naphthylcarbamoyl, anthrylcarbamoyl, phenanthryloxycarbamoyl, acenaphthylenyloxycarbamoyl, and the like), N-mono-$C_{7-10}$ aralkyl-carbamoyl (e.g., benzylcarbamoyl, and the like), and the like.

Examples of "alkylenedioxy" of "aryl group which may have 1 to 5 substituent(s) selected from the group consisting of (i) a halogen, (ii) a nitro, (iii) a cyano, (iv) an amino, (v) a carboxyl group which may be esterified or amidated, (vi) an alkylenedioxy, (vii) an alkyl, (viii) an alkoxy, (ix) an alkylthio, (x) an alkylsulfinyl and (xi) an alkylsulfonyl" represented by $R^a$ are a $C_{1-6}$ alkylenedioxy (e.g., —OCH$_2$O—, —O(CH$_2$)$_2$O—, —O(CH$_2$)$_3$O—, —O(CH$_2$)$_4$O—, —O(CH$_2$)$_5$O—, —O(CH$_2$)$_6$O—).

Examples of "alkyl" of "aryl group which may have 1 to 5 substituent(s) selected from the group consisting of (i) a halogen, (ii) a nitro, (iii) a cyano, (iv) an amino, (v) a carboxyl group which may be esterified or amidated, (vi) an alkylenedioxy, (vii) an alkyl, (viii) an alkoxy, (ix) an alkylthio, (x) an alkylsulfinyl and (xi) an alkylsulfonyl" represented by $R^a$ are a $C_{1-6}$ alkyl (e.g., methyl, ethyl, propyl, isopropyl, butyl, isobutyl, sec-butyl, tert-butyl, pentyl, hexyl, and the like), and the like.

Examples of "alkoxy" of "aryl group which may have 1 to 5 substituent(s) selected from the group consisting of (i) a halogen, (ii) a nitro, (iii) a cyano, (iv) an amino, (v) a carboxyl group which may be esterified or amidated, (vi) an alkylenedioxy, (vii) an alkyl, (viii) an alkoxy, (ix) an alkylthio, (x) an alkylsulfinyl and (xi) an alkylsulfonyl" represented by $R^a$ are a $C_{1-6}$ alkoxy (e.g., methoxy, ethoxy, propoxy, isopropoxy, butoxy, isobutoxy, sec-butoxy, tert-butoxy, pentyloxy, hexyloxy, and the like), and the like.

Examples of "alkylthio" of "aryl group which may have 1 to 5 substituent(s) selected from the group consisting of (i) a halogen, (ii) a nitro, (iii) a cyano, (iv) an amino, (v) a carboxyl group which may be esterified or amidated, (vi) an alkylenedioxy, (vii) an alkyl, (viii) an alkoxy, (ix) an alkylthio, (x) an alkylsulfinyl and (xi) an alkylsulfonyl" represented by $R^a$ are a $C_{1-6}$ alkylthio (e.g., methylthio, ethylthio, propylthio, isopropylthio, butylthio, isobutylthio, sec-butylthio, tert-butylthio, pentylthio, hexylthio, and the like), and the like.

Examples of "alkylsulfinyl" of "aryl group which may have 1 to 5 substituent(s) selected from the group consisting of (i) a halogen, (ii) a nitro, (iii) a cyano, (iv) an amino, (v) a carboxyl group which may be esterified or amidated, (vi) an alkylenedioxy, (vii) an alkyl, (viii) an alkoxy, (ix) an alkylthio, (x) an alkylsulfinyl and (xi) an alkylsulfonyl" represented by $R^a$ are a $C_{1-6}$ alkylsulfinyl (e.g., methylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl, hexylsulfinyl, and the like), and the like.

Examples of "alkylsulfonyl" of "aryl group which may have 1 to 5 substituent(s) selected from the group consisting of (i) a halogen, (ii) a nitro, (iii) a cyano, (iv) an amino, (v) a carboxyl group which may be esterified or amidated, (vi) an alkylenedioxy, (vii) an alkyl, (viii) an alkoxy, (ix) an alkylthio, (x) an alkylsulfinyl and (xi) an alkylsulfonyl" represented by $R^a$ are a $C_{1-6}$ alkylsulfonyl (e.g., methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, hexylsulfonyl, and the like), and the like.

Examples of "cycloalkyl group" of "cycloalkyl group which may have a substituent" represented by $R^a$ are a $C_{3-6}$ cycloalkyl (e.g., cyclopropyl, cyclobutyl, cyclopentyl, cyclohexyl, and the like), and the like.

Examples of "heterocyclic group" of "heterocyclic group which may have a substituent" represented by $R^a$ are (1) a 5-membered cyclic group which contains 1 to 4 heteroatom(s) selected from an oxygen atom, a sulfur atom, a nitrogen atom and the like in addition to a carbon atom (e.g., 2-thienyl, 3-thienyl, 2-furyl, 3-furyl, 2-pyrrolyl, 3-pyrrolyl, 2-oxazolyl, 4-oxazolyl, 5-oxazolyl, 2-thiazolyl, 4-thiazolyl, 5-thiazolyl, 3-pyrazolyl, 4-pyrazolyl, 5-pyrazolyl, 2-imidazolyl, 4-imidazolyl, 5-imidazolyl, 3-isoxazolyl, 4-isoxazolyl, 5-isoxazolyl, 3-isothiazolyl, 4-isothiazolyl, 5-isothiazolyl, 3-(1,2,4-oxadiazolyl), 5-(1,2,4-oxadiazolyl), 1,3,4-oxadiazolyl, 3-(1,2,4-thiadiazolyl), 5-(1,2,4-thiadiazolyl), 1,3,4-thiadiazolyl, 4-(1,2,3-thiadiazolyl), 5-(1,2,3-thiadiazolyl), 1,2,5-thiadiazolyl, 1,2,3-triazolyl, 1,2,4-triazolyl, 1H-tetrazolyl, 2H-tetrazolyl, oxoimidazinyl, dioxotriazinyl, pyrrolidinyl, and the like), (2) a 6-membered cyclic group which contains 1 to 4 heteroatom(s) selected from an oxygen atom, a sulfur atom, a nitrogen atom and the like in addition to a carbon atom (e.g., 2-pyridyl, 3-pyridyl, 4-pyridyl, N-oxido-2-pyridyl, N-oxido-3-pyridyl, N-oxido-4-pyridyl, 2-pyrimidinyl, 4-pyrimidinyl, 5-pyrimidinyl, N-oxido-2-pyrimidinyl, N-oxido-4-pyrimidinyl, N-oxido-5-pyrimidinyl, 2-thiomorpholinyl, 3-thiomorpholinyl, 2-morpholinyl, 3-morpholinyl, piperidinyl, pyranyl, thiopyranyl, 1,4-oxazinyl, 1,4-thiazinyl, 1,3-thiazinyl, 2-piperazinyl, 3-piperazinyl, triazinyl, oxotriazinyl, 3-pyridazinyl, 4-pyridazinyl, pyrazinyl, N-oxido-3-pyridazinyl, N-oxido-4-pyridazinyl, and the like), and (3) a bicyclic or tricyclic condensed cyclic group which contains 1 to 4 heteroatom(s) selected from an oxygen atom, a sulfur atom, a nitrogen atom and the like in addition to a carbon atom (e.g., benzofuryl, benzothiazolyl, benzoxazolyl, tetrazolo[1,5-b]pyridazinyl, triazolo[4,5-b]pyridazinyl, benzoimidazolyl, quinolyl, isoquinolyl, cinnolinyl, phthalazinyl, quinazolinyl, quinoxalinyl, indolizinyl, quinolizinyl, 1,8-naphthylidinyl, purinyl, pteridinyl, dibenzofuranyl, carbazolyl, acridinyl, phenanthrydinyl, chromanyl, benzoxazinyl, phenazinyl, phenothiazinyl, phenoxazinyl, and the like).

Examples of "substituent" of "cycloalkyl group which may have a substituent" and "heterocyclic group which may have a substituent" represented by $R^a$ are (i) a $C_{1-6}$ alkyl (e.g., methyl, ethyl, propyl, isopropyl, butyl, isobutyl, sec-butyl, tert-butyl, pentyl, hexyl, and the like), (ii) a $C_{2-6}$ alkenyl (e.g., vinyl, allyl, 1-butenyl, 2-butenyl, and the like), (iii) a $C_{2-6}$ alkynyl (e.g., ethynyl, propargyl, 2-butynyl, 5-hexynyl, and the like), (iv) a $C_{3-6}$ cycloalkyl (e.g., cyclopropyl, cyclobutyl, cyclopentyl, cyclohexyl, and the like), (v) a $C_{6-14}$ aryl (e.g., phenyl, 1-naphthyl, 2-naphthyl, and the like), (vi) a $C_{7-14}$ aralkyl (e.g., benzyl, phenethyl, and the like), (vii) a nitro, (viii) a hydroxy, (ix) a mercapto, (x) a cyano, (xi) a carbamoyl, (xii) a carboxyl, (xiii) a $C_{1-6}$ alkoxy-carbonyl (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl, and the like), (xiv) a sulfo, (xv) a halogen (e.g., fluorine, chlorine, bromine and iodine), (xvi) a $C_{1-6}$ alkoxy (e.g., methoxy, ethoxy, propoxy, isopropoxy, butoxy, isobutoxy, sec-butoxy, tert-butoxy, pentyloxy, hexyloxy, and the like), which may have a $C_{1-6}$ alkoxy (e.g., methoxy, ethoxy, propoxy, isopropoxy, butoxy, isobutoxy, sec-butoxy, tert-butoxy, pentyloxy, hexyloxy, and the like), (xvii) a $C_{6-10}$ aryloxy (e.g., phenoxy, 1-naphthyloxy, 2-naphthyloxy, and the like), (xviii) a $C_{1-6}$ alkylthio (e.g., methylthio, ethylthio, propylthio, isopropylthio, butylthio, isobutylthio, sec-butylthio, tert-butylthio, pentylthio, hexylthio, and the like), (xix) a $C_{6-10}$ arylthio (e.g., phenylthio, 1-naphthylthio, 2-naphthylthio, and the like), (xx) a $C_{1-6}$ alkylsulfinyl (e.g., methylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl, hexylsulfinyl, and the like), (xxi) a $C_{6-10}$ arylsulfinyl (e.g., phenylsulfinyl, 1-naphthylsulfinyl, 2-naphthylsulfinyl, and the like), (xxii) a $C_{1-6}$ alkylsulfonyl (e.g., methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, hexylsulfonyl, and the like), (xxiii) a $C_{6-10}$ arylsulfinyl (e.g., phenylsulfonyl, 1-naphthylsulfonyl, 2-naphthylsulfonyl, and the like), (xxiv) an amino, (xxv) a $C_{1-6}$ acylamino, (e.g., formylamino, acetylamino, propionylamino, butyrylamino, isobutyrylamino, valerylamino, and the like), (xxvi) a mono-$C_{1-6}$ alkylamino (e.g., methylamino, ethylamino, propylamino, isopropylamino, butylamino, and the like), (xxvii) a di-$C_{1-6}$ alkylamino (e.g., dimethylamino, diethylamino, dipropylamino, diisopropylamino, dibutylamino, and the like), (xxviii) a $C_{3-6}$ cycloalkylamino (e.g., cyclopropylamino, cyclobutylamino, cyclopentylamino, cyclohexylamino, and the like), (xxix) a $C_{6-10}$ arylamino (e.g., anilino, 1-naphthylamino, 2-naphthylamino, and the like), (xxx) a $C_{1-6}$ acyl (e.g., formyl, acetyl, propionyl, butyryl, isobutyryl, valeryl, and the like), (xxxi) a $C_{6-10}$ arylcarbonyl (e.g., benzoyl, 1-naphthylcarbonyl, 2-naphthylcarbonyl, and the like), (xxxii) a $C_{1-4}$ alkylenedioxy (e.g., —OCH$_2$O—, —O(CH$_2$)$_2$O—, —O(CH$_2$)$_3$O— and —O(CH$_2$)$_4$O—), (xxxiii) a 5- or 6-membered heterocyclic group which contains 1 to 4 heteroatom(s) selected from an oxygen atom, a sulfur atom, a nitrogen atom and the like in addition to a carbon atom (e.g., 2-thienyl, 3-thienyl, 2-furyl, 3-furyl, 2-pyrrolyl, 3-pyrrolyl, 2-oxazolyl, 4-oxazolyl, 5-oxazolyl, 2-thiazolyl, 4-thiazolyl, 5-thiazolyl, 3-pyrazolyl, 4-pyrazolyl, 5-pyrazolyl, 2-imidazolyl, 4-imidazolyl, 5-imidazolyl, 3-isoxazolyl, 4-isoxazolyl, 5-isoxazolyl, 3-isothiazolyl, 4-isothiazolyl, 5-isothiazolyl, 3-(1,2,4-oxadiazolyl), 5-(1,2,4-oxadiazolyl), 1,3,4-oxadiazolyl, 3-(1,2,4-thiadiazolyl), 5-(1,2,4-thiadiazolyl), 1,3,4-thiadiazolyl, 4-(1,2,3-thiadiazolyl), 5-(1,2,3-thiadiazolyl), 1,2,5-thiadiazolyl, 1,2,3-triazolyl, 1,2,4-triazolyl, 1H-tetrazolyl, 2H-tetrazolyl, oxoimidazinyl, dioxotriazinyl, pyrrolidinyl, 2-pyridyl, 3-pyridyl, 4-pyridyl, 2-pyrimidinyl, 4-pyrimidinyl, 5-pyrimidinyl, 2-thiomorpholinyl, 3-thiomorpholinyl, 2-morpholinyl, 3-morpholinyl, piperidinyl, pyranyl, thiopyranyl, 1,4-oxazinyl, 1,4-thiazinyl, 1,3-thiazinyl, 2-piperazinyl, 3-piperazinyl, triazinyl, oxotriazinyl, 3-pyridazinyl, 4-pyridazinyl, pyrazinyl, and the like), (xxxiv) oxo, (xxxv) thioxo, and the like. The number of substituents is 1 to 6, preferably 1 to 3, and the substitution position may be any place on which the substitution is possible.

Examples of "nitrogen-containing heterocyclic group" of "nitrogen-containing heterocyclic group which may have a substituent" represented by $R^b$ are a 5- to 7-membered nitrogen-containing heterocyclic group (e.g., pyrrolidin-1-yl, pyrrolidin-2-yl, pyrrolidin-3-yl, oxazolidin-3-yl, thiazolidin-3-yl, isoxazolidin-2-yl, isothiazolidin-2-yl, imidazolidin-1-yl, imidazolidin-2-yl, imidazolidin-4-yl, pyrazolidin-2-yl, pyrazolidin-3-yl, pyrazolidin-4-yl, pyrrol-1-yl, pyrrol-2-yl, pyrrol-3-yl, imidazol-1-yl, imidazol-2-yl, imidazol-4-yl, pyrazol-1-yl, pyrazol-3-yl, pyrazol-4-yl, 1,2,3-triazol-1-yl, 1,2,5-triazol-1-yl, tetrazol-1-yl, tetrazol-2-yl, tetrazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, piperidin-1-yl, piperidin-2-yl, piperidin-3-yl, piperidin-4-yl, piperazin-1-yl, piperazin-2-yl, morpholin-2-yl, morpholin-3-yl, morpholin-4-yl, pyridin-2-yl, pyridin-3-yl, pyridin-4-yl, pyrazin-2-yl, pyrimidin-2-yl, pyrimidin-4-yl, pyrimidin-5-yl, pyridazin-3-yl, pyridazin-4-yl, 1,2,3-triazin-4-yl, 1,2,3-triazin-5-yl, 1,2,4-triazin-3-yl, 1,2,4-triazin-5-yl, 1,2,4-triazin-6-yl, 1,3,5-triazin-2-yl, 1,2,3,4-tetrazin-5-yl, 1,2,3,5-tetrazin-4-yl, azepan-1-yl, azepan-2-yl, 1,2-diazepan-3-yl, 1,2-diazepan-4-yl, 1,2-diazepan-5-yl, 1,3-diazepan-2-yl, 1,3-diazepan-4-yl, 1,3-diazepan-5-yl, 1,4-diazepan-2-yl, 1,4-diazepan-3-yl, 1,4-diazepan-5-yl, 1,2,3-triazepan-4-yl, 1,2,3-triazepan-5-yl, 1,2,4-triazepan-3-yl, 1,2,4-triazepan-5-yl, and the like), and the like.

Examples of "substituent" of "nitrogen-containing heterocyclic group which may have a substituent" represented by $R^b$ are same number and same kind as "substituent" of "cycloalkyl group which may have a substituent" and "heterocyclic group which may have a substituent" represented by $R^a$.

Example of "amino group which may have a substituent" represented by $R^c$ is a group of the formula: —$NR^eR^f$ wherein $R^e$ is (1) a hydrogen atom, (2) a $C_{1-6}$ alkyl which may have a substituent, (3) a $C_{3-6}$ cycloalkyl which may have a substituent, (4) a $C_{6-14}$ aryl which may have a substituent, (5) a $C_{7-20}$ aralkyl which may have a substituent, (6) a carbamoyl which may have a substituent or (7) a heterocyclic group; and $R^f$ is a hydrogen atom or a $C_{1-6}$ alkyl whish may have a substituent.

Examples of "$C_{1-6}$ alkyl" of "$C_{1-6}$ alkyl which may have a substituent" represented by $R^e$ and $R^f$ are methyl, ethyl, propyl, isopropyl, butyl, isobutyl, sec-butyl, tert-butyl, pentyl, hexyl, and the like.

Examples of the substituent of "$C_{1-6}$ alkyl which may have a substituent" represented by $R^e$ and $R^f$ are (1) a $C_{1-6}$ alkyl (e.g., methyl, ethyl, propyl, isopropyl, butyl, isobutyl, sec-butyl, tert-butyl, pentyl, hexyl, and the like), (2) a $C_{2-6}$ alkenyl (e.g., vinyl, 1-methylvinyl, 1-propenyl, allyl, and the like), (3) a $C_{2-6}$ alkynyl (e.g., ethynyl, 1-propynyl, propargyl and the like), (4) a $C_{3-5}$ cycloalkyl (e.g., cyclopropyl, cyclobutyl, cyclopentyl, cyclohexyl, and the like), (5) a $C_{5-7}$ cycloalkenyl (e.g., cyclopentenyl, cyclohexenyl, and the like), (6) a $C_{7-11}$ aralkyl (e.g., benzyl, α-methylbenzyl, phenethyl, and the like), (7) a $C_{6-14}$ aryl (e.g., phenyl, naphthyl, and the like), (8) a $C_{1-6}$ alkoxy (e.g., methoxy, ethoxy, propoxy, isopropoxy, butoxy, isobutoxy, sec-butoxy, tert-butoxy, and the like), (9) a $C_{6-14}$ aryloxy (e.g., phenoxy, 1-naphthoxy, 2-naphthoxy, and the like), (10) a $C_{1-6}$ alkanoyl (e.g., formyl, acetyl, propionyl, butyryl, isobutyryl, and the like), (11) a $C_{6-14}$ aryl-carbonyl (e.g., benzoyl, 1-naphthylcarbonyl, 2-naphthylcarbonyl, and the like), (12) a $C_{1-6}$ alkanoyloxy (e.g., formyloxy, acetoxy, propionyloxy, butyryloxy, isobutyryloxy, and the like), (13) a $C_{6-14}$ aryl-carbonyloxy (e.g., benzoyloxy, 1-naphthylcarbonyloxy, 2-naphthylcarbonyloxy, and the like), (14) a carboxy, (15) a $C_{1-6}$ alkoxy-carbonyl (e.g., methoxycarbonyl, ethoxycarbonyl, propoxycarbonyl, isopropoxycarbonyl, butoxycarbonyl, isobutoxycarbonyl, tert-butoxycarbonyl, and the like), (16) a carbamoyl, (17) a N-mono-$C_{1-4}$ alkylcarbamoyl (e.g., N-methylcarbamoyl, N-ethylcarbamoyl, N-propylcarbamoyl, N-isopropylcarbamoyl, N-butylcarbamoyl, and the like), (18) a N,N-di-$C_{1-4}$ alkylcarbamoyl (e.g., N,N-dimethylcarbamoyl, N,N-diethylcarbamoyl, N,N-dipropylcarbamoyl, N,N-dibutylcarbamoyl, and the like), (19) a cyclic aminocarbonyl (e.g., 1-aziridinylcarbonyl, 1-azetidinylcarbonyl, 1-pyrrolidinylcarbonyl, 1-piperidinylcarbonyl, N-methylpiperazinylcarbonyl, morpholinocarbonyl, and the like), (20) a halogen (e.g., fluorine, chlorine, bromine, iodine), (21) a $C_{1-4}$ alkyl substituted by 1 to 3 halogen(s) (e.g., chloromethyl, dichloromethyl, trifluoromethyl, trifluoroethyl, and the like), (22) an oxo, (23) an amidino, (24) an imino, (25) an amino, (26) a mono- or di-$C_{1-4}$ alkylamino (e.g., methylamino, ethylamino, propylamino, isopropylamino, butylamino, isobutylamino, sec-butylamino, tert-butylamino, pentylamino, hexylamino, dimethylamino, diethylamino, dipropylamino, and the like), (27) a 3- to 6-membered cyclic amino which may contain 1 to 3 heteroatom(s) selected from an oxygen atom, a sulfur atom, a nitrogen atom, and the like in addition to carbon atom (e.g., aziridinyl, azetidinyl, pyrrolidinyl, pyrrolinyl, pyrrolyl, imidazolyl, pyrazolyl, imidazolidinyl, piperidino, morpholino, dihydropyridyl, pyridyl, N-methylpiperazinyl, N-ethylpiperazinyl, and the like), (28) a $C_{1-6}$ alkanoylamino (e.g., formylamino, acetylamino, trifluoroacetylamino, propionylamino, butyrylamino, isobutyrylamino, and the like), (29) a benzamido, (30) carbamoylamino, (31) a (N—$C_{1-4}$ alkylcarbamoyl)amino (e.g., (N-methylcarbamoyl)amino, (N-ethylcarbamoyl)amino, (N-propylcarbamoyl)amino, (N-isopropylcarbamoyl)amino, (N-butylcarbamoyl)amino, and the like), (32) a (N,N-di-$C_{1-4}$ alkylcarbamoyl)amino (e.g., (N,N-dimethylcarbamoyl)amino, (N,N-diethylcarbamoyl)amino, (N,N-dipropylcarbamoyl)amino, (N,N-dibutylcarbamoyl)amino, and the like), (33) a $C_{1-6}$ alkylenedioxy (e.g., —$OCH_2O$—, —$O(CH_2)_2O$—, —$O(CH_2)_3O$—, —$O(CH_2)_4O$—, —$O(CH_2)_5O$—, —$O(CH_2)_6O$—), (34) a dihydroboryl, (35) a hydroxy, (36) an epoxy, (37) a nitro, (38) a cyano, (39) a mercapto, (40) a sulfo, (41) a sulfino, (42) a phosphono, (43) a sulfamoyl, (44) a N—$C_{1-6}$ alkylsulfamoyl (e.g., N-methylsulfamoyl, N-ethylsulfamoyl, N-propylsulfamoyl, N-isopropylsulfamoyl, N-butylsulfamoyl, and the like), (45) a N,N-di-$C_{1-6}$ alkylsulfamoyl (e.g., N,N-dimethylsulfamoyl, N,N-diethylsulfamoyl, N,N-dipropylsulfamoyl, N,N-dibutylsulfamoyl, and the like), (46) a $C_{1-6}$ alkylthio (e.g., methylthio, ethylthio, propylthio, isopropylthio, butylthio, sec-butylthio, tert-butylthio, and the like), (47) a phenylthio, (48) a $C_{1-6}$ alkylsulfinyl (e.g., methylsulfinyl, ethylsulfinyl, propylsulfinyl, butylsulfinyl, and the like), (49) a phenylsulfinyl, (50) a $C_{1-6}$ alkylsulfonyl (e.g., methylsulfonyl, ethylsulfonyl, propylsulfonyl, butylsulfonyl, and the like), (51) a phenylsulfonyl, and the like. The number of substituent is 1 to 6, preferably 1 to 3, and the substitution position may be any place on which the substitution is possible.

Examples of "$C_{3-6}$ cycloalkyl" of "$C_{3-6}$ cycloalkyl which may have a substituent" represented by $R^e$ are cyclopropyl, cyclobutyl, cyclopentyl, cyclohexyl, and the like.

Examples of the substituent of "$C_{3-6}$ cycloalkyl which may have a substituent" represented by $R^e$ are the same as the substituent of "$C_{1-6}$ alkyl which may have a substituent" represented by $R^e$ and $R^f$ above. The number of substituents is 1 to 6, preferably 1 to 3, and the substitution position may be any place on which the substitution is possible.

Examples of $C_{6-14}$ aryl of "$C_{6-14}$ aryl which may have a substituent" represented by Re are phenyl, naphthyl, anthracenyl, and the like.

Examples of the substituent of "$C_{6-14}$ aryl which may have a substituent" are the same as the substituent of "$C_{1-6}$ alkyl which may have a substituent" represented by $R^e$ and $R^f$ above except for oxo and epoxy. The number of substituents is 1 to 6, preferably 1 to 3, and the substitution position may be any place on which the substitution is possible.

Examples of $C_{7-20}$ aralkyl of "$C_{7-20}$ aralkyl which may have a substituent" represented by $R^e$ are benzyl, phenethyl, phenylpropyl, benzhydroryl, trityl and the like.

Examples of the substituent of "$C_{7-20}$ aralkyl which may have a substituent" are the same as the substituent of "$C_{1-6}$ alkyl which may have a substituent" represented by $R^e$ and $R^f$ above. The number of substituent is 1 to 6, preferably 1 to 3, and the substitution position may be any place on which the substitution is possible.

Examples of the substituent of "carbamoyl which may have a substituent" represented by $R^e$ are (1) a $C_{1-6}$ alkyl which may have a substituent, (2) a $C_{3-6}$ cycloalkyl which may have a substituent, (3) a $C_{6-14}$ aryl which may have a substituent, (4) a $C_{7-20}$ aralkyl which may have a substituent, (5) a hydroxy, (6) a $C_{1-6}$ alkoxy which may have a substituent, (7) a $C_{1-6}$ alkoxy-carbonyl which may have a substituent, and the like. The number of the substituent may be 1 or 2.

Examples of "$C_{1-6}$ alkyl which may have a substituent" as a substituent of "carbamoyl which may have a substituent" represented by $R^e$ are the same as "$C_{1-6}$ alkyl which may have a substituent" represented by $R^e$ and $R^f$ above. Examples of "$C_{3-6}$ cycloalkyl which may have a substituent", "$C_{6-14}$ aryl which may have a substituent" and "$C_{7-20}$ aralkyl which may have a substituent" as a substituent of "carbamoyl which may have a substituent" represented by $R^e$ are the same as "$C_{3-6}$ cycloalkyl which may have a substituent", "$C_{6-14}$ aryl which may have a substituent" and "07-20 aralkyl which may have a substituent" represented by $R^e$ above.

Examples of the $C_{1-6}$ alkoxy of "$C_{1-6}$ alkoxy which may have a substituent" as a substituent of "carbamoyl which may have a substituent" represented by $R^e$ are methoxy, ethoxy, propoxy, isopropoxy, butoxy, isobutoxy, sec-butoxy, tert-butoxy, pentyloxy, hexyloxy, and the like. Examples of the substituent of "$C_{1-6}$ alkoxy which may have a substituent" are the same as the substituent of "$C_{1-6}$ alkyl which may have a substituent" represented by $R^e$ above. The number of substituents is 1 to 6, preferably 1 to 3, and the substitution position may be any place on which the substitution is possible.

Example of "$C_{1-6}$ alkoxy-carbonyl which may have a substituent" as a substituent of "carbamoyl which may have a substituent" represented by $R^e$ is a group comprising combining "$C_{1-6}$ alkoxy which may have a substituent" as a substituent of "carbamoyl which may have a substituent" represented by $R^e$ above with carbonyl.

Examples of "heterocyclic group" represented by $R^e$ are (1) a 5-membered cyclic group containing 1 to 4 heteroatom(s) selected from an oxygen atom, a sulfur atom, a nitrogen atom, and the like in addition to carbon atom (e.g., 2-thienyl, 3-thienyl, 2-furyl, 3-furyl, 2-pyrrolyl, 3-pyrrolyl, 2-oxazolyl, 4-oxazolyl, 5-oxazolyl, 2-thiazolyl, 4-thiazolyl, 5-thiazolyl, 3-pyrazolyl, 4-pyrazolyl, 5-pyrazolyl, 2-imidazolyl, 4-imidazolyl, 5-imidazolyl, 3-isoxazolyl, 4-isoxazolyl, 5-isoxazolyl, 3-isothiazolyl, 4-isothiazolyl, 5-isothiazolyl, 3-(1,2,4-oxadiazolyl), 5-(1,2,4-oxadiazolyl), 1,3,4-oxadiazolyl, 3-(1,2,4-thiadiazolyl), 5-(1,2,4-thiadiazolyl), 1,3,4-thiadiazolyl, 4-(1,2,3-thiadiazolyl), 5-(1,2,3-thiadiazolyl), 1,2,5-thiadiazolyl, 1,2,3-triazolyl, 1,2,4-triazolyl, 1H-tetrazolyl, 2H-tetrazolyl, oxoimidazinyl, dioxotriazinyl, pyrrolidinyl, and the like), (2) a 6-membered cyclic group containing 1 to 4 heteroatom(s) selected from an oxygen atom, a sulfur atom, a nitrogen atom, and the like in addition to carbon atom (e.g., 2-pyridyl, 3-pyridyl, 4-pyridyl, N-oxido-2-pyridyl, N-oxido-3-pyridyl, N-oxido-4-pyridyl, 2-pyrimidinyl, 4-pyrimidinyl, 5-pyrimidinyl, N-oxido-2-pyrimidinyl, N-oxido-4-pyrimidinyl, N-oxido-5-pyrimidinyl, 2-thiomorpholinyl, 3-thiomorpholinyl, 2-morpholinyl, 3-morpholinyl, piperidinyl, pyranyl, thiopyranyl, 1,4-oxazinyl, 1,4-thiazinyl, 1,3-thiazinyl, 2-piperazinyl, 3-piperazinyl, triazinyl, oxotriazinyl, 3-pyridazinyl, 4-pyridazinyl, pyrazinyl, N-oxido-3-pyridazinyl, N-oxido-4-pyridazinyl, and the like), and (3) a bicyclic or tricyclic condensed cyclic group which contains 1 to 4 heteroatom(s) selected from an oxygen atom, a sulfur atom, a nitrogen atom and the like in addition to a carbon atom (e.g., benzofuryl, benzothiazolyl, benzoxazolyl, tetrazolo[1,5-b]pyridazinyl, triazolo[4,5-b]pyridazinyl, benzoimidazolyl, quinolyl, isoquinolyl, cinnolinyl, phthalazinyl, quinazolinyl, quinoxalinyl, indolizinyl, quinolizinyl, 1,8-naphthylidinyl, purinyl, pteridinyl, dibenzofuranyl, carbazolyl, acridinyl, phenanthrydinyl, chromanyl, benzoxazinyl, phenazinyl, phenothiazinyl, phenoxazinyl, and the like).

Examples of the aryl of "aryl which may have a substituent" represented by $R^d$ are phenyl, naphthyl, anthracenyl, and the like.

Examples of the substituent of "aryl which may have a substituent" represented by $R^d$ are (1) a $C_{6-14}$ aryl (e.g., phenyl, naphthyl, and the like) which may have 1 to 4 substituent(s) selected from the group consisting of (i) a hydroxy, (ii) an amino, (iii) a mono- or di-$C_{1-6}$ alkylamino (e.g., methylamino, ethylamino, propylamino, dimethylamino, diethylamino, and the like), (iv) a $C_{1-6}$ alkoxy (e.g., methoxy, ethoxy, propoxy, butoxy, pentyloxy, hexyloxy, and the like), and (v) a halogen (e.g., fluorine, chlorine, bromine and iodine), (2) a hydroxy, (3) a carboxy, (4) a nitro, (5) a $C_{1-6}$ alkoxy (e.g., methoxy, ethoxy, propoxy, isopropoxy, butoxy, pentyloxy, hexyloxy, and the like), (6) a $C_{1-6}$ alkyl-carbonyloxy (e.g., acetoxy, propionyloxy, butyryloxy, isobutyryloxy, valeryloxy, isovaleryloxy, pivaloyloxy, pentylcarbonyloxy, hexylcarbonyloxy, and the like), (7) a $C_{1-6}$ alkylthio (e.g., methylthio, ethylthio, propylthio, isopropylthio, butylthio, isobutylthio, sec-butylthio, tert-butylthio, pentylthio, hexylthio, and the like), (8) a $C_{1-6}$ alkylsulfinyl (e.g., methylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl, hexylsulfinyl, and the like), (9) a $C_{1-6}$ alkylsulfonyl (e.g., methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, hexylsulfonyl, and the like), (10) a halogen (e.g., fluorine, chlorine, bromine and iodine), (11) a group of the formula: —$NR^gR^h$ wherein $R^g$ is (a) a hydrogen atom, (b) a $C_{1-6}$ alkyl which may have a substituent, (c) a $C_{3-6}$ cycloalkyl which may have a substituent, (d) a $C_{6-14}$ aryl which may have a substituent, (e) a $C_{7-20}$ aralkyl which may have a substituent, (f) a carbamoyl which may have 1 or 2 substituent(s) selected from the group consisting of (i) a $C_{3-6}$ cycloalkyl which may have a substituent, (ii) a $C_{6-14}$ aryl which may have a substituent, (iii) a $C_{7-20}$ aralkyl which may have a substituent, (iv) hydroxy, (v) a $C_{1-6}$ alkoxy which may have a substituent and (vi) a $C_{1-6}$ alkoxy-carbonyl which may have a substituent, (g) a heterocyclic group; and $R^h$ is a hydrogen atom or a $C_{1-6}$ alkyl which may have a substituent, (12) a 5-membered cyclic group containing 1 to 4 heteroatom(s) selected from an oxygen atom, a sulfur atom, a nitrogen atom, and the like in addition to carbon atom (e.g., 2-thienyl, 3-thienyl, 2-furyl, 3-furyl, 2-pyrrolyl, 3-pyrrolyl, 2-oxazolyl, 4-oxazolyl, 5-oxazolyl, 2-thiazolyl, 4-thiazolyl, 5-thiazolyl, 3-pyrazolyl, 4-pyrazolyl, 5-pyrazolyl, 2-imidazolyl, 4-imidazolyl, 5-imidazolyl, 3-isoxazolyl, 4-isoxazolyl, 5-isoxazolyl, 3-isothiazolyl, 4-isothiazolyl, 5-isothiazolyl, 3-(1,2,4-oxadiazolyl), 5-(1,2,4-oxadiazolyl), 1,3,4-oxadiazolyl, 3-(1,2,4-thiadiazolyl), 5-(1,2,4-thiadiazolyl), 1,3,4-thiadiazolyl, 4-(1,2,3-thiadiazolyl), 5-(1,2,3-thiadiazolyl), 1,2,5-thiadiazolyl, 1,2,3-triazolyl, 1,2,4-triazolyl, 1H-tetrazolyl, 2H-tetrazolyl, oxoimidazinyl, dioxotriazinyl, pyrrolidinyl, and the like), (13) a 6-membered cyclic group containing 1 to 4 heteroatom(s) selected from an oxygen atom, a sulfur atom, a nitrogen atom, and the like in addition to carbon atom (e.g., 2-pyridyl, 3-pyridyl, 4-pyridyl, N-oxido-2-pyridyl, N-oxido-3-pyridyl, N-oxido-4-pyridyl, 2-pyrimidinyl, 4-pyrimidinyl, 5-pyrimidinyl, N-oxido-2-pyrimidinyl, N-oxido-4-pyrimidinyl, N-oxido-5-pyrimidinyl, 2-thiomorpholinyl, 3-thiomorpholinyl, 2-morpholinyl, 3-morpholinyl, piperidinyl, pyranyl, thiopyranyl, 1,4-oxazinyl, 1,4-thiazinyl, 1,3-thiazinyl, 2-piperazinyl, 3-piperazinyl, triazinyl, oxotriazinyl, 3-pyridazinyl, 4-pyridazinyl, pyrazinyl, N-oxido-3-pyridazinyl, N-oxido-4-pyridazinyl, and the like), (14) a bicyclic or tricyclic condensed cyclic group which contains 1 to 4 heteroatom(s) selected from an oxygen atom, a sulfur atom, a nitrogen atom and the like in addition to a carbon atom (e.g., benzofuryl, benzothiazolyl, benzoxazolyl, tetrazolo[1,5-b]pyridazinyl, triazolo[4,5-b]pyridazinyl, benzoimidazolyl, quinolyl, isoquinolyl, cinnolinyl, phthalazinyl, quinazolinyl, quinoxalinyl, indolizinyl, quinolizinyl, 1,8-naphthylidinyl, purinyl, pteridinyl, dibenzofuranyl, carbazolyl, acridinyl, phenanthrydinyl, chromanyl, benzoxazinyl, phenazinyl, phenothiazinyl, phenoxazinyl, and the like), (15) a $C_{1-6}$ alkoxycarbonyl (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl, and the like), (16) a carbamoyl, (17) a N-mono-$C_{1-6}$ alkylcarbamoyl (e.g., N-methylcarbamoyl, N-ethylcarbamoyl, N-propylcarbamoyl, N-isopropylcarbamoyl, and the like), (18) a N,N-di-$C_{1-6}$ alkylcarbamoyl (e.g., N,N-dimethylcarbamoyl, N,N-diethylcarbamoyl, N,N-dipropylcarbamoyl, and the like), and the like. The number of substituent is 1 to 6, preferably 1 to 3, and the substitution position may be any place on which the substitution is possible.

The definitions of $R^g$ and $R^f$ utilized in the group of the formula: —$NR^gR^h$ wherein $R^g$ and $R^h$ have the same meanings defined above as a substituent of "aryl which may have a substituent" represented by $R^d$ are shown below.

Examples of "$C_{1-6}$ alkyl which may have a substituent" represented by $R^g$ and $R^h$ are the same as "$C_{1-6}$ alkyl which may have a substituent" represented by $R^e$ and $R^f$ described above.

Examples of "$C_{3-6}$ cycloalkyl which may have a substituent", "$C_{6-14}$ aryl which may have a substituent", "$C_{7-20}$ aralkyl which may have a substituent" and "heterocyclic group" represented by $R^g$ are the same as "$C_{3-6}$ cycloalkyl which may have a substituent", "$C_{6-14}$ aryl which may have a substituent", "$C_{7-20}$ aralkyl which may have a substituent" and "heterocyclic group" represented by $R^e$ described above.

Examples of "$C_{3-6}$ cycloalkyl which may have a substituent", "$C_{6-14}$ aryl which may have a substituent" and "$C_{7-20}$ aralkyl which may have a substituent" of "carbamoyl which may have 1 or 2 substituent(s) selected from the group consisting of (i) a $C_{3-6}$ cycloalkyl which may have a substituent, (ii) a $C_{6-14}$ aryl which may have a substituent, (iii) a $C_{7-20}$ aralkyl which may have a substituent, (iv) a hydroxy, (v) a $C_{1-6}$ alkoxy which may have a substituent and (vi) a $C_{1-6}$ alkoxy-carbonyl which may have a substituent" represented by $R^g$ are the same as "$C_{3-6}$ cycloalkyl which may have a substituent", "$C_{6-14}$ aryl which may have a substituent" and "$C_{7-20}$ aralkyl which may have a substituent" represented by $R^e$ described above.

Examples of "$C_{1-6}$ alkoxy which may have a substituent" of "carbamoyl which may have 1 or 2 substituent(s) selected from the group consisting of (i) a $C_{3-6}$ cycloalkyl which may have a substituent, (ii) a $C_{6-14}$ aryl which may have a substituent, (iii) a $C_{7-20}$ aralkyl which may have a substituent, (iv) a hydroxy, (v) a $C_{1-6}$ alkoxy which may have a substituent and (vi) a $C_{1-6}$ alkoxy-carbonyl which may have a substituent" represented by $R^g$ are methoxy, ethoxy, propoxy, isopropoxy, butoxy, isobutoxy, sec-butoxy, tert-butoxy, pentyloxy, hexyloxy, and the like. Examples of the substituent of said "$C_{1-6}$ alkoxy which may have a substituent" are the same as the substituent of "$C_{1-6}$ alkyl which may have a substituent" represented by $R^e$ described above. The number of substituents is 1 to 6, preferably 1 to 3, and the substitution position may be any place on which the substitution is possible.

Example of "$C_{1-6}$ alkoxy-carbonyl which may have a substituent" of "carbamoyl which may have 1 or 2 substituent(s) selected from the group consisting of (i) a $C_{3-6}$ cycloalkyl which may have a substituent, (ii) a $C_{6-14}$ aryl which may have a substituent, (iii) a $C_{7-20}$ aralkyl which may have a substituent, (iv) a hydroxy, (v) a $C_{1-6}$ alkoxy which may have a substituent and (vi) a $C_{1-6}$ alkoxy-carbonyl which may have a substituent" represented by $R^g$ is a group comprising combining "$C_{1-6}$ alkoxy which may have a substituent" as a substituent of "carbamoyl which may have a substituent" represented by $R^g$ above with carbonyl.

Preferable examples of $R^a$ are an aryl group which may have 1 to 5 substituent(s) selected from the group consisting of (i) a halogen, (ii) a nitro, (iii) a cyano, (iv) an amino, (v) a carboxyl group which may be esterified or amidated, (vi) an alkylenedioxy, (vii) an alkyl, (viii) an alkoxy, (ix) an alkylthio, (x) an alkylsulfinyl and (xi) an alkylsulfonyl. Among them, a phenyl which is mono- or di-substituted by a halogen, especially 2,6-difluorophenyl, are preferable.

Preferable examples of $R^b$ are pyrrolidin-1-yl, pyrrolidin-2-yl, imidazol-1-yl, imidazol-2-yl, 1,2,3-triazol-1-yl, 1,2,5-triazol-1-yl, tetrazol-1-yl, tetrazol-2-yl, pyridin-2-yl, pyridin-4-yl. Among them, pyridin-2-yl is preferable.

Preferable example of $R^c$ is a group represented by the formula: —$NR^{e'}R^{f'}$ wherein $R^{e'}$ is (1) a $C_{1-6}$ alkyl which may have a substituent or (2) a $C_{7-20}$ aralkyl; $R^{f'}$ is a $C_{1-6}$ alkyl. Among them, a group of the formula: —$N(Me)R^{e''}$ wherein $R^{e''}$ is a $C_{1-6}$ alkyl which is substituted by a $C_{1-6}$ alkoxy; or benzyl is preferable.

Preferable example of $R^d$ is phenyl which may have a substituent. Among them, phenyl group which is substituted at its 4-position by a group represented by the formula —$NR^gR^h$: wherein each $R^g$ and $R^h$ has the meaning defined above, is preferable, and especially, phenyl group which is substituted at its 4-position by a group represented by the formula —$NHR^{g'}$ wherein $R^{g'}$ is carbamoyl which may have 1 or 2 substituent(s) selected from the group consisting of (i) a $C_{3-6}$ cycloalkyl which may have a substituent, (ii) a $C_{6-14}$ aryl which may have a substituent, (iii) a $C_{7-20}$ aralkyl which may have a substituent, (iv) hydroxy, (v) a $C_{1-6}$ alkoxy which may have a substituent and (vi) a $C_{1-6}$ alkoxy-carbonylamino is preferable. Especially, a phenyl group substituted at its 4-position by a $C_{1-6}$ alkoxyamino-carbonylamino (e.g. 4-methoxyaminocarbonylaminophenyl, 4-ethoxyaminocarbonylaminophenyl, and the like) is more preferable.

p is preferably 1. And q is preferably 1.

Salts of Compound (A) are preferably physiologically acceptable acid addition salts. Such salts include, for example, salts with inorganic acids (e.g., hydrochloric acid, hydrobromic acid, nitric acid, sulfuric acid, phosphoric acid), salts with organic acids (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.), and the like. When Compound (A) has an acidic group, it may form a physiologically acceptable salt with an inorganic base (e.g., alkali metals and alkaline earth metals such as sodium, potassium, calcium and magnesium, ammonia, and the like) or an organic base (e.g., trimethylamine, triethylamine, pyridine, picoline, ethanolamine, diethanolamine, triethanolamine, dicyclohexylamine, N,N'-dibenzylethylenediamine, and the like).

Compound (A) can be produced by the method described in JP-A-9-169768 (WO 96/24597) and JP-A-2001-278884 (WO 00/56739) and its analogous method.

Compound (A) may be a hydrate or a non-hydrate. The hydrate is exemplified by monohydrate, sesquihydrate and dihydrate.

When Compound (A) is obtained as a mixture of optically active configurations, it can be resolved into the (R)- and (S)-forms by the conventional optical resolution techniques.

Compound (A) can be used as a prodrug. The prodrug of Compound (A) or a salt thereof means a compound which is converted to Compound (A) of the present invention under physiological conditions or with a reaction due to an enzyme, a gastric acid, and the like in the living body, that is, a compound which is converted to Compound (A) of the present invention with oxidation, reduction, hydrolysis, and the like with an enzyme; a compound which is converted to Compound (A) of the present invention with gastric acid, etc. The prodrug for Compound (A) may for example be a compound obtained by subjecting an amino group in Compound (A) to an acylation, alkylation or phosphorylation (e.g., a compound obtained by subjecting an amino group in Compound (A) or to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in Compound (A) to an acylation, alkylation, phosphorylation or boration (e.g., a compound obtained by subjecting an hydroxy in Compound (A) to an acetylation, palmitoylation, propanoylation, pivaloylation, succinylation, fumarylation, alanylation, dimethylaminomethylcarbonylation, etc.); a compound obtained by subjecting a carboxy group in Compound (A) to an esterification or amidation (e.g., a compound obtained by subjecting a carboxyl group in compound (A) to an ethylesterification, phenylesterification, carboxymethylesterification, dimethylaminomethylesterification, pivaloyloxymethylesterification, ethoxycarbonyloxyethylesterification, phthalidylesterification, (5-methyl-2-oxo-1,3-dioxolen-4-yl)methylesterification, cyclohexyloxycarbonylethylesterification and methylamidation, etc.) and the like. Any of these compounds can be produced from the compound of the present invention by a method known per se.

A prodrug of Compound (A) may also be one which is converted into Compound (A) under a physiological condition, such as those described in "IYAKUHIN no KAIHATSU (Development of Pharmaceuticals)", Vol. 7, Design of Molecules, p. 163-198, Published by HIROKAWA SHOTEN (1990).

Compound (A) may be labeled with an isotope (e.g., $^3$H, $^{14}$C, $^{35}$S) and the like.

The present invention is hereinafter described in more detail by means of, but is not limited to, the following Reference Examples, Examples, Preparation Examples and Experimental Examples.

$^1$H-NMR spectra are determined with tetramethylsilane as the internal standard, using the Varian GEMINI 200 (200 MHz) spectrometer, the JEOL LAMBDA 300 (300 MHz) spectrometer or the Bruker AM500 (500 MHz) spectrometer; all δ values are shown in ppm. Unless otherwise specifically indicated, "%" is by weight. Yield indicates mol/mol %. The other symbols used herein have the following definitions:

s: singlet
d: doublet
t: triplet
dt: double triplet
m: multiplet
br: broad
AIBN: 2,2-azobisisobutyronitrile
DMF: N,N-dimethylformamide
NBS: N-bromosuccinimide
TFA: trifluoroacetic acid
THF: tetrahydrofuran
Me: methyl
Et: ethyl
Ph: phenyl
TBS: tert-butyl dimethyl silyl
Ms: methanesulfonyl The term "room temperature" indicates the range from about 15 to 25° C., but is not to be construed as strictly limitative. Each of lactose, corn starch, D-mannitol, low substituted hydroxypropylcellulose, talc, hydroxypropylcellulose, hydroxypropylmethylcellulose 2910, titanium oxide and light silicic acid anhydride used in the following Preparation is suited for standard of Pharmacopoeia, Fourteenth Edition.

EXAMPLES

Reference Example 1

Production of ethyl 2-[(2,6-difluorobenzyl)(ethoxycarbonyl)amino]-5-(4-{[(methoxyamino)carbonyl]amino}phenyl)-4-[(methylamino)methyl]thiophene-3-carboxylate

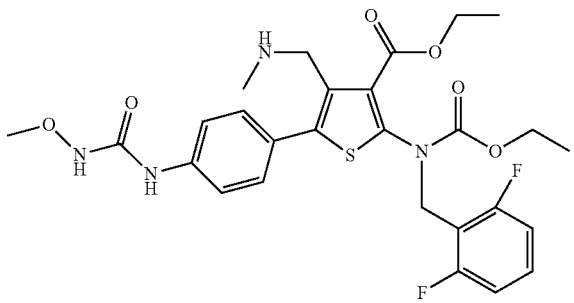 [SMILES: CCOC(=O)c1c(N(Cc2c(F)cccc2F)C(=O)OCC)sc(-c2ccc(NC(=O)NOC)cc2)c1CNC]

To a solution of ethyl 4-(N-benzyl-N-methylaminomethyl)-2-[N-(2,6-difluorobenzyl)-N-ethoxycarbonylamino]-5-[4-(3-methoxyureido)phenyl]thiophene-3-carboxylate (3.64 g, 5.47 mmol) in ethanol (100 ml) were added 1N hydrochloric acid (8 ml) and 10% palladium-carbon (50% wet, 1.82 g). The mixture was stirred vigorously under hydrogen atmosphere for 6 hours. The catalyst was removed, and the filtrate was neutralized with 1N sodium hydroxide solution. The solvent was distilled off, and the residue was distributed between ethyl acetate and water. The organic layer was washed with saturated brine and dried over anhydrous magnesium sulfate. The solvent was distilled off under reduced pressure. The residue was subjected to an NH-silica gel (Fuji Silysia Chemical) chromatography to give the title compound (2.43 g, 77%) as yellow powders.

$^1$H-NMR (CDCl$_3$) δ: 1.18 (3H, t, J=7.0 Hz), 1.33 (3H, t, J=7.2 Hz), 2.33 (3H, s), 3.65 (2H, s), 3.82 (5H, s), 4.16 (2H, q, J=7.0 Hz), 4.24 (2H, q, J=7.2 Hz), 4.96 (2H, s), 6.84 (2H, t, J=7.8 Hz), 7.1-7.35 (3H, m), 7.44 (2H, d, J=8.6 Hz), 7.53 (2H, d, J=8.6 Hz), 7.63 (1H, s).

Reference Example 2

Production of ethyl 2-[(2,6-difluorobenzyl)(ethoxycarbonyl)amino]-5-(4-{[(methoxyamino)carbonyl]amino}phenyl)-4-{[methyl(pyridin-2-ylmethyl)amino]methyl}thiophene-3-carboxylate

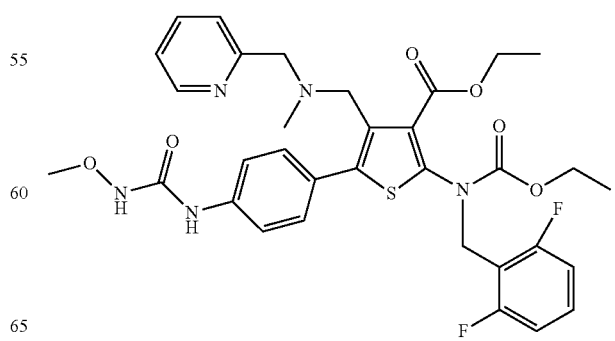

The compound obtained in Reference Example 1 (2.43 g, 4.21 mmol) was dissolved in DMF (20 ml), and N,N-diisopropylethylamine (2.93 ml, 16.84 mmol) and 2-chloromethylpyridine hydrochloride (1.04 g, 6.32 mmol) were added thereto. The mixture was stirred at room temperature for 24 hours, combined with saturated aqueous solution of sodium hydrogen carbonate and extracted with ethyl acetate. The organic layer was washed with saturated brine, dried over magnesium sulfate and concentrated under reduced pressure. The residue was purified by silica gel column chromatography (eluent: ethyl acetate) to give the title compound (2.34 g, 83%) as yellow powders.

Reference Example 3

Production of 2-[(2,6-difluorobenzyl)(ethoxycarbonyl)amino]-5-(4-{[(methoxyamino)carbonyl]amino}phenyl)-4-{[methyl(pyridin-2-ylmethyl)amino]methyl}thiophene-3-carboxylic acid

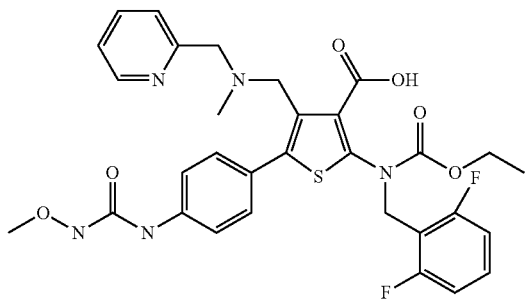 [SMILES: CCOC(=O)N(Cc1c(F)cccc1F)c1sc(-c2ccc(NC(=O)NOC)cc2)c(CN(C)Cc2ccccn2)c1C(=O)O]

To a solution of the compound obtained in Reference Example 2 (2.34 g, 3.5 mmol) in ethanol (40 ml) was added 2N sodium hydroxide solution (8.75 ml), and the mixture was stirred at 50-60° C. for 14 hours. The reaction mixture was cooled to room temperature and neutralized with 1N hydrochloric acid. The solvent was distilled off and the obtained residue was distributed between ethyl acetate and water. The organic layer was washed with saturated brine and dried over magnesium sulfate. The solvent was distilled off under reduced pressure to give the title compound (2.06 g, 92%) as pale yellow powders.

$^1$H-NMR (CDCl$_3$) δ: 1.1-1.3 (3H, m), 2.28 (3H, s), 3.7-3.9 (2H, brm), 3.84 (3H, s), 3.91 (3H, s), 4.1-4.3 (2H, m), 5.07 (2H, s), 6.7-6.85 (2H, m), 7.15-7.8 (10H, m), 8.5-8.6 (1H, m).

Reference Example 4

Production of methyl 6-(bromomethyl)nicotinate

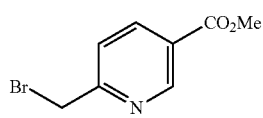 [SMILES: COC(=O)c1ccc(CBr)nc1]

Methyl 6-methylnicotinate (1.05 g, 10 mmol) was dissolved in ethyl acetate (50 ml), and NBS (3.56 g, 20 mmol) and AIBN (329 mg, 2 mmol) were added thereto. The reaction mixture was stirred at 80° C. for 3 hours, combined with an aqueous solution of sodium hydrogen carbonate and extracted with ethyl acetate. The organic layer was washed with saturated brine, dried over magnesium sulfate and concentrated under reduced pressure. The residue was purified by silica gel column chromatography (eluent: ethyl acetate/hexane=1/4) to give the title compound (682 mg, 28%) as an orange amorphous compound.

$^1$H-NMR (CDCl$_3$) δ: 3.96 (3H, s), 4.58 (2H, s), 7.53 (1H, d, J=8.2 Hz), 8.30 (2H, dd, J=1.8, 8.2 Hz), 9.17 (1H, d, J=1.8 Hz).

Reference Example 5

Production of ethyl 2-[N-(2,6-difluorobenzyl)-N-ethoxycarbonylamino]-4-[N-(2-methoxyethyl)-N-methylaminomethyl]-5-(4-aminophenyl)thiophene-3-carboxylate

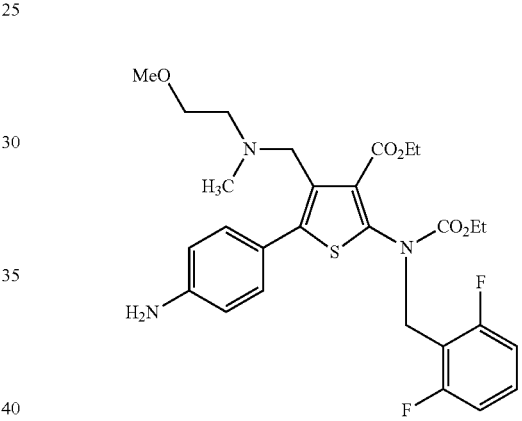

A solution of 2N hydrochloride in diethyl ether (21 ml) and 10% palladium-carbon (50% wet, 3.73 g) were added to a solution of ethyl 2-[N-(2,6-difluorobenzyl)-N-ethoxycarbonylamino]-4-[N-(2-methoxyethyl)-N-methylaminomethyl]-5-(4-nitrophenyl)thiophene-3-carboxylate (12.43 g) (JP-A-2001-278884, WO 00/56739) in ethanol (315 ml). The mixture was stirred vigorously under hydrogen atmosphere for 1 hour. The catalyst was removed, and the filtrate was neutralized with sodium hydrogen carbonate solution. The solvent was distilled off, and the residue was distributed between ethyl acetate and water. The organic layer was washed with saturated brine and dried over anhydrous magnesium sulfate. The solvent was distilled off under reduced pressure. The residue was subjected to an NH-silica gel (Fuji Silysia Chemical) chromatography to give the title compound (11.44 g) as an oil.

$^1$H-NMR (CDCl$_3$) δ: 1.12-1.30 (3H, br), 2.05 (3H, s), 2.39 (2H, t, J=6.3 Hz), 3.27 (3H, s), 3.32 (3H, t, J=6.3 Hz), 3.59 (2H, s), 3.78 (2H, s), 4.20 (2H, q, J=7.1 Hz), 4.10-4.23 (2H, br), 5.00 (2H, s), 6.66 (2H, d, J=8.6 Hz), 6.84 (2H, t, J=8.2 Hz), 7.18 (2H, d, J=8.6 Hz), 7.15-7.30 (1H, m).

IR (KBr): 1717, 1626, 1609, 1472, 1406, 1300, 1246 cm$^{-1}$.

Reference Example 6

Production of ethyl 2-[(2,6-difluorobenzyl)(ethoxycarbonyl)amino]-5-(4-{[(methoxyamino)carbonyl]amino}phenyl)-4-{[(2-methoxyethyl)(methyl)amino]methyl}-3-thiophenecarboxylate

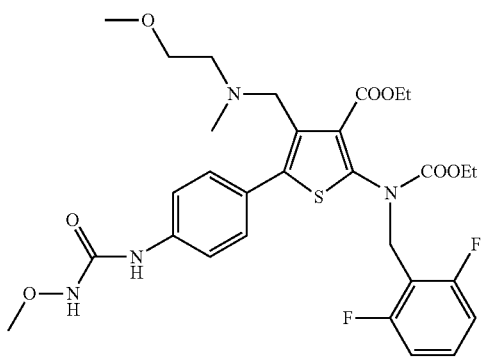 [SMILES: CCOC(=O)c1c(N(Cc2c(F)cccc2F)C(=O)OCC)sc(-c2ccc(NC(=O)NOC)cc2)c1CN(C)CCOC]

N-ethyldiisopropylamine (3.06 ml) was added to a solution of the compound obtained in Reference Example 5 (4.89 g) in dichloromethane (113 ml) under ice cooling, and the mixture was stirred. N,N'-carbonyldiimidazole (2.82 g) was added to the mixture under ice cooling. The reaction mixture was warmed to room temperature and stirred for 67 hours. The reaction mixture was cooled under ice cooling, and O-methylhydroxyamine hydrochloride (7.26 g) and N-ethyldiisopropylamine (15.6 ml) were added thereto. The reaction mixture was warmed to room temperature and stirred at room temperature for 19 hours. The reaction mixture was distributed between chloroform and saturated aqueous solution of sodium hydrogen carbonate, and extracted with chloroform. The combined extract was washed with brine and dried over magnesium sulfate. The solvent was distilled off under reduced pressure. The residue was purified by silica gel column chromatography to give the title compound (4.89 g) as a pale yellow caramelized product.

$^1$H-NMR (CDCl$_3$) δ: 1.19 (3H, brs), 1.30 (3H, t, J=6.9 Hz), 2.04 (3H, s), 2.40 (2H, t, J=6.0 Hz), 3.27 (3H, s), 3.33 (2H, t, J=6.0 Hz), 3.60 (2H, s), 3.81 (3H, s), 4.13-4.24 (4H, m), 5.00 (2H, s), 6.84 (2H, t, J=7.8 Hz), 7.19-7.29 (2H, m), 7.36 (2H, d, J=8.7 Hz), 7.50 (2H, d, J=8.7 Hz), 7.60 (1H, s).

IR (KBr): 1717, 1590, 1528, 1472, 1408, 1304 cm$^{-1}$.

Reference Example 7

Production of 2-[(2,6-difluorobenzyl)(ethoxycarbonyl)amino]-5-(4-{[(methoxyamino)carbonyl]amino}phenyl)-4-{[(2-methoxyethyl)(methyl)amino]methyl}-3-thiophenecarboxylic acid

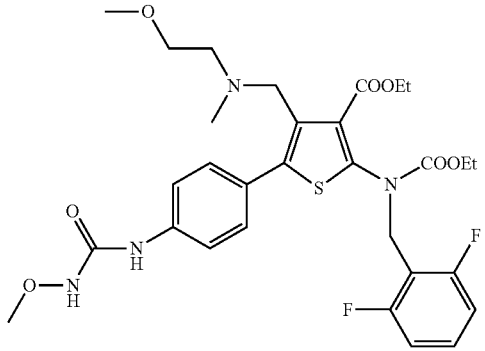 [SMILES: CCOC(=O)c1c(N(Cc2c(F)cccc2F)C(=O)OCC)sc(-c2ccc(NC(=O)NOC)cc2)c1CN(C)CCOC]

An aqueous solution of 2N sodium hydroxide (18.9 ml) was added to a solution of the compound obtained in Reference Example 6 (4.81 g) in ethanol (114 ml), and the mixture was stirred at 60° C. for 5 hours. The reaction mixture was warmed to room temperature and combined with 1N hydrochloric acid (37.8 ml). The solvent was distilled off. The residue was dissolved in ethanol and toluene, and the solvent was distilled off. The residue was combined with anhydrous ethanol (30 ml), and the inorganic products were filtered off. The filtrate was concentrated to dryness. The obtained residue was fined by anhydrous ether, collected by filtration and dried to give the title compound (4.43 g).

$^1$H-NMR (CDCl$_3$) δ: 1.17 (3H, brs), 2.45 (3H, s), 2.81 (2H, brs), 3.28 (3H, s), 3.55 (2H, t, J=4.8 Hz), 3.82 (3H, s), 3.92 (2H, s), 4.10-4.35 (2H, m), 5.06 (2H, s), 6.82 (2H, t, J=7.8 Hz), 7.16 (2H, d, J=8.4 Hz), 7.22-7.35 (1H, m), 7.60 (2H, d, J=8.4 Hz), 8.00-8.50 (2H, br).

IR (KBr): 1713, 1605, 1528, 1472, 1408 cm$^{-1}$.

Reference Example 8

Production of 4-(1-hydroxy-1-methylethyl)aniline (1) and 4-(1-methoxy-1-methylethyl)aniline (2)

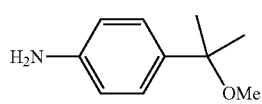

To a solution of 2-methyl-2-(4-nitrophenyl)-2-propanol (2.0 g) in methanol (55 ml) was added 5% platinum-carbon (0.3 g), and the mixture was stirred under hydrogen atmosphere for 4 hours. The catalyst was filtered off, and the filtrate was concentrated to dryness. The obtained residue was purified by aminopropylsilica gel column chromatography (Fuji Silysia Chemical) (120 g; eluent hexane/ethyl acetate 9/1 to 1/4) to give 4-(1-hydroxy-1-methylethyl)aniline (1) (1.0 g) and 4-(1-methoxy-1-methylethyl)aniline (2) (0.35 g).

4-(1-hydroxy-1-methylethyl)aniline (1)

$^1$H-NMR (CDCl$_3$) δ: 1.45 (1H, s), 1.55 (6H, s), 3.64 (2H, brs), 6.66 (2H, d, J=8.8 Hz), 7.28 (2H, d, J=8.8 Hz).

IR (KBr): 3335, 2975, 1613, 1516, 1256 cm$^{-1}$.

4-(1-methoxy-1-methylethyl)aniline (2)

$^1$H-NMR (CDCl$_3$) δ: 1.49 (6H, s), 3.03 (3H, s), 3.64 (2H, brs), 6.67 (2H, d, J=8.7 Hz), 7.20 (2H, d, J=8.7 Hz).

IR (KBr): 2978, 1630, 1613, 1518, 1358, 1264 cm$^{-1}$.

Reference Example 9

Production of 3-methoxy-6-methyl-2-nitropyridine

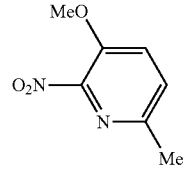 [SMILES: COc1ccc(C)nc1[N+](=O)[O-]]

Potassium carbonate (4.15 g) and methyl iodide (2.80 ml) were added to a solution of 6-methyl-2-nitro-3-hydroxypyridine (4.63 g) in DMF (120 ml), and the mixture was stirred at room temperature for 14 hours. The reaction mixture was distributed between ethylacetate and water. The organic layer was washed with saturated brine and dried over anhydrous sodium sulfate. The solvent was distilled off under reduced pressure, and the residue was recrystallized from ethyl acetate/hexane to give the title compound (3.94 g) as needle crystals.

$^1$H-NMR (CDCl$_3$) δ: 2.54 (3H, s), 3.95 (3H, s), 7.37 (1H, d, J=8.8 Hz), 7.44 (1H, d, J=8.8 Hz).

IR (KBr): 1541, 1489, 1381, 1308, 1289 cm$^{-1}$.

Reference Example 10

Production of 2-amino-3-methoxy-6-methylpyridine

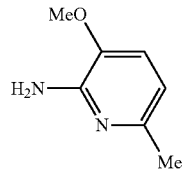

To a solution of 3-methoxy-6-methyl-2-nitropyridine (3.85 g) in ethanol (91.6 ml) was added 10% palladium-carbon (50% wet, 0.96 g), and the mixture was stirred under hydrogen atmosphere for 2 hours. The catalyst was filtered off, and the filtrate was concentrated to dryness. The residue was recrystallized from ethyl acetate/hexane to give the title compound (2.89 g).

$^1$H-NMR (CDCl$_3$) δ: 2.32 (3H, s), 3.81 (3H, s), 4.61 (2H, s), 6.44 (1H, d, J=8.4 Hz), 6.81 (1H, d, J=8.4 Hz).

IR (KBr): 1624, 1576, 1480, 1439, 1258 cm$^{-1}$.

Reference Example 11

Production of 2-amino-3-hydroxy-6-methylpyridine

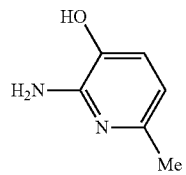

The similar reaction as described in Reference Example 10 by using 6-methyl-2-nitro-3-hydroxypyridine (4.63 g) gave the title compound (2.81 g) as crystalline powders.

$^1$H-NMR (DMSO-d$_6$) δ: 2.14 (3H, s), 5.29 (2H, s), 6.20 (1H, d, J=7.5 Hz), 6.70 (1H, d, J=7.5 Hz), 9.09 (1H, s).

Reference Example 12

Production of 3-methoxy-2-nitropyridine

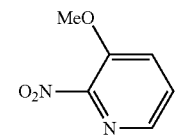

The similar reaction as described in Reference Example 9 by using 2-nitro-3-hydroxypyridine (7.0 g), potassium carbonate (6.91 g) and methyl iodide (4.67 ml) gave the title compound (7.5 g) as crystalline powders.

$^1$H-NMR (CDCl$_3$) δ: 3.99 (3H, s), 7.54-7.56 (2H, m), 8.09-8.12 (1H, m).

IR (KBr): 1601, 1537, 1530, 1422, 1364, 1275 cm$^{-1}$.

Reference Example 13

Production of 2-amino-3-methoxypyridine

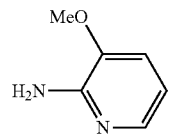

The similar reaction as described in Reference Example 10 by using 3-methoxy-2-nitropyridine (7.5 g) gave the title compound (5.42 g) as crystalline powders.

$^1$H-NMR (CDCl$_3$) δ: 3.84 (3H, s), 4.65 (2H, brs), 6.62 (1H, d, J=5.0 Hz, 7.6 Hz), 6.90 (1H, dd, J=1.4 Hz, 7.6 Hz), 7.66 (1H, dd, J=1.4 Hz, 5.0 Hz).

IR (KBr): 3443, 3142, 1634, 1601, 1570, 1483, 1460, 1441 cm$^{-1}$.

Example 1

Production of N-(4-(5-((benzyl(methyl)amino)methyl)-1-(2,6-difluorobenzyl)-2,4-dioxo-3-(2-pyridinyl)-1,2,3,4-tetrahydrothieno[2,3-d]pyrimidin-6-yl)phenyl)-N'-methoxyurea

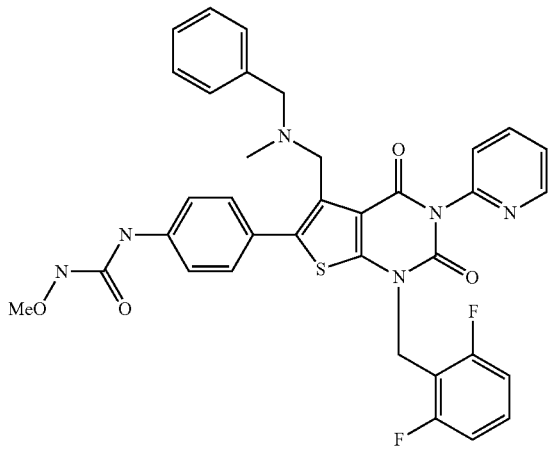 [SMILES: CONC(=O)Nc1ccc(-c2sc3c(c2CN(C)Cc2ccccc2)c(=O)n(-c2ccccn2)c(=O)n3Cc2c(F)cccc2F)cc1]

Ethyldiisopropylamine (1.05 ml, 6.02 mmol) and diethyl cyanophosphate (0.86 ml, 5.64 mmol) were added to a solution of 4-(N-benzyl-N-methylaminomethyl)-2-[N-(2,6-difluorobenzyl)-N-ethoxycarbonylamino]-5-[4-(3-methoxyureido)phenyl]thiophene-3-carboxylic acid (2.40 g, 3.76 mmol) and 2-aminopyridine (1.06 g, 11.28 mmol) in DMF (20 ml), and the mixture was stirred at room temperature for 3 days. The reaction mixture was combined with sodium hydrogen carbonate solution and extracted with ethyl acetate. The organic layer was washed with brine, dried over magnesium sulfate and concentrated under reduced pressure. The residue was purified by silica gel column chromatography (eluent: ethyl acetate) to give an amide compound. The obtained amide compound was dissolved in methanol (40 ml), and sodium methoxide (2.03 mg, 37.6 mmol) was added thereto. The reaction mixture was stirred at room temperature for 5 hours, concentrated, neutralized with 1N hydrochloric acid and extracted with ethyl acetate. The organic layer was washed with brine, dried over magnesium sulfate and concentrated under reduced pressure. The residue was purified by NH-silica gel column chromatography (Fuji Silysia Chemical) (eluent: ethyl acetate) to give the title compound (1.59 g, 63%) as a pale yellow amorphous compound.

$^1$H-NMR (CDCl$_3$) δ: 2.05 (3H, s), 3.56 (2H, s), 3.82 (3H, s), 3.89 (2H, s), 5.34 (2H, brs), 6.91 (2H, t, J=8.0 Hz), 7.1-7.45 (9H, m), 7.56 (2H, d, J=8.8 Hz), 7.65 (1H, s), 7.75 (2H, d, J=8.8 Hz), 7.91 (1H, dt, J=2.0, 7.7 Hz), 8.7-8.75 (1H, m).

Elemental analysis for C$_{35}$H$_{30}$F$_2$N$_6$O$_4$S$_2$

Calcd.: C, 62.86; H, 4.52; N, 12.57.

Found: C, 62.72; H, 4.31; N, 12.40.

mp 179-182° C.

Reference Example 14

Production of N-(4-(1-(2,6-difluorobenzyl)-5-((methylamino)methyl)-2,4-dioxo-3-(2-pyridinyl)-1,2,3,4-tetrahydrothieno[2,3-d]pyrimidin-6-yl)phenyl)-N'-methoxyurea

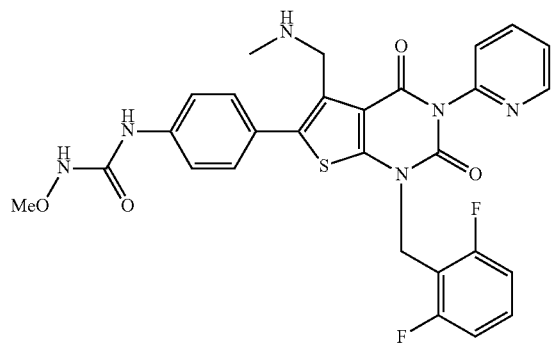 [SMILES: CNCc1c(-c2ccc(NC(=O)NOC)cc2)sc2c1c(=O)n(-c1ccccn1)c(=O)n2Cc1c(F)cccc1F]

To a solution of the compound obtained in Example 1 (1.59 g, 2.38 mmol) in ethanol (40 ml) were added 1N hydrochloric acid (7 ml) and 10% palladium-carbon (50% wet, 0.63 g), and the mixture was stirred vigorously under hydrogen atmosphere for 20 hours. The catalyst was removed, and the filtrate was neutralized with 1N sodium hydroxide solution. The solvent was distilled off. The residue was distributed between ethyl acetate and water, and the organic layer was washed with saturated brine and dried over anhydrous magnesium sulfate. The solvent was distilled off, and the obtained powders were washed with diethyl ether to give the title compound (980 mg, 71%) as pale yellow powders.

$^1$H-NMR (CDCl$_3$) δ: 2.34 (3H, s), 3.78 (2H, s), 3.82 (2H, s), 5.38 (2H, brs), 6.92 (2H, t, J=8.2 Hz), 7.2-7.8 (9H, m), 7.92 (1H, dt, J=1.8 Hz, 7.6 Hz), 8.72 (1H, d, J=4.8 Hz).

Example 2

Production of N-{2-[{[1-(2,6-difluorobenzyl)-6-(4-{[(methoxyamino)carbonyl]amino}phenyl)-2,4-dioxo-3-(2-pyridinyl)-1,2,3,4-tetrahydrothieno[2,3-d]pyrimidin-5-yl]methyl}(methyl)amino]ethyl}-N-methylsulfonamide

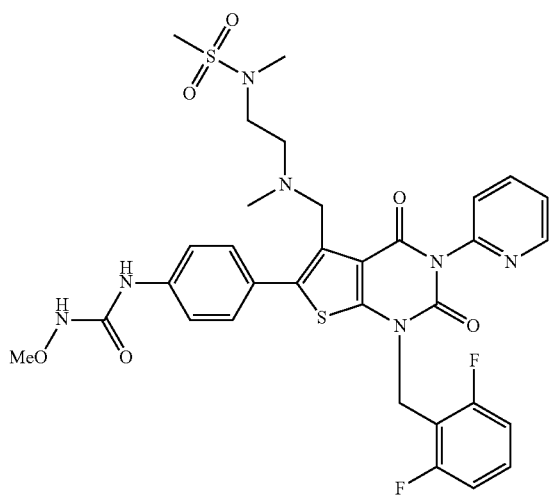 [SMILES: CONC(=O)Nc1ccc(-c2sc3c(c2CN(C)CCN(C)S(C)(=O)=O)c(=O)n(-c2ccccn2)c(=O)n3Cc2c(F)cccc2F)cc1]

2-(Methylamino)ethanol (0.14 g, 1.903 mmol) was dissolved in THF (10 ml), and triethylamine (0.58 ml, 4.15 mmol) and methanesulfonyl chloride (0.27 ml, 3.46 mmol) were added thereto. The reaction mixture was stirred at room temperature for 1 hour. The reaction mixture was combined with an aqueous solution of sodium hydrogen carbonate and extracted with ethyl acetate. The water layer was salted out and extracted with ethyl acetate. The combined organic layer was dried over magnesium sulfate and concentrated under reduced pressure to give a mesylate. A solution of the obtained mesylate, the compound obtained in Reference Example 14 (200 mg, 0.346 mmol), N,N-diisopropylethylamine (0.12 ml, 0.692 mmol) and potassium iodide (230 mg, 1.38 mmol) in DMF (8 ml) was stirred at 50-60° C. for 16 hours. The reaction mixture was combined with an aqueous solution of sodium hydrogen carbonate and extracted with ethyl acetate. The organic layer was washed with brine, dried over magnesium sulfate and concentrated under reduced pressure. The residue was purified by silica gel column chromatography (eluent: ethyl acetate/methanol=80/1) and recrystallized from dichloromethane/methanol/diethyl ether to give the title compound (115 mg, 47%) as pale yellow crystals.

$^1$H-NMR (CDCl$_3$) δ: 2.11 (3H, s), 2.45-2.6 (2H, m), 2.70 (3H, s), 2.75 (3H, s), 3.1-3.25 (2H, m), 3.80 (2H, s), 3.83 (3H, s), 5.36 (2H, brs), 6.93 (2H, t, J=8.2 Hz), 7.14 (1H, s), 7.2-7.6 (7H, m), 7.65 (1H, s), 7.85-7.95 (1H, m), 8.65-8.75 (1H, m).

IR (KBr): 1715, 1669, 1530, 1462, 1333, 1146, 1032, 781 cm$^{-1}$.

Elemental analysis for C$_{32}$H$_{33}$F$_2$N$_7$O$_6$S$_2$.0.3H$_2$O

Calcd.: C, 53.44; H, 4.71; N, 13.63.

Found: C, 53.76; H, 4.75; N, 13.21.

mp 185-187° C.

Example 3

Production of N-(4-(1-(2,6-difluorobenzyl)-5-((methyl(2-(2-oxo-1-pyrrolidinyl)ethyl)amino)methyl)-2,4-dioxo-3-(2-pyridinyl)-1,2,3,4-tetrahydrothieno[2,3-d]pyrimidin-6-yl)phenyl)-N'-methoxyurea

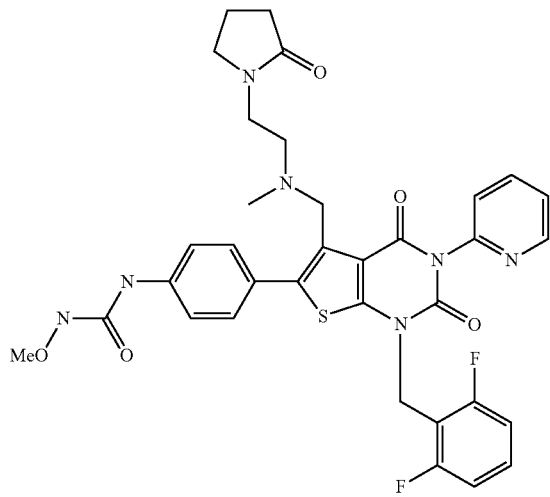 [SMILES: CONC(=O)Nc1ccc(-c2sc3c(c2CN(C)CCN2CCCC2=O)c(=O)n(-c2ccccn2)c(=O)n3Cc2c(F)cccc2F)cc1]

The similar reaction as described in Example 2 by using the compound obtained in Reference Example 14 (200 mg, 0.346 mmol) and 1-(2-hydroxyethyl)-2-pyrrolidone (0.25 g, 1.903 mmol) gave the title compound (97 mg, 41%) as colorless crystals.

$^1$H-NMR (CDCl$_3$) δ: 1.7-1.85 (2H, m), 2.17 (3H, s), 2.15-2.3 (2H, m), 2.5-2.6 (2H, m), 3.15 (2H, t, J=7.0 Hz), 3.2-3.4 (2H, m), 3.76 (2H, s), 3.83 (3H, s), 5.36 (2H, brs), 6.93 (2H, t, J=8.4 Hz), 7.16 (1H, s), 7.2-7.7 (8H, m), 7.85-7.95 (1H, m), 8.65-8.75 (1H, m).

IR (KBr): 1715, 1672, 1526, 1464, 1329, 1032, 783 cm$^{-1}$.
Elemental analysis for C$_{34}$H$_{33}$F$_2$N$_7$O$_5$S.0.5H$_2$O
Calcd.: C, 58.44; H, 4.90; N, 14.03.
Found: C, 58.75; H, 4.98; N, 13.71.
mp 199-201° C.

Example 4

Production of N-(4-(1-(2,6-difluorobenzyl)-5-((methyl(2-pyridinylmethyl)amino)methyl)-2,4-dioxo-3-(2-pyridinyl)-1,2,3,4-tetrahydrothieno[2,3-d]pyrimidin-6-yl)phenyl)-N'-methoxyurea

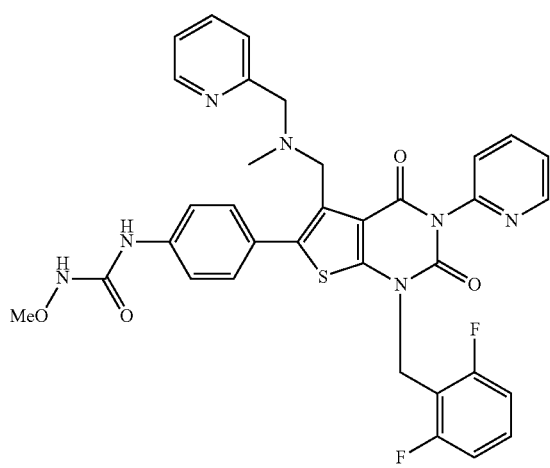 [SMILES: CONC(=O)Nc1ccc(-c2sc3c(c2CN(C)Cc2ccccn2)c(=O)n(-c2ccccn2)c(=O)n3Cc2c(F)cccc2F)cc1]

The compound obtained in Reference Example 14 (150 mg, 0.259 mmol) was dissolved in DMF (4 ml), and N,N-diisopropylethylamine (0.20 ml, 1.14 mmol) and 2-chloromethylpyridine hydrochloride (85 mg, 0.518 mmol) were added thereto. The reaction mixture was stirred at room temperature for 1 hour, combined with an aqueous solution of sodium hydrogen carbonate and extracted with ethyl acetate. The organic layer was washed with brine, dried over magnesium sulfate and concentrated under reduced pressure. The residue was purified by silica gel column chromatography (eluent: ethyl acetate/methanol=40/1), and recrystallized from dichloromethane/methanol/diethyl ether to give the title compound (70 mg, 40%) as pale yellow crystals.

$^1$H-NMR (CDCl$_3$) δ: 2.10 (3H, s), 3.70 (2H, s), 3.82 (3H, s), 3.96 (3H, s), 5.34 (2H, brs), 6.85-7.7 (14H, m), 7.85-7.95 (1H, m), 8.4-8.5 (1H, m), 8.65-8.75 (1H, m).

IR (KBr): 1717, 1672, 1526, 1464, 1331, 1236, 1036, 772 cm$^{-1}$.
Elemental analysis for C$_{34}$H$_{29}$F$_2$N$_7$O$_4$S.0.3H$_2$O
Calcd.: C, 62.36; H, 4.58; N, 12.47.
Found: C, 62.22; H, 4.32; N, 12.57.
mp 165-167° C.

Example 5

Production of N-(4-(5-((benzyl(methyl)amino)methyl)-1-(2,6-difluorobenzyl)-3-(2-hydroxyethyl)-2,4-dioxo-1,2,3,4-tetrahydrothieno[2,3-d]pyrimidin-6-yl)phenyl)-N'-methoxyurea

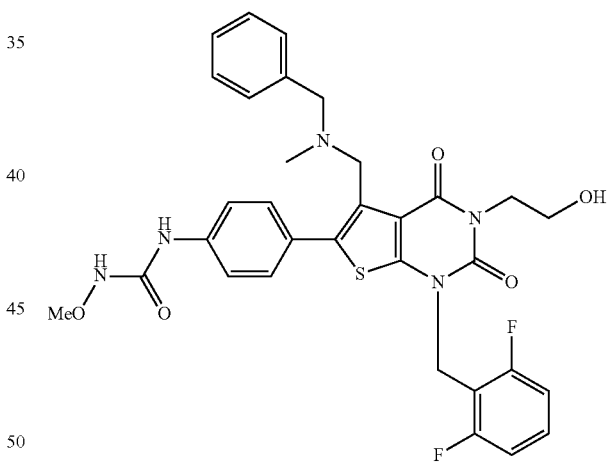

Ethyldiisopropylamine (0.56 ml, 3.2 mmol) and diethylcyanophosphate (0.46 ml, 3 mmol) were added to a solution of 4-(N-benzyl-N-methylaminomethyl)-2-[N-(2,6-difluorobenzyl)-N-ethoxycarbonylamino]-5-[4-(3-methoxyureido)phenyl]thiophene-3-carboxylic acid (1.28 g, 2 mmol) and 2-aminoethanol (183 mg, 3 mmol) in DMF (12 ml), and the mixture was stirred at room temperature for 3 days. The reaction mixture was combined with an aqueous solution of sodium hydrogen carbonate, extracted with ethyl acetate, dried over magnesium sulfate and concentrated under reduced pressure. The residue was purified by NH-silica gel column chromatography (Fuji Silysia Chemical) (eluent: ethyl acetate/methanol=80/1) to give an amide. The obtained amide was dissolved in methanol (20 ml), and sodium methoxide (589 mg, 10.9 mmol) was added thereto. The reaction mixture was stirred at 50-60° C. for 3 hours, concentrated under reduced pressure, neutralized with 1N hydrochloric acid and extracted with ethyl acetate. The extract was washed with brine, dried over magnesium sulfate and concentrated under reduced pressure. The residue was purified by silica gel column chromatography (eluent: ethyl acetate) and recrystallized from dichloromethane/methanol/diethyl ether to give the title compound (511 mg, 74%) as colorless crystals.

$^1$H-NMR (CDCl$_3$) δ: 2.04 (3H, s), 2.5-2.65 (1H, m), 3.58 (2H, s), 3.83 (3H, s), 3.91 (2H, s), 3.9-4.0 (2H, m), 4.37 (2H, t, J=5.0 Hz), 5.34 (2H, s), 6.92 (2H, t, J=8.2 Hz), 7.1-7.4 (7H, m), 7.54 (2H, d, J=8.6 Hz), 7.66 (2H, d, J=8.6 Hz), 7.6-7.7 (1H, m).

IR (KBr): 1711, 1649, 1535, 1470, 1323, 1236, 1028, 785 cm$^{-1}$.

Elemental analysis for C$_{32}$H$_{31}$F$_2$N$_5$O$_5$S.0.5H$_2$O
Calcd.: C, 59.62; H, 5.00; N, 10.86.
Found: C, 59.75; H, 4.81; N, 10.93.

Example 6

Production of N-(4-(5-((benzyl(methyl)amino)methyl)-1-(2,6-difluorobenzyl)-2,4-dioxo-3-(2-(2H-1,2,3-triazol-2-yl)ethyl)-1,2,3,4-tetrahydrothieno[2,3-d]pyrimidin-6-yl)phenyl)-N'-methoxyurea (1)

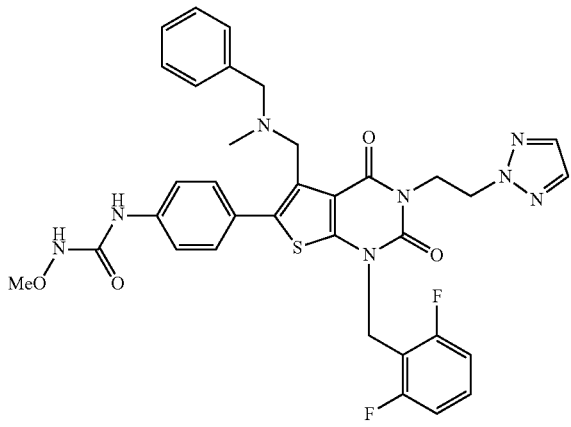 [SMILES: CONC(=O)Nc1ccc(-c2sc3c(c2CN(C)Cc2ccccc2)c(=O)n(CCn2nccn2)c(=O)n3Cc2c(F)cccc2F)cc1]

Production of N-(4-(5-((benzyl(methyl)amino)methyl)-1-(2,6-difluorobenzyl)-2,4-dioxo-3-(2-(1H-1,2,3-triazol-1-yl)ethyl)-1,2,3,4-tetrahydrothieno[2,3-d]pyrimidin-6-yl)phenyl)-N'-methoxyurea (2)

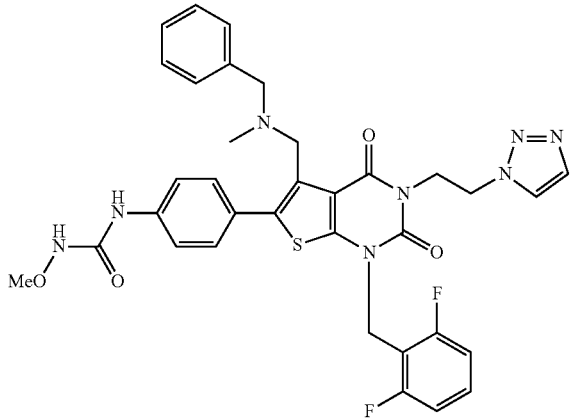 [SMILES: CONC(=O)Nc1ccc(-c2sc3c(c2CN(C)Cc2ccccc2)c(=O)n(CCn2ccnn2)c(=O)n3Cc2c(F)cccc2F)cc1]

The similar reaction as described in Example 2 by using the compound obtained in Example 5 (450 mg, 0.708 mmol) gave a mesylate. A solution of the obtained mesylate, 1,2,3-triazole (148 mg, 2.12 mmol and potassium carbonate (294 mg, 2.12 mmol) in DMF (8 ml) was stirred at room temperature for 18 hours, and at 50-60° C. for 3 hours. The reaction mixture was combined with an aqueous solution of sodium hydrogen carbonate and extracted with ethyl acetate. The organic layer was washed with brine, dried over magnesium sulfate and concentrated under reduced pressure. The residue was purified by silica gel column chromatography (eluent: ethyl acetate) to give the title compound 2-yl form (243 mg, 50%) as a white amorphous compound. On the other hand, the residue was recrystallized from dichloromethane/methanol/diethyl ether to give the title compound 1-yl form (177 mg, 36%) as colorless crystals.

2-yl form (1)

$^1$H-NMR (CDCl$_3$) δ: 2.04 (3H, s), 3.51 (2H, s), 3.82 (3H, s), 3.86 (2H, s), 4.57 (2H, t, J=6.2 Hz), 4.81 (2H, t, J=6.2 Hz), 5.28 (2H, s), 6.91 (2H, t, J=8.4 Hz), 7.15-7.35 (6H, m), 7.46 (2H, s), 7.53 (2H, d, J=8.6 Hz), 7.62 (1H, s), 7.70 (2H, t, J=8.6 Hz), 7.75 (1H, s).

IR (KBr): 1705, 1663, 1530, 1472, 1323, 1034, 786 cm$^{-1}$.

1-yl form (2)

$^1$H-NMR (CDCl$_3$) δ: 2.02 (3H, s), 3.52 (2H, s), 3.82 (3H, s), 3.85 (2H, s), 4.58 (2H, t, J=6.4 Hz), 4.78 (2H, t, J=6.4 Hz), 5.30 (2H, s), 6.92 (2H, t, J=8.2 Hz), 7.12 (1H, s), 7.15-7.4 (7H, m), 7.54 (2H, d, J=8.8 Hz), 7.55-7.65 (2H, m), 7.67 (2H, d, J=8.8 Hz).

IR (KBr): 1709, 1659, 1526, 1472, 1319, 1028, 799 cm$^{-1}$.

Elemental analysis for C$_{34}$H$_{32}$F$_2$N$_8$O$_4$S.0.8H$_2$O
Calcd.: C, 58.24; H, 4.83; N, 15.98.
Found: C, 58.48; H, 4.89; N, 15.65.

Example 7

Production of N-(4-(5-((benzyl(methyl)amino)methyl)-1-(2,6-difluorobenzyl)-2,4-dioxo-3-(2-(2H-tetrazol-2-yl)ethyl)-1,2,3,4-tetrazolothieno[2,3-d]pyrimidin-6-yl)phenyl)-N'-methoxyurea (1)

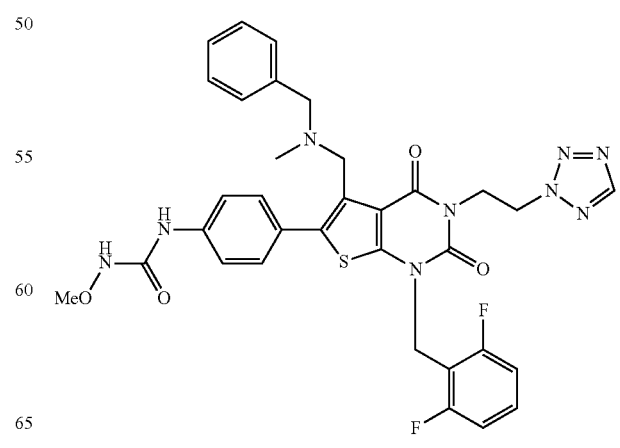

Production of N-(4-(5-((benzyl(methyl)amino)methyl)-1-(2,6-difluorobenzyl)-2,4-dioxo-3-(2-(1H-tetrazol-1-yl)ethyl)-1,2,3,4-tetrahydrothieno[2,3-d]pyrimidin-6-yl)phenyl)-N'-methoxyurea (2)

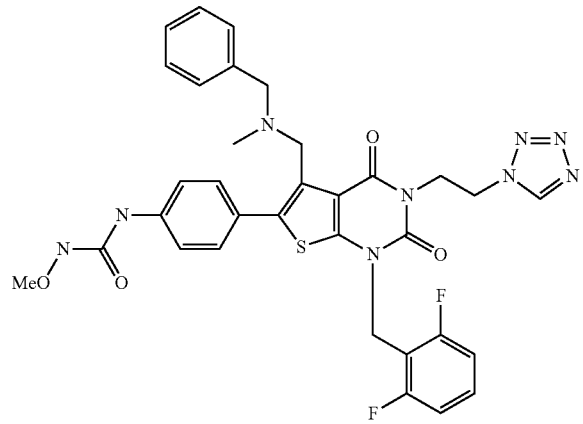 [SMILES: CONC(=O)Nc1ccc(-c2sc3c(c2CN(C)Cc2ccccc2)c(=O)n(CCn2cnnn2)c(=O)n3Cc2c(F)cccc2F)cc1]

The similar reaction as described in Example 6 by using the compound obtained in Reference Example 5 (636 mg, 1 mmol) and tetrazole (210 mg, 3 mmol) gave the title compound 2-yl form (234 mg, 34%) as a white amorphous compound. On the other hand, the residue was powdered by diethylether to give the title compound, 1-yl form, (34 mg, 5%) as pale yellow crystals.
2-yl form (1)
$^1$H-NMR (CDCl$_3$) δ: 2.02 (3H, s), 3.51 (2H, s), 3.83 (5H, s), 4.6-4.7 (2H, m), 5.0-5.1 (2H, m), 5.28 (2H, s), 6.92 (2H, t, J=8.2 Hz), 7.12 (1H, s), 7.2-7.75 (11H, m), 8.38 (1H, s). IR (KBr): 1705, 1663, 1530, 1472, 1323, 1236, 1032, 777 cm$^{-1}$.
1-yl form (2)
$^1$H-NMR (CDCl$_3$) δ: 2.01 (3H, s), 3.51 (2H, s), 3.83 (3H, s), 3.8-4.0 (2H, m), 4.6-4.7 (2H, m), 4.8-4.9 (2H, m), 5.30 (2H, s), 6.65-6.75 (1H, m), 6.85-7.0 (2H, m), 7.1-7.7 (11H, m), 8.68 (1H, s).

Example 8

Production of N-(4-(1-(2,6-difluorobenzyl)-3-(2-hydroxyethyl)-5-(((2-methoxyethyl)(methyl)amino)methyl)-2,4-dioxo-1,2,3,4-tetrahydrothieno[2,3-d]pyrimidin-6-yl)phenyl)-N'-methoxyurea

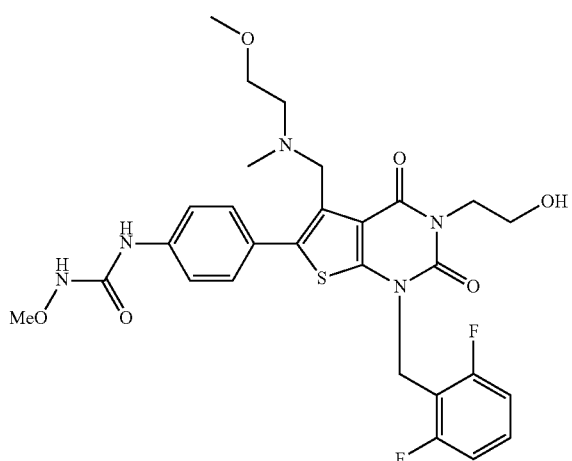

The similar reaction as described in Example 5 by using 4-(N-benzyl-N-methylaminomethyl)-2-[N-(2,6-difluorobenzyl)-N-ethoxycarbonylamino]-5-[4-(3-methoxyureido)phenyl]thiophen-3-carboxylic acid (1.21 g, 2 mmol) and 2-aminoethanol (0.18 ml, 3 mmol) to give the title compound (302 mg, 25%) as a pale yellow amorphous compound.
$^1$H-NMR(CDCl$_3$) δ: 2.11 (3H, s), 2.65 (2H, t, J=5.8 Hz), 3.30 (3H, s), 3.46 (2H, t, J=5.8 Hz), 3.82 (5H, s), 3.9-4.0 (2H, m), 4.35 (2H, t, J=5.2 Hz), 5.34 (2H, s), 6.92 (2H, t, J=8.0 Hz), 7.14 (1H, s), 7.2-7.35 (1H, m), 7.5-7.65 (5H, m).

Example 9

Production of N-(4-(1-(2,6-difluorobenzyl)-5-(((2-methoxyethyl)(methyl)amino)methyl)-2,4-dioxo-3-(2-(2H-tetrazol-2-yl)ethyl)-1,2,3,4-tetrahydrothieno[2,3-d]pyrimidin-6-yl)phenyl)-N'-methoxyurea (1)

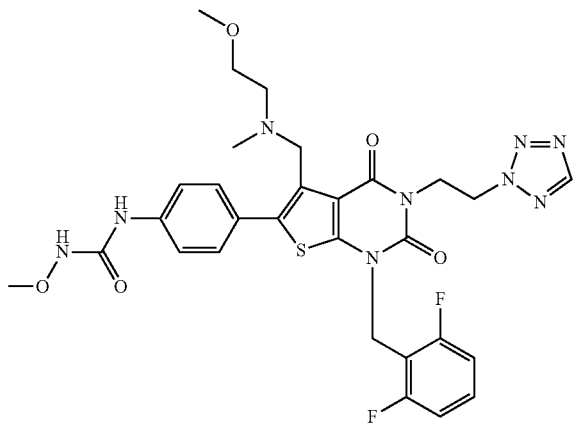 [SMILES: COCCN(C)Cc1c(-c2ccc(NC(=O)NOC)cc2)sc2c1c(=O)n(CCn1ncnn1)c(=O)n2Cc1c(F)cccc1F]

Production of N-(4-(1-(2,6-difluorobenzyl)-5-(((2-methoxyethyl)(methyl)amino)methyl)-2,4-dioxo-3-(2-(1H-tetrazol-1-yl)ethyl)-1,2,3,4-tetrahydrothieno[2,3-d]pyrimidin-6-yl)phenyl)-N'-methoxyurea (2)

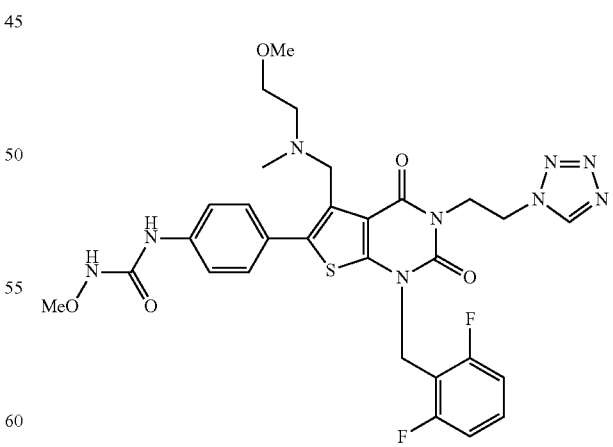

The similar reaction as described in Example 6 by using the compound obtained in Example 8 (250 mg, 0.414 mmol) and tetrazole (145 mg, 2.07 mmol) gave the title compound 2-yl form (66 mg, 24%) and 1-yl form (27 mg, 10%) as white amorphous compounds.

2-yl form (1)

¹H-NMR (CDCl₃) δ: 2.10 (3H, brs), 2.55-2.65 (2H, m), 3.31 (3H, s), 3.4-3.5 (2H, m), 3.76 (2H, s), 3.82 (3H, s), 4.62 (2H, t, J=5.8 Hz), 5.02 (2H, t, J=5.8 Hz), 5.27 (2H, s), 6.92 (2H, t, J=8.2 Hz), 7.13 (1H, s), 7.25-7.4 (1H, m), 7.5-7.65 (5H, m), 8.43 (1H, s).

1-yl form (2)

¹H-NMR (CDCl₃) δ: 2.07 (3H, s), 2.55-2.65 (2H, m), 3.30 (3H, s), 3.4-3.5 (2H, m), 3.74 (2H, s), 3.82 (3H, s), 4.55-4.65 (2H, m), 4.8-4.9 (2H, m), 5.30 (2H, s), 6.93 (2H, t, J=7.8 Hz), 7.10 (1H, s), 7.2-7.4 (1H, m), 7.5-7.65 (5H, m), 8.69 (1H, s).

Example 10

Production of N-(4-(1-(2,6-difluorobenzyl)-5-(((2-methoxyethyl)(methyl)amino)methyl)-2,4-dioxo-3-(2-(2H-1,2,3-triazol-2-yl)ethyl)-1,2,3,4-tetrahydrothieno[2,3-d]pyrimidin-6-yl)phenyl)-N'-methoxyurea

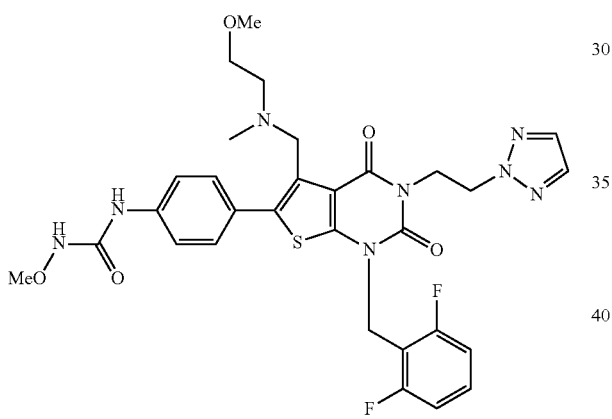

The similar reaction as described in Reference Example 14 by using the compound obtained in Example 6 (1-yl form) (200 mg, 0.291 mmol) gave de-benzyl-form (0.11 g, 63%) as colorless powders. The similar reaction as described in Example 4 by using the de-benzyl-form (0.11 g, 0.184 mmol) and 2-(chloromethyl)methylether (0.10 ml, 1.104 mmol) gave the title compound (35 mg, 29%) as colorless crystals.

¹H-NMR (CDCl₃) δ: 2.11 (3H, s), 2.62 (2H, t, J=5.8 Hz), 3.31 (3H, s), 3.44 (2H, t, J=5.8 Hz), 3.78 (2H, s), 3.82 (3H, s), 4.55 (2H, t, J=5.6 Hz), 4.79 (2H, t, J=5.6 Hz), 5.27 (2H, s), 6.91 (2H, t, J=8.2 Hz), 7.10 (1H, s), 7.2-7.4 (2H, m), 7.51 (2H, s), 7.45-7.65 (4H, m).

Elemental analysis for $C_{30}H_{32}F_2N_8O_5S$

Calcd.: C, 55.04; H, 4.93; N, 17.12.

Found: C, 55.02; H, 4.85; N, 16.83.

Reference Example 15

Production of N-(4-(1-(2,6-difluorobenzyl)-5-((methylamino)methyl)-2,4-dioxo-3-phenyl-1,2,3,4-tetrahydrothieno[2,3-d]pyrimidin-6-yl)phenyl)-N'-methoxyurea

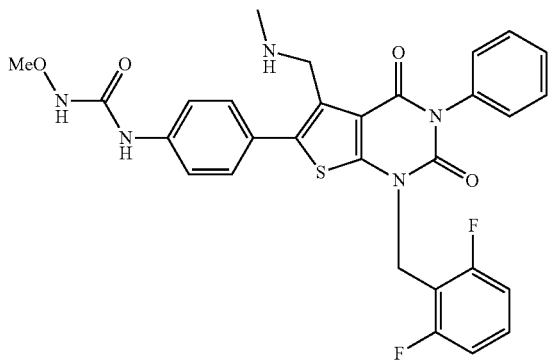 [SMILES: CNCc1c(-c2ccc(NC(=O)NOC)cc2)sc2c1c(=O)n(-c1ccccc1)c(=O)n2Cc1c(F)cccc1F]

The similar reaction as described in Reference Example 14 by using 5-(N-benzyl-N-methylaminomethyl)-1-(2,6-difluorobenzyl)-6-[4-(3-methoxyureido)phenyl]-3-phenylthieno[2,3-d]pyrimidin-2,4(1H,3H)-dione (6.68 g, 10 mmol) gave the title compound (5.52 g, 96%) as white powders.

¹H-NMR (CDCl₃) δ: 2.35 (3H, s), 3.76 (2H, s), 3.82 (3H, s), 5.37 (2H, s), 6.92 (2H, t, J=8.2 Hz), 7.25-7.7 (12H, m).

Example 11

Production of N-(4-(1-(2,6-difluorobenzyl)-5-((methyl(2-(2H-1,2,3-triazol-2-yl)ethyl)amino)methyl)-2,4-dioxo-3-phenyl-1,2,3,4-tetrahydrothieno[2,3-d]pyrimidin-6-yl)phenyl)-N'-methoxyurea (1)

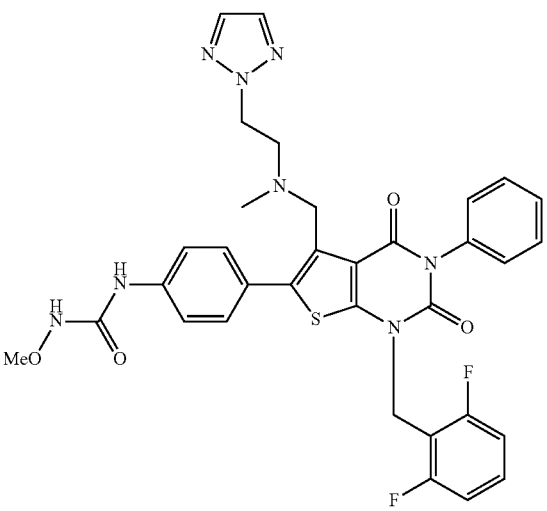 [SMILES: CONC(=O)Nc1ccc(-c2sc3c(c2CN(C)CCn2nccn2)c(=O)n(-c2ccccc2)c(=O)n3Cc2c(F)cccc2F)cc1]

Production of N-(4-(1-(2,6-difluorobenzyl)-5-((methyl(2-(1H-1,2,3-triazol-1-yl)ethyl)amino)methyl)-2,4-dioxo-3-phenyl-1,2,3,4-tetrahydrothieno[2,3-d]pyrimidin-6-yl)phenyl)-N'-methoxyurea (2)

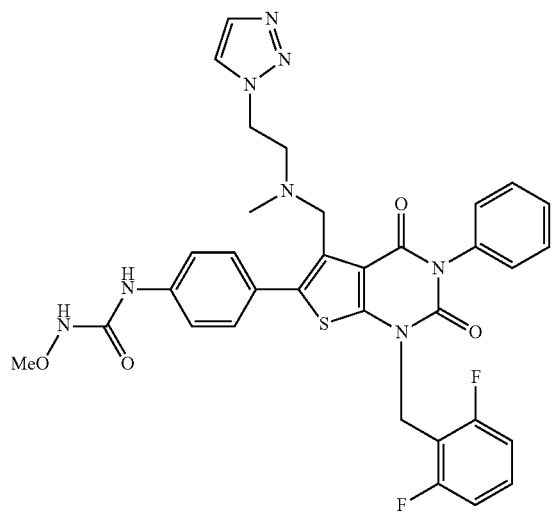 [SMILES: CONC(=O)Nc1ccc(-c2sc3c(c2CN(C)CCn2ccnn2)c(=O)n(-c2ccccc2)c(=O)n3Cc2c(F)cccc2F)cc1]

Potassium carbonate (1.33 g, 10 mmol) was added to a solution of 1,2,3-triazole (0.46 g, 6.67 mmol) and 1-bromo-2-chloroethane (0.83 ml, 10 mmol) in DMF (5 ml), and the mixture was stirred at room temperature for 1 hour, and 50-60° C. for 3 hours. The reaction mixture was combined with saturated brine and extracted twice with ethyl acetate. The combined organic layer was dried over magnesium sulfate and concentrated to give a halide.

The compound obtained in Reference Example 15 (700 mg, 1.21 mmol) was dissolved in DMF (12 ml), and N,N-diisopropylethylamine (1.16 ml, 6.67 mmol) and the halide obtained above were added thereto. The mixture was stirred at 50-60° C. for 16 hours, combined with an aqueous solution of sodium hydrogen carbonate and extracted with ethyl acetate. The organic layer was washed with brine, dried over magnesium sulfate and concentrated under reduced pressure. The residue was purified by NH-silica gel column chromatography (eluent: ethyl acetate) and recrystallized from dichloromethane/methanol/diethyl ether to give the title compound 2-yl form (140 mg, 17%) and 1-yl form (332 mg, 41%) as colorless crystals.

2-yl form (1)
$^1$H-NMR (CDCl$_3$) δ: 2.23 (3H, s), 3.00 (2H, t, J=6.3 Hz), 3.78 (2H, s), 3.82 (3H, s), 4.45 (2H, t, J=6.3 Hz), 5.37 (2H, s), 6.92 (2H, t, J=8.2 Hz), 6.85-6.95 (1H, m), 7.11 (1H, s), 7.2-7.6 (12H, m).
IR (KBr): 1715, 1671, 1530, 1470, 1331, 1236, 1032, 822, 735 cm$^{-1}$.
Elemental analysis for C$_{33}$H$_{30}$F$_2$N$_8$O$_4$S·0.3H$_2$O
Calcd.: C, 58.45; H, 4.55; N, 16.52.
Found: C, 58.75; H, 4.27; N, 16.20.
mp 166-168° C.

1-yl form (2)
$^1$H-NMR (CDCl$_3$) δ: 2.14 (3H, s), 2.82 (2H, t, J=6.0 Hz), 3.80 (2H, s), 3.82 (3H, s), 4.39 (2H, t, J=6.0 Hz), 5.37 (2H, s), 6.92 (2H, t, J=8.2 Hz), 6.85-6.95 (1H, m), 7.14 (1H, s), 7.2-7.55 (11H, m), 7.63 (1H, s).
IR (KBr): 1719, 1672, 1526, 1470, 1236, 1231, 1028, 824, 733 cm$^{-1}$.
Elemental analysis for C$_{33}$H$_{30}$F$_2$N$_8$O$_4$S·0.4H$_2$O
Calcd.: C, 58.30; H, 4.57; N, 16.48.
Found: C, 58.53; H, 4.50; N, 16.29.
mp 194-196° C.

Example 12

Production of N-(4-(1-(2,6-difluorobenzyl)-5-((methyl(2-(2-pyridinyl)ethyl)amino)methyl)-2,4-dioxo-3-phenyl-1,2,3,4-tetrahydrothieno[2,3-d]pyrimidin-6-yl)phenyl)-N'-methoxyurea

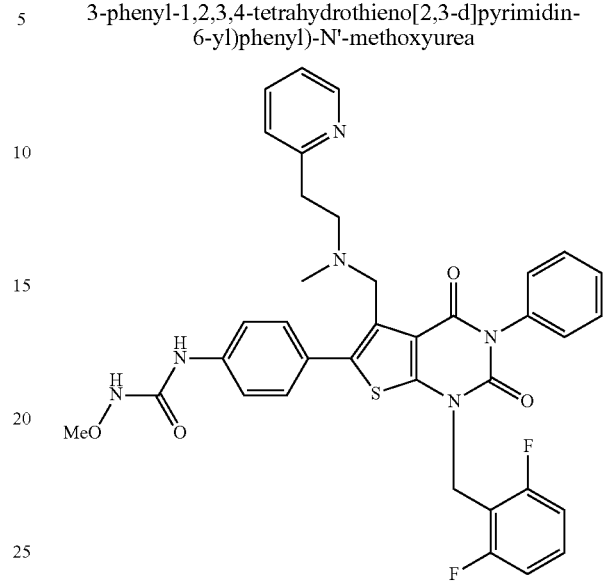

The similar reaction as described in Example 2 by using the compound obtained in Reference Example 15 (350 mg, 0.606 mmol) and 2-(2-hydroxyethyl)pyridine (0.45 g, 3.64 mmol) gave the title compound (233 mg, 56%) as colorless crystals.
$^1$H-NMR (CDCl$_3$) δ: 2.20 (3H, s), 2.85 (4H, s), 3.82 (5H, s), 5.37 (2H, s), 6.93 (2H, t, J=8.2 Hz), 6.95-7.1 (2H, m), 7.14 (1H, s), 7.2-7.55 (11H, m), 7.60 (1H, s), 8.43 (1H, d, J=4.0 Hz).
IR (KBr): 1717, 1667, 1530, 1470, 1331, 1236, 1030, 735 cm$^{-1}$.
Elemental analysis for C$_{36}$H$_{32}$F$_2$N$_6$O$_4$S
Calcd.: C, 63.33; H, 4.72; N, 12.31.
Found: C, 63.17; H, 4.56; N, 12.31.
mp 159-160° C.

Example 13

Production of N-(4-(1-(2,6-difluorobenzyl)-5-((methyl(2-(4-pyridinyl)ethyl)amino)methyl)-2,4-dioxo-3-phenyl-1,2,3,4-tetrahydrothieno[2,3-d]pyrimidin-6-yl)phenyl)-N'-methoxyurea

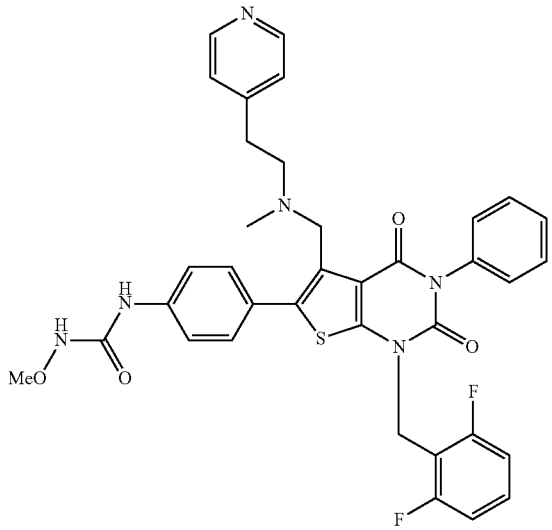 [SMILES: CONC(=O)Nc1ccc(-c2sc3c(c2CN(C)CCc2ccncc2)c(=O)n(-c2ccccc2)c(=O)n3Cc2c(F)cccc2F)cc1]

The similar reaction as described in Example 2 by using the compound obtained in Reference Example 15 (350 mg, 0.606 mmol) and 4-(2-hydroxyethyl)pyridine hydrochloride (0.58 g, 3.64 mmol) gave the title compound (166 mg, 40%) as colorless crystals.

$^1$H-NMR (CDCl$_3$) δ: 2.18 (3H, s), 2.68 (4H, s), 3.83 (5H, s), 5.37 (2H, s), 6.85-7.0 (5H, m), 7.16 (1H, s), 7.2-7.65 (10H, m), 8.35-8.4 (2H, m).

IR (KBr): 1715, 1667, 1532, 1470, 735 cm$^{-1}$.

Elemental analysis for C$_{36}$H$_{32}$F$_2$N$_6$O$_4$S.0.1H$_2$O

Calcd.: C, 63.16; H, 4.74; N, 12.28.

Found: C, 62.91; H, 4.68; N, 12.26.

mp 194-196° C.

Example 14

Production of N-(4-(1-(2,6-difluorobenzyl)-5-((methyl(2-pyridinylmethyl)amino)methyl)-2,4-dioxo-3-phenyl-1,2,3,4-tetrahydrothieno[2,3-d]pyrimidin-6-yl)phenyl)-N'-methoxyurea

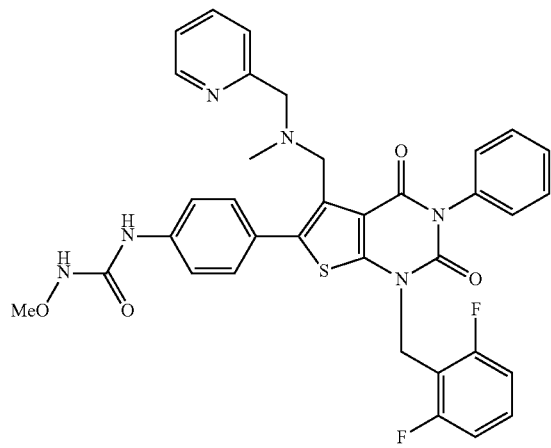 [SMILES: CONC(=O)Nc1ccc(-c2sc3c(c2CN(C)Cc2ccccn2)c(=O)n(-c2ccccc2)c(=O)n3Cc2c(F)cccc2F)cc1]

The similar reaction as described in Example 4 by using the compound obtained in Reference Example 15 (350 mg, 0.606 mmol) and 2-chloromethylpyridine hydrochloride (149 mg, 0.908 mmol) gave the title compound (297 mg, 73%) as colorless crystals.

$^1$H-NMR (CDCl$_3$) δ: 2.10 (3H, s), 3.71 (2H, s), 3.83 (3H, s), 3.99 (2H, s), 5.36 (2H, s), 6.92 (2H, t, J=8.2 Hz), 7.0-7.1 (1H, m), 7.15 (1H, s), 7.2-7.35 (4H, m), 7.4-7.65 (9H, m), 8.4-8.5 (1H, m).

IR (KBr): 1715, 1667, 1532, 1472, 735 cm$^{-1}$.

Elemental analysis for C$_{35}$H$_{30}$F$_2$N$_6$O$_4$S.0.5H$_2$O

Calcd.: C, 62.03; H, 4.61; N, 12.40.

Found: C, 62.13; H, 4.59; N, 12.47.

mp 181-182° C.

Reference Example 16

Production of N-(4-(5-((benzyl(methyl)amino)methyl)-1-(2,6-difluorobenzyl)-2,4-dioxo-3-(4-fluorophenyl)-1,2,3,4-tetrahydrothieno[2,3-d]pyrimidin-6-yl)phenyl)-N'-methoxyurea

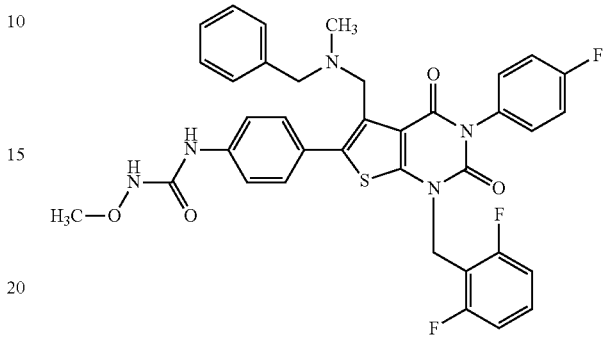

The similar reaction as described in Example 5 by using 4-(N-benzyl-N-methylaminomethyl)-2-[N-(2,6-difluorobenzyl)-N-ethoxycarbonylamino]-5-[4-(3-methoxyureido)phenyl]thiophene-3-carboxylic acid (2.87 g, 4.49 mmol) and 4-fluoroaniline (0.64 ml, 6.735 mmol) gave the title compound (2.71 g, 88%) as pale yellow powders.

$^1$H-NMR (CDCl$_3$) δ: 2.05 (3H, s), 3.56 (2H, s), 3.83 (3H, s), 3.89 (2H, s), 5.36 (2H, s), 6.93 (2H, t, J=8.0 Hz), 7.1-7.35 (11H, m), 7.56 (2H, d, J=8.4 Hz), 7.63 (1H, s), 7.72 (2H, d, J=8.4 Hz).

Elemental analysis for C$_{36}$H$_{30}$F$_3$N$_5$O$_4$S.0.5H$_2$O

Calcd.: C, 62.24; H, 4.50; N, 10.08.

Found: C, 62.43; H, 4.21; N, 9.84.

Reference Example 17

Production of N-(4-(1-(2,6-difluorobenzyl)-3-(4-fluorophenyl)-5-((methylamino)methyl)-2,4-dioxo-1,2,3,4-tetrahydrothieno[2,3-d]pyrimidin-6-yl)phenyl)-N'-methoxyurea

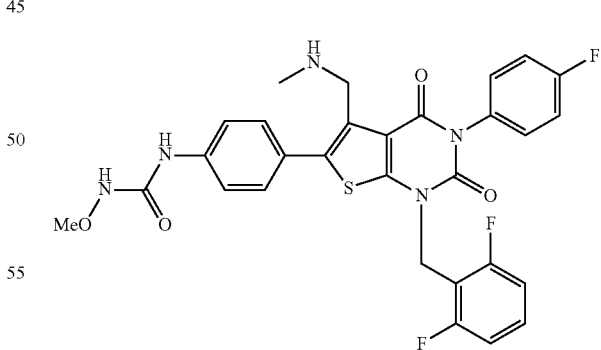

The similar reaction as described in Reference Example 14 by using the compound obtained in Reference Example 16 (2.50 g, 3.65 mmol) gave the title compound (1.85 g, 85%) as white powder.

$^1$H-NMR (CDCl$_3$) δ: 2.37 (3H, s), 3.76 (2H, s), 3.82 (3H, s), 5.37 (2H, s), 6.92 (2H, t, J=8.2 Hz), 6.85-7.0 (1H, brs), 7.15-7.35 (6H, m), 7.42 (2H, d, J=8.4 Hz), 7.57 (2H, d, J=8.4 Hz), 7.63 (1H, s).

Example 15

Production of N-(4-(1-(2,6-difluorobenzyl)-3-(4-fluorophenyl)-5-((methyl(2-pyridinylmethyl)amino)methyl)-2,4-dioxo-1,2,3,4-tetrahydrothieno[2,3-d]pyrimidin-6-yl)phenyl)-N'-methoxyurea

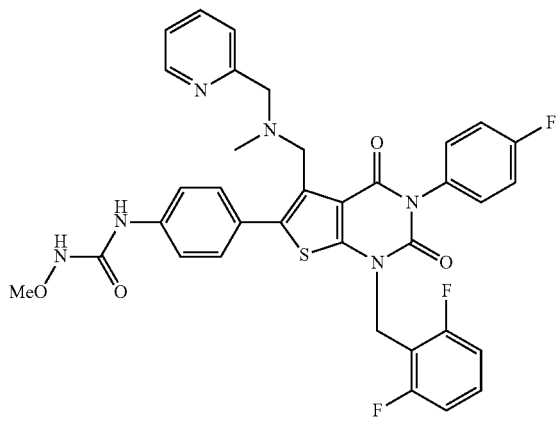 [SMILES: CONC(=O)Nc1ccc(-c2sc3c(c2CN(C)Cc2ccccn2)c(=O)n(-c2ccc(F)cc2)c(=O)n3Cc2c(F)cccc2F)cc1]

The similar reaction as described in Example 4 by using the compound obtained in Reference Example 17 (150 mg, 0.25 mmol) and 2-chloromethylpyridine hydrochloride (85 mg, 0.52 mmol) gave the title compound (105 mg, 61%) as colorless crystals.

$^1$H-NMR (CDCl$_3$) δ: 2.10 (3H, s), 3.71 (2H, s), 3.83 (3H, s), 3.97 (2H, s), 5.35 (2H, s), 6.93 (2H, t, J=8.2 Hz), 7.0-7.7 (14H, m), 8.4-8.5 (1H, m).

IR (KBr): 1723, 1665, 1532, 1510, 1474, 1236, 1032, 761 cm$^{-1}$.

Elemental analysis for C$_{35}$H$_{29}$F$_3$N$_6$O$_4$S.0.7H$_2$O
Calcd.: C, 60.11; H, 4.38; N, 12.02.
Found: C, 59.76; H, 4.03; N, 11.71.
mp 183-185° C.

Example 16

Production of N-(4-(1-(2,6-difluorobenzyl)-3-(4-fluorophenyl)-5-((methyl(2-(2-pyridinyl)ethyl)amino)methyl)-2,4-dioxo-1,2,3,4-tetrahydrothieno[2,3-d]pyrimidin-6-yl)phenyl)-N'-methoxyurea

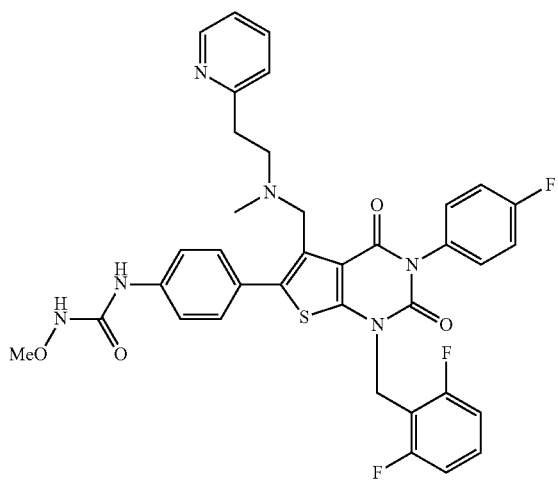 [SMILES: CONC(=O)Nc1ccc(-c2sc3c(c2CN(C)CCc2ccccn2)c(=O)n(-c2ccc(F)cc2)c(=O)n3Cc2c(F)cccc2F)cc1]

The similar reaction as described in Example 2 by using the compound obtained in Reference Example 17 (150 mg, 0.25 mmol) and 2-(2-hydroxyethyl)pyridine (0.19 g, 1.512 mmol) gave the title compound (100 mg, 57%) as colorless crystals.

$^1$H-NMR (CDCl$_3$) δ: 2.19 (3H, s), 2.85 (4H, s), 3.82 (5H, s), 5.36 (2H, s), 6.9-7.55 (13H, m), 7.60 (1H, s), 8.4-8.45 (1H, m).

IR (KBr): 1723, 1665, 1534, 1510, 1474, 1464, 1238, 1034, 762 cm$^{-1}$.

Elemental analysis for C$_{36}$H$_{31}$F$_3$N$_6$O$_4$S.0.5H$_2$O
Calcd.: C, 60.92; H, 4.54; N, 11.84.
Found: C, 61.12; H, 4.63; N, 11.78.
mp 185-187° C.

Example 17

Production of N-(4-(1-(2,6-difluorobenzyl)-5-((methyl(2-(2-pyridinyl)ethyl)amino)methyl)-2,4-dioxo-3-(2-pyridinyl)-1,2,3,4-tetrahydrothieno[2,3-d]pyrimidin-6-yl)phenyl)-N'-methoxyurea

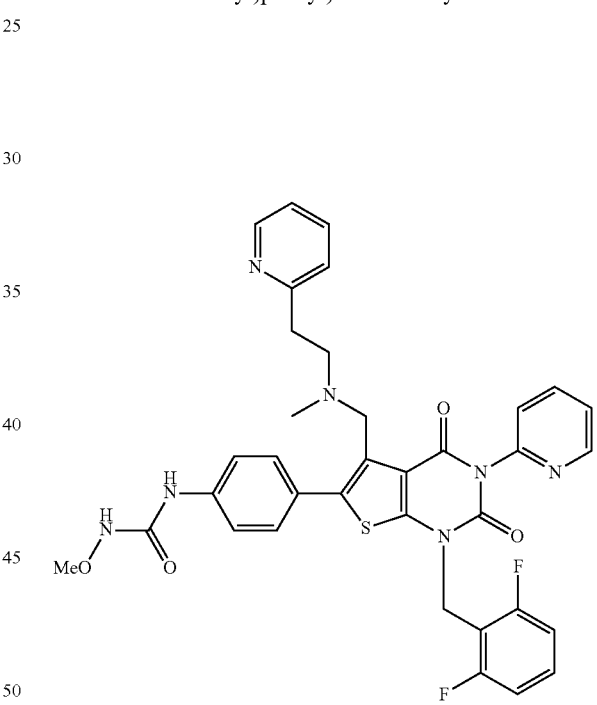

The similar reaction as described in Example 2 by using the compound obtained in Reference Example 14 (150 mg, 0.259 mmol) and 2-(2-hydroxyethyl)pyridine (0.18 g, 1.425 mmol) gave the title compound (83 mg, 47%) as pale yellow crystals.

$^1$H-NMR (CDCl$_3$) δ: 2.21 (3H, s), 2.8-2.9 (4H, m), 3.82 (5H, s), 5.34 (2H, brs), 6.85-7.75 (13H, m), 7.60 (1H, s), 7.85-7.95 (1H, m), 8.4-8.5 (1H, m), 8.65-8.75 (1H, m).

IR (KBr): 1715, 1671, 1530, 1458, 1329, 1032, 781 cm$^{-1}$.
mp 194-196° C.

Example 18

Production of N-(4-(1-(2,6-difluorobenzyl)-5-((methyl(3-pyridinylmethyl)amino)methyl)-2,4-dioxo-3-phenyl-1,2,3,4-tetrahydrothieno[2,3-d]pyrimidin-6-yl)phenyl)-N'-methoxyurea

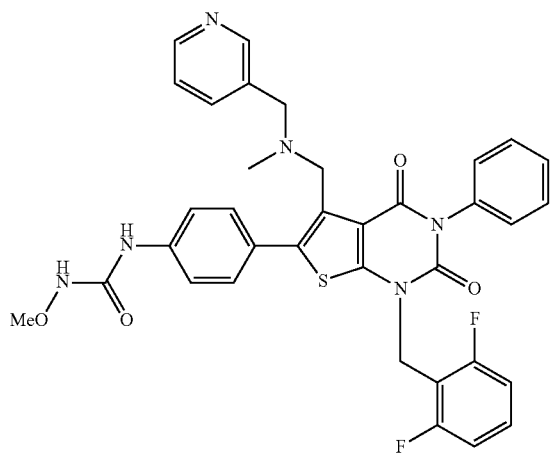 [SMILES: CONC(=O)Nc1ccc(-c2sc3c(c2CN(C)Cc2cccnc2)c(=O)n(-c2ccccc2)c(=O)n3Cc2c(F)cccc2F)cc1]

The similar reaction as described in Example 4 by using the compound obtained in Reference Example 15 (150 mg, 0.26 mmol) and 3-chloromethylpyridine hydrochloride (85 mg, 0.52 mmol) gave the title compound (117 mg, 67%) as colorless crystals.

$^1$H-NMR (CDCl$_3$) δ: 2.04 (3H, s), 3.58 (2H, s), 3.83 (3H, s), 3.92 (2H, s), 5.37 (2H, s), 6.92 (2H, t, J=8.2 Hz), 7.05-7.7 (14H, m), 8.35-8.45 (2H, m).

IR (KBr): 1713, 1669, 1532, 1464, 1329, 1238, 1032, 787 cm$^{-1}$.

Elemental analysis for C$_{35}$H$_{30}$F$_2$N$_6$O$_4$S·0.3H$_2$O
Calcd.: C, 62.36; H, 4.58; N, 12.47.
Found: C, 62.22; H, 4.32; N, 12.57.
mp 184-185° C.

Example 19

Production of N-(4-(1-(2,6-difluorobenzyl)-5-((((6-(hydroxymethyl)-2-pyridinyl)methyl)(methyl)amino)methyl)-2,4-dioxo-3-phenyl-1,2,3,4-tetrahydrothieno[2,3-d]pyrimidin-6-yl)phenyl)-N'-methoxyurea

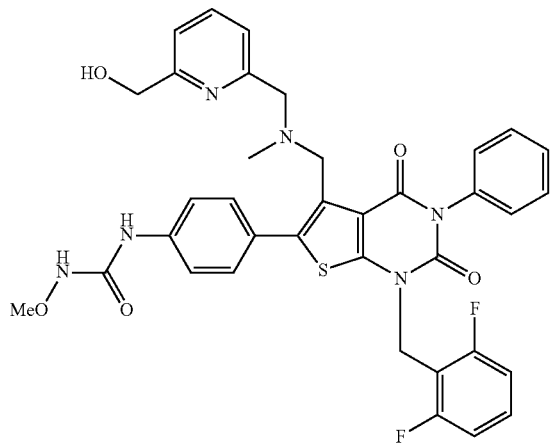 [SMILES: CONC(=O)Nc1ccc(-c2sc3c(c2CN(C)Cc2cccc(CO)n2)c(=O)n(-c2ccccc2)c(=O)n3Cc2c(F)cccc2F)cc1]

The similar reaction as described in Example 4 by using the compound obtained in Reference Example 15 (150 mg, 0.26 mmol) and 6-bromomethyl-2-pyridinemethanol (105 mg, 0.52 mmol) gave the title compound (115 mg, 63%) as colorless crystals.

$^1$H-NMR (CDCl$_3$) δ: 2.13 (3H, s), 3.72 (2H, s), 3.83 (3H, s), 3.97 (2H, s), 4.05-4.1 (1H, m), 4.65-4.75 (2H, m), 5.37 (2H, s), 6.93 (2H, t, J=8.2 Hz), 6.9-7.05 (1H, m), 7.1-7.2 (2H, m), 7.2-7.7 (12H, m).

IR (KBr): 1713, 1669, 1534, 1472, 1032, 789, 735 cm$^{-1}$.

Elemental analysis for C$_{36}$H$_{32}$F$_2$N$_6$O$_5$S·1.1H$_2$O
Calcd.: C, 60.17; H, 4.80; N, 11.70.
Found: C, 60.02; H, 4.70; N, 11.53.

Example 20

Production of methyl 6-(((((1-(2,6-difluorobenzyl)-6-(4-(((methoxyamino)carbonyl)amino)phenyl)-2,4-dioxo-3-phenyl-1,2,3,4-tetrahydrothieno[2,3-d]pyrimidin-5-yl)methyl)(methyl)amino)methyl)nicotinate

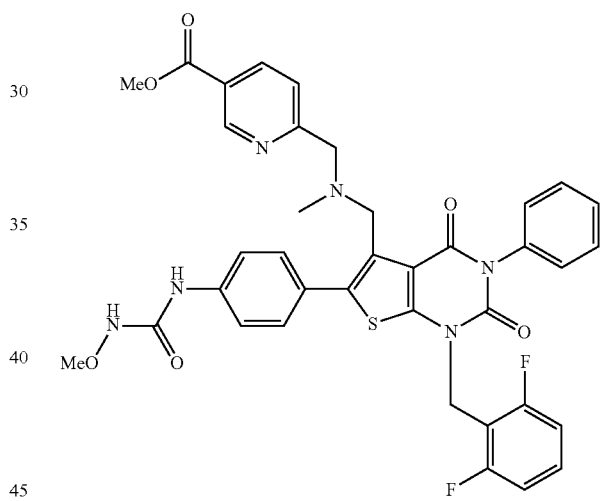

The similar reaction as described in Example 4 by using the compound obtained in Reference Example 15 (280 mg, 0.485 mmol) and methyl 6-(bromomethyl)nicotinate (0.19 g, 0.825 mmol) gave the title compound (267 mg, 76%) as colorless crystals.

$^1$H-NMR (CDCl$_3$) δ: 2.09 (3H, s), 3.76 (2H, s), 3.83 (3H, s), 3.93 (3H, s), 3.99 (2H, s), 5.35 (2H, s), 6.92 (2H, t, J=8.2 Hz), 7.26 (1H, s), 7.2-7.6 (11H, m), 7.64 (1H, s), 8.05-8.15 (1H, m), 9.0-9.05 (1H, s).

IR (KBr): 1732, 1715, 1669, 1526, 1470, 1296, 1032, 789, 735 cm$^{-1}$.

Elemental analysis for C$_{37}$H$_{32}$F$_2$N$_6$O$_6$S
Calcd.: C, 61.15; H, 4.44; N, 11.56.
Found: C, 60.96; H, 4.47; N, 11.52.

Example 21

Production of 6-((((1-(2,6-difluorobenzyl)-6-(4-(((methoxyamino)carbonyl)amino)phenyl)-2,4-dioxo-3-phenyl-1,2,3,4-tetrahydrothieno[2,3-d]pyrimidin-5-yl)methyl)(methyl)amino)methyl)-N-methylnicotinamide

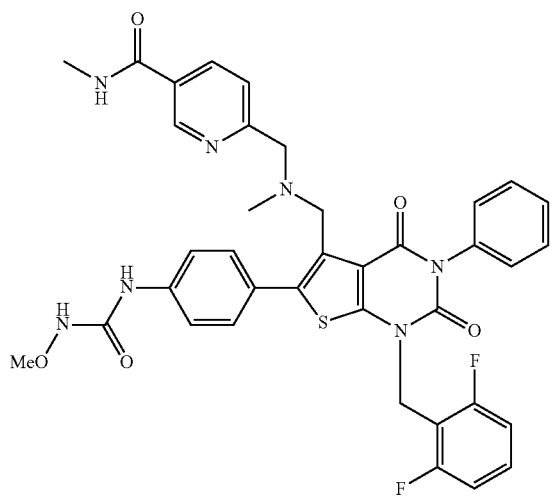 [SMILES: CNC(=O)c1ccc(CN(C)Cc2c(-c3ccc(NC(=O)NOC)cc3)sc3c2c(=O)n(-c2ccccc2)c(=O)n3Cc2c(F)cccc2F)nc1]

Ethyldiisopropylamine (0.48 ml, 2.76 mmol) and a solution of dimethylaluminium chloride in hexane (0.98 M, 1.69 ml, 1.656 mmol) were added dropwise to a solution of methylamine (2M in THF) (1.38 ml, 2.76 mmol) in dichloromethane (4 ml) under ice cooling, and the mixture was stirred at room temperature for 30 minutes. A solution of the compound obtained in Example 20 (200 mg, 0.275 mmol) in dichloromethane (14 ml) was added to the mixture, and the mixture was stirred at room temperature for 2 days. The reaction mixture was combined with an aqueous solution of sodium hydrogen carbonate and extracted with chloroform. The organic layer was washed with brine, dried over magnesium sulfate and concentrated under reduced pressure. The residue was purified by NH-silica gel column chromatography (Fuji Silysia Chemical) (eluent: ethyl acetate/methanol=40/1) and recrystallized from dichloromethane/methanol/diethyl ether to give the title compound (68 mg, 34%) as colorless crystals.

$^1$H-NMR (CDCl$_3$) δ: 2.21 (3H, s), 3.00 (3H, d, J=4.6 Hz), 3.74 (2H, s), 3.84 (3H, s), 3.92 (2H, s), 5.36 (2H, s), 6.5-6.65 (1H, m), 6.92 (2H, t, J=8.0 Hz), 7.15-7.6 (12H, m), 7.71 (1H, s), 7.9-8.0 (1H, m), 8.80-8.85 (1H, m). IR (KBr): 1713, 1665, 1534, 1470, 1327, 1032, 735 cm$^{-1}$.

Elemental analysis for C$_{37}$H$_{33}$F$_2$N$_7$O$_5$S.1.6H$_2$O
Calcd.: C, 58.89; H, 4.84; N, 12.99.
Found: C, 59.12; H, 5.06; N, 12.66.

Example 22

Production of ethyl 6-((((1-(2,6-difluorobenzyl)-6-(4-(((methoxyamino)carbonyl)amino)phenyl)-2,4-dioxo-3-phenyl-1,2,3,4-tetrahydrothieno[2,3-d]pyrimidin-5-yl)methyl)(methyl)amino)methyl)-2-pyridinecarboxylate

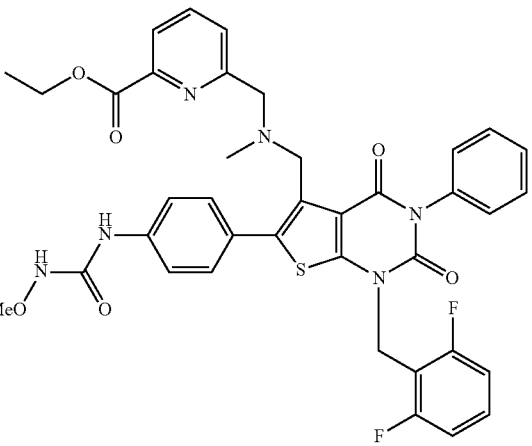

The similar reaction as described in Example 2 by using the compound obtained in Reference Example 15 (578 mg, 1 mmol) and ethyl 6-hydroxymethyl-2-pyridinecarboxylate (797 mg, 4.4 mmol) gave the title compound (590 mg, 80%) as colorless crystals.

$^1$H-NMR(CDCl$_3$) δ: 1.40 (3H, t, J=7.2 Hz), 2.10 (3H, s), 3.79 (2H, s), 3.83 (3H, s), 4.01 (2H, s), 4.43 (2H, q, J=7.2 Hz), 5.35 (2H, s), 6.92 (2H, t, J=8.2 Hz), 7.15 (1H, s), 7.2-7.7 (13H, m), 7.88 (1H, d, J=7.4 Hz).
IR (KBr): 1717, 1667, 1530, 1464, 1310, 1236, 1032, 747 cm$^{-1}$.

Elemental analysis for C$_{38}$H$_{34}$F$_2$N$_6$O$_6$S
Calcd.: C, 61.61; H, 4.63; N, 11.34.
Found: C, 61.39; H, 4.65; N, 11.17.

Example 23

Production of 6-((((1-(2,6-difluorobenzyl)-6-(4-(((methoxyamino)carbonyl)amino)phenyl)-2,4-dioxo-3-phenyl-1,2,3,4-tetrahydrothieno[2,3-d]pyrimidin-5-yl)methyl)(methyl)amino)methyl)-N-methyl-2-pyridinecarboxamide

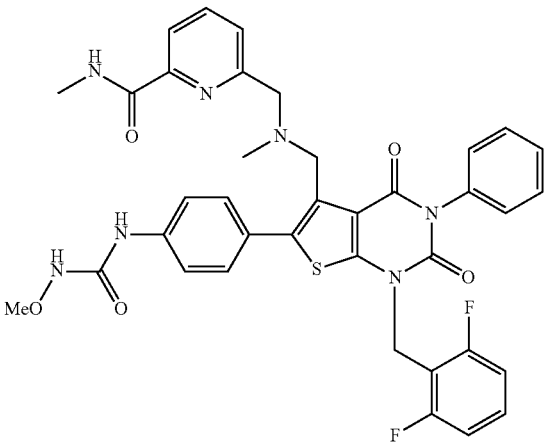 [SMILES: CNC(=O)c1cccc(CN(C)Cc2c(-c3ccc(NC(=O)NOC)cc3)sc3c2c(=O)n(-c2ccccc2)c(=O)n3Cc2c(F)cccc2F)n1]

The similar reaction as described in Example 21 by using the compound obtained in Example 22 (300 mg, 0.413 mmol) and a solution of methylamine in THF (2 M, 2.07 ml, 4.13 mmol) gave the title compound (158 mg, 53%) as colorless crystals.

$^1$H-NMR (CDCl$_3$) δ: 2.13 (3H, s), 2.95 (3H, d, J=5.2 Hz), 3.74 (2H, s), 3.84 (3H, s), 3.99 (2H, s), 5.36 (2H, s), 6.93 (2H, t, J=8.2 Hz), 7.15-7.7 (13H, m), 7.9-8.1 (3H, m).

IR (KBr): 1719, 1663, 1534, 1472, 1331, 1032, 737 cm$^{-1}$.

Elemental analysis for C$_{37}$H$_{33}$F$_2$N$_7$O$_5$S.1.0H$_2$O

Calcd.: C, 59.75; H, 4.74; N, 13.18.

Found: C, 59.60; H, 4.77; N, 13.12.

Example 24

Production of N-(4-(1-(2,6-difluorobenzyl)-5-(((2-(1H-imidazol-1-yl)ethyl)(methyl)amino)methyl)-2,4-dioxo-3-phenyl-1,2,3,4-tetrahydrothieno[2,3-d]pyrimidin-6-yl)phenyl)-N'-methoxyurea

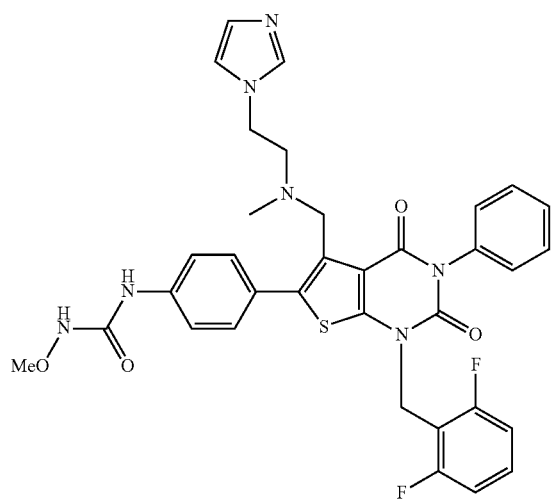 [SMILES: CONC(=O)Nc1ccc(-c2sc3c(c2CN(C)CCn2ccnc2)c(=O)n(-c2ccccc2)c(=O)n3Cc2c(F)cccc2F)cc1]

The compound obtained in Reference Example 15 (289 mg, 0.5 mmol) was dissolved in DMF (30 ml), and ethyldiisopropylamine (0.44 ml, 2.5 mmol) and 1-bromo-2-chloroethane (0.17 ml, 2.5 mmol) were added thereto. The reaction mixture was stirred at 50-60° C. for 1 hour, combined with an aqueous solution of sodium hydrogen carbonate and extracted with ethyl acetate. The combined organic layer was dried over magnesium sulfate and concentrated under reduced pressure to give a halide. A solution of the obtained halide, imidazole (177 mg, 2.6 mmol) and potassium carbonate (72 mg, 0.52 mmol) in DMF (4 ml) was stirred at room temperature for 18 hours and at 50-60° C. for 1 hour, combined with water and extracted with ethyl acetate. The organic layer was washed with brine, dried over magnesium sulfate and concentrated under reduced pressure. The residue was purified by NH-silica gel column chromatography (Fuji Silysia Chemical) (eluent: ethyl acetate/methanol=80/1 to 20/1) and recrystallized from dichloromethane/methanol/diethyl ether to give the title compound (40 mg, 23%) as colorless crystals.

$^1$H-NMR (CDCl$_3$) δ: 2.17 (3H, s), 2.6-2.8 (2H, m), 3.80 (2H, s), 3.83 (3H, s), 3.9-4.0 (2H, m), 5.38 (2H, s), 6.78 (1H, s), 6.85-7.0 (3H, m), 7.2-7.6 (12H, m), 7.71 (1H, s).

Example 25

Production of N-(4-(1-(2,6-difluorobenzyl)-5-(((2-(2-(2-hydroxyethyl)-1H-imidazol-1-yl)ethyl)(methyl)amino)methyl)-2,4-dioxo-3-phenyl-1,2,3,4-tetrahydrothieno[2,3-d]pyrimidin-6-yl)phenyl)-N'-methoxyurea

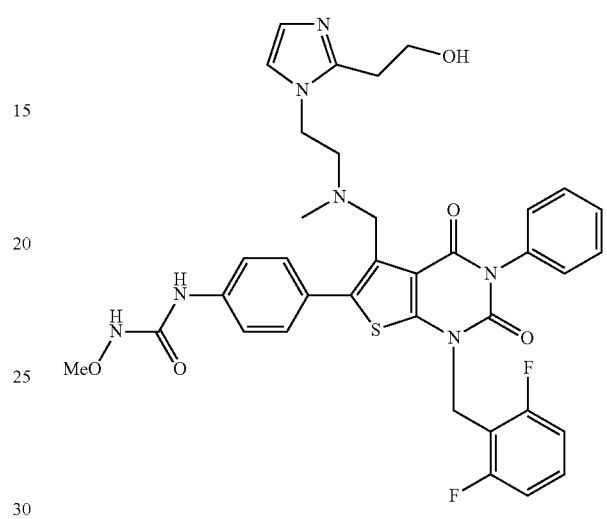

The similar reaction as described in Example 24 by using the compound obtained in Reference Example 15 (289 mg, 0.5 mmol) and 2-(2-hydroxyethyl)imidazole (292 mg, 2.6 mmol) gave the title compound (19 mg, 10%) as colorless crystals.

$^1$H-NMR (CDCl$_3$) δ: 1.9-2.1 (2H, m), 2.16 (3H, s), 2.6-2.8 (4H, m), 3.78 (2H, s), 3.83 (2H, s), 3.9-4.0 (2H, m), 5.38 (2H, s), 6.70 (1H, s), 6.80 (1H, s), 6.94 (2H, t, J=8.0 Hz), 7.2-7.6 (11H, m), 7.73 (1H, s).

Example 26

Production of 2-(4-(1-(2,6-difluorobenzyl)-6-(4-(((methoxyamino)carbonyl)amino)phenyl)-5-((methyl(2-pyridinylmethyl)amino)methyl)-2,4-dioxo-1,4-dihydrothieno[2,3-d]pyrimidin-3(2H)-yl)phenoxy)-N-methylacetamide

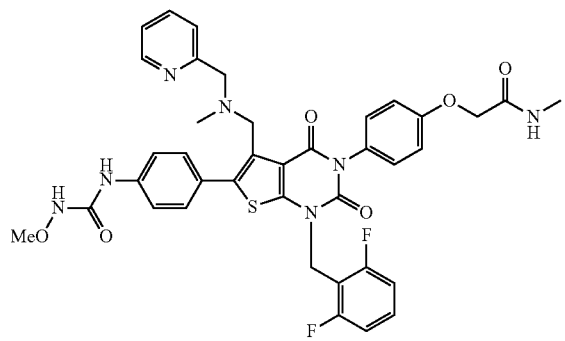 [SMILES: CNC(=O)COc1ccc(-n2c(=O)c3c(CN(C)Cc4ccccn4)c(-c4ccc(NC(=O)NOC)cc4)sc3n(Cc3c(F)cccc3F)c2=O)cc1]

The similar reaction as described in Example 5 by using the compound obtained in Reference Example 3 (320 mg, 0.5 mmol) and 4-aminophenoxy-N-methylacetamide (135 mg, 0.75 mmol) gave the title compound (192 mg, 51%) as colorless crystals.

¹H-NMR (CDCl₃) δ: 2.09 (3H, s), 2.93 (3H, d, J=4.8 Hz), 3.72 (2H, s), 3.83 (3H, s), 3.97 (2H, s), 4.55 (2H, s), 5.35 (2H, s), 6.55-6.65 (1H, m), 6.92 (2H, t, J=8.0 Hz), 7.0-7.65 (14H, m), 8.44 (1H, d, J=6.0 Hz).

IR (KBr): 1721, 1669, 1532, 1472, 1236, 1032, 764 cm⁻¹.

Elemental analysis for $C_{38}H_{35}F_2N_7O_6S \cdot 0.5H_2O$
Calcd.: C, 59.68; H, 4.74; N, 12.82.
Found: C, 59.51; H, 4.66; N, 12.68.

Example 27

Production of 2-(4-(1-(2,6-difluorobenzyl)-6-(4-(((methoxyamino)carbonyl)amino)phenyl)-5-((methyl(2-pyridinylmethyl)amino)methyl)-2,4-dioxo-1,4-dihydrothieno[2,3-d]pyrimidin-3(2H)-yl)phenyl)-N-ethylacetamide

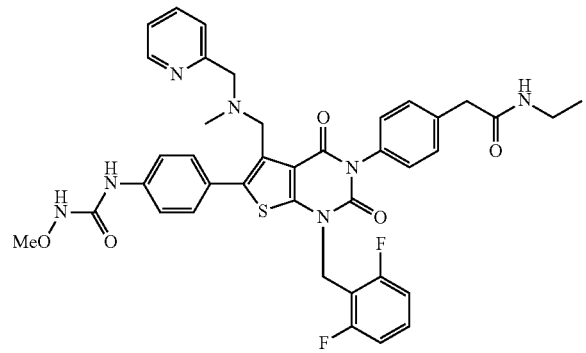 [SMILES: CCNC(=O)Cc1ccc(-n2c(=O)c3c(CN(C)Cc4ccccn4)c(-c4ccc(NC(=O)NOC)cc4)sc3n(Cc3c(F)cccc3F)c2=O)cc1]

The similar reaction as described in Example 5 by using the compound obtained in Reference Example 3 (320 mg, 0.5 mmol) and 4-aminophenyl-N-ethylacetamide (134 mg, 0.75 mmol) gave the title compound (145 mg, 38%) as pale yellow crystals.

¹H-NMR (CDCl₃) δ: 1.10 (3H, t, J=7.2 Hz), 2.10 (3H, s), 3.2-3.4 (2H, m), 3.64 (2H, s), 3.72 (2H, s), 3.83 (3H, s), 3.98 (2H, s), 5.36 (2H, s), 5.45-5.55 (1H, m), 6.93 (2H, t, J=8.0 Hz), 7.0-7.1 (1H, m), 7.16 (1H, s), 7.25-7.7 (12H, m), 8.44 (1H, d, J=4.0 Hz).

IR (KBr): 1721, 1672, 1534, 1470, 1032, 762 cm⁻¹.

Elemental analysis for $C_{39}H_{37}F_2N_7O_5S \cdot 0.5H_2O$
Calcd.: C, 61.41; H, 5.02; N, 12.85.
Found: C, 61.44; H, 4.90; N, 12.75.

Example 28

Production of methyl 3-(1-(2,6-difluorobenzyl)-6-(4-(((methoxyamino)carbonyl)amino)phenyl)-5-((methyl(2-pyridinylmethyl)amino)methyl)-2,4-dioxo-1,4-dihydrothieno[2,3-d]pyrimidin-3(2H)-yl)propanate

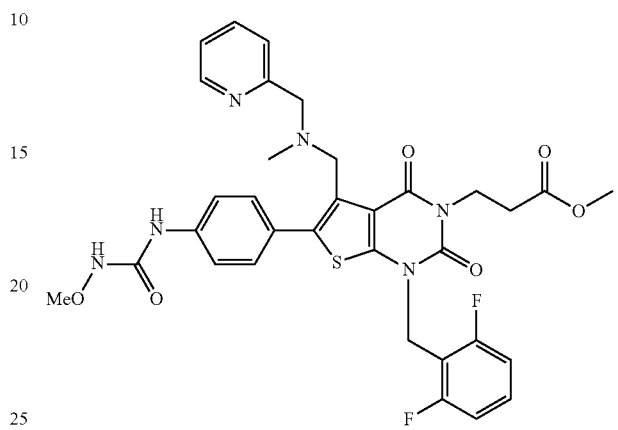

The similar reaction as described in Example 5 by using the compound obtained in Reference Example 3 (320 mg, 0.5 mmol) and β-alanine methyl ester (115 mg, 0.75 mmol) gave the title compound (255 mg, 75%) as a pale yellow amorphous compound.

¹H-NMR (CDCl₃) δ: 2.10 (3H, s), 2.65-2.8 (2H, m), 3.68 (3H, s), 3.72 (2H, s), 3.83 (3H, s), 3.98 (2H, s), 4.3-4.5 (2H, m), 5.31 (2H, s), 6.91 (2H, t, J=7.6 Hz), 7.0-7.4 (5H, m), 7.45-7.65 (5H, m), 8.4-8.5 (1H, m).

Example 29

Production of 3-(1-(2,6-difluorobenzyl)-6-(4-(((methoxyamino)carbonyl)amino)phenyl)-5-((methyl(2-pyridinylmethyl)amino)methyl)-2,4-dioxo-1,4-dihydrothieno[2,3-d]pyrimidin-3(2H)-yl)-N,N-dimethylpropanamide

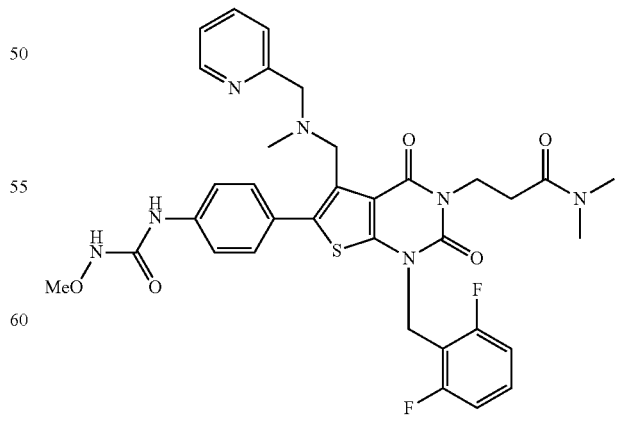

The similar reaction as described in Example 21 by using the compound obtained in Example 28 (300 mg, 0.413 mmol)

and a solution of dimethylamine in THF (2M) (1.63 ml, 3.26 mmol) gave the title compound (73 mg, 33%) as pale yellow powders.

$^1$H-NMR (CDCl$_3$) δ: 2.09 (3H, s), 2.75 (3H, d, J=7.8 Hz), 2.94 (3H, s), 3.02 (3H, s), 3.73 (2H, s), 3.83 (3H, s), 4.07 (2H, s), 4.40 (2H, t, J=7.8 Hz), 5.33 (2H, s), 6.91 (2H, t, J=8.2 Hz), 7.0-7.35 (5H, m), 7.5-7.65 (5H, m), 8.45 (1H, d, J=4.0 Hz).

IR (KBr): 1703, 1659, 1530, 1472, 1321, 1034, 779 cm$^{-1}$.

Elemental analysis for C$_{34}$H$_{35}$F$_2$N$_7$O$_5$S.1.0H$_2$O

Calcd.: C, 57.54; H, 5.25; N, 13.81.

Found: C, 57.56; H, 5.05; N, 13.59.

Example 30

Production of N-(4-(1-(2,6-difluorobenzyl)-3-(4-hydroxycyclohexyl)-5-((methyl(2-pyridinylmethyl)amino)methyl)-2,4-dioxo-1,2,3,4-tetrahydrothieno[2,3-d]pyrimidin-6-yl)phenyl)-N'-methoxyurea

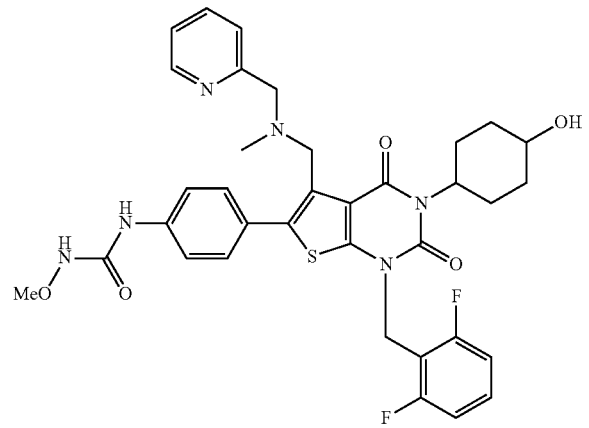 [SMILES: CONC(=O)Nc1ccc(-c2sc3c(c2CN(C)Cc2ccccn2)c(=O)n(C2CCC(O)CC2)c(=O)n3Cc2c(F)cccc2F)cc1]

The similar reaction as described in Example 5 by using the compound obtained in Example 28 (320 mg, 0.5 mmol) and 4-aminohexanol (86 mg, 0.75 mmol) gave the title compound (154 mg, 45%) as colorless crystals.

$^1$H-NMR (CDCl$_3$) δ: 1.4-1.8 (4H, m), 2.0-2.1 (2H, m), 2.12 (3H, s), 2.55-2.75 (2H, m), 3.73 (2H, s), 3.7-3.8 (1H, m), 3.82 (3H, s), 3.98 (2H, s), 4.9-5.1 (1H, brm), 5.29 (2H, s), 6.91 (2H, t, J=8.2 Hz), 7.0-7.4 (7H, m), 7.45-7.65 (5H, m), 8.45 (1H, d, J=4.8 Hz).

IR (KBr): 1705, 1659, 1530, 1470, 1312, 1236, 1069, 1034, 783 cm$^{-1}$.

Elemental analysis for C$_{35}$H$_{36}$F$_2$N$_6$O$_5$S.1.5H$_2$O

Calcd.: C, 58.57; H, 5.48; N, 11.71.

Found: C, 58.65; H, 5.35; N, 11.64.

Example 31

Production of N-(4-(1-(2,6-difluorobenzyl)-5-((methyl(2-(2H-tetrazol-2-yl)ethyl)aminomethyl))-2,4-dioxo-3-phenyl-1,2,3,4-tetrahydrothieno[2,3-d]pyrimidin-6-yl)phenyl)-N'-methoxyurea (1)

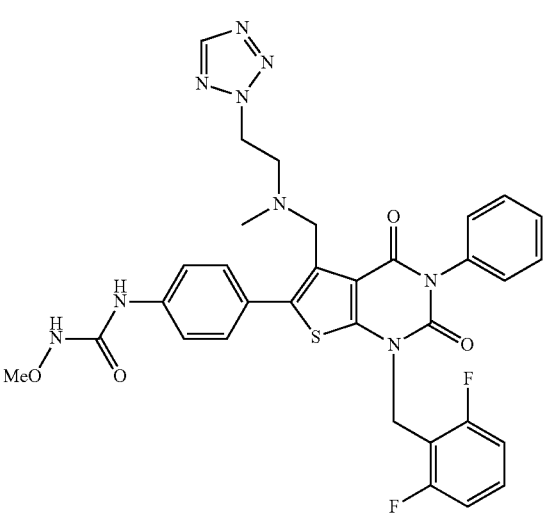 [SMILES: CONC(=O)Nc1ccc(-c2sc3c(c2CN(C)CCn2ncnn2)c(=O)n(-c2ccccc2)c(=O)n3Cc2c(F)cccc2F)cc1]

Production of N-(4-(1-(2,6-difluorobenzyl)-5-((methyl(2-(1H-tetrazol-1-yl)ethyl)amino)methyl)-2,4-dioxo-3-phenyl-1,2,3,4-tetrahydrothieno[2,3-d]pyrimidin-6-yl)phenyl)-N'-methoxyurea (2)

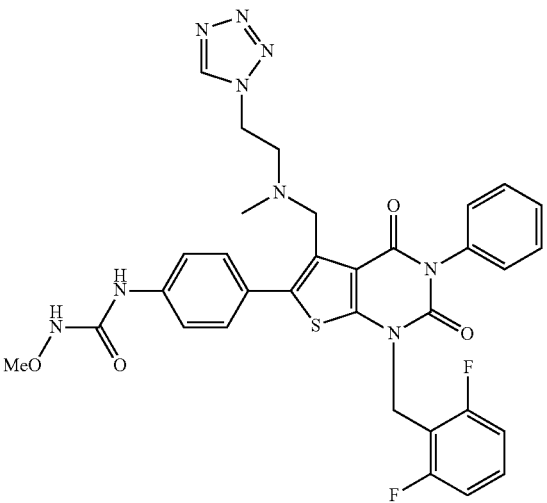 [SMILES: CONC(=O)Nc1ccc(-c2sc3c(c2CN(C)CCn2cnnn2)c(=O)n(-c2ccccc2)c(=O)n3Cc2c(F)cccc2F)cc1]

Potassium carbonate (2.075 g, 15 mmol) was added to a solution of tetrazole (0.70 g, 10 mmol) and 1-bromo-2-chloroethane (1.25 ml, 15 mmol) in DMF (5 ml), and the mixture was stirred at room temperature for 16 hours. The reaction mixture was combined with saturated brine and extracted twice with ethyl acetate. The combined extract was dried over magnesium sulfate and concentrated under reduced pressure to give a halide (4.23 g including DMF).

N,N-diisopropylethylamine (1.16 ml, 6.67 mmol) and the halide obtained above were added to a solution of the compound obtained in Reference Example 15 (578 mg, 1 mmol) in DMF (10 ml), and the mixture was stirred at 60-70° C. for 16 hours. The reaction mixture was combined with an aqueous solution of sodium hydrogen carbonate and extracted with ethyl acetate. The organic layer was washed with brine, dried over magnesium sulfate and concentrated under reduced pressure. The residue was purified by silica gel column chromatography (eluent: ethyl acetate/hexane=9/1) and recrystallized from dichloromethane/methanol/diethyl ether to give the title compound 2-yl form (80 mg, 12%) and 1-yl form (38 mg, 57%) as colorless crystals.

2-yl form (1)

$^1$H-NMR (CDCl$_3$) δ: 2.25 (3H, s), 3.04 (2H, t, J=6.2 Hz), 3.78 (2H, s), 3.83 (3H, s), 4.66 (2H, t, J=6.2 Hz), 5.38 (2H, s), 6.94 (2H, t, J=8.0 Hz), 7.16 (1H, s), 7.2-7.6 (10H, m), 7.64 (1H, s), 8.30 (1H, s).

IR (KBr): 1713, 1669, 1530, 1470, 1325, 1032, 735 cm$^{-1}$.

Elemental analysis for C$_{32}$H$_{29}$F$_2$N$_9$O$_4$S.0.5H$_2$O

Calcd.: C, 56.30; H, 4.43; N, 18.46.

Found: C, 56.18; H, 4.42; N, 18.19.

1-yl form (2)

$^1$H-NMR (CDCl$_3$) δ: 2.02 (3H, s), 2.7-2.8 (2H, m), 3.78 (2H, s), 3.83 (3H, s), 4.4-4.5 (2H, m), 5.38 (2H, s), 6.92 (2H, t, J=8.0 Hz), 7.17 (1H, s), 7.25-7.65 (10H, m), 7.66 (1H, s).

IR (KBr): 1713, 1669, 1530, 1470, 1327, 1236, 1032, 735 cm$^{-1}$.

Elemental analysis for C$_{32}$H$_{29}$F$_2$N$_9$O$_4$S.0.5H$_2$O

Calcd.: C, 56.30; H, 4.43; N, 18.46.

Found: C, 56.54; H, 4.30; N, 18.27.

Example 32

Production of N-(4-(1-(2,6-difluorobenzyl)-3-(2-hydroxyethyl)-5-((methyl(2-pyridinylmethyl)amino)methyl)-2,4-dioxo-1,2,3,4-tetrahydrothieno[2,3-d]pyrimidin-6-yl)phenyl)-N'-methoxyurea

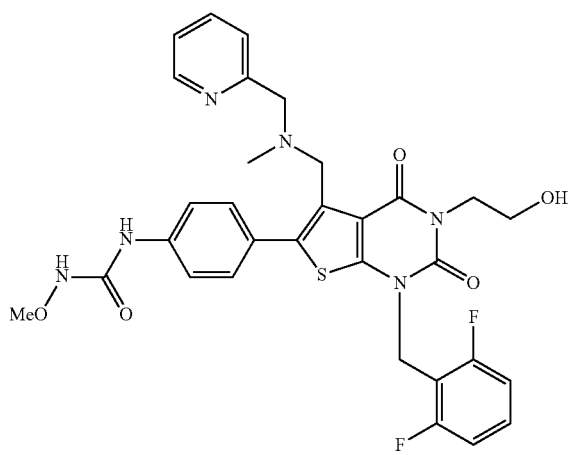 [SMILES: CONC(=O)Nc1ccc(-c2sc3c(c2CN(C)Cc2ccccn2)c(=O)n(CCO)c(=O)n3Cc2c(F)cccc2F)cc1]

The similar reaction as described in Example 5 by using the compound obtained in Reference Example 3 (410 mg, 0.64 mmol) and 2-aminoethanol (0.06 ml, 0.96 mmol) gave the title compound (76 mg, 19%) as colorless crystals.

$^1$H-NMR (CDCl$_3$) δ: 2.22 (3H, s), 3.3-3.5 (1H, br), 3.78 (2H, s), 3.83 (3H, s), 3.9-4.05 (2H, m), 3.99 (2H, s), 4.35-4.4 (2H, m), 5.27 (2H, s), 6.91 (2H, t, J=8.0 Hz), 6.9-7.1 (1H, m), 7.15 (1H, s), 7.2-7.65 (8H, m), 8.35-8.4 (1H, m).

IR (KBr): 1709, 1649, 1470, 1323, 1030, 787 cm$^{-1}$.

Elemental analysis for C$_{31}$H$_{30}$F$_2$N$_6$O$_5$S.0.5H$_2$O

Calcd.: C, 57.67; H, 4.84; N, 13.02.

Found: C, 57.77; H, 4.90; N, 12.82.

Example 33

Production of N-(4-(1-(2,6-difluorobenzyl)-5-((methyl(3-(2-oxo-1-pyrrolidinyl)propyl)amino)methyl)-2,4-dioxo-3-phenyl-1,2,3,4-tetrahydrothieno[2,3-d]pyrimidin-6-yl)phenyl)-N'-methoxyurea

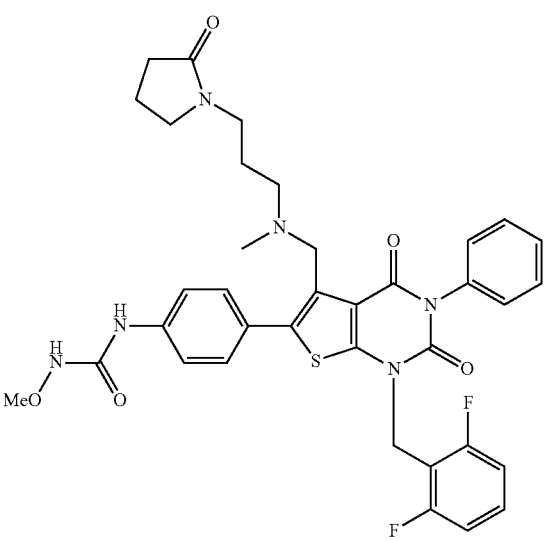 [SMILES: CONC(=O)Nc1ccc(-c2sc3c(c2CN(C)CCCN2CCCC2=O)c(=O)n(-c2ccccc2)c(=O)n3Cc2c(F)cccc2F)cc1]

The similar reaction as described in Example 2 by using the compound obtained in Reference Example 15 (404 mg, 0.7 mmol) and 1-(3-hydroxypropyl)-2-pyrrolidone (0.55 g, 3.85 mmol) gave the title compound (322 mg, 66%) as colorless crystals.

$^1$H-NMR (CDCl$_3$) δ: 1.5-1.7 (2H, m), 1.8-2.0 (2H, m), 2.05 (3H, s), 2.25-2.45 (4H, m), 3.15 (2H, t, J=7.8 Hz), 3.23 (2H, t, J=7.2 Hz), 3.76 (2H, s), 3.83 (3H, s), 5.37 (2H, s), 6.93 (2H, t, J=8.0 Hz), 7.15 (1H, s), 7.2-7.6 (10H, m), 7.67 (1H, s).

IR (KBr): 1715, 1671, 1532, 1470, 1327, 1032, 735 cm$^{-1}$.

Elemental analysis for C$_{36}$H$_{36}$F$_2$N$_6$O$_5$S.1.0H$_2$O

Calcd.: C, 59.99; H, 5.31; N, 11.66.

Found: C, 60.21; H, 5.18; N, 11.74.

mp 128-129° C.

Example 34

Production of N-(4-(1-(2,6-difluorobenzyl)-5-((methyl(2-(2-oxo-1-pyrrolidinyl)ethyl)amino)methyl)-2,4-dioxo-3-phenyl-1,2,3,4-tetrahydrothieno[2,3-d]pyrimidin-6-yl)phenyl)-N'-methoxyurea

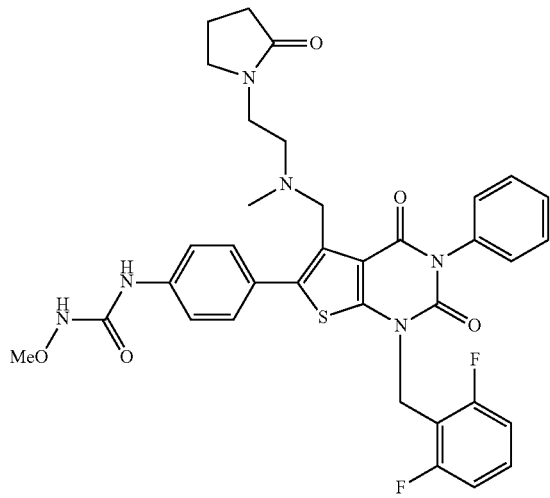 [SMILES: CONC(=O)Nc1ccc(-c2sc3c(c2CN(C)CCN2CCCC2=O)c(=O)n(-c2ccccc2)c(=O)n3Cc2c(F)cccc2F)cc1]

The similar reaction as described in Example 2 by using the compound obtained in Reference Example 15 (404 mg, 0.7 mmol) and 1-(3-hydroxyethyl)-2-pyrrolidone (0.50 g, 3.85 mmol) gave the title compound (290 mg, 60%) as colorless crystals.

$^1$H-NMR (CDCl$_3$) δ: 1.7-1.85 (2H, m), 2.14 (3H, s), 2.21 (2H, t, J=8.1 Hz), 2.54 (2H, t, J=6.2 Hz), 3.19 (2H, t, J=7.0 Hz), 3.29 (2H, t, J=6.2 Hz), 3.77 (2H, s), 3.83 (3H, s), 5.38 (2H, s), 6.93 (2H, t, J=8.1 Hz), 7.18 (1H, s), 7.25-7.7 (11H, m).

IR (KBr): 1715, 1672, 1530, 1470, 1323, 1238, 1032, 735 cm$^{-1}$.

Elemental analysis for C$_{35}$H$_{34}$F$_2$N$_6$O$_5$S.0.5H$_2$O
Calcd.: C, 60.25; H, 5.06; N, 12.04.
Found: C, 60.29; H, 5.04; N, 12.13.
mp 134-136° C.

Example 35

Production of N-(4-(1-(2,6-difluorobenzyl)-3-(4-fluorophenyl)-5-((methyl-(2-(2-oxo-1-pyrrolidinyl)ethyl)amino)methyl)-2,4-dioxo-1,2,3,4-tetrahydrothieno[2,3-d]pyrimidin-6-yl)phenyl)-N'-methoxyurea

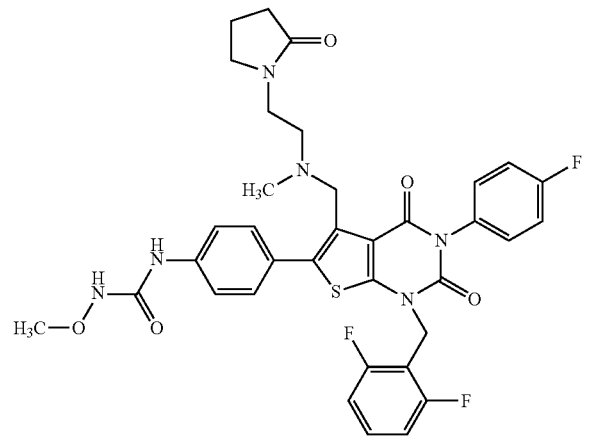 [SMILES: CONC(=O)Nc1ccc(-c2sc3c(c2CN(C)CCN2CCCC2=O)c(=O)n(-c2ccc(F)cc2)c(=O)n3Cc2c(F)cccc2F)cc1]

The similar reaction as described in Example 2 by using the compound obtained in Reference Example 17 (350 mg, 0.588 mmol) and 1-(3-hydroxyethyl)-2-pyrrolidone (0.50 g, 3.85 mmol) gave the title compound (283 mg, 68%) as pale yellow crystals.

$^1$H-NMR (CDCl$_3$) δ: 1.7-1.9 (2H, m), 2.15 (3H, s), 2.15-2.3 (2H, m), 2.52 (2H, t, J=6.2 Hz), 3.20 (2H, t, J=6.8 Hz), 3.29 (2H, t, J=6.2 Hz), 3.77 (2H, s), 3.83 (3H, s), 5.37 (2H, s), 6.93 (2H, t, J=8.2 Hz), 7.1-7.35 (6H, m), 7.5-7.65 (4H, m), 7.64 (1H, s).

IR (KBr): 1723, 1667, 1532, 1472, 1236, 1034, 837, 762 cm$^{-1}$.

Elemental analysis for C$_{35}$H$_{33}$F$_3$N$_6$O$_5$S.0.5H$_2$O
Calcd.: C, 58.73; H, 4.79; N, 11.74.
Found: C, 58.99; H, 4.98; N, 11.92.
mp 198-200° C.

Example 36

Production of N-(2-(((1-(2,6-difluorobenzyl)-3-(4-fluorophenyl)-6-(4-(((methoxyamino)carbonyl)amino)phenyl)-2,4-dioxo-1,2,3,4-tetrahydrothieno[2,3-d]pyrimidin-5-ylmethyl)(methyl)amino)ethyl)-N-methylmethanesulfonamide

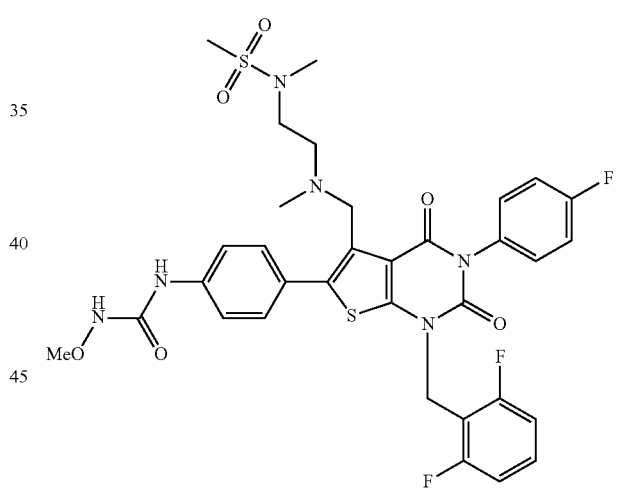

The similar reaction as described in Example 2 by using the compound obtained in Reference Example 17 (350 mg, 0.588 mmol) and 2-methylaminoethanol (0.29 g, 3.85 mmol) gave the title compound (263 mg, 61%) as pale yellow crystals.

$^1$H-NMR (CDCl$_3$) δ: 2.13 (3H, s), 2.55 (2H, t, J=6.4 Hz), 2.70 (3H, s), 2.71 (3H, s), 3.15 (2H, t, J=6.4 Hz), 3.81 (2H, s), 3.83 (3H, s), 5.37 (2H, s), 6.93 (2H, t, J=8.2 Hz), 7.1-7.7 (11H, m).

IR (KBr): 1725, 1663, 1534, 1474, 1331, 1236, 1142, 1034, 793 cm$^{-1}$.

Elemental analysis for C$_{33}$H$_{33}$F$_3$N$_6$O$_6$S$_2$
Calcd.: C, 54.24; H, 4.55; N, 11.50.
Found: C, 54.10; H, 4.45; N, 11.36.
mp 218-220° C.

Example 37

Production of N-(4-(1-(2,6-difluorobenzyl)-5-((methyl(((2S)-1-(methylsulfonyl)-2-pyrrolidinyl)methyl)amino)methyl)-2,4-dioxo-3-phenyl-1,2,3,4-tetrahydrothieno[2,3-d]pyrimidin-6-yl)phenyl)-N'-methoxyurea

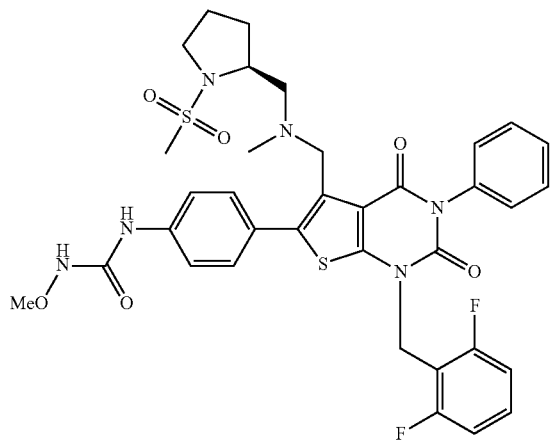 [SMILES: CONC(=O)Nc1ccc(-c2sc3c(c2CN(C)C[C@@H]2CCCN2S(C)(=O)=O)c(=O)n(-c2ccccc2)c(=O)n3Cc2c(F)cccc2F)cc1]

The similar reaction as described in Example 2 by using the compound obtained in Reference Example 15 (404 mg, 0.7 mmol) and (L)-2-hydroxymethylpyrrolidine (0.39 g, 3.85 mmol) gave the title compound (262 mg, 51%) as colorless crystals.

$^1$H-NMR (CDCl$_3$) δ: 1.7-1.85 (4H, m), 2.08 (3H, s), 2.2-2.4 (1H, m), 2.5-2.65 (1H, m), 2.72 (3H, s), 3.15-3.3 (2H, m), 3.7-3.9 (3H, m), 3.83 (3H, s), 5.37 (2H, s), 6.92 (2H, t, J=8.2 Hz), 7.13 (1H, s), 7.2-7.7 (11H, m).

IR (KBr): 1713, 1667, 1528, 1470, 1333, 1148, 1030, 785 cm$^{-1}$.

Elemental analysis for $C_{35}H_{36}F_2N_6O_6S_2$

Calcd.: C, 56.90; H, 4.91; N, 11.37.

Found: C, 56.55; H, 4.87; N, 11.23.

mp 195-197° C.

Example 38

Production of N-(4-(1-(2,6-difluorobenzyl)-3-(4-fluorophenyl)-5-((methyl(((2S)-1-(methylsulfonyl)-2-pyrrolidinylmethyl)amino)methyl)-2,4-dioxo-1,2,3,4-tetrahydrothieno[2,3-d]pyrimidin-6-yl)phenyl)-N'-methoxyurea

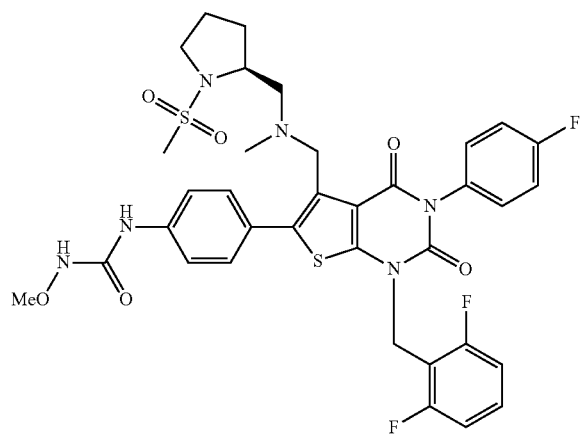 [SMILES: CONC(=O)Nc1ccc(-c2sc3c(c2CN(C)C[C@@H]2CCCN2S(C)(=O)=O)c(=O)n(-c2ccc(F)cc2)c(=O)n3Cc2c(F)cccc2F)cc1]

The similar reaction as described in Example 2 by using the compound obtained in Reference Example 17 (400 mg, 0.672 mmol) and (L)-2-hydroxymethylpyrrolidine (0.39 g, 3.85 mmol) gave the title compound (222 mg, 44%) as colorless crystals.

$^1$H-NMR (CDCl$_3$) δ: 1.7-1.85 (4H, m), 2.09 (3H, s), 2.25-2.35 (1H, m), 2.55-2.65 (1H, m), 2.71 (3H, s), 3.15-3.3 (2H, m), 3.65-3.7 (2H, m), 3.74 (1H, d, J=12.0 Hz), 3.83 (3H, s), 3.87 (1H, d, J=12.0 Hz), 5.36 (2H, s), 6.92 (2H, t, J=8.2 Hz), 6.85-6.95 (1H, m), 7.1-7.35 (5H, m), 7.49 (2H, d, J=8.4 Hz), 7.55 (2H, d, J=8.4 Hz), 7.62 (1H, s).

IR (KBr): 1715, 1667, 1530, 1470, 1333, 1236, 1152, 1032, 795 cm$^{-1}$.

Elemental analysis for $C_{35}H_{35}F_3N_6O_6S_2$

Calcd.: C, 55.55; H, 4.66; N, 11.10.

Found: C, 55.42; H, 4.45; N, 11.01.

mp 202-204° C.

Example 39

Production of N-(4-(1-(2,6-difluorobenzyl)-5-((methyl(((2R)-1-(methylsulfonyl)-2-pyrrolidinyl)methyl)amino)methyl)-2,4-dioxo-3-phenyl-1,2,3,4-tetrahydrothieno[2,3-d]pyrimidin-6-yl)phenyl)-N'-methoxyurea

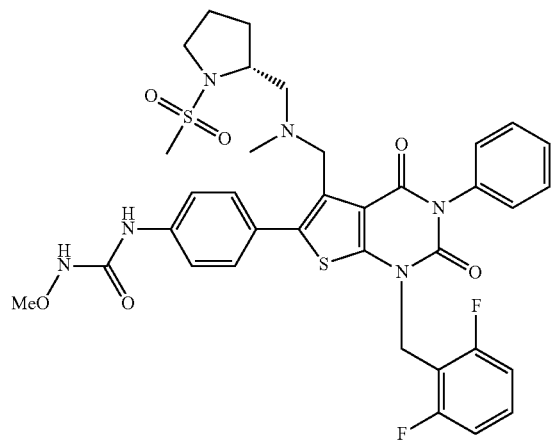 [SMILES: CONC(=O)Nc1ccc(-c2sc3c(c2CN(C)C[C@H]2CCCN2S(C)(=O)=O)c(=O)n(-c2ccccc2)c(=O)n3Cc2c(F)cccc2F)cc1]

The similar reaction as described in Example 2 by using the compound obtained in Reference Example 15 (188 mg, 0.325 mmol) and (R)-2-hydroxymethylpyrrolidine (0.14 g, 1.38 mmol) gave the title compound (136 mg, 57%) as colorless crystals.

$^1$H-NMR (CDCl$_3$) δ: 1.7-1.85 (4H, m), 2.08 (3H, s), 2.2-2.4 (1H, m), 2.5-2.65 (1H, m), 2.72 (3H, s), 3.15-3.3 (2H, m), 3.7-3.9 (3H, m), 3.83 (3H, s), 5.37 (2H, s), 6.92 (2H, t, J=8.2 Hz), 7.13 (1H, s), 7.2-7.7 (11H, m).

IR (KBr): 1713, 1665, 1530, 1470, 1333, 1148, 1030, 785 cm$^{-1}$.

Elemental analysis for $C_{35}H_{36}F_2N_6O_6S_2 \cdot 0.5H_2O$

Calcd.: C, 56.21; H, 4.99; N, 11.24.

Found: C, 56.29; H, 4.79; N, 11.11.

mp 208-210° C.

Example 40

Production of N-(4-(1-(2,6-difluorobenzyl)-5-(((2-methoxyethyl)(methyl)amino)methyl)-2,4-dioxo-3-(2-pyridinyl)-1,2,3,4-tetrahydrothieno[2,3-d]pyrimidin-6-yl)phenyl)-N'-methoxyurea

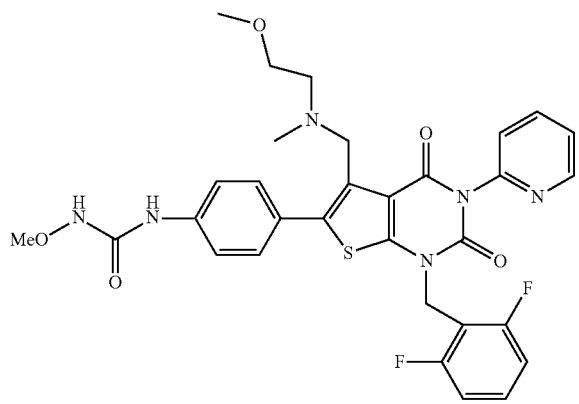 [SMILES: COCCN(C)Cc1c(-c2ccc(NC(=O)NOC)cc2)sc2c1c(=O)n(-c1ccccn1)c(=O)n2Cc1c(F)cccc1F]

Diethyl cyanophosphate (245 mg) and N-ethyldiisopropylamine (284 μl) were added to a solution of the compound obtained in Reference Example 7 (607 mg) and 2-aminopyridine (142 mg) in DMF (10 ml) under ice cooling, and the reaction mixture was warmed gradually to room temperature and stirred for 13 hours. The reaction mixture was distributed between ethyl acetate and water. The organic layer was successively washed with water and saturated brine, dried over magnesium sulfate, and concentrated under reduced pressure. The obtained residue was roughly purified by aminopropyl silica gel column chromatography (Fuji Silysia Chemical). The obtained crude amide (350 mg) was dissolved in ethanol (25.5 ml), and a solution of 28% sodium methoxide in methanol (196 mg) was added thereto. The mixture was stirred at room temperature for 15 hours. The reaction mixture was neutralized with 1N hydrochloric acid (1 ml), and the solvent was distilled off. The residue was distributed between ethyl acetate and water. The organic layer was successively washed with water and saturated brine, and dried over anhydrous sodium sulfate. The solvent was distilled off under reduced pressure. The obtained residue was purified by aminopropyl silica gel column chromatography (45 g, eluent: ethyl acetate/hexane 7/3 to ethyl acetate) and recrystallized from THF-ethanol to give the title compound (210 mg) as colorless crystals.

Elemental analysis for $C_{31}H_{30}N_6O_5SF_2$

Calcd.: C, 58.48; H, 4.75; N, 13.20.

Found: C, 58.46; H, 4.68; N, 12.93.

$^1$H-NMR (CDCl$_3$) δ: 2.15 (3H, s), 2.62 (2H, t, J=5.9 Hz), 3.26 (3H, s), 3.41 (2H, t, J=5.9 Hz), 3.80 (3H, s), 3.81 (2H, brs), 5.34 (2H, brs), 6.91 (2H, t, J=8.1 Hz), 7.24-7.40 (4H, m), 7.53 (2H, d, J=8.4 Hz), 7.62 (2H, d, J=8.4 Hz), 7.65 (1H, s), 7.88 (1H, dt, J=1.5 Hz, 7.8 Hz), 8.67-8.69 (1H, m).

IR (KBr): 1717, 1674, 1591, 1530, 1460, 1329 cm$^{-1}$.

Example 41

Production of N-(4-(1-(2,6-difluorobenzyl)-5-(((2-ethoxyethyl)(methyl)amino)methyl)-2,4-dioxo-3-(2-pyridinyl)-1,2,3,4-tetrahydrothieno[2,3-d]pyrimidin-6-yl)phenyl)-N'-methoxyurea

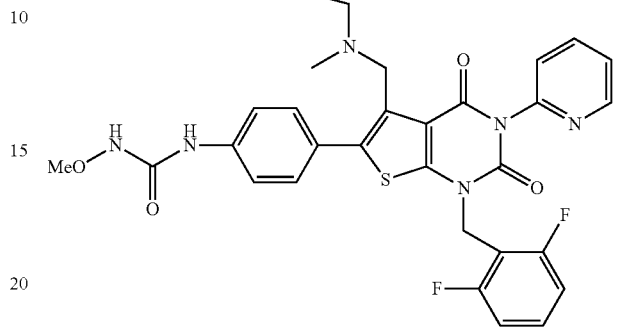

To a solution of the compound obtained in Reference Example 14 (251 mg) in DMF (4.3 ml) were added 2-ethoxyethyl chloride (141 mg), N-ethyldiisopropylamine (245 μl) and potassium iodide (107 mg), and the mixture was stirred at 60° C. for 24 hours. The reaction mixture was distributed between ethyl acetate and water. The organic layer was washed with saturated brine and dried over magnesium sulfate. The solvent was distilled off, and the residue was purified by aminopropyl silica gel column chromatography (Fuji Silysia Chemical) (45 g, eluent: ethyl acetate/hexane=3/2 to 4/1) and recrystallized from ethyl acetate to give the title compound (62 mg) as colorless crystals.

Elemental analysis for $C_{32}H_{32}N_6O_5SF_2$.0.1AcOEt

Calcd.: C, 59.01; H, 5.01; N, 12.74.

Found: C, 59.11; H, 5.13; N, 12.55.

$^1$H-NMR (CDCl$_3$) δ: 1.13 (3H, t, J=6.9 Hz), 2.15 (3H, s), 2.63 (2H, t, J=6.2 Hz), 3.39 (2H, q, J=6.9 Hz), 3.44 (2H, t, J=6.2 Hz), 3.80 (2H, brs), 3.81 (3H, s), 5.34 (2H, brs), 6.91 (2H, t, J=8.1 Hz), 7.19 (1H, s), 7.27-7.32 (1H, m), 7.35-7.41 (2H, m), 7.53 (2H, d, J=8.4 Hz), 7.63 (1H, s), 7.64 (2H, d, J=8.4 Hz), 7.88 (1H, dt, J=1.2 Hz, 7.5 Hz), 8.68 (1H, dt, J=0.9 Hz, 4.8 Hz).

IR (KBr): 1717, 1674, 1591, 1530, 1460, 1329 cm$^{-1}$.

Example 42

Production of N-(4-(1-(2,6-difluorobenzyl)-3-(5-fluoro-2-pyridinyl)-5-(((2-methoxyethyl)(methyl)amino)methyl)-2,4-dioxo-1,2,3,4-tetrahydrothieno[2,3-d]pyrimidin-6-yl)phenyl)-N'-methoxyurea

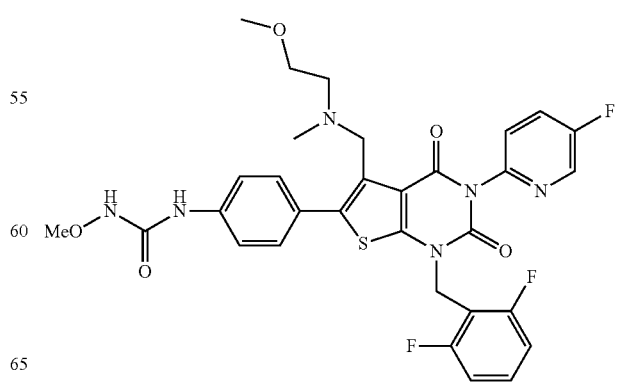

By a similar manner to Example 40, a crude amide (270 mg) was obtained from the compound obtained in Reference Example 7 (304 mg), diethyl cyanophosphate (153 μl), 2-amino-5-fluoropyridine (113 mg) and N-ethyldiisopropylamine (190 μl), and the title compound (113 mg) was obtained from the crude amide by using methanol (19 ml) and a solution of 28% sodium methoxide in methanol (146 mg).

Elemental analysis for $C_{31}H_{29}N_6O_5SF_3$

Calcd.: C, 56.87; H, 4.46; N, 12.84.

Found: C, 56.69; H, 4.57; N, 12.83.

$^1$H-NMR (CDCl$_3$) δ: 2.13 (3H, s), 2.62 (2H, t, J=5.9 Hz), 3.26 (3H, s), 3.41 (2H, t, J=5.9 Hz), 3.80 (2H, brs), 3.82 (3H, s), 5.33 (2H, brs), 6.92 (2H, t, J=8.3 Hz), 7.19 (1H, s), 7.28-7.38 (2H, m), 7.52-7.63 (6H, m), 8.51 (1H, d, J=3.0 Hz).

IR (KBr): 1715, 1674, 1586, 1530, 1462 cm$^{-1}$.

Example 43

Production of N-(4-(3-(5-bromo-2-pyridinyl)-1-(2,6-difluorobenzyl)-5-(((2-methoxyethyl)(methyl)amino)methyl)-2,4-dioxo-1,2,3,4-tetrahydrothieno[2,3-d]pyrimidin-6-yl)phenyl)-N'-methoxyurea

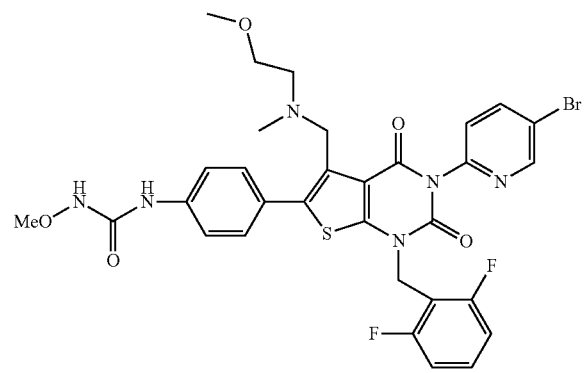 [SMILES: COCCN(C)Cc1c(-c2ccc(NC(=O)NOC)cc2)sc2c1c(=O)n(-c1ccc(Br)cn1)c(=O)n2Cc1c(F)cccc1F]

The similar reaction as described in Example 40 by using the compound obtained in Reference Example 7 (304 mg), diethyl cyanophosphate (153 μl), 2-amino-5-bromopyridine (173 mg) and N-ethyldiisopropylamine (190 μl) gave a crude amide (228 mg). Furthermore, the similar reaction by using methanol (14.5 ml) and a solution of 28% sodium methoxide in methanol (112 mg) gave the title compound (113 mg).

Elemental analysis for $C_{31}H_{29}N_6O_5SBrF_2 \cdot 0.5H_2O$

Calcd.: C, 51.39; H, 4.17; N, 11.60.

Found: C, 51.68; H, 4.25; N, 11.53.

$^1$H-NMR (CDCl$_3$) δ: 2.13 (3H, s), 2.62 (2H, t, J=5.9 Hz), 3.26 (3H, s), 3.41 (2H, t, J=5.9 Hz), 3.78 (2H, brs), 3.80 (3H, s), 5.32 (2H, brs), 6.92 (2H, t, J=8.1 Hz), 7.27 (1H, d, J=8.4 Hz), 7.27-7.33 (1H, m), 7.37 (1H, s), 7.54 (2H, d, J=9.0 Hz), 7.60 (2H, d, J=9.0 Hz), 7.64 (1H, s), 7.98 (1H, dd, J=2.7 Hz, 8.4 Hz), 8.72 (1H, d, J=2.7 Hz).

IR (KBr): 2938, 1717, 1674, 1590, 1456 cm$^{-1}$.

Example 44

Production of N-(4-(1-(2,6-difluorobenzyl)-5-(((2-methoxyethyl)(methyl)amino)methyl)-3-(5-methyl-2-pyridinyl)-2,4-dioxo-1,2,3,4-tetrahydrothieno[2,3-d]pyrimidin-6-yl)phenyl)-N'-methoxyurea

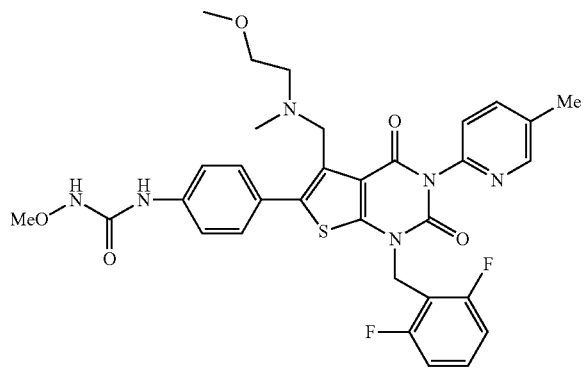 [SMILES: COCCN(C)Cc1c(-c2ccc(NC(=O)NOC)cc2)sc2c1c(=O)n(-c1ccc(C)cn1)c(=O)n2Cc1c(F)cccc1F]

The similar reaction as described in Example 40 by using the compound obtained in Reference Example 7 (304 mg), diethyl cyanophosphate (153 μl), 2-amino-5-methylpyridine (109 mg) and N-ethyldiisopropylamine (190 μl) gave a crude amide (188 mg). Furthermore, the similar reaction by using methanol (13.5 ml), a solution of 28% sodium methoxide in methanol (103 mg) gave the title compound (122 mg).

Elemental analysis for $C_{32}H_{32}N_6O_5SF_2 \cdot 0.5H_2O$

Calcd.: C, 58.26; H, 5.04; N, 12.74.

Found: C, 58.55; H, 5.14; N, 12.67.

$^1$H-NMR (CDCl$_3$) δ: 2.14 (3H, s), 2.39 (3H, s), 2.62 (2H, t, J=5.7 Hz), 3.26 (3H, s), 3.41 (2H, t, J=5.7 Hz), 3.77 (2H, brs), 3.80 (3H, s), 5.26 (1H, brs), 5.38 (1H, brs), 6.91 (2H, t, J=8.3 Hz), 7.23-7.34 (2H, m), 7.42 (1H, s), 7.53 (2H, d, J=8.7 Hz), 7.62 (2H, d, J=8.7 Hz), 7.66 (1H, s), 7.66-7.69 (1H, m), 8.48 (1H, d, J=2.4 Hz).

IR (KBr): 2938, 1717, 1675, 1586, 1530, 1462 cm$^{-1}$.

Example 45

Production of N-(4-(1-(2,6-difluorobenzyl)-5-(((2-methoxyethyl)(methyl)amino)methyl)-3-(6-methyl-2-pyridinyl)-2,4-dioxo-1,2,3,4-tetrahydrothieno[2,3-d]pyrimidin-6-yl)phenyl)-N'-methoxyurea

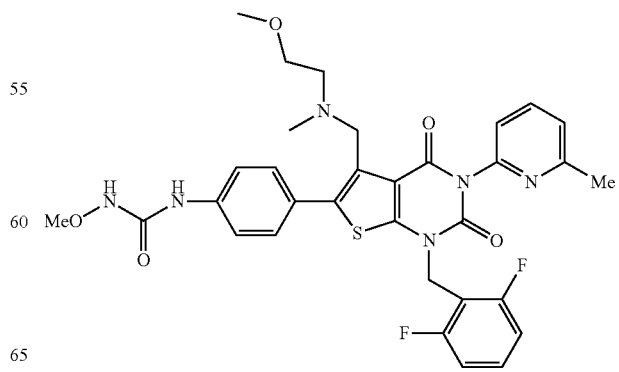

The similar reaction as described in Example 40 by using the compound obtained in Reference Example 7 (423 mg), diethyl cyanophosphate (212 µl), 2-amino-6-methylpyridine (151 mg) and N-ethyldiisopropylamine (265 µl) gave a crude amide (242 mg). Furthermore, the similar reaction by using methanol (17 ml), a solution of 28% sodium methoxide in methanol (131 mg) gave the title compound (145 mg).

Elemental analysis for $C_{32}H_{32}N_6O_5SF_2 \cdot 0.5H_2O$

Calcd.: C, 58.26; H, 5.04; N, 12.74.

Found: C, 58.39; H, 4.86; N, 12.79.

$^1$H-NMR (CDCl$_3$) δ: 2.15 (3H, s), 2.60 (3H, s), 2.62 (2H, t, J=5.8 Hz), 3.27 (3H, s), 3.41 (2H, t, J=5.8 Hz), 3.66-3.94 (2H, m), 3.81 (3H, s), 5.15 (1H, d, J=15.3 Hz), 5.48 (1H, d, J=15.3 Hz), 6.91 (2H, t, J=8.1 Hz), 7.16 (1H, d, J=7.8 Hz), 7.21 (1H, d, J=7.8 Hz), 7.25 (1H, s), 7.26-7.35 (1H, m), 7.53 (2H, d, J=8.7 Hz), 7.63 (1H, s), 7.53 (2H, d, J=8.7 Hz), 7.64 (2H, d, J=8.7 Hz), 7.76 (1H, t, J=7.8 Hz).

IR (KBr): 2936, 1715, 1672, 1603, 1530, 1472 cm$^{-1}$.

Example 46

Production of N-(4-(1-(2,6-difluorobenzyl)-5-(((2-methoxyethyl)(methyl)amino)methyl)-3-(3-methoxy-6-methyl-2-pyridinyl)-2,4-dioxo-1,2,3,4-tetrahydrothieno[2,3-d]pyrimidin-6-yl)phenyl)-N'-methoxyurea

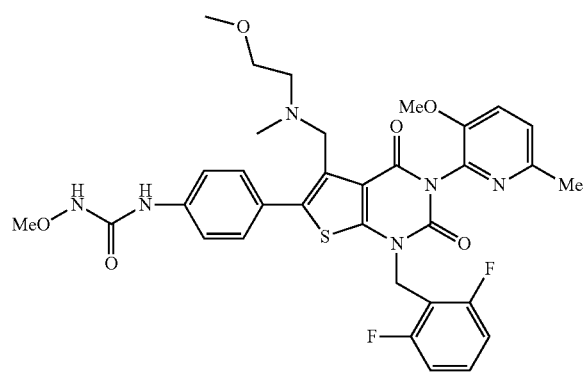 [SMILES: COCCN(C)Cc1c(-c2ccc(NC(=O)NOC)cc2)sc2c1c(=O)n(-c1nc(C)ccc1OC)c(=O)n2Cc1c(F)cccc1F]

The similar reaction as described in Example 40 by using the compound obtained in Reference Example 7 (455 mg), diethyl cyanophosphate (227 µl), 2-amino-3-methoxy-6-methylpyridine (208 mg) and N-ethyldiisopropylamine (310 µl) gave a crude amide (130 mg).

Furthermore, the similar reaction by using methanol (8.5 ml), a solution of 28% sodium methoxide in methanol (666 mg) gave the title compound (107 mg).

Elemental analysis for $C_{33}H_{34}N_6O_6SF_2 \cdot 0.5H_2O$

Calcd.: C, 57.47; H, 5.11; N, 12.18.

Found: C, 57.54; H, 5.03; N, 12.26.

$^1$H-NMR (CDCl$_3$) δ: 2.13 (3H, s), 2.51 (3H, s), 2.62 (2H, t, J=5.9 Hz), 3.26 (3H, s), 3.40 (2H, t, J=5.9 Hz), 3.77 (1H, d, J=12.3 Hz), 3.77 (3H, s), 3.79 (3H, s), 3.86 (1H, d, J=12.3 Hz), 5.24 (1H, d, J=15.6 Hz), 5.40 (1H, d, J=15.6 Hz), 6.90 (2H, t, J=8.1 Hz), 7.19 (1H, d, J=8.4 Hz), 7.23-7.34 (1H, m), 7.27 (1H, d, J=8.4 Hz), 7.51 (2H, d, J=8.7 Hz), 7.58 (2H, d, J=8.7 Hz), 7.65 (1H, s), 7.69 (1H, s).

IR (KBr): 2938, 1715, 1674, 1589, 1532, 1470 cm$^{-1}$.

Example 47

Production of N-(4-(1-(2,6-difluorobenzyl)-3-(3-hydroxy-6-methyl-2-pyridinyl)-5-(((2-methoxyethyl)(methyl)amino)methyl)-2,4-dioxo-1,2,3,4-tetrahydrothieno[2,3-d]pyrimidin-6-yl)phenyl)-N'-methoxyurea

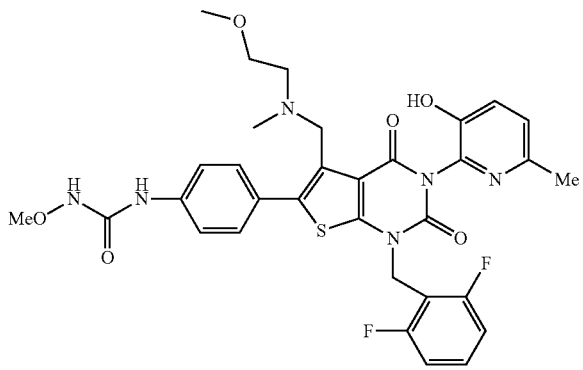 [SMILES: COCCN(C)Cc1c(-c2ccc(NC(=O)NOC)cc2)sc2c1c(=O)n(-c1nc(C)ccc1O)c(=O)n2Cc1c(F)cccc1F]

A crude amide (163 mg) was produced by reacting the compound obtained in Reference Example 7 (455 mg) with 1-ethyl-3-(3-dimethylaminopropyl)-carbodiimide hydrochloride (306 mg), 1-hydroxybenzotriazole (288 mg), 2-amino-3-hydroxy-6-methylpyridine (187 mg) and N-ethyldiisopropylamine (517 µl). Furthermore, the title compound (127 mg) was obtained from the crude amide by using methanol (11 ml) and a solution of 28% sodium methoxide in methanol (85 mg).

Elemental analysis for $C_{33}H_{34}N_6O_6SF_2 \cdot H_2O$

Calcd.: C, 56.13; H, 5.01; N, 12.27.

Found: C, 56.03; H, 5.21; N, 12.05.

$^1$H-NMR (CDCl$_3$) δ: 2.11 (3H, s), 2.48 (3H, s), 2.51-2.59 (2H, m), 3.20 (3H, s), 3.30-3.46 (4H, m), 3.60 (1H, d, J=12.3 Hz), 3.79 (3H, s), 4.05 (1H, d, J=12.3 Hz), 5.21 (1H, d, J=15.6 Hz), 5.31 (1H, d, J=15.6 Hz), 6.88 (2H, t, J=8.1 Hz), 7.07 (1H, d, J=8.1 Hz), 7.21-7.31 (2H, m), 7.43-7.51 (4H, m), 7.69 (1H, s).

IR (KBr): 2936, 1715, 1669, 1591, 1530, 1472 cm$^{-1}$.

Example 48

Production of N-(4-(1-(2,6-difluorobenzyl)-5-(((2-methoxyethyl)(methyl)amino)methyl)-3-(3-methoxy-2-pyridinyl)-2,4-dioxo-1,2,3,4-tetrahydrothieno[2,3-d]pyrimidin-6-yl)phenyl)-N'-methoxyurea

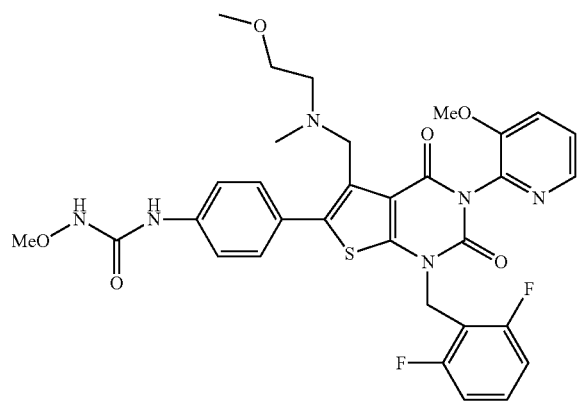 [SMILES: COCCN(C)Cc1c(-c2ccc(NC(=O)NOC)cc2)sc2c1c(=O)n(-c1ncccc1OC)c(=O)n2Cc1c(F)cccc1F]

The similar reaction as described in Example 40 by using the compound obtained in Reference Example 7 (455 mg), diethyl cyanophosphate (285 μl), 2-amino-3-methoxypyridine (233 mg) and N-ethyldiisopropylamine (388 μl) gave a crude amide (226 mg). Furthermore, the similar reaction by using methanol (15.5 ml), a solution of 28% sodium methoxide in methanol (120 mg) gave the title compound (115 mg).

Elemental analysis for $C_{32}H_{32}N_6O_6SF_2 \cdot 0.5H_2O$

Calcd.: C, 56.88; H, 4.92; N, 12.44.

Found: C, 56.88; H, 4.96; N, 12.31.

$^1$H-NMR (CDCl$_3$) δ: 2.20 (3H, s), 2.63 (2H, t, J=6.2 Hz), 3.28 (3H, s), 3.41 (2H, t, J=6.2 Hz), 3.78 (1H, d, J=12.3 Hz), 3.82 (3H, s), 3.84 (3H, s), 3.88 (1H, d, J=12.3 Hz), 5.35 (2H, s), 6.92 (2H, t, J=8.1 Hz), 7.17 (1H, s), 7.23-7.39 (3H, m), 7.54 (2H, d, J=8.8 Hz), 7.57 (1H, s), 7.69 (2H, d, J=8.8 Hz), 8.23-8.27 (1H, m).

IR (KBr): 1717, 1674, 1590, 1530, 1470 cm$^{-1}$.

Example 49

Production of N-(4-(1-(2,6-difluorobenzyl)-3-(4-(1-hydroxy-1-methylethyl)phenyl)-5-(((2-methoxyethyl)(methyl)amino)methyl)-2,4-dioxo-1,2,3,4-tetrahydrothieno[2,3-d]pyrimidin-6-yl)phenyl)-N'-methoxyurea

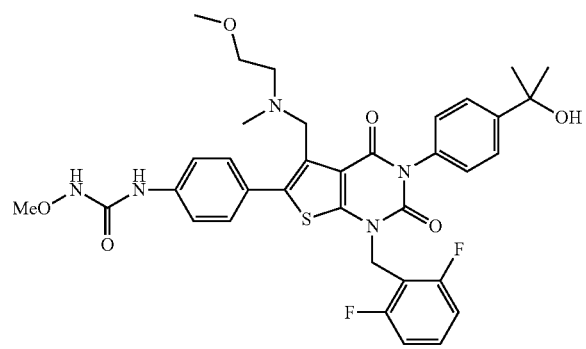 [SMILES: COCCN(C)Cc1c(-c2ccc(NC(=O)NOC)cc2)sc2c1c(=O)n(-c1ccc(C(C)(C)O)cc1)c(=O)n2Cc1c(F)cccc1F]

The similar reaction as described in Example 40 by using the compound obtained in Reference Example 7 (1.22 g), diethyl cyanophosphate (456 μl), 4-(1-hydroxy-1-methylethyl)aniline (454 mg) and N-ethyldiisopropylamine (569 μl) gave a crude amide (1.12 g). Furthermore, the similar reaction by using ethanol (60 ml), a solution of 28% sodium methoxide in methanol (579 mg) gave the title compound (849 mg).

Elemental analysis for $C_{35}H_{37}N_5O_6SF_2 \cdot 0.5H_2O$

Calcd.: C, 59.82; H, 5.45; N, 9.97.

Found: C, 60.09; H, 5.40; N, 10.06.

$^1$H-NMR (CDCl$_3$) δ: 1.60 (6H, s), 1.79 (1H, s), 2.14 (3H, s), 2.63 (2H, t, J=5.9 Hz), 3.27 (3H, s), 3.41 (2H, t, J=5.9 Hz), 3.81 (3H, s), 3.82 (2H, s), 5.36 (2H, s), 6.92 (2H, t, J=8.3 Hz), 7.20-7.34 (4H, m), 7.53 (2H, d, J=8.7 Hz), 7.60-7.63 (5H, m).

IR (KBr): 1713, 1669, 1590, 1532, 1470 cm$^{-1}$.

Example 50

Production of N-(4-(5-((benzyl(methyl)amino)methyl)-1-(2,6-difluorobenzyl)-3-(4-(1-hydroxy-1-methylethyl)phenyl)-2,4-dioxo-1,2,3,4-tetrahydrothieno[2,3-d]pyrimidin-6-yl)phenyl)-N'-methoxyurea

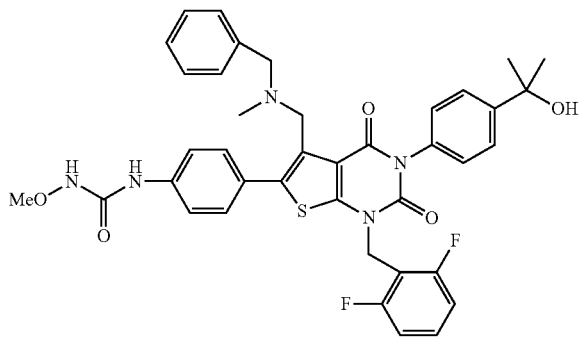 [SMILES: CONC(=O)Nc1ccc(-c2sc3c(c2CN(C)Cc2ccccc2)c(=O)n(-c2ccc(C(C)(C)O)cc2)c(=O)n3Cc2c(F)cccc2F)cc1]

The similar reaction as described in Example 40 by using 4-(N-benzyl-N-methylaminomethyl)-2-[N-(2,6-difluorobenzyl)-N-ethoxycarbonylamino]-5-[4-(3-methoxyureido)phenyl]thiophene-3-carboxylic acid (470 mg), diethyl cyanophosphate (167 μl), 4-(1-hydroxy-1-methylethyl)aniline (166 mg) and N-ethyldiisopropylamine (209 μl) gave a crude amide (422 mg). Furthermore, the similar reaction by using ethanol (25.5 ml) and sodium ethoxide (70 mg) gave the title compound (113 mg).

Elemental analysis for $C_{39}H_{37}N_5O_5SF_2$

Calcd.: C, 64.54; H, 5.14; N, 9.65.

Found: C, 64.46; H, 5.05; N, 9.70.

$^1$H-NMR (CDCl$_3$) δ: 1.62 (6H, s), 1.77 (1H, s), 2.05 (3H, s), 3.56 (2H, s), 3.82 (3H, s), 3.90 (2H, s), 5.36 (2H, s), 6.91 (2H, t, J=8.1 Hz), 7.14-7.38 (9H, m), 7.55 (2H, d, J=9.0 Hz), 7.62 (1H, s), 7.64 (2H, d, J=8.7 Hz), 7.72 (2H, d, J=8.4 Hz).

IR (KBr): 1713, 1669, 1590, 1530, 1470 cm$^{-1}$.

Example 51

Production of N-(4-(1-(2,6-difluorobenzyl)-5-(((2-methoxyethyl)(methyl)amino)methyl)-3-(4-(1-methoxy-1-methylethyl)phenyl)-2,4-dioxo-1,2,3,4-tetrahydrothieno[2,3-d]pyrimidin-6-yl)phenyl)-N'-methoxyurea

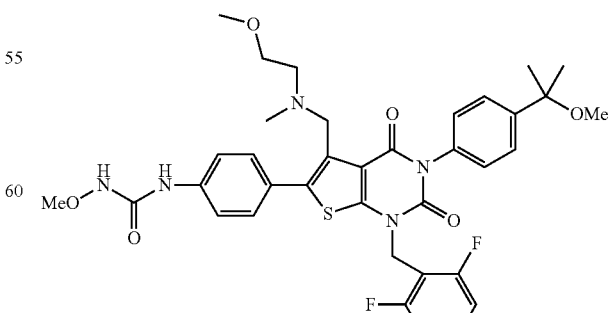

The similar reaction as described in Example 40 by using the compound obtained in Reference Example 7 (364 mg), diethyl cyanophosphate (136 µl), 4-(1-methoxy-1-methylethyl)aniline (149 mg) and N-ethyldiisopropylamine (171 µl) gave a crude amide (292 mg). Furthermore, the similar reaction by using ethanol (19 ml) and a solution of 28% sodium methoxide in methanol (146 mg) gave the title compound (146 mg).

Elemental analysis for $C_{36}H_{39}N_5O_6SF_2$
Calcd.: C, 61.09; H, 5.55; N, 9.89.
Found: C, 60.97; H, 5.54; N, 9.92.
$^1$H-NMR (CDCl$_3$) δ: 1.55 (6H, s), 2.15 (3H, s), 2.64 (2H, t, J=5.9 Hz), 3.11 (3H, s), 3.27 (3H, s), 3.41 (2H, t, J=5.9 Hz), 3.82 (3H, s), 3.83 (2H, s), 5.36 (2H, s), 6.92 (2H, t, J=8.3 Hz), 7.16 (1H, s), 7.24-7.36 (4H, m), 7.51-7.63 (6H, m).
IR (KBr): 1715, 1674, 1590, 1532, 1464, 1327 cm$^{-1}$.

Example 52

Production of N-(4-(1-(2,6-difluorobenzyl)-5-(((2-methoxyethyl)(methyl)amino)methyl)-3-(1-methyl-1H-imidazol-2-yl)-2,4-dioxo-1,2,3,4-tetrahydrothieno[2,3-d]pyrimidin-6-yl)phenyl)-N'-methoxyurea

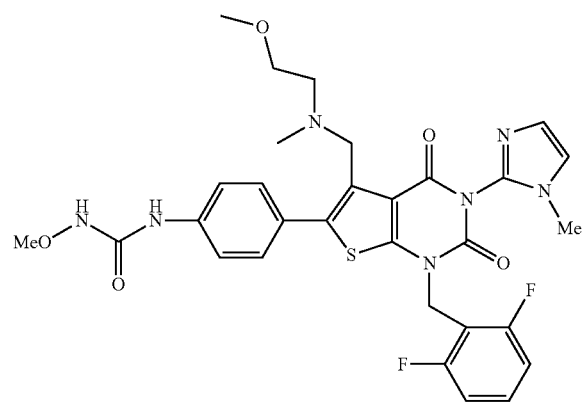 [SMILES: COCCN(C)Cc1c(-c2ccc(NC(=O)NOC)cc2)sc2c1c(=O)n(-c1nccn1C)c(=O)n2Cc1c(F)cccc1F]

The similar reaction as described in Example 40 by using the compound obtained in Reference Example 7 (455 mg), diethyl cyanophosphate (228 µl), 2-amino-1-methyl-1H-imidazole hydrochloride (214 mg) and N-ethyldiisopropylamine (586 µl) gave a crude amide (48 mg). Furthermore, the similar reaction by using methanol (3.3 ml) and a solution of 28% sodium methoxide in methanol (25 mg) gave the title compound (17 mg).

$^1$H-NMR (CDCl$_3$) δ: 2.15 (3H, s), 2.61 (2H, dt, J=1.8 Hz, 6.90 Hz), 3.27 (3H, s), 3.40 (2H, dt, J=1.8 Hz, 6.0 Hz), 3.53 (3H, s), 3.75 (1H, d, J=12.3 Hz), 3.80 (3H, s), 3.81 (1H, d, J=12.3 Hz), 5.12 (1H, d, J=15.9 Hz), 5.57 (1H, d, J=15.9 Hz), 6.91 (2H, t, J=8.1 Hz), 6.99 (1H, d, J=1.5 Hz), 7.14 (1H, d, J=1.5 Hz), 7.28 (1H, s), 7.25-7.34 (1H, m), 7.53 (2H, d, J=9.0 Hz), 7.60 (2H, d, J=9.0 Hz), 7.70 (1H, s).
IR (KBr): 1725, 1682, 1590, 1530, 1470 cm$^{-1}$.

Example 53

Production of N-(4-(1-(2,6-difluorobenzyl)-5-(((2-methoxyethyl)(methyl)amino)methyl)-3-(3-methylbutyl)-2,4-dioxo-1,2,3,4-tetrahydrothieno[2,3-d]pyrimidin-6-yl)phenyl)-N'-methoxyurea

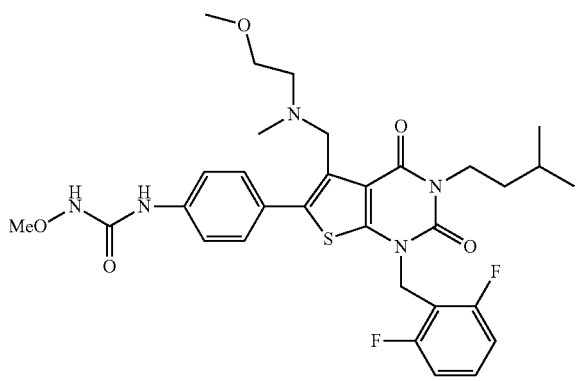 [SMILES: COCCN(C)Cc1c(-c2ccc(NC(=O)NOC)cc2)sc2c1c(=O)n(CCC(C)C)c(=O)n2Cc1c(F)cccc1F]

The similar reaction as described in Example 40 by using the compound obtained in Reference Example 7 (455 mg), diethyl cyanophosphate (228 µl), isoamylamine (139 mg) and N-ethyldiisopropylamine (310 µl) gave a crude amide (102 mg). Furthermore, the stirring with methanol (7 ml), a solution of 28% sodium methoxide in methanol (55 mg) at 55° C. for 20 hours and the similar treatment gave the title compound (80 mg).

Elemental analysis for $C_{31}H_{37}N_5O_5SF_2$
Calcd.: C, 59.13; H, 5.92; N, 11.12.
Found: C, 58.97; H, 5.99; N, 10.90.
$^1$H-NMR (CDCl$_3$) δ: 0.98 (6H, d, J=6.3 Hz), 1.52-1.58 (2H, m), 1.64-1.71 (1H, m), 2.14 (3H, s), 2.66 (2H, t, J=5.9 Hz), 3.30 (3H, s), 3.45 (2H, t, J=5.9 Hz), 3.81 (3H, s), 3.85 (2H, s), 4.04-4.09 (2H, m), 5.33 (2H, s), 6.90 (2H, t, J=8.3 Hz), 7.17 (1H, s), 7.24-7.35 (1H, m), 7.51 (2H, d, J=8.7 Hz), 7.57 (2H, d, J=8.7 Hz), 7.60 (1H, s).
IR (KBr): 2959, 1705, 1659, 1590, 1531, 1472 cm$^{-1}$.

Example 54

Production of N-(4-(1-(2,6-difluorobenzyl)-3-(2-methoxyethyl)-5-(((2-methoxyethyl)(methyl)amino)methyl)-2,4-dioxo-1,2,3,4-tetrahydrothieno[2,3-d]pyrimidin-6-yl)phenyl)-N'-methoxyurea

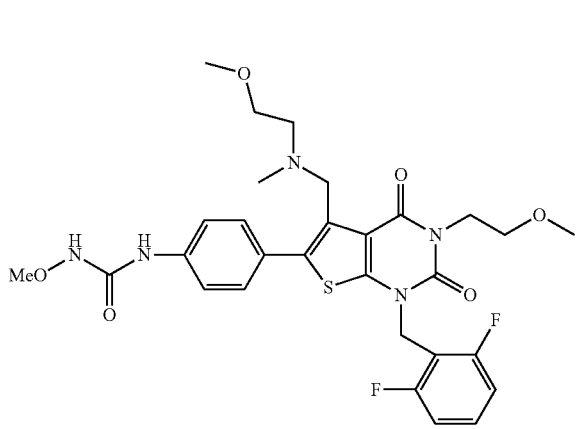 [SMILES: COCCN(C)Cc1c(-c2ccc(NC(=O)NOC)cc2)sc2c1c(=O)n(CCOC)c(=O)n2Cc1c(F)cccc1F]

The similar reaction as described in Example 40 by using the compound obtained in Reference Example 7 (455 mg), diethyl cyanophosphate (228 μl), 2-methoxyethylamine (120 mg) and N-ethyldiisopropylamine (310 μl) gave a crude amide (266 mg). Furthermore, the similar reaction by using methanol (19.6 ml) and a solution of 28% sodium methoxide in methanol (152 mg) gave the title compound (140 mg).

Elemental analysis for $C_{29}H_{33}N_5O_6SF_2$

Calcd.: C, 56.39; H, 5.39; N, 11.34.

Found: C, 56.40; H, 5.35; N, 11.15.

$^1$H-NMR (CDCl$_3$) δ: 2.14 (3H, s), 2.65 (2H, t, J=5.9 Hz), 3.30 (3H, s), 3.36 (3H, s), 3.45 (2H, t, J=5.9 Hz), 3.66 (2H, t, J=5.9 Hz), 3.81 (3H, s), 3.84 (2H, s), 4.30 (2H, t, J=5.9 Hz), 5.33 (2H, s), 6.90 (2H, t, J=8.3 Hz), 7.15 (1H, s), 7.24-7.34 (1H, m), 7.51 (2H, d, J=9.0 Hz), 7.56 (2H, d, J=9.0 Hz), 7.60 (1H, m).

IR (KBr): 2936, 1705, 1663, 1590, 1532, 1472 cm$^{-1}$.

Example 55

Production of N-(4-(1-(2,6-difluorobenzyl)-3-(2-ethoxyethyl)-5-(((2-methoxyethyl)(methyl)amino)methyl)-2,4-dioxo-1,2,3,4-tetrahydrothieno[2,3-d]pyrimidin-6-yl)phenyl)-N'-methoxyurea

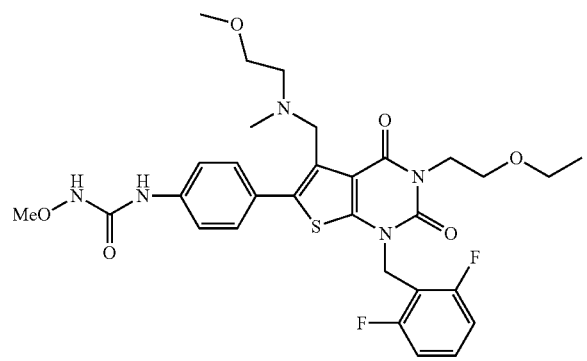 [SMILES: CCOCCn1c(=O)c2c(CN(C)CCOC)c(-c3ccc(NC(=O)NOC)cc3)sc2n(Cc2c(F)cccc2F)c1=O]

The similar reaction as described in Example 40 by using the compound obtained in Reference Example 7 (455 mg), diethyl cyanophosphate (228 μl), 2-ethoxyethylamine (143 mg) and N-ethyldiisopropylamine (310 μl) gave a crude amide (259 mg). Furthermore, the similar reaction by using methanol (18.7 ml) and a solution of 28% sodium methoxide in methanol (144 mg) gave the title compound (193 mg).

Elemental analysis for $C_{30}H_{35}N_5O_6SF_2$

Calcd.: C, 57.04; H, 5.58; N, 11.09.

Found: C, 57.01; H, 5.66; N, 10.93.

$^1$H-NMR (CDCl$_3$) δ: 1.15 (3H, t, J=6.9 Hz), 2.14 (3H, s), 2.66 (2H, t, J=6.0 Hz), 3.30 (3H, s), 3.45 (2H, t, J=6.0 Hz), 3.54 (2H, q, J=6.9 Hz), 3.69 (2H, t, J=6.0 Hz), 3.81 (3H, s), 3.84 (2H, s), 4.29 (2H, t, J=6.0 Hz), 5.32 (2H, s), 6.89 (2H, t, J=8.1 Hz), 7.17 (1H, s), 7.23-7.34 (1H, m), 7.52 (2H, d, J=8.7 Hz), 7.57 (2H, d, J=8.7 Hz), 7.60 (1H, m).

IR (KBr): 2975, 1705, 1663, 1590, 1532, 1472 cm$^{-1}$.

Example 56

Production of N-(4-(1-(2,6-difluorobenzyl)-3-isopropyl-5-(((2-methoxyethyl)(methyl)amino)methyl)-2,4-dioxo-1,2,3,4-tetrahydrothieno[2,3-d]pyrimidin-6-yl)phenyl)-N'-methoxyurea

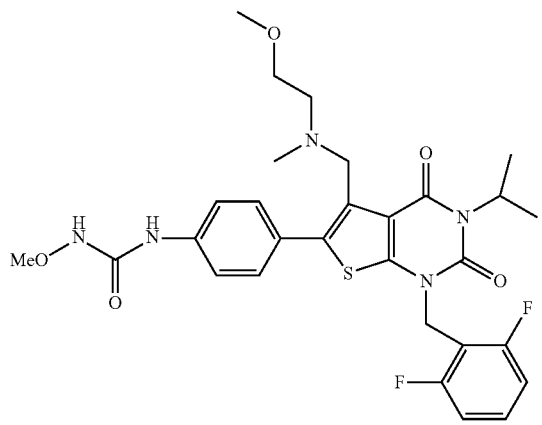 [SMILES: COCCN(C)Cc1c(-c2ccc(NC(=O)NOC)cc2)sc2c1c(=O)n(C(C)C)c(=O)n2Cc1c(F)cccc1F]

The similar reaction as described in Example 40 by using the compound obtained in Reference Example 7 (455 mg), diethyl cyanophosphate (228 μl), isopropylamine (95 mg) and N-ethyldiisopropylamine (310 μl) gave a crude amide (306 mg). Furthermore, the stirring with methanol (23.2 ml) and a solution of 28% sodium methoxide in methanol (179 mg) at 60° C. for 17 hours and the similar treatment gave the title compound (192 mg).

Elemental analysis for $C_{29}H_{33}N_5O_5SF_2$

Calcd.: C, 57.89; H, 5.53; N, 11.64.

Found: C, 57.98; H, 5.49; N, 11.72.

$^1$H-NMR (CDCl$_3$) δ: 1.52 (6H, d, J=6.9 Hz), 2.13 (3H, s), 2.66 (2H, t, J=5.9 Hz), 3.31 (3H, s), 3.46 (2H, t, J=5.9 Hz), 3.82 (3H, s), 3.84 (2H, s), 5.31 (2H, s), 5.34 (1H, m), 6.90 (2H, t, J=8.1 Hz), 7.16 (1H, s), 7.24-7.35 (1H, m), 7.52 (2H, d, J=8.4 Hz), 7.55 (2H, d, J=8.4 Hz), 7.60 (1H, m). IR (KBr): 2973, 1703, 1659, 1590, 1534, 1472 cm$^{-1}$.

Example 57

Production of N-(4-(1-(2,6-difluorobenzyl)-5-(((2-methoxyethyl)(methyl)amino)methyl)-3-(6-methoxy-3-pyridazinyl)-2,4-dioxo-1,2,3,4-tetrahydrothieno[2,3-d]pyrimidin-6-yl)phenyl)-N'-methoxyurea

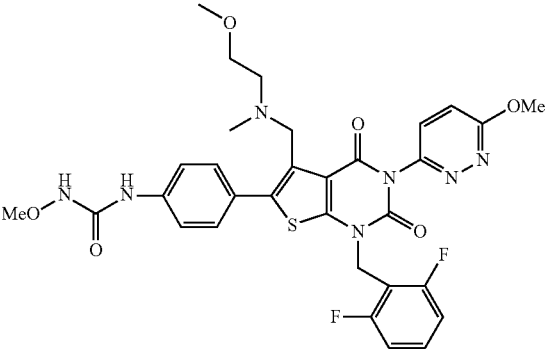 [SMILES: COCCN(C)Cc1c(-c2ccc(NC(=O)NOC)cc2)sc2c1c(=O)n(-c1ccc(OC)nn1)c(=O)n2Cc1c(F)cccc1F]

The similar reaction as described in Example 40 by using the compound obtained in Reference Example 7 (455 mg), diethyl cyanophosphate (285 μl), 3-amino-6-chloropyridine (243 mg) and N-ethyldiisopropylamine (388 μl) gave a crude amide (207 mg). Furthermore, the similar reaction by using methanol (14.2 ml) and a solution of 28% sodium methoxide in methanol (109 mg) gave the title compound (132 mg).

$^1$H-NMR (CDCl$_3$) δ: 2.13 (3H, s), 2.62 (2H, t, J=5.7 Hz), 3.26 (3H, s), 3.41 (2H, t, J=5.7 Hz), 3.74 (2H, brs), 3.82 (3H, s), 4.18 (3H, s), 5.32 (2H, brs), 6.92 (2H, t, J=8.3 Hz), 7.12 (1H, d, J=9.3 Hz), 7.24 (1H, s), 7.29-7.35 (1H, m), 7.41 (2H, d, J=9.3 Hz), 7.54 (2H, d, J=9.0 Hz), 7.59 (2H, d, J=8.7 Hz), 7.66 (1H, s).

IR (KBr): 2936, 1717, 1674, 1591, 1530, 1460 cm$^{-1}$.

Example 58

Production of N-(4-(1-(2,6-difluorobenzyl)-5-(((2-methoxyethyl)(methyl)amino)methyl)-2,4-dioxo-3-(3-pyridazinyl)-1,2,3,4-tetrahydrothieno[2,3-d]pyrimidin-6-yl)phenyl)-N'-methoxyurea

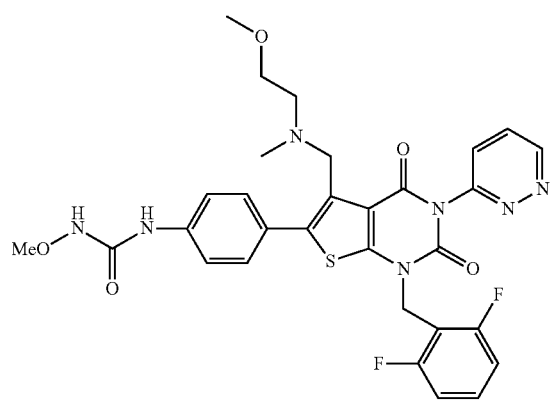 [SMILES: COCCN(C)Cc1c(-c2ccc(NC(=O)NOC)cc2)sc2c1c(=O)n(-c1cccnn1)c(=O)n2Cc1c(F)cccc1F]

The similar reaction as described in Example 40 by using the compound obtained in Reference Example 7 (364 mg), diethyl cyanophosphate (182 μl), 3-aminopyridazine hydrochloride (158 mg) and N-ethyldiisopropylamine (414 μl) gave a crude amide (55 mg). Furthermore, the similar reaction by using methanol (4 ml) and a solution of 28% sodium methoxide in methanol (30 mg) gave the title compound (15 mg).

$^1$H-NMR (CDCl$_3$) δ: 2.12 (3H, s), 2.61 (2H, t, J=5.7 Hz), 3.26 (3H, s), 3.39 (2H, t, J=5.7 Hz), 3.78 (2H, brs), 3.82 (3H, s), 5.34 (2H, brs), 6.93 (2H, t, J=8.1 Hz), 7.26 (1H, s), 7.29-7.37 (1H, m), 7.53-7.61 (5H, m), 7.67 (1H, s), 7.69 (1H, dd, J=4.8 Hz, 8.4 Hz), 9.28 (1H, dd, J=1.8 Hz, 4.8 Hz).

IR (KBr): 2936, 1717, 1674, 1590, 1530, 1470 cm$^{-1}$.

Example 59

Production of N-(4-(1-(2,6-difluorobenzyl)-5-(((2-methoxyethyl)(methyl)amino)methyl)-3-methoxy-2,4-dioxo-1,2,3,4-tetrahydrothieno[2,3-d]pyrimidin-6-yl)phenyl)-N'-methoxyurea

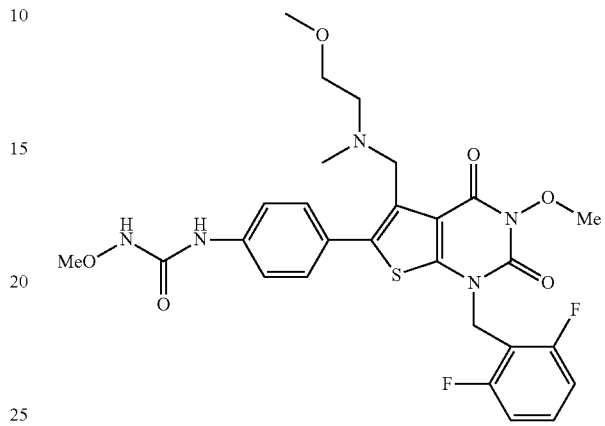

The similar reaction as described in Example 40 by using the compound obtained in Reference Example 7 (607 mg), diethyl cyanophosphate (304 μl), o-methylhydroxylamine hydrochloride (334 mg) and N-ethyldiisopropylamine (1.04 ml) gave a crude product, which was purified by aminopropyl silica gel column chromatography (Fuji Silysia Chemical) to give the title compound (283 mg).

$^1$H-NMR (CDCl$_3$) δ: 2.14 (3H, s), 2.68 (2H, t, J=6.0 Hz), 3.31 (3H, s), 3.47 (2H, t, J=6.0 Hz), 3.82 (3H, s), 3.83 (2H, s), 4.06 (3H, s), 5.35 (2H, s), 6.92 (2H, t, J=8.3 Hz), 7.20 (1H, s), 7.29-7.35 (1H, m), 7.55 (4H, s), 7.63 (1H, s).

IR (KBr): 1725, 1684, 1590, 1530, 1472 cm$^{-1}$.

Example 60

Production of N-(4-(1-(2,6-difluorobenzyl)-5-(((2-methoxyethyl)(methyl)amino)methyl)-3-methyl-2,4-dioxo-1,2,3,4-tetrahydrothieno[2,3-d]pyrimidin-6-yl)phenyl)-N'-methoxyurea

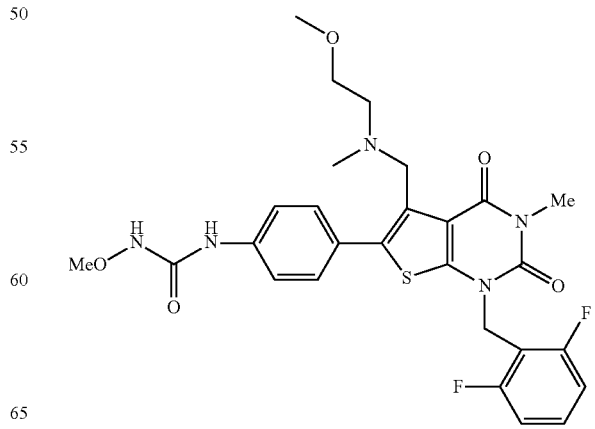

The similar reaction as described in Example 40 by using the compound obtained in Reference Example 7 (607 mg), diethyl cyanophosphate (304 µl), methylamine hydrochloride (270 mg) and N-ethyldiisopropylamine (1.04 ml) gave a crude amide (133 mg). Furthermore, the stirring with methanol (9.1 ml) and a solution of 28 sodium methoxide in methanol (70 mg) at 60° C. for 17 hours and the similar treatment gave the title compound (83 mg).

$^1$H-NMR (CDCl$_3$) δ: 2.13 (3H, s), 2.66 (2H, t, J=5.9 Hz), 3.31 (3H, s), 3.45 (3H, s), 3.48 (2H, t, J=5.9 Hz), 3.82 (3H, s), 3.84 (2H, s), 5.33 (2H, s), 6.91 (2H, t, J=8.3 Hz), 7.17 (1H, s), 7.25-7.35 (1H, m), 7.55 (4H, s), 7.62 (1H, s).

IR (KBr): 1705, 1661, 1590, 1532, 1472 cm$^{-1}$.

Reference Example 18 production of N-(4-(5-chloromethyl-1-(2,6-difluorobenzyl)-1,2,3,4-tetrahydro-2,4-dioxo-3-phenylthieno[2,3-d]pyrimidin-6-yl)phenyl)-N'-methoxyurea

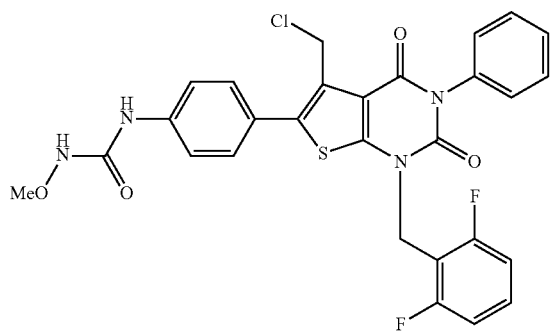 [SMILES: CONC(=O)Nc1ccc(-c2sc3c(c2CCl)c(=O)n(-c2ccccc2)c(=O)n3Cc2c(F)cccc2F)cc1]

Into a solution of N-(4-(5-((benzyl(methyl)amino)methyl)-1-(2,6-difluorobenzyl)-1,2,3,4-tetrahydro-2,4-dioxo-3-phenylthieno[2,3-d]pyrimidin-6-yl)phenyl)-N'-methoxyurea (7.7 g, 11.53 mmol) in THF (200 ml) which was cooled with a dry ice-acetone bath was added α-choloroethyl chloroformate (1.7 ml, 11.64 mmol). The temperature of the mixture was elevated up to room temperature, and the mixture was stirred for 2.5 hours. The reaction mixture was diluted with saturated aqueous solution of sodium bicarbonate and extracted with chloroform. The organic layer was washed with saturated aqueous solution of sodium chloride, dried over magnesium sulfate and concentrated under reduced pressure.

The residue was purified with silica gel chromatography (eluent; ethyl acetate/chloroform; from 1/4 to 1/3) and recrystallized from chloroform/diethylether, whereby the title compound (5.66 g, 84%) was obtained as white crystals.

$^1$H NMR (CDCl$_3$) δ 3.83 (3H, s), 4.84 (2H, s), 5.27 (2H, s), 5.37 (2H, s), 6.92 (2H, t, J=7.8 Hz), 7.23-7.35 (4H, m), 7.41-7.66 (8H, m).

Reference Example 19

Production of N-(4-(5-chloromethyl-1-(2,6-difluorobenzyl)-1,2,3,4-tetrahydro-2,4-dioxo-3-(4-methoxyphenyl)thieno[2,3-d]pyrimidin-6-yl)phenyl)-N'-methoxyurea

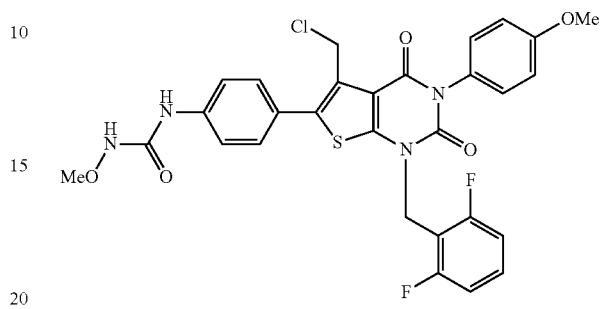

The similar reaction as described in Example 5 by using 4-(N-benzyl-N-methylaminomethyl)-2-(N-(2,6-difluorobenzyl)-N-ethoxycarbonylamino)-5-(4-(3-methoxyureido)phenyl)thiophene-3-carboxylic acid (5.0 g, 7.83 mmol) and p-anisidine (1.93 g, 15.65 mmol) gave N-(4-(5-((benzyl(methyl)amino)methyl)-1-(2,6-difluorobenzyl)-3-(4-methoxyphenyl)-2,4-dioxo-1,2,3,4-tetrahydrothieno[2,3-d]pyrimidin-6-yl)phenyl)-N'-methoxyurea (3.39 g, 62%) as white solids. The similar reaction as described in Reference Example 18 by using the compound (80 mg, 0.11 mmol) gave the title compound (50 mg, 74%) as white crystals.

$^1$H NMR (CDCl$_3$) δ 3.81 (3H, s), 3.83 (3H, s), 4.83 (2H, s), 5.35 (2H, s), 6.92 (2H, t, J=8.1 Hz), 7.00 (2H, d, J=10.2 Hz), 7.18-7.35 (3H, m), 7.48-7.65 (5H, m).

Reference Example 20

Production of N-(4-(5-chloromethyl-1-(2,6-difluorobenzyl)-1,2,3,4-tetrahydro-2,4-dioxo-3-(4-hydroxycyclohexyl)thieno[2,3-d]pyrimidin-6-yl)phenyl)-N'-methoxyurea

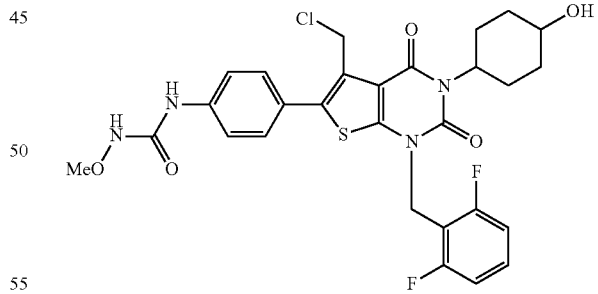

The similar reaction as described in Example 5 by using 4-(N-benzyl-N-methylaminomethyl)-2-(N-(2,6-difluorobenzyl)-N-ethoxycarbonylamino)-5-(4-(3-methoxyureido)phenyl)thiophene-3-carboxylic acid (10.0 g, 15.65 mmol) and 4-aminocyclohexanol (3.61 g, 31.30 mmol) gave N-(4-(5-((benzyl(methyl)amino)methyl)-1-(2,6-difluorobenzyl)-3-(4-hydroxycyclohexyl)-2,4-dioxo-1,2,3,4-tetrahydrothieno[2,3-d]pyrimidin-6-yl)phenyl)-N'-methoxyurea (5.20 g, 48%) as white crystals. The similar reaction as described in Reference Example 18 by using the compound (500 mg, 0.72 mmol) gave the title compound (180 mg, 41%) as white crystals.

$^1$H NMR (CDCl$_3$) δ 1.41-1.55 (2H, m), 1.71 (2H, d, J=11.7 Hz), 2.07 (2H, d, J=12.4 Hz), 2.63 (2H, q, J=11.1 Hz), 3.70-3.82 (4H, m), 4.84 (2H, s), 4.90-5.06 (1H, m), 5.29 (2H, s), 6.91 (2H, t, J=8.1 Hz), 7.13 (1H, s), 7.25-7.33 (1H, m), 7.47 (2H, d, J=8.4 Hz), 7.58 (2H, d, J=9.0 Hz), 7.63 (1H, s).

Reference Example 21

Production of N-(4-(5-chloromethyl-1-(2,6-difluorobenzyl)-3-(5-fluoropyridin-2-yl)-1,2,3,4-tetrahydro-2,4-dioxothieno[2,3-d]pyrimidin-6-yl)phenyl)-N'-methoxyurea

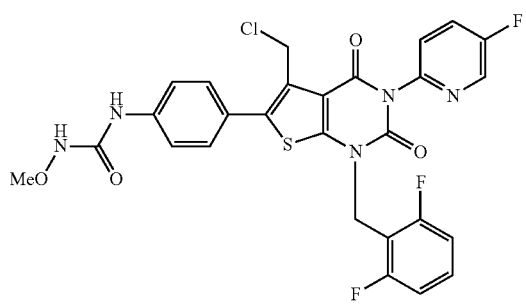 [SMILES: CONC(=O)Nc1ccc(-c2sc3c(c2CCl)c(=O)n(-c2ccc(F)cn2)c(=O)n3Cc2c(F)cccc2F)cc1]

The similar reaction as described in Example 5 by using 4-(N-benzyl-N-methylaminomethyl)-2-(N-(2,6-difluorobenzyl)-N-ethoxycarbonylamino)-5-(4-(3-methoxyureido)phenyl)thiophene-3-carboxylic acid (10.0 g, 15.65 mmol) and 2-amino-5-fluoropyridine (3.51 g, 31.30 mmol) gave N-(4-(5-((benzyl(methyl)amino)methyl)-1-(2,6-difluorobenzyl)-3-(5-fluoropyridin-2-yl)-2,4-dioxo-1,2,3,4-tetrahydrothieno[2,3-d]pyrimidin-6-yl)phenyl)-N'-methoxyurea (3.39 g, 32%) as white solids. The similar reaction as described in Reference Example 18 by using the compound (1.0 g, 1.46 mmol) gave the title compound (560 mg, 64%) as white solids.

$^1$H NMR (CDCl$_3$) δ 3.83 (1H, s), 4.79 (2H, br), 5.34 (2H, br), 6.93 (2H, t, J=8.0 Hz), 7.14 (1H, s), 7.29-7.40 (2H, m), 7.50-7.65 (5H, m), 8.51 (1H, d, J=3.0 Hz).

Reference Example 22

Production of N-(4-(5-chloromethyl-1-(2,6-difluorobenzyl)-1,2,3,4-tetrahydro-2,4-dioxo-3-(pyridin-2-yl)thieno[2,3-d]pyrimidin-6-yl)phenyl)-N'-methoxyurea

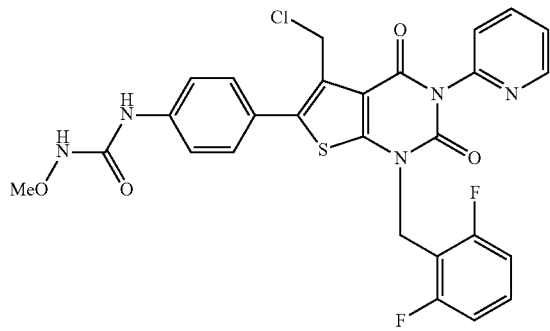 [SMILES: CONC(=O)Nc1ccc(-c2sc3c(c2CCl)c(=O)n(-c2ccccn2)c(=O)n3Cc2c(F)cccc2F)cc1]

The similar reaction as described in Reference Example 18 by using compound (500 mg, 0.75 mmol) obtained in Example 1 gave the title compound (270 mg, 62%) as white solids.

$^1$H NMR (DMDO-d$_6$) δ 3.63 (3H, s), 4.85 (2H, s), 5.10-5.24 (2H, br), 7.13 (2H, t, J=8.3 Hz), 7.41-7.54 (4H, m), 7.78 (2H, d, J=8.4 Hz), 8.01 (1H, t, J=8.0 Hz), 8.30 (1H, s), 8.59-8.61 (1H, m), 9.14 (1H, s), 9.66 (1H, s)

Reference Example 23

Production of N-(4-(1-(2,6-difluorobenzyl)-3-(4-hydroxycyclohexyl)-5-(methylamino)methyl-1,2,3,4-tetrahydro-2,4-dioxo-thieno[2,3-d]pyrimidin-6-yl)phenyl)-N'-methoxyurea

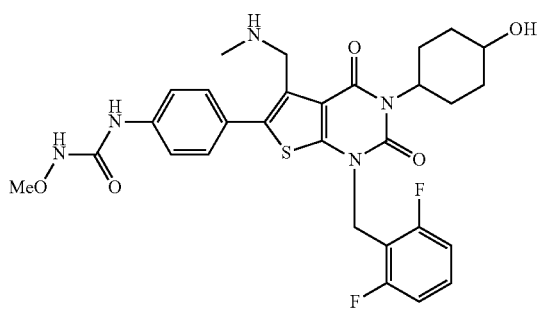 [SMILES: CNCc1c(-c2ccc(NC(=O)NOC)cc2)sc2c1c(=O)n(C1CCC(O)CC1)c(=O)n2Cc1c(F)cccc1F]

The similar reaction as described in Reference Example 14 by using N-(4-(5-((benzyl(methyl)amino)methyl)-1-(2,6-difluorobenzyl)-3-(4-hydroxycyclohexyl)-2,4-dioxo-1,2,3,4-tetrahydrothieno[2,3-d]pyrimidin-6-yl)phenyl)-N'-methoxyurea (5.20 g, 48%) obtained in Reference Example 20 gave the title compound (5.20 g, 48%) as white crystals.

$^1$H NMR (DMDO-d$_6$) δ 3.63 (3H, s), 4.85 (2H, s), 5.10-5.24 (2H, br), 7.13 (2H, t, J=8.3 Hz), 7.41-7.54 (4H, m), 7.78 (2H, d, J=8.4 Hz), 8.01 (1H, t, J=8.0 Hz), 8.30 (1H, s), 8.59-8.61 (1H, m), 9.14 (1H, s), 9.66 (1H, s)

Reference Example 24

Production of N-(2-methoxy-1-methylethyl)-N-methylamine

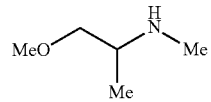

A mixture of a solution of methoxyacetone (2.92 g, 33.14 mmol) and methylamine in 2.0 M THF (100 ml, 200.0 mmol) and a solution of acetic acid (0.5 ml) in THF (100 ml) was stirred under ice cooling for 30 minutes. To the mixture was added triacetoxy sodium borohydride (14.05 g, 66.28 mmol), and the mixture was stirred at room temperature for 4 days. To the reaction mixture were added saturated aqueous solution of sodium bicarbonate (100 ml), ethyl acetate ethyl acetate (100 ml) and benzyloxycarbonylchloride (8.48 g, 49.71 mmol), successively, and the mixture was stirred at room temperature for 5 hours. The reaction mixture was distributed between saturated aqueous solution of sodium bicarbonate and ethyl acetate. The ethyl acetate layer was washed with saturated brine and dried over magnesium sulfate, and the solvent was distilled off. The residue was purified by silica gel chromatography (eluent: ethyl acetate/hexane; from 6/1 to 4/1) to obtain colorless liquid (4.24 g, 54%). A mixed solution of the colorless liquid (0.94 g, 3.96 mmol) and 10% palladium-carbon (94 mg) in ethanol (10 ml) was stirred at room temperature under hydrogen atmosphere for 2 hours, and subjected to filtration. The filtrate was concentrated under reduced pressure to give the title compound (220 mg, 54%) as pale yellow liquid.

$^1$H NMR (CDCl$_3$) δ 1.15 (3H, d, J=6.6 Hz), 2.50 (3H, s), 2.90-2.99 (1H, m), 3.29-3.44 (5H, m).

Reference Example 25

Production of N-(4-(5-methylaminomethyl-1-(2,6-difluorobenzyl)-1,2,3,4-tetrahydro-2,4-dioxo-3-(4-methoxyphenyl)thieno[2,3-d]pyrimidin-6-yl)phenyl)-N'-methoxyureahydrochloride

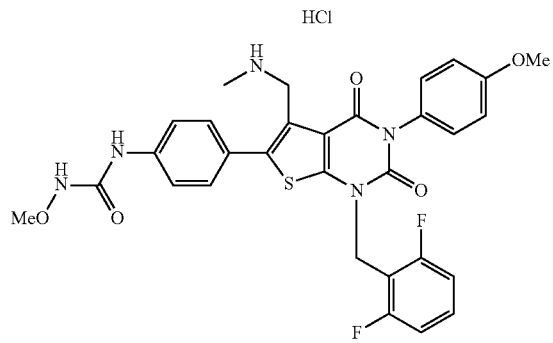 [SMILES: Cl ; CNCc1c(-c2ccc(NC(=O)NOC)cc2)sc2c1c(=O)n(-c1ccc(OC)cc1)c(=O)n2Cc1c(F)cccc1F]

A mixed solution of N-(4-(5-((benzyl(methyl)amino)methyl)-1-(2,6-difluorobenzyl)-3-(4-methoxyphenyl)-2,4-dioxo-1,2,3,4-tetrahydrothieno[2,3-d]pyrimidin-6-yl)phenyl)-N'-methoxyurea (2.0 g, 2.87 mmol) synthesized in Reference Example 19, 10%-palladium-carbon (200 mg), 1N hydrochloric acid (3 ml) in ethanol (40 ml) was stirred under hydrogen atmosphere at room temperature for 72 hours. The reaction mixture was subjected to filtration and the filtrate was concentrated to dryness to give the title compound (1.77 g, 96%) as white powders.

$^1$H NMR (CDCl$_3$) δ 2.73 (3H, s), 3.80 (3H, s), 3.85 (3H, s), 4.00-4.18 (2H, br), 5.35 (2H, s), 5.37 (2H, s), 6.90-7.08 (4H, m), 7.20-7.38 (5H, m), 7.61 (4H, s), 7.77 (1H, s), 7.95 (1H, s).

Reference Example 26

Production of N-(4-(5-(((1R)-1-phenylethyl(methyl)amino)methyl)-1-(2,6-difluorobenzyl)-1,2,3,4-tetrahydro-2,4-dioxo-3-phenylthieno[2,3-d]pyrimidin-6-yl)phenyl)-N'-methoxyurea

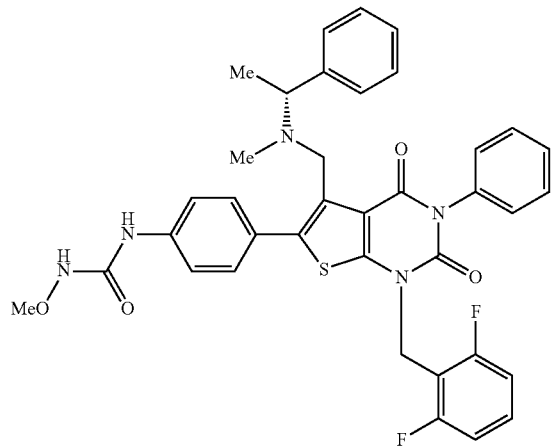

A solution of the compound (100 mg, 0.17 mmol) obtained in Reference Example 18, (R)-(+)-N-α-dimethylbenzylamine (28 mg, 0.21 mmol) and N-ethyldiisopropylamine (29 mg, 0.22 mmol) in DMF (200 ml) was stirred at room temperature for 24 hours. The reaction mixture was diluted with saturated aqueous solution of sodium bicarbonate and extracted with ethyl acetate. The organic layer was washed with saturated aqueous solution of sodium chloride, dried over magnesium sulfate and concentrated under reduced pressure. The residue was purified by silica gel chromatography (eluent: from ethyl acetate/chloroform (2/3) to chloroform/methanol (20/1)) and recrystallized from chloroform/diethylether to give the title compound (58 mg, 50%) as white crystals.

$^1$H NMR (CDCl$_3$) δ 1.25 (3H, d, J=6.6 Hz), 1.89 (3H, s), 3.82 (3H, s), 3.82-3.87 (1H, m), 3.91 (2H, d, J=4.5 Hz), 5.35 (2H, s), 6.91 (2H, t, J=8.3 Hz), 7.14-7.30 (9H, m), 7.43-7.61 (8H, m).

mp 192-193° C.

Reference Example 27

Production of N-(4-(5-((methyl((1S)-1-phenylethyl)amino)methyl)-1-(2,6-difluorobenzyl)-1,2,3,4-tetrahydro-2,4-dioxo-3-phenylthieno[2,3-d]pyrimidin-6-yl)phenyl)-N'-methoxyurea

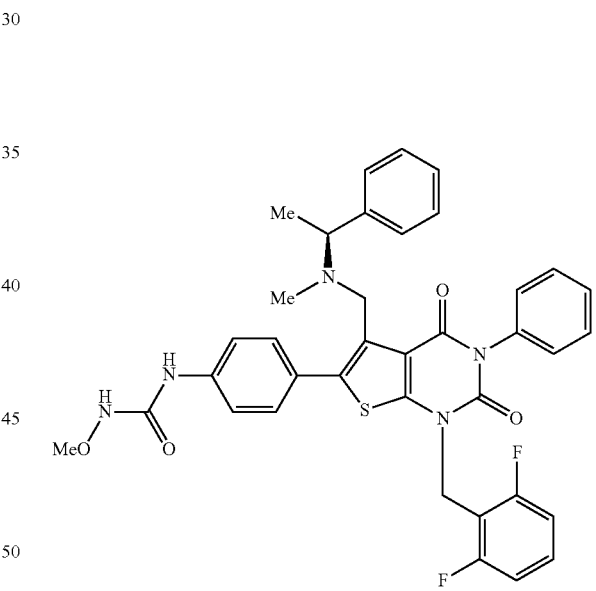

The similar reaction as described in Reference Example 26 by using compound (100 mg, 0.17 mmol) obtained in Reference Example 18 and (S)-(−)-N-α-dimethylbenzylamine (28 mg, 0.21 mmol) gave the title compound (61 mg, 53%) as white crystals.

$^1$H NMR (CDCl$_3$) δ 1.25 (3H, d, J=6.6 Hz), 1.89 (3H, s), 3.82 (3H, s), 3.82-3.90 (1H, m), 3.91 (2H, d, J=4.5 Hz), 5.35 (2H, s), 6.91 (2H, t, J=8.0 Hz), 7.19-7.30 (9H, m), 7.43-7.61 (8H, m).

mp 191-192° C.

Reference Example 28

Production of N-(4-(5-(((1R)-1-phenylethylamino)methyl)-1-(2,6-difluorobenzyl)-1,2,3,4-tetrahydro-2,4-dioxo-3-phenylthieno[2,3-d]pyrimidin-6-yl)phenyl)-N'-methoxyurea

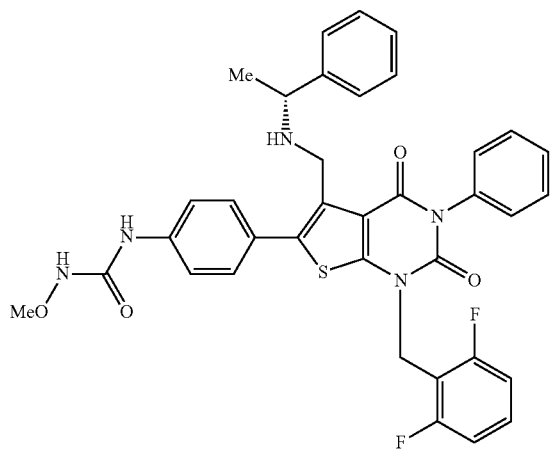 [SMILES: CONC(=O)Nc1ccc(-c2sc3c(c2CN[C@H](C)c2ccccc2)c(=O)n(-c2ccccc2)c(=O)n3Cc2c(F)cccc2F)cc1]

The similar reaction as described in Reference Example 26 by using compound (100 mg, 0.17 mmol) obtained in Reference Example 18 and (R)-(+)-1-phenylethylamine (25 mg, 0.21 mmol) gave the title compound (56 mg, 49%) as white crystals.

$^1$H NMR (CDCl$_3$) δ 1.32 (3H, d, J=6.6 Hz), 3.59 (1H, d, J=12.0 Hz), 3.65-3.82 (5H, m), 5.25-5.46 (2H, AB), 6.90 (2H, t, J=8.1 Hz), 7.11-7.59 (13H, m).

Elemental analysis C$_{36}$H$_{31}$F$_2$N$_5$O$_4$S.0.2H$_2$O
Calcd.: C, 64.41; H, 4.71; N, 10.43.
Found: C, 64.29; H, 4.64; N, 10.46.
mp 180-182° C.

Reference Example 29

Production of N-(4-(5-(((1S)-1-phenylethylamino)methyl)-1-(2,6-difluorobenzyl)-1,2,3,4-tetrahydro-2,4-dioxo-3-phenylthieno[2,3-d]pyrimidin-6-yl)phenyl)-N'-methoxyurea

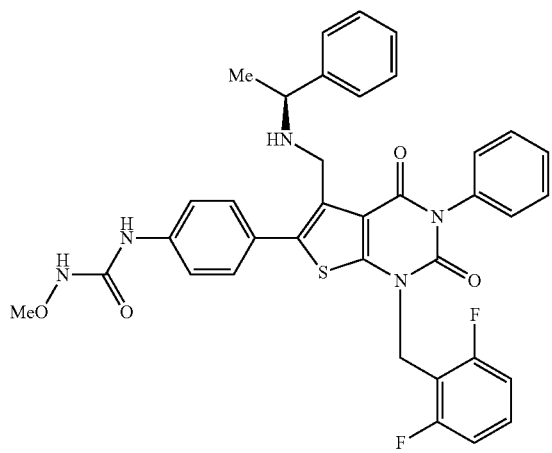

The similar reaction as described in Reference Example 26 by using the compound (100 mg, 0.17 mmol) obtained in Reference Example 18 and (S)-(−)-1-phenylethylamine (25 mg, 0.21 mmol) gave the title compound (56 mg, 49%) as white crystals.

$^1$H NMR (CDCl$_3$) δ 1.31 (3H, d, J=6.6 Hz), 3.58 (1H, d, J=12.3 Hz), 3.72-3.82 (5H, m), 5.24-5.46 (2H, AB), 6.90 (2H, t, J=8.1 Hz), 7.12 (1H, s), 7.16-7.37 (8H, m), 7.43-7.56 (4H, m).

Elemental analysis C$_{36}$H$_{31}$F$_2$N$_5$O$_4$S
Calcd.: C, 64.76; H, 4.68; N, 10.49.
Found: C, 64.46; H, 4.57; N, 10.60.
mp 182-185° C.

Reference Example 30

Production of N-(4-(5-((methyl(1-phenylpropyl)amino)methyl)-1-(2,6-difluorobenzyl)-1,2,3,4-tetrahydro-2,4-dioxo-3-phenylthieno[2,3-d]pyrimidin-6-yl)phenyl)-N'-methoxyurea

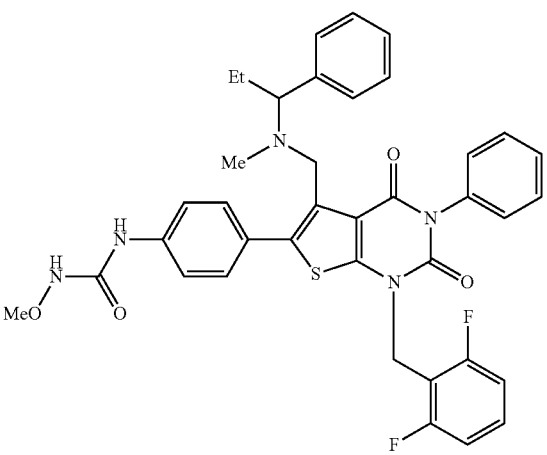 [SMILES: CCC(c1ccccc1)N(C)Cc1c(-c2ccc(NC(=O)NOC)cc2)sc2c1c(=O)n(-c1ccccc1)c(=O)n2Cc1c(F)cccc1F]

Under ice cooling, to a solution of 1-phenyl-1-propanol (1.0 g, 7.34 mmol) and N-ethyldiisopropylamine (1.42 g, 11.01 mmol) in dichloromethane (10 ml) was added methanesulfonyl chloride (690 μl, 8.81 mmol), and the mixture was stirred at room temperature for 5 hours. The reaction mixture was diluted with saturated aqueous solution of sodium bicarbonate and extracted with ethyl acetate. The extract was washed with saturated brine, dried over magnesium sulfate, and solvent was distilled off under reduced pressure. The residue was purified by silica gel chromatography (eluent:ethyl acetate/hexane:5/1) to give 1-chloro-1-phenylpropane (610 mg, 54%) as pale yellow liquid.

The similar reaction as described in Reference Example 26 by using the compound (100 mg, 0.17 mmol) obtained in Reference Example 15 and the 1-chloro-1-phenylpropane (32 mg, 0.21 mmol) obtained above gave the title compound (45 mg, 38%) as white crystals.

$^1$H NMR (CDCl$_3$) δ 0.67 (3H, t, J=7.2 Hz), 1.63-1.91 (5H, m), 3.52-3.57 (1H, m), 3.73-3.93 (5H, m), 3.91 (2H, d, J=4.5 Hz), 5.35 (2H, s), 6.91 (2H, t, J=8.1 Hz), 7.08-7.34 (8H, m), 7.41-7.55 (8H, m), 7.64 (1H, s).

mp 171-172° C.

Reference Example 31

Production of methyl (((1-(2,6-difluorobenzyl)-6-(4-(((methoxyamino)carbonyl)amino)phenyl)-2,4-dioxo-3-phenyl-1,2,3,4-tetrahydrothieno[2,3-d]pyrimidin-5-ylmethyl)(methyl)amino)(phenyl)acetic acid

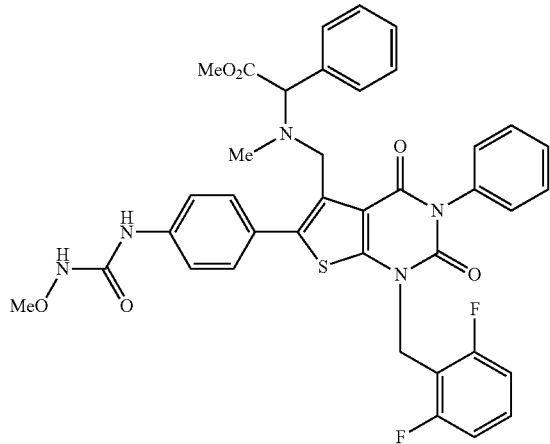 [SMILES: CONC(=O)Nc1ccc(-c2sc3c(c2CN(C)C(C(=O)OC)c2ccccc2)c(=O)n(-c2ccccc2)c(=O)n3Cc2c(F)cccc2F)cc1]

The similar reaction as described in Example 20 by using the compound (150 mg, 0.17 mmol) obtained in Reference Example 15 and α-bromophenylmethyl acetate (71 mg, 0.31 mmol) gave the title compound (73 mg, 39%) as white crystals.

$^1$H NMR (CDCl$_3$) δ 2.08 (3H, s), 3.54 (32H, s), 3.79 (3H, s), 3.89-4.20 (2H, AB), 4.67 (1H, s), 5.35 (2H, brs), 6.92 (2H, t, J=8.2 Hz), 7.22-7.37 (6H, m), 7.44-7.56 (7H, m) 7.71 (2H, d, J=8.0 Hz).

Elemental analysis C$_{38}$H$_{33}$F$_2$N$_5$O$_6$S
Calcd.: C, 62.89; H, 4.58; N, 9.65.
Found: C, 62.70; H, 4.61; N, 9.78.
mp 147-149° C.

Reference Example 32

Production of N-(4-(1-(2,6-difluorobenzyl)-5-((2-methoxy-1-phenylethyl(methyl)amino)methyl)-1,2,3,4-tetrahydro-2,4-dioxo-3-phenylthieno[2,3-d]pyrimidin-6-yl)phenyl)-N'-methoxyurea

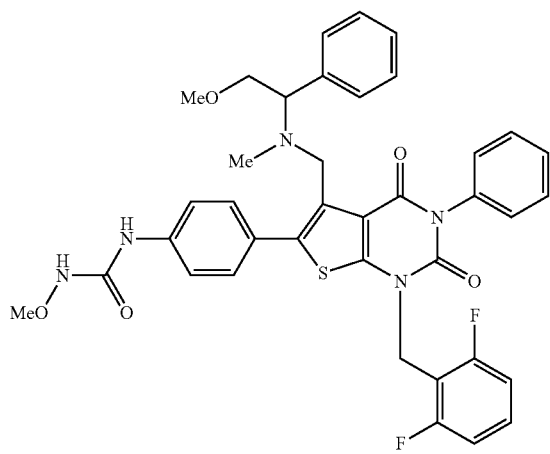 [SMILES: COCC(c1ccccc1)N(C)Cc1c(-c2ccc(NC(=O)NOC)cc2)sc2c1c(=O)n(-c1ccccc1)c(=O)n2Cc1c(F)cccc1F]

A solution of methylphenethylether (1.0 g, 7.34 mmol), NBS (1.96 g, 11.01 mmol) and AIBN (240 mg, 1.47 mmol) in carbon tetrachloride (30 ml) was heated under reflux for 2 hours. After cooling, the reaction mixture was diluted with saturated aqueous solution of sodium bicarbonate and extracted with chloroform. The extract was washed with saturated brine, dried over magnesium sulfate and concentrated under reduced pressure to give a crude 2-methoxy-1-phenyl-bromoethane (1.33 g, 84%) as brown liquid.

The similar reaction as described in Example 14 by using the compound (200 mg, 0.34 mmol) obtained in Reference Example 15 and the crude bromide (50 mg) obtained above gave the title compound (42 mg, 18%) as white crystals.

$^1$H NMR (CDCl$_3$) δ 1.97 (3H, s), 3.24 (3H, s), 3.55-3.61 (1H, m), 3.80 (3H, s), 3.86-3.96 (3H, m), 4.67 (1H, s), 5.36 (2H, s), 6.91 (2H, t, J=8.1 Hz), 7.14-7.31 (8H, m), 7.33-7.56 (8H, m), 7.63 (1H, s).

Elemental analysis C$_{38}$H$_{35}$F$_2$N$_5$O$_5$S.0.2H$_2$O
Calcd.: C, 63.80; H, 4.99; N, 9.79.
Found: C, 63.64; H, 4.95; N, 9.89.
mp 169-172° C.

Reference Example 33

Production of N-(4-(1-(2,6-difluorobenzyl)-5-((methyl(1-pyridin-2-ylethyl)amino)methyl)-1,2,3,4-tetrahydro-2,4-dioxo-3-phenylthieno[2,3-d]pyrimidin-6-yl)phenyl)-N'-methoxyurea

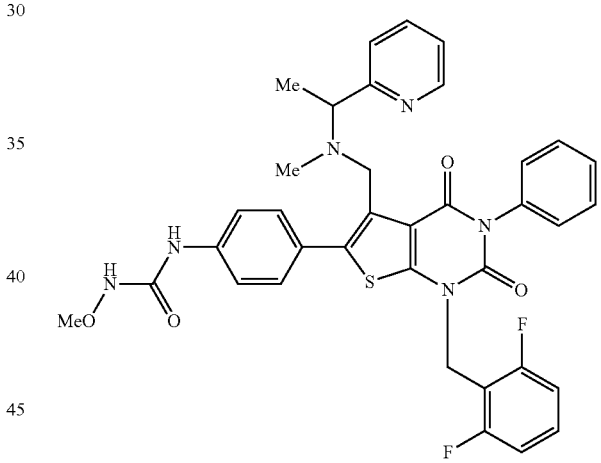

A solution of 2-ethylpyridine (10.0 g, 93.34 mmol), N-bromosuccinimide (17.44 g, 98.00 mmol) and azobisisobutyronitrile (1.53 g, 9.33 mmol) in carbon tetrachloride (300 ml) was stirred at 90° C. for 1 hour. After cooling, the reaction mixture was subjected to filtration. The filtrate was washed with saturated aqueous solution of sodium bicarbonate and saturated aqueous solution of sodium chloride, dried over magnesium sulfate and concentrated. The residue was purified by silica gel chromatography to give a bromide (15.68 g, 90%) as pale yellow liquid.

The similar reaction as described in Example 14 by using the compound (160 mg, 0.26 mmol) obtained in Reference Example 15 and the above bromide (62 mg, 0.33 mmol) obtained above gave the title compound (133 mg, 75%) as white crystals.

$^1$H NMR (CDCl$_3$) δ 1.30 (3H, d, J=6.9 Hz), 1.92 (3H, s), 3.80 (3H, s), 4.00 (2H, s), 4.04 (1H, q, J=6.6 Hz), 5.35 (2H, s), 6.91 (2H, t, J=8.0 Hz), 7.02-7.06 (1H, m), 7.24-7.30 (4H, m), 7.40-7.54 (8H, m), 7.65 (1H, s), 8.44 (1H, d, J=5.7 Hz).

mp 146-148° C.

The title compound (40 mg) was optically resolved by a preparative HPLC by using CHIRALPAK AD (50 mmI.D.× 500 mL), in which mobile phase is hexane/2-propanol (=3/2), to obtain 19 mg of an optical isomer having an retention time of 25 minutes (99.9% ee) and 19 mg of another isomer having retention time of 29 minutes (99.0% ee) in an analysis using CHIRALPAK AD (4.6 mmI.D.×250 mL), both of which are white powders.

Reference Example 34

Production of N-(4-(1-(2,6-difluorobenzyl)-5-(((2-methoxy-1-methylethyl)methylamino)methyl)-1,2,3,4-tetrahydro-2,4-dioxo-3-phenylthieno[2,3-d]pyrimidin-6-yl)phenyl)-N'-methoxyurea

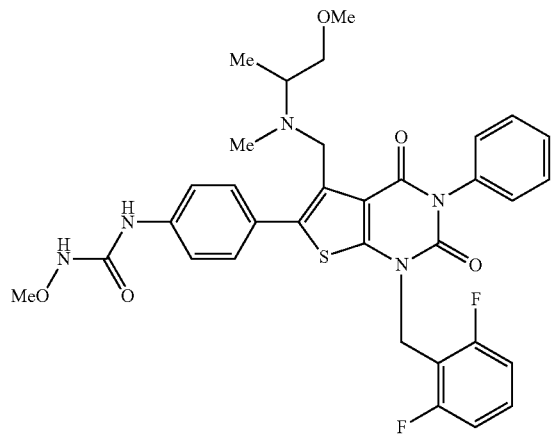 [SMILES: COCC(C)N(C)Cc1c(-c2ccc(NC(=O)NOC)cc2)sc2c1c(=O)n(-c1ccccc1)c(=O)n2Cc1c(F)cccc1F]

The similar reaction as described in Reference Example 26 by using the compound (100 mg, 0.17 mmol) obtained in Reference Example 18 and the compound (21 mg, 0.21 mmol) obtained in Reference Example 24 gave the title compound (24 mg, 21%) as white crystals.

$^1$H NMR (CDCl$_3$) δ 0.90 (3H, d, J=6.3 Hz), 2.04 (3H, s), 3.06-3.16 (2H, m), 3.26 (3H, s), 3.40-3.46 (1H, m), 3.51-3.98 (4H, m), 5.35 (2H, s), 6.90 (2H, t, J=8.4 Hz), 7.09 (1H, s), 7.25-7.32 (5H, m), 7.39-7.60 (6H, m).

Elemental analysis C$_{33}$H$_{33}$F$_2$N$_5$O$_5$S.0.3H$_2$O

Calcd.: C, 60.50; H, 5.17; N, 10.69.

Found: C, 60.28; H, 5.21; N, 10.53.

mp 154-155° C.

The title compound (48 mg) was optically resolved by preparative HPLC by using CHIRALPAK AD (50 mmI.D.× 500 mL), in which mobile phase is hexane/2-propanol (65/35), to obtain 22 mg of an optical isomer having an retention time of 49 minutes (99.0% ee) and 21 mg of another isomer having retention time of 54 minutes (99.0% ee) in an analysis using CHIRALPAK OD (4.6 mmI.D.×250 mL), both of which are white powders.

Reference Example 35

Production of N-(4-(1-(2,6-difluorobenzyl)-5-((methyl(1-pyridin-2-ylethyl)amino)methyl)-1,2,3,4-tetrahydro-2,4-dioxo-3-(pyridin-2-yl)thieno[2,3-d]pyrimidin-6-yl)phenyl)-N'-methoxyurea

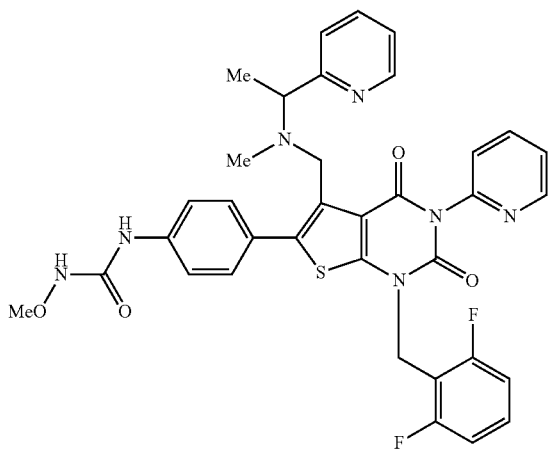

The similar reaction as described in Reference Example 33 by using the compound (100 mg, 0.17 mmol) obtained in Reference Example 14 gave the title compound (31 mg, 27%) as white crystals.

$^1$H NMR (CDCl$_3$) δ 1.30 (3H, d, J=6.9 Hz), 1.92 (3H, s), 3.80 (3H, s), 3.98-4.10 (3H, m), 5.33 (2H, brs), 6.90 (2H, t, J=8.1 Hz), 7.01-7.06 (1H, m), 7.23-7.42 (5H, m), 7.49-7.56 (4H, m) 7.65 (1H, s), 7.90 (1H, t, J=7.8 Hz), 8.44 (1H, d, J=3.9 Hz), 8.68 (1H, d, J=5.7 Hz).

mp 143-144° C.

The title compound (20 mg) was optically resolved by a preparative HPLC by using CHIRALPAK AD (50 mmI.D.× 500 mL), in which mobile phase is hexane/2-propanol (1/1), to obtain 10 mg of an optical isomer having an retention time of 23 minutes (99.9% ee) and 11 mg of another isomer having retention time of 28 minutes (99.2% ee) in an analysis using CHIRALPAK AD (4.6 mmI.D.×250 mL), each of which is colorless oily substance.

Reference Example 36

Production of N-(4-(1-(2,6-difluorobenzyl)-3-(4-hydroxycyclohexyl)-5-((methyl(1-pyridin-2-ylethyl)amino)methyl)-1,2,3,4-tetrahydro-2,4-dioxothieno[2,3-d]pyrimidin-6-yl)phenyl)-N'-methoxyurea

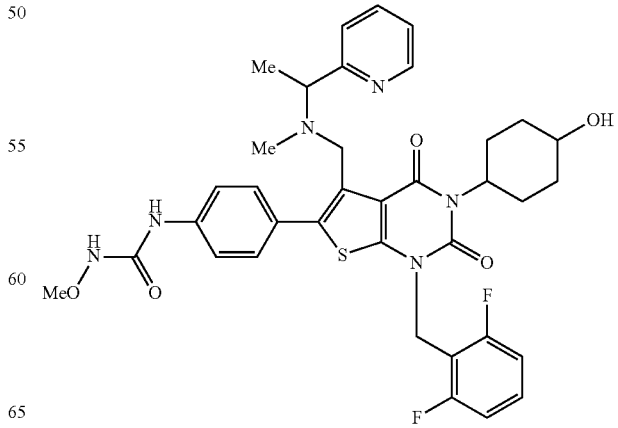

The similar reaction as described in Reference Example 33 by using the compound (100 mg, 0.17 mmol) obtained in Reference Example 23 gave the title compound (17 mg, 14%) as white crystals.

$^1$H NMR (CDCl$_3$) δ 1.35 (3H, d, J=6.9 Hz), 1.43-1.54 (2H, m), 1.91 (3H, s), 2.09 (2H, d, J=12.3 Hz), 2.65 (2H, q, J=12.8 Hz), 3.73-3.81 (4H, m), 3.98-4.13 (3H, m), 4.60 (1H, t, J=12.0 Hz), 5.28 (2H, brs), 6.88 (2H, t, J=8.1 Hz), 6.89-7.08 (1H, m), 7.22-7.31 (3H, m), 7.40-7.54 (4H, m) 7.62 (1H, s), 8.45 (1H, d, J=4.89 Hz).

mp 144-145° C.

Reference Example 37

Production of N-(4-(5-(((1R)-1-phenylethylamino)methyl)-1-(2,6-difluorobenzyl)-3-(4-hydroxycyclohexyl)-1,2,3,4-tetrahydro-2,4-dioxothieno[2,3-d]pyrimidin-6-yl)phenyl)-N'-methoxyurea

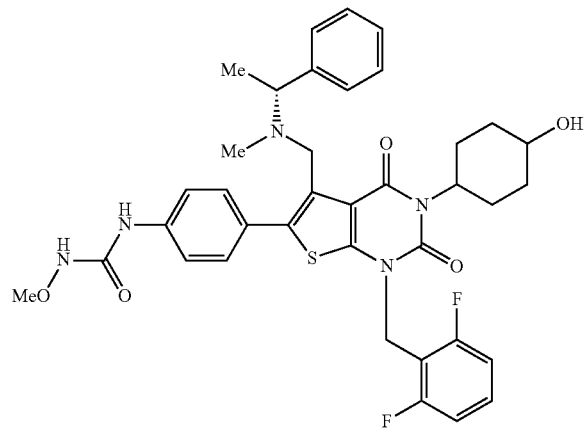 [SMILES: CONC(=O)Nc1ccc(-c2sc3c(c2CN(C)[C@H](C)c2ccccc2)c(=O)n(C2CCC(O)CC2)c(=O)n3Cc2c(F)cccc2F)cc1]

The similar reaction as described in Reference Example 26 by using the compound (180 mg, 0.30 mmol) obtained in Reference Example 20 gave the title compound (77 mg, 37%) as white crystals.

$^1$H NMR (CDCl$_3$) δ 1.30 (3H, d, J=6.6 Hz), 1.43-1.57 (2H, m), 1.71 (2H, d, J=9.9 Hz), 1.88 (3H, s), 2.04-2.15 (2H, m), 2.62-2.71 (2H, m), 3.70-3.93 (7H, m), 4.90-5.10 (1H, m), 5.28 (2H, s), 6.89 (2H, t, J=8.1 Hz), 7.11-7.30 (8H, m), 7.51 (3H, s), 7.60 (1H, s).

Elemental analysis C$_{37}$H$_{39}$F$_2$N$_5$O$_5$S.1.5H$_2$O

Calcd.: C, 60.81; H, 5.79; N, 9.58.

Found: C, 60.77; H, 5.72; N, 9.41.

mp 137-138° C.

Reference Example 38

Production of N-(4-(5-((methyl((1R)-1-phenylethyl)amino)methyl)-1-(2,6-difluorobenzyl)-1,2,3,4-tetrahydro-2,4-dioxo-3-pyridin-2-ylthieno[2,3-d]pyrimidin-6-yl)phenyl)-N'-methoxyurea

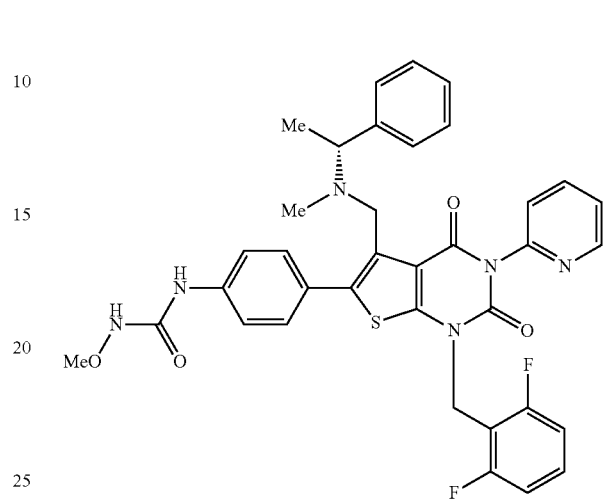

The similar reaction as described in Reference Example 26 by using the compound (270 mg, 0.46 mmol) obtained in Reference Example 22 gave the title compound (178 mg, 57%) as white crystals.

$^1$H NMR (CDCl$_3$) δ 1.27 (3H, d, J=6.8 Hz), 1.91 (3H, s), 2.04-2.15 (2H, m), 2.62-2.71 (2H, m), 3.75-4.00 (4H, m), 5.30 (2H, brs), 6.91 (2H, t, J=8.1 Hz), 7.13-7.42 (10H, m), 7.54 (2H, d, J=8.6 Hz), 7.61 (2H, d, J=8.5 Hz), 7.91 (1H, t, J=7.7 Hz), 8.70 (1H, d, J=4.8 Hz).

Elemental analysis C$_{36}$H$_{32}$F$_2$N$_6$O$_4$S.0.5H$_2$O

Calcd.: C, 62.51; H, 4.81; N, 12.15.

Found: C, 62.34; H, 4.71; N, 12.12.

mp 168-170° C.

Reference Example 39

Production of N-(4-(5-((methyl((1R)-1-phenylethyl)amino)methyl)-1-(2,6-difluorobenzyl)-1,2,3,4-tetrahydro-2,4-dioxo-3-(5-fluoropyridin-2-yl)thieno[2,3-d]pyrimidin-6-yl)phenyl)-N'-methoxyurea

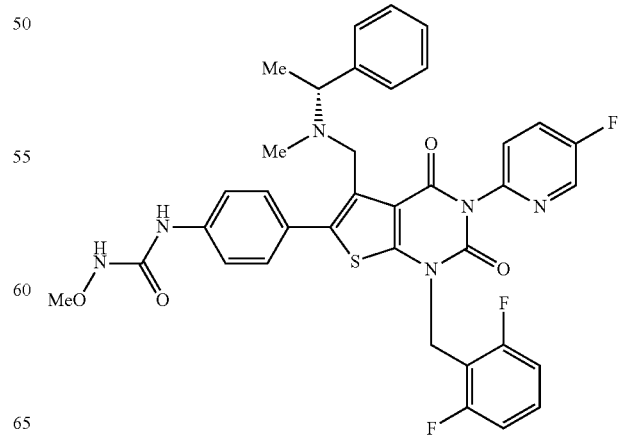

The similar reaction as described in Reference Example 26 by using the compound (280 mg, 0.46 mmol) obtained in Reference Example 21 gave the title compound (187 mg, 58%) as white crystals.

$^1$H NMR (CDCl$_3$) δ 1.27 (3H, d, J=6.6 Hz), 1.90 (3H, s), 3.78-3.99 (5H, m), 5.33 (2H, brs), 6.91 (2H, t, J=8.1 Hz), 7.12-7.38 (9H, m), 7.51-7.63 (5H, m), 8.52 (1H, d, J=3.0 Hz).

Elemental analysis C$_{36}$H$_{31}$F$_3$N$_6$O$_4$S.0.2H$_2$O
Calcd.: C, 61.39; H, 4.49; N, 11.93.
Found: C, 61.22; H, 4.56; N, 11.96.
mp 128-130° C.

Reference Example 40

Production of N-(4-(5-(((2-methoxyethyl)methylamino)methyl)-1-(2,6-difluorobenzyl)-1,2,3,4-tetrahydro-2,4-dioxo-3-(4-methoxyphenyl)thieno[2,3-d]pyrimidin-6-yl)phenyl)-N'-methoxyurea

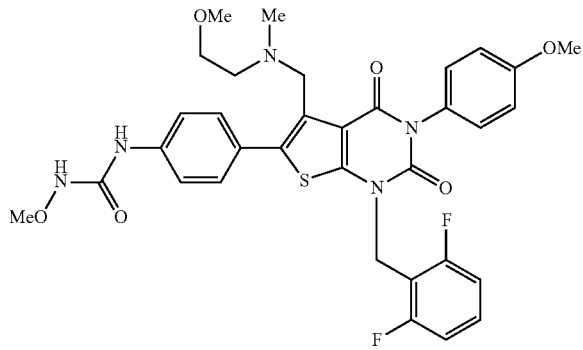 [SMILES: COCCN(C)Cc1c(-c2ccc(NC(=O)NOC)cc2)sc2c1c(=O)n(-c1ccc(OC)cc1)c(=O)n2Cc1c(F)cccc1F]

The similar reaction as described in Example 4 by using the compound (800 mg, 1.24 mmol) obtained in Reference Example 25 and 2-bromoethylethylether (207 mg, 1.49 mmol) gave the title compound (407 mg, 58%) as white solids.

$^1$H NMR (CDCl$_3$) δ 2.13 (3H, s), 2.64 (2H, t, J=5.7 Hz), 3.27 (3H, s), 3.41 (2H, t, J=5.6 Hz), 3.82 (3H, s), 3.84 (3H, s), 5.36 (2H, s), 6.92 (2H, t, J=8.1 Hz), 7.01 (2H, d, J=8.7 Hz), 7.11 81H, s), 7.19 (2H, d, J=8.7 Hz), 7.26-7.33 (3H, m), 7.53-7.70 (5H, m).
mp 181-184° C.

Reference Example 41

Production of 1-amino-2-methyl-2-propanol

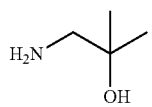

To a suspension of lithium aluminum hydride (2.85 g, 75 mmol) in diethylether (120 ml) was dropwise added a solution of acetone cyanhydrin (4.73 g, 50 mmol) in diethylether (30 ml) under ice cooling. The reaction liquid was stirred at room temperature for 4 hours. To the reaction liquid were dropwise added water (2.85 ml), 1N sodium hydroxide (2.85 ml) and water (8.55 ml), successively. Insoluble matters are filtered off, and the filtrate was concentrated to give the title compound (1.32 g, 30%) as colorless oily substance.

$^1$H-NMR (CDCl$_3$) δ: 1.17 (6H, s), 2.60 (2H, s).

Reference Example 42

Production of tert-butyl(3-ethoxy-2,2-dimethylpropoxy)dimethylsilane

To a solution of 3-{[tert-butyl(dimethyl)silyl]oxy}-2,2-dimethylpropan-1-ol (Registry No. 117932-70-4) (2.18 g, 10 mmol) in THF (30 ml) were added triethylamine (1.67 ml, 12 mmol) and methanesulfonyl chloride (0.85 ml, 11 mmol) under ice cooling. The reaction liquid was stirred at room temperature for 30 minutes, and to the reaction liquid was added an aqueous solution of sodium bicarbonate. The mixture was extracted with ethyl acetate. The organic layer was washed with brine, dried over anhydrous magnesium sulfate and concentrated under reduced pressure to give the title compound (2.98 g, quant.) as colorless oily substance.

$^1$H-NMR (CDCl$_3$) δ: 0.04 (6H, s), 0.89 (9H, s), 0.93 (6H, s), 2.98 (3H, s), 3.34 (9H, s), 4.00 (2H, s).

Reference Example 43

Production of 2-(3-{[tert-butyl(dimethyl)silyl]oxy}-2,2-dimethylpropyl)-1H-isoindol-1,3(2H)-dione

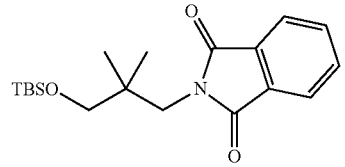 [SMILES: CC(C)(CO[Si](C)(C)C(C)(C)C)CN1C(=O)c2ccccc2C1=O]

To a solution of compound (2.96 g, 10 mmol) obtained in Reference Example 42 in DMF (10 ml) was added potassium phthalimide (1.85 g, 10 mmol). The reaction liquid was stirred at 140° C. for 30 hours, and water was added. The mixture was extracted with ethyl acetate. The organic layer was washed with brine, dried over anhydrous magnesium sulfate and concentrated under reduced pressure. The residue was purified by silica gel column chromatography (eluent; ethyl acetate/hexane=1/10) to give the title compound (2.79 g, 80%) as pale yellow oily substance.

$^1$H-NMR (CDCl$_3$) δ: 0.01 (6H, s), 0.87 (9H, s), 0.93 (6H, s), 3.39 (2H, s), 3.61 (2H, s), 7.65-7.75 (2H, m), 7.8-7.9 (2H, m).

Reference Example 44

Production of 3-amino-2,2-dimethylpropan-1-ol hydrochloride

A mixture of compound (1.395 g, 4.0 mmol) obtained in Reference Example 43, concentrated hydrochloric acid (10 ml), acetic acid (7 ml) and water (10 ml) was refluxed for 24 hours. The reaction liquid was concentrated and water was added. The precipitated phthalic acid was filtered off and filtrate was concentrated. The residue was recrystallized from ethyl acetate to give the title compound (257.2 mg, 46%) as pale purple crystals.

$^1$H-NMR(CDCl$_3$+CD$_3$OD) δ: 2.91 (2H, brs), 3.38 (6H, brs), 3.52 (2H, brs).

Reference Example 45

Production of [1-({[tert-butyl(dimethyl)silyl]oxy}methyl)cyclopropyl]methanol

To a solution of lithium aluminum hydride (9.34 g, 246 mmol) in THF (150 ml) was dropwise added a solution of dimethylcyclopropane-1,1-dicarboxylate (25.95 g, 164.1 mmol) in THF (150 ml) under ice cooling. The solution was stirred at 0° C. for 2 hours, and to the solution were slowly added water (9.5 ml), 15% aqueous solution of NaOH (9.5 ml) and water (30 ml), successively. Insoluble matters were filtered off, and the filtrate was concentrated to give cyclopropane-1,1-dimethylmethanol as colorless oily substance.

To a solution of the above oily substance in 1,2-dimethoxyethane (150 ml) was added sodium hydride (60% oil, 6.56 g, 164 mmol), and the mixture was stirred at room temperature for 1 hour. To the reaction liquid was dropwise added a solution of tert-butylchlorodimethylsilane (24.7 g, 164 mmol) in 1,2-dimethoxyethane (100 ml), and the mixture was stirred at room temperature over night. The reaction liquid was poured into water and extracted twice with ethyl acetate. The organic layer was dried over magnesium sulfate and concentrated under reduced pressure. The residue was purified by silicagel column chromatography (eluent; ethyl acetate/hexane=1/15-1/9) to give the title compound (28.19 g, 79%) as colorless oily substance.

$^1$H-NMR (CDCl$_3$) δ: 0.07 (6H, s), 0.45-0.54 (4H, m), 0.91 (9H, s), 2.35 (1H, brs), 3.56 (2H, s), 3.61 (2H, s).

IR (neat) 3361, 2953, 2856, 1466, 1254, 1088, 1030, 837, 777 cm$^{-1}$.

Reference Example 46

Production of tert-butyl{[1-(ethoxymethyl)cyclopropyl]methoxy}dimethylsilane

The similar reaction as described in Reference Example 42 by using the compound (4.33 g, 20 mmol) obtained in Reference Example 45 gave the title compound (5.71 g, 97%) as colorless oily substance.

$^1$H-NMR (CDCl$_3$) δ: 0.05 (6H, s), 0.55-0.65 (4H, m), 0.89 (9H, s), 3.01 (3H, s), 3.52 (2H, s), 4.17 (2H, s).

Reference Example 47

Production of 2-{[1-({[tert-butyl(dimethyl)silyl]oxy}methyl)cyclopropyl]methyl}-1H-isoindol-1,3(2H)-dione

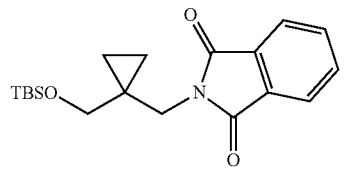 [SMILES: CC(C)(C)[Si](C)(C)OCC1(CN2C(=O)c3ccccc3C2=O)CC1]

The similar reaction as described in Reference Example 43 by using the compound (5.71 g, 19.39 mmol) obtained in Reference Example 46 gave the title compound (5.02 g, 75%) as colorless oily substance.

$^1$H-NMR (CDCl$_3$) δ: −0.07 (6H, s), 0.45-0.55 (2H, m), 0.65-0.75 (2H, m), 0.79 (9H, s), 3.53 (2H, s), 3.74 (2H, s), 7.65-7.75 (2H, m), 7.80-7.90 (2H, m).

Reference Example 48

Production of 1-[1-({[tert-butyl(dimethyl)silyl]oxy}methyl)cyclopropyl]methanamine

To a solution of compound (2.0 g, 5.79 mmol) obtained in Reference Example 47 in ethanol (20 ml) was added hydrazine monohydrate (0.42 ml, 8.68 mmol) and the mixture was refluxed for 2 hours. Insoluble matters were filtered off and the filtrate was concentrated. The residue was distributed between ethyl acetate and aqueous solution of 1N-sodium hydroxide, and extracted with ethyl acetate. The organic layer was washed with brine, dried over magnesium sulfate and concentrated to give the title compound (1.15 g, 92%) as pale yellow oily substance.

$^1$H-NMR (CDCl$_3$) δ: 0.0-0.1 (6H, m), 0.3-0.4 (4H, m), 0.85 (9H, s), 2.61 (2H, s), 3.49 (2H, s).

Reference Example 49

Production of N-(4-(5-chloromethyl-1-(2,6-difluorobenzyl)-1,2,3,4-tetrahydro-2,4-dioxo-3-(6-methoxy-3-pyridinyl)thieno[2,3-d]pyrimidin-6-yl)phenyl)-N'-methoxyurea

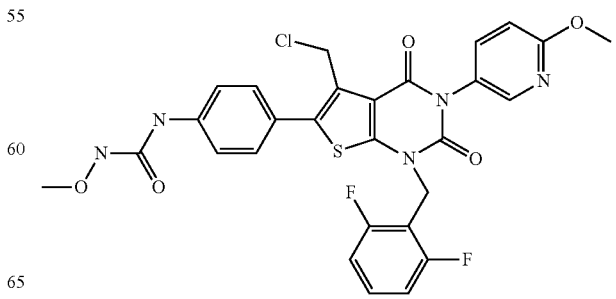

The similar reaction as described in Reference Example 18 by using the N-(4-(1-(2,6-difluorobenzyl)-5-(((2-methoxyethyl)(methyl)amino)methyl)-3-(6-methoxy-3-pyridinyl)-2,4-dioxo-1,2,3,4-tetrahydrothieno[2,3-d]pyrimidin-6-yl)phenyl)-N'-methoxyurea (49.3 mg, 0.074 mmol) gave the title compound (44.1 mg, quant.) as white powders.

¹H-NMR (CDCl₃) δ: 3.83 (3H, s), 3.97 (3H, s), 4.83 (2H, s), 5.37 (2H, s), 6.87 (1H, d, J=9.0 Hz), 6.94 (2H, t, J=8.4 Hz), 7.13 (1H, s), 7.25-7.35 (1H, m), 7.5-7.6 (3H, m), 7.52 (2H, d, J=9.0 Hz), 7.66 (1H, s), 8.1-8.15 (1H, m).

Reference Example 50

Production of N-(4-(5-chloromethyl-1-(2,6-difluorobenzyl)-1,2,3,4-tetrahydro-2,4-dioxo-3-(6-methoxy-3-pyridazinyl)thieno[2,3-d]pyrimidin-6-yl)phenyl)-N'-methoxyurea

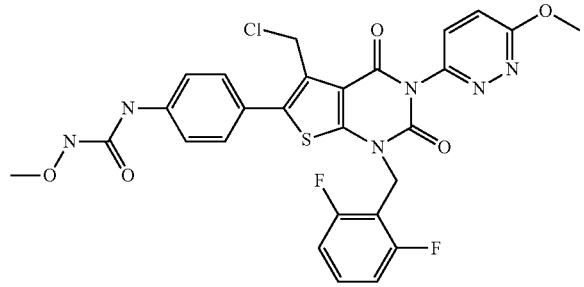

The similar reaction as described in Reference Example 18 by using the N-(4-(1-(2,6-difluorobenzyl)-5-(((2-methoxyethyl)(methyl)amino)methyl)-3-(6-methoxy-3-pyridazinyl)-2,4-dioxo-1,2,3,4-tetrahydrothieno[2,3-d]pyrimidin-6-yl) phenyl)-N'-methoxyurea (1.34 g, 2 mmol) gave the title compound (888.5 mg, 71%) as pale yellow powders.

¹H-NMR (CDCl₃) δ: 3.83 (3H, s), 4.19 (3H, s), 4.7-4.9 (2H, brm), 5.3-5.45 (2H, m), 6.93 (2H, t, J=8.0 Hz), 7.14 (1H, d, J=9.0 Hz), 7.16 (1H, s), 7.2-7.4 (1H, m), 7.42 (1H, d, J=9.0 Hz), 7.52 (2H, d, J=8.6 Hz), 7.62 (2H, d, J=8.6 Hz), 7.69 (1H, s).

Reference Example 51

Production of N-(4-(1-(2,6-difluorobenzyl)-3-(4-hydroxycyclohexyl)-5-((methylamino)methyl)-2,4-dioxo-1,2,3,4-tetrahydrothieno[2,3-d]pyrimidin-6-yl)phenyl)-N'-methoxyurea

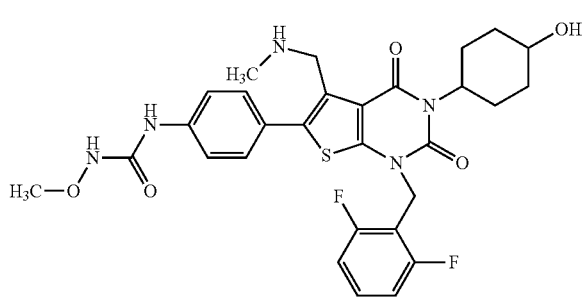 [SMILES: CNCc1c(-c2ccc(NC(=O)NOC)cc2)sc2c1c(=O)n(C1CCC(O)CC1)c(=O)n2Cc1c(F)cccc1F]

The similar reaction as described in Reference Example 14 by using the compound (1.75 g, 2.54 mmol) obtained in Example 69 described later gave the title compound (1.60 g, quant.) as colorless crystals.

¹H-NMR (CDCl₃) δ: 1.4-1.9 (3H, m), 2.0-2.2 (2H, m), 2.40 (3H, s), 2.5-2.75 (2H, m), 3.77 (2H, s), 3.7-3.85 (1H, m), 3.82 (3H, s), 4.9-5.1 (1H, m), 5.30 (2H, s), 6.90 (2H, t, J=8.0 Hz), 7.2-7.35 (2H, m), 7.38 (2H, d, J=8.4 Hz), 7.54 (2H, d, J=8.4 Hz), 7.61 (1H, s).

Reference Example 52

Production of N-(4-(1-(2,6-difluorobenzyl)-3-(2-hydroxypropyl)-5-((methylamino)methyl)-2,4-dioxo-1,2,3,4-tetrahydrothieno[2,3-d]pyrimidin-6-yl)phenyl)-N'-methoxyurea

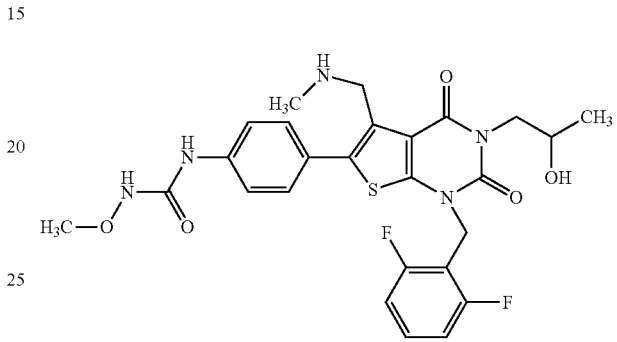

The similar reaction as described in Reference Example 14 by using the compound (360 mg, 0.554 mmol) obtained in Example 72 described later gave the title compound (281 mg, 91%) as white powders.

¹H-NMR (CDCl₃) δ: 1.29 (3H, d, J=6.0 Hz), 2.39 (3H, s), 3.80 (2H, s), 3.82 (3H, s), 4.1-4.25 (3H, m), 5.34 (2H, s), 6.91 (2H, t, J=8.2 Hz), 7.25-7.35 (2H, m), 7.40 (2H, d, J=8.6 Hz), 7.56 (2H, d, J=8.6 Hz), 7.63 (1H, s).

Reference Example 53

Production of N-(4-(1-(2,6-difluorobenzyl)-3-(2-hydroxy-2-methylpropyl)-5-((methylamino)methyl)-2,4-dioxo-1,2,3,4-tetrahydrothieno[2,3-d]pyrimidin-6-yl)phenyl)-N'-methoxyurea

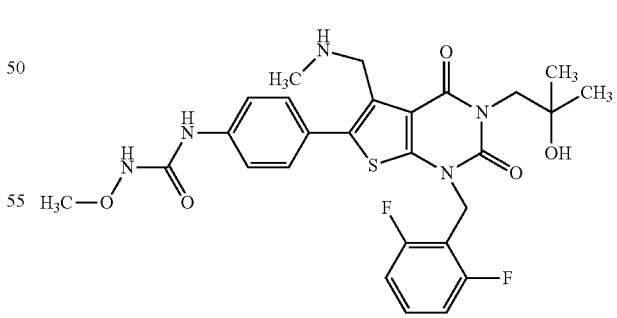

The similar reaction as described in Reference Example 14 by using the compound (310 mg, 0.467 mmol) obtained in Example 73 described later gave the title compound (241 mg, 90%) as white powders.

¹H-NMR (CDCl₃) δ: 1.28 (6H, s), 2.38 (3H, s), 3.80 (2H, s), 3.82 (3H, s), 3.88 (1H, brs), 4.26 (2H, s), 5.37 (2H, s), 6.91

(2H, t, J=8.1 Hz), 7.25-7.35 (2H, m), 7.40 (2H, d, J=8.6 Hz), 7.56 (2H, d, J=8.6 Hz), 7.63 (1H, s).

Reference Example 54

Production of N-(4-(1-(2,6-difluorobenzyl)-3-(6-methoxy-3-pyridazinyl)-5-((methylamino)methyl)-2,4-dioxo-1,2,3,4-tetrahydrothieno[2,3-d]pyrimidin-6-yl)phenyl)-N'-methoxyurea

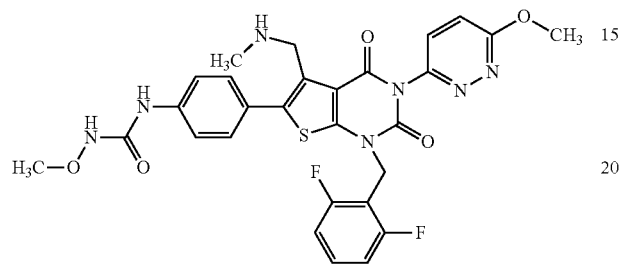

The similar reaction as described in Reference Example 14 by using the compound (320 mg, 0.457 mmol) obtained in Example 77 described later gave the title compound (138 mg, 50%) as white powders.

¹H-NMR (CDCl₃) δ: 2.34 (3H, s), 3.77 (2H, s), 3.82 (3H, s), 4.19 (3H, s), 5.35 (2H, s), 6.92 (2H, t, J=8.0 Hz), 7.14 (1H, t, J=9.2 Hz), 7.25-7.5 (5H, m), 7.57 (2H, d, J=8.6 Hz), 7.64 (1H, s).

Reference Example 55

Production of N-{4-[1-(2,6-difluorobenzyl)-5-[(dimethylamino)methyl]-3-(4-methoxyphenyl)-2,4-dioxo-1,2,3,4-tetrahydrothieno[2,3-d]pyrimidin-6-yl]phenyl}-N'-methoxyurea

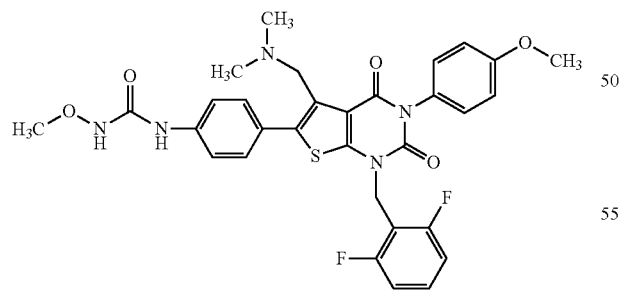

The similar reaction as described in Reference Example 26 by using the compound (130 mg, 0.192 mmol) obtained in Reference Example 19 described later and a solution of dimethylamine in THF (0.96 ml, 1.92 mmol) gave the title compound (43.4 mg, 36%) as colorless crystals.

¹H-NMR (CDCl₃) δ: 2.14 (6H, s), 3.70 (2H, s), 3.82 (3H, s), 3.83 (3H, s), 5.36 (2H, s), 6.92 (2H, t, J=7.8 Hz), 7.01 (1H, d, J=8.7 Hz), 7.1-7.35 (4H, m), 7.51 (2H, d, J=8.7 Hz), 7.56 (2H, d, J=8.7 Hz), 7.63 (1H, s).

Reference Example 56

Production of N-{4-[1-(2,6-difluorobenzyl)-3-(6-methoxypyridazin-3-yl)-2,4-dioxo-5-(pyrrolidin-1-ylmethyl)-1,2,3,4-tetrahydrothieno[2,3-d]pyrimidin-6-yl]phenyl}-N'-methoxyurea

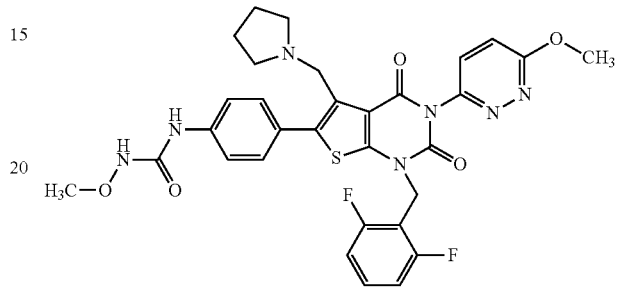

The similar reaction as described in Reference Example 26 by using the compound (110 mg, 0.175 mmol) obtained in Reference Example 50 and pyrrolidine (124 mg, 1.75 mmol) gave the title compound (68.1 mg, 60%) as colorless crystals.

¹H-NMR (CDCl₃) δ: 1.5-1.7 (4H, m), 2.35-2.5 (4H, m), 3.82 (3H, s), 3.89 (2H, brs), 4.18 (3H, s), 5.34 (2H, brs), 6.92 (2H, t, J=8.8 Hz), 7.12 (2H, d, J=9.2 Hz), 7.2-7.35 (2H, m), 7.41 (1H, d, J=9.2 Hz), 7.5-7.6 (3H, m), 7.64 (1H, s).

Reference Example 57

Production of N-{4-[1-(2,6-difluorobenzyl)-3-(6-methoxypyridazin-3-yl)-5-(morpholin-4-ylmethyl)-2,4-dioxo-1,2,3,4-tetrahydrothieno[2,3-d]pyrimidin-6-yl]phenyl}-N'-methoxyurea

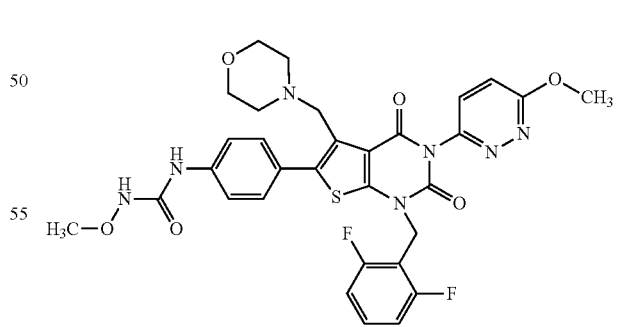

The similar reaction as described in Reference Example 26 by using the compound (110 mg, 0.175 mmol) obtained in Reference Example 50 and morpholine (152 mg, 1.75 mmol) gave the title compound (78.0 mg, 67%) as colorless crystals.

¹H-NMR (CDCl₃) δ: 2.35-2.5 (4H, m), 3.5-3.65 (4H, m), 3.76 (2H, s), 3.83 (3H, s), 4.19 (3H, s), 5.35 (2H, s), 6.93 (2H, t, J=8.0 Hz), 7.1-7.2 (2H, m), 7.2-7.3 (1H, m), 7.40 (1H, d, J=9.0 Hz), 7.5-7.7 (5H, m).

Reference Example 58

Production of N-(4-(5-((benzyl(2-methoxyethyl)amino)methyl)-1-(2,6-difluorobenzyl)-3-(6-methoxy-3-pyridazinyl)-2,4-dioxo-1,2,3,4-tetrahydrothieno[2,3-d]pyrimidin-6-yl)phenyl)-N'-methoxyurea

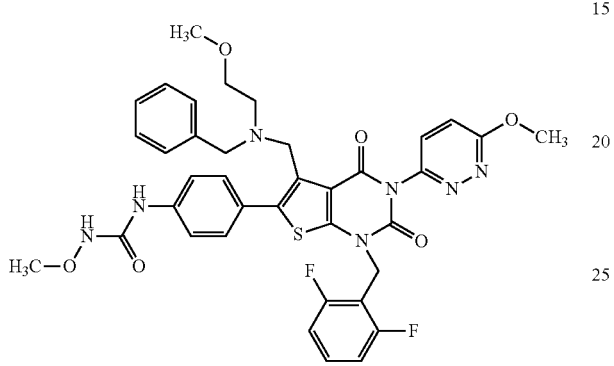

The similar reaction as described in Reference Example 26 by using the compound (120 mg, 0.191 mmol) obtained in Reference Example 50 and N-benzyl-N-(2-methoxyethyl)amine (316 mg, 1.91 mmol) gave the title compound (105.1 mg, 74%) as white powders.
¹H-NMR (CDCl₃) δ: 2.67 (2H, t, J=6.2 Hz), 3.18 (3H, s), 3.34 (2H, t, J=6.2 Hz), 3.65 (2H, s), 3.83 (3H, s), 4.03 (2H, s), 4.20 (3H, s), 5.32 (2H, brs), 6.92 (2H, t, J=8.2 Hz), 7.1-7.25 (6H, m), 7.25-7.35 (2H, m), 7.40 (1H, d, J=9.0 Hz), 7.55 (2H, d, J=8.7 Hz), 7.64 (1H, s), 7.75 (2H, d, J=8.7 Hz).
Elemental analysis C₃₇H₃₅F₂N₇O₆S.1.0H₂O
Calcd.: C, 58.34; H, 4.90; N, 12.87.
Found: C, 58.51; H, 4.58; N, 12.56.

Reference Example 59

Production of N-(4-(1-(2,6-difluorobenzyl)-5-(((2-methoxyethyl)amino)methyl)-3-(6-methoxy-3-pyridazinyl)-2,4-dioxo-1,2,3,4-tetrahydrothieno[2,3-d]pyrimidin-6-yl)phenyl)-N'-methoxyurea

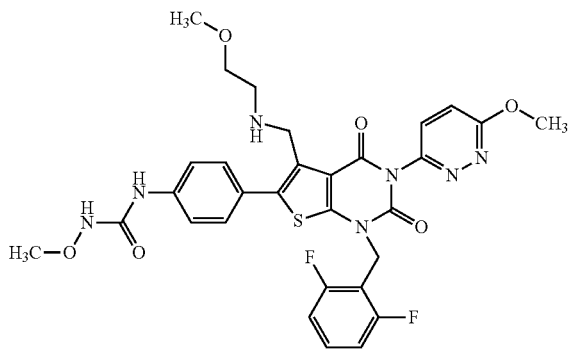

The similar reaction as described in Reference Example 14 by using the compound (400 mg, 0.538 mmol) obtained in Reference Example 58 gave the title compound (215.9 mg, 61%) as colorless crystals.
¹H-NMR (CDCl₃) δ: 2.72 (2H, t, J=5.6 Hz), 3.28 (3H, s), 3.40 (2H, t, J=5.6 Hz), 3.82 (3H, s), 3.86 (2H, s), 4.19 (3H, s), 5.35 (2H, brs), 6.92 (2H, t, J=8.4 Hz), 7.14 (2H, d, J=9.0 Hz), 7.25-7.35 (1H, m), 7.39 (2H, d, J=9.0 Hz), 7.43 (2H, d, J=8.8 Hz), 7.56 (2H, d, J=8.8 Hz), 7.64 (1H, s).
Elemental analysis C₃₀H₂₉F₂N₇O₆S.0.5H₂O
Calcd.: C, 54.38; H, 4.56; N, 14.80.
Found: C, 54.62; H, 4.39; N, 14.62.

Example 61

Production of N-(4-(1-(2,6-difluorobenzyl)-3-(2-hydroxypropyl)-5-(((2-methoxyethyl)(methyl)amino)methyl)-2,4-dioxo-1,2,3,4-tetrahydrothieno[2,3-d]pyrimidin-6-yl)phenyl)-N'-methoxyurea

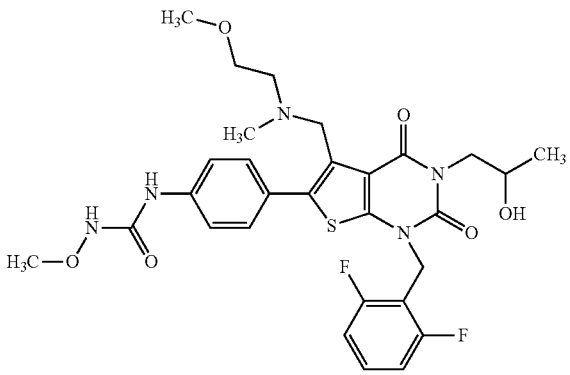 [SMILES: COCCN(C)Cc1c(-c2ccc(NC(=O)NOC)cc2)sc2c1c(=O)n(CC(C)O)c(=O)n2Cc1c(F)cccc1F]

The similar reaction as described in Example 5 by using the compound (1.82 g, 3 mmol) obtained in Reference Example 7 and 1-amino-2-propanol (0.45 g, 6 mmol) gave the title compound (1.11 g, 60%) as white powders.
¹H-NMR (CDCl₃) δ: 1.27 (3H, d, J=5.6 Hz), 2.12 (3H, s), 2.64 (2H, t, J=5.8 Hz), 2.9-3.05 (1H, m), 3.30 (3H, s), 3.45 (2H, d, J=5.8 Hz), 3.82 (5H, s), 4.05-4.25 (1H, m), 4.18 (2H, s), 5.34 (2H, s), 6.91 (2H, t, J=8.2 Hz), 7.2-7.4 (1H, m), 7.5-7.6 (3H, m), 7.63 (1H, s).
Elemental analysis C₂₉H₃₃F₂N₅O₆S.0.7H₂O
Calcd.: C, 55.26; H, 5.50; N, 11.11.
Found: C, 55.42; H, 5.52; N, 10.75.

Example 62

Production of N-(4-(1-(2,6-difluorobenzyl)-5-(((2-methoxyethyl)(methyl)amino)methyl)-2,4-dioxo-3-(2-oxopropyl)-1,2,3,4-tetrahydrothieno[2,3-d]pyrimidin-6-yl)phenyl)-N'-methoxyurea

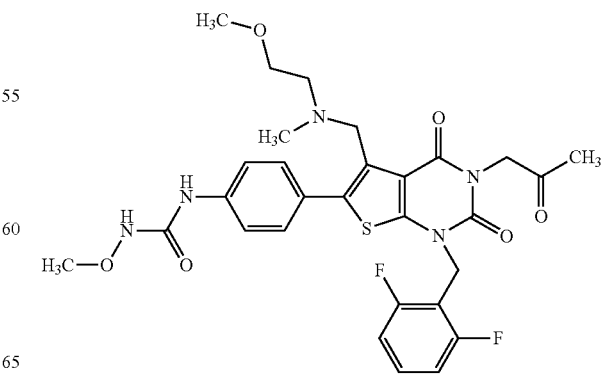

To a solution of oxalyl chloride (0.20 g, 1.58 mmol) in dichloromethane (2 ml) was dropwise added a solution of dimethylsulfoxide (163 mg, 2.09 mmol) in dichloromethane (2 ml) under cooling at −78° C. After stirring for 10 minutes, a solution of the compound (308 mg, 0.5 mmol) obtained in Example 61 in dichloromethane (2 ml) was dropwise added. After stirring for further 30 minutes, triethylamine (0.40 ml, 2.88 mmol) was dropwise added, and the mixture was stirred at 0° C. for 2 hours. To the mixture was added an aqueous solution of ammonium chloride at 0° C., and the mixture was extracted with ethyl acetate. The organic layer was washed with brine, dried over anhydrous magnesium sulfate, and concentrated with under reduced pressure. The residue was purified by NH-silica gel (Produced by Fuji Silysia Chemical Ltd.) column chromatography (eluent; ethyl acetate), and the obtained powders was washed with diisopropyl ether and hexane to give the title compound (40.7 mg, 13%) as pale yellow powders.

$^1$H-NMR (CDCl$_3$) δ: 2.13 (3H, s), 2.27 (3H, s), 2.55-2.65 (2H, m), 3.29 (3H, s), 3.4-3.5 (2H, m), 3.82 (5H, s), 4.88 (2H, s), 5.33 (2H, s), 6.91 (2H, t, J=8.0 Hz), 7.2-7.35 (1H, m), 7.5-7.65 (4H, m).

Example 63

Production of N-(4-(1-(2,6-difluorobenzyl)-3-(3,3-dimethyl-2-oxobutyl)-5-(((2-methoxyethyl)(methyl)amino)methyl)-2,4-dioxo-1,2,3,4-tetrahydrothieno[2,3-d]pyrimidin-6-yl)phenyl)-N'-methoxyurea

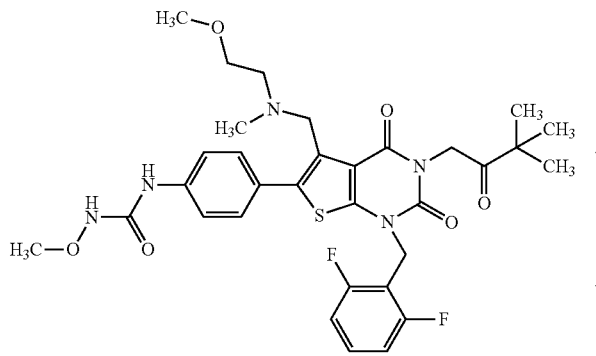

The similar reaction as described in Example 5 by using the compound (303 mg, 0.5 mmol) obtained in Reference Example 7 and 3,3-dimethyl-2-oxobutylamine hydrochloride (U.S. Pat. No. 6,096,688) (152 mg, 1 mmol) gave the title compound (195.7 mg, 60%) as pale yellow crystals.

$^1$H-NMR (CDCl$_3$) δ: 1.30 (9H, s), 2.12 (3H, s), 2.62 (2H, t, J=5.8 Hz), 3.29 (3H, s), 3.44 (2H, d, J=5.8 Hz), 3.80 (2H, s), 3.82 (3H, s), 5.04 (2H, s), 5.33 (2H, s), 6.91 (2H, t, J=8.2 Hz), 7.14 (1H, s), 7.2-7.3 (1H, m), 7.5-7.6 (4H, m), 7.61 (1H, s).

Elemental analysis C$_{32}$H$_{37}$F$_2$N$_5$O$_6$S

Calcd.: C, 58.43; H, 5.67; N, 10.65.

Found: C, 58.15; H, 5.71; N, 10.42.

Example 64

Production of N-(4-(1-(2,6-difluorobenzyl)-5-(((2-methoxyethyl)(methyl)amino)methyl)-2,4-dioxo-3-(2,2,2-trifluoroethyl)-1,2,3,4-tetrahydrothieno[2,3-d]pyrimidin-6-yl)phenyl)-N'-methoxyurea

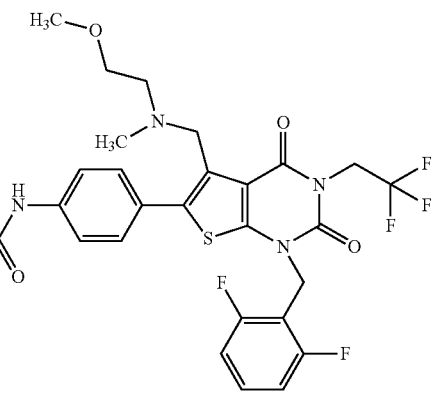

The similar reaction as described in Example 5 by using the compound (303 mg, 0.5 mmol) obtained in Reference Example 7 and 2,2,2-trifluoroethylamine (99 mg, 1 mmol) gave the title compound (52.9 mg, 16%) as colorless crystals.

$^1$H-NMR (CDCl$_3$) δ: 2.12 (3H, s), 2.65 (2H, t, J=6.0 Hz), 3.31 (3H, s), 3.45 (2H, d, J=6.0 Hz), 3.82 (5H, s), 4.75-4.85 (2H, m), 5.36 (2H, s), 6.92 (2H, t, J=8.2 Hz), 7.13 (1H, s), 7.2-7.35 (1H, m), 7.55-7.6 (4H, m), 7.62 (1H, s).

Elemental analysis C$_{28}$H$_{28}$F$_5$N$_5$O$_5$S·1.0H$_2$O

Calcd.: C, 50.98; H, 4.58; N, 10.62.

Found: C, 51.14; H, 4.44; N, 10.34.

Example 65

Production of N-(4-(1-(2,6-difluorobenzyl)-3-(2-hydroxy-3,3-dimethylbutyl)-5-(((2-methoxyethyl)(methyl)amino)methyl)-2,4-dioxo-1,2,3,4-tetrahydrothieno[2,3-d]pyrimidin-6-yl)phenyl)-N'-methoxyurea

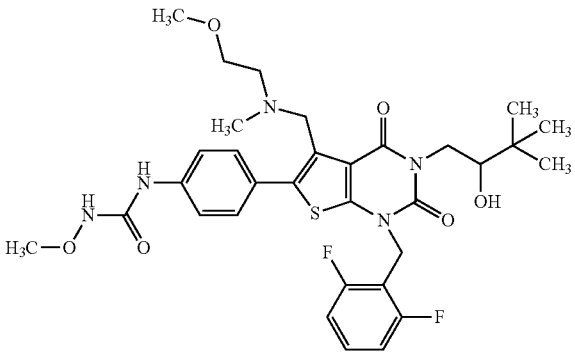 [SMILES: COCCN(C)Cc1c(-c2ccc(NC(=O)NOC)cc2)sc2c1c(=O)n(CC(O)C(C)(C)C)c(=O)n2Cc1c(F)cccc1F]

To a mixed solution of compound (120 mg, 0.182 mmol) obtained in Example 63 in methanol (6 ml) and THF (4 ml) was added sodium borohydride (6.9 mg, 0.182 mmol) under ice cooling. The reaction liquid was stirred at room temperature for 1.5 hours and concentrated under reduced pressure. The residue was distributed between water and ethyl acetate, and the organic layer was extracted. The extract was washed with brine, dried over anhydrous magnesium sulfate and concentrated under reduced pressure. The residue was purified by NH-silica gel (Produced by Fuji Silysia Chemical Ltd.) column chromatography (eluent; ethyl acetate), and recrystallized from ethyl acetate and diethylether to give the title compound (81.1 mg, 68%) as colorless crystals.

$^1$H-NMR (CDCl$_3$) δ: 1.04 (9H, s), 2.12 (3H, s), 2.64 (2H, t, J=6.0 Hz), 2.96 (1H, d, J=6.0 Hz), 3.31 (3H, s), 3.46 (2H, d, J=6.0 Hz), 3.5-3.6 (1H, m), 3.82 (3H, s), 3.75-3.9 (2H, m), 4.05-4.2 (1H, m), 4.3-4.45 (1H, m), 5.25-5.45 (2H, m), 6.91 (2H, t, J=8.2 Hz), 7.14 (1H, s), 7.2-7.35 (1H, m), 7.5-7.6 (4H, m), 7.61 (1H, s).

Elemental analysis C$_{32}$H$_{39}$F$_2$N$_5$O$_6$S.0.2H$_2$O

Calcd.: C, 57.94; H, 5.99; N, 10.56.

Found: C, 57.89; H, 5.91; N, 10.43.

Example 66

Production of N-(4-(1-(2,6-difluorobenzyl)-3-(2-hydroxy-2-methylpropyl)-5-(((2-methoxyethyl)(methyl)amino)methyl)-2,4-dioxo-1,2,3,4-tetrahydrothieno[2,3-d]pyrimidin-6-yl)phenyl)-N'-methoxyurea

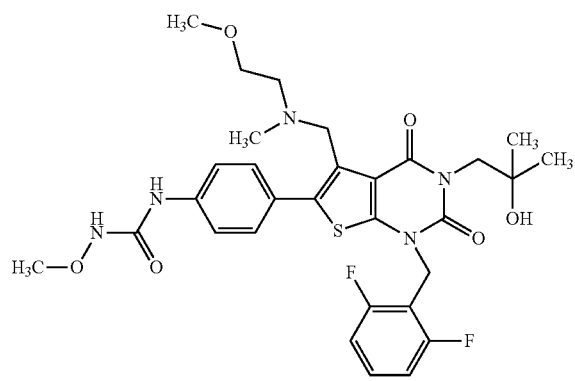 [SMILES: COCCN(C)Cc1c(-c2ccc(NC(=O)NOC)cc2)sc2c1c(=O)n(CC(C)(C)O)c(=O)n2Cc1c(F)cccc1F]

The similar reaction as described in Example 5 by using the compound (303 mg, 0.5 mmol) obtained in Reference Example 7 and compound (89 mg, 1 mmol) obtained in Reference Example 41 gave the title compound (133.9 mg, 42%) as colorless crystals.

$^1$H-NMR (CDCl$_3$) δ: 1.28 (6H, s), 2.3 (3H, s), 2.64 (2H, t, J=5.8 Hz), 3.30 (3H, s), 3.45 (2H, t, J=5.8 Hz), 3.82 (5H, s), 3.99 (1H, s), 4.25 (2H, s), 5.36 (2H, s), 6.91 (2H, t, J=8.2 Hz), 7.12 (1H, s), 7.2-7.4 (1H, m), 7.5-7.6 (4H, m), 7.61 (1H, s).

Elemental analysis C$_{30}$H$_{35}$F$_2$N$_5$O$_6$S.0.1H$_2$O

Calcd.: C, 56.88; H, 5.60; N, 11.06.

Found: C, 56.65; H, 5.54; N, 10.85.

Example 67

Production of N-[4-(1-(2,6-difluorobenzyl)-3-(3-hydroxy-2,2-dimethylpropyl)-5-{[(2-methoxyethyl)(methyl)amino]methyl}-2,4-dioxo-1,2,3,4-tetrahydrothieno[2,3-d]pyrimidin-6-yl)phenyl]-N'-methoxyurea

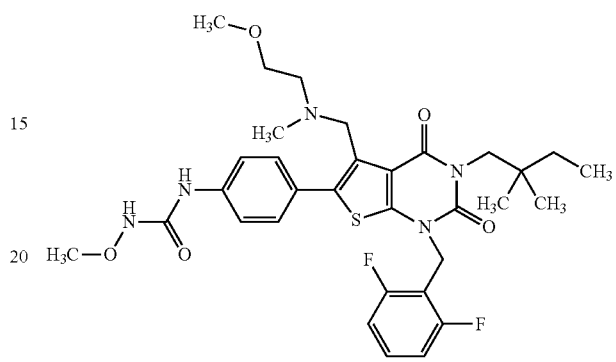

The similar reaction as described in Example 5 by using the compound (303 mg, 0.5 mmol) obtained in Reference Example 7 and compound (140 mg, 1 mmol) obtained in Reference Example 44 gave the title compound (36.8 mg, 11%) as pale yellow crystals.

$^1$H-NMR (CDCl$_3$) δ: 0.96 (6H, s), 2.13 (3H, s), 2.64 (2H, t, J=6.2 Hz), 3.13 (2H, s), 3.30 (3H, s), 3.45 (2H, t, J=6.2 Hz), 3.82 (5H, s), 3.95-4.15 (2H, brm), 5.1-5.5 (2H, br), 6.91 (2H, t, J=8.2 Hz), 7.14 (1H, s), 7.2-7.4 (1H, m), 7.5-7.6 (4H, m), 7.61 (1H, s). HPLC (220 nm) Purity 90% (Retention time 1.83 minutes)

MS (ESI$_+$, m/e) 646 (M+1)

Example 68

Production of N-(4-(1-(2,6-difluorobenzyl)-3-((1-(hydroxymethyl)cyclopropylmethyl)-5-(((2-methoxyethyl)(methyl)amino)methyl)-2,4-dioxo-1,2,3,4-tetrahydrothieno[2,3-d]pyrimidin-6-yl)phenyl)-N'-methoxyurea

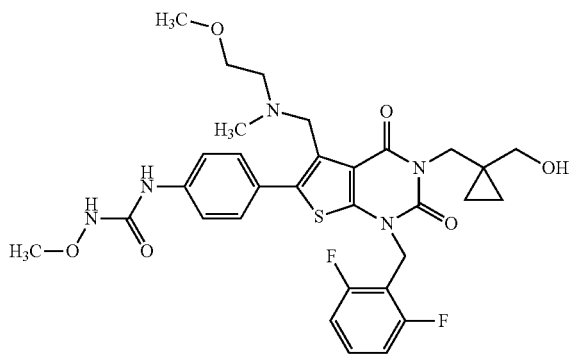 [SMILES: COCCN(C)Cc1c(-c2ccc(NC(=O)NOC)cc2)sc2c1c(=O)n(CC1(CO)CC1)c(=O)n2Cc1c(F)cccc1F]

The similar reaction as described in Example 5 by using the compound (606 mg, 1 mmol) obtained in Reference Example 7 and compound (431 mg, 2 mmol) obtained in Reference Example 47 gave the thienopyrimidine cyclized form (549.3 mg, 72%). The above cyclized form was dissolved in THF (10 ml), and a solution of tetrabutylammoniumfluoride in 1M THF (1.7 ml, 1.7 mmol) was added. The mixture was stirred at room temperature for 20 hours. The reaction liquid was distributed between water and ethyl acetate, and the organic layer was extracted. The organic layer was washed with brine, dried over anhydrous magnesium sulfate and concentrated under reduced pressure. The residue was purified by NH-silica gel (Produced by Fuji Silysia Chemical Ltd.) column chromatography (eluent; ethyl acetate), and recrystallized from ethyl acetate and diethylether to give the title compound (196.1 mg, 43%) as colorless crystals.

$^1$H-NMR (CDCl$_3$) δ: 0.46 (2H, t, J=5.4 Hz), 0.85 (2H, t, J=5.4 Hz), 2.11 (3H, s), 2.64 (2H, t, J=6.0 Hz), 3.25 (2H, s), 3.31 (3H, s), 3.46 (2H, t, J=6.0 Hz), 3.82 (5H, s), 3.95-4.15 (1H, br), 4.14 (2H, s), 5.37 (2H, s), 6.91 (2H, t, J=8.0 Hz), 7.12 (1H, s), 7.2-7.4 (1H, m), 7.54 (4H, s), 7.61 (1H, s).

Elemental analysis C$_{31}$H$_{35}$F$_2$N$_5$O$_6$S

Calcd.: C, 57.84; H, 5.48; N, 10.88.

Found: C, 57.63; H, 5.46; N, 10.86.

Example 69

Production of N-(4-(5-((benzyl(methyl)amino)methyl)-1-(2,6-difluorobenzyl)-3-(4-hydroxycyclohexyl)-2,4-dioxo-1,2,3,4-tetrahydrothieno[2,3-d]pyrimidin-6-yl)phenyl)-N'-methoxyurea

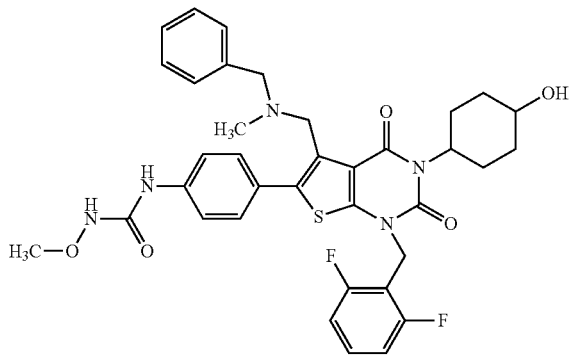 [SMILES: CONC(=O)Nc1ccc(-c2sc3c(c2CN(C)Cc2ccccc2)c(=O)n(C2CCC(O)CC2)c(=O)n3Cc2c(F)cccc2F)cc1]

The similar reaction as described in Example 5 by using 4-(N-benzyl-N-methylaminomethyl)-2-[N-(2,6-difluorobenzyl)-N-ethoxycarbonylamino]-5-[4-(3-methoxyureido)phenyl]thiophene-3-carboxylic acid (3.19 g, 5 mmol) and trans-4-aminocyclohexanol (1.44 g, 12.5 mmol) gave the title compound (1.80 g, 52%) as colorless crystals.

$^1$H-NMR (CDCl$_3$) δ: 1.35-1.65 (3H, m), 1.65-1.8 (2H, m), 2.07 (3H, s), 2.5-2.8 (2H, m), 3.58 (2H, s), 3.7-3.9 (1H, m), 3.82 (3H, s), 3.91 (2H, s), 4.9-5.1 (1H, m), 5.29 (2H, s), 6.90 (2H, t, J=7.8 Hz), 7.13 (1H, s), 7.15-7.35 (6H, m), 7.53 (2H, d, J=8.6 Hz), 7.61 (1H, s), 7.66 (2H, d, J=8.6 Hz).

Elemental analysis C$_{36}$H$_{37}$F$_2$N$_5$O$_6$S.0.5H$_2$O

Calcd.: C, 61.09; H, 5.55; N, 9.89.

Found: C, 61.41; H, 5.65; N, 9.56.

Example 70

Production of N-[4-(1-(2,6-difluorobenzyl)-3-(4-hydroxycyclohexyl)-5-{[(2-methoxyethyl)(methyl)amino]methyl}-2,4-dioxo-1,2,3,4-tetrahydrothieno[2,3-d]pyrimidin-6-yl)phenyl]-N'-methoxyurea

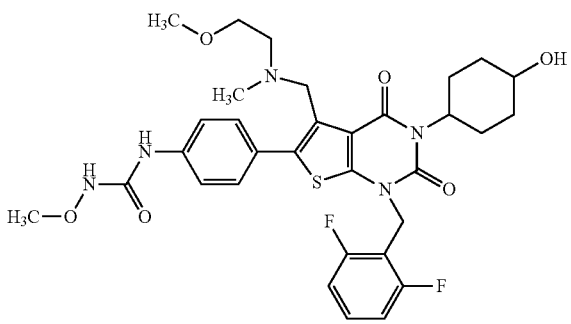 [SMILES: COCCN(C)Cc1c(-c2ccc(NC(=O)NOC)cc2)sc2c1c(=O)n(C1CCC(O)CC1)c(=O)n2Cc1c(F)cccc1F]

The similar reaction as described in Example 4 by using the compound (300 mg, 0.5 mmol) obtained in Reference Example 51 and 2-bromoethylmethylether (0.69 g, 5 mmol) gave the title compound (75.1 mg, 23%) as colorless crystals.

$^1$H-NMR (CDCl$_3$) δ: 1.2-1.6 (3H, m), 1.6-1.8 (2H, m), 2.0-2.1 (2H, m), 2.14 (3H, s), 2.5-2.75 (4H, m), 3.31 (3H, s), 3.45 (2H, t, J=5.8 Hz), 3.65-3.85 (3H, m), 3.82 (3H, s), 4.9-5.05 (1H, br), 5.30 (2H, s), 6.90 (2H, t, J=8.0 Hz), 7.12 (1H, s), 7.25-7.4 (1H, m), 7.5-7.6 (4H, m), 7.60 (1H, s).

Elemental analysis C$_{32}$H$_{33}$F$_2$N$_5$O$_6$S.0.5H$_2$O

Calcd.: C, 57.65; H, 5.74; N, 10.50.

Found: C, 57.54; H, 5.75; N, 10.64.

Example 71

Production of N-{4-[1-(2,6-difluorobenzyl)-5-{[(2-methoxyethyl)(methypamino]methyl}-3-(6-methylpyridazin-3-yl)-2,4-dioxo-1,2,3,4-tetrahydrothieno[2,3-d]pyrimidin-6-yl]phenyl}-N'-methoxyurea

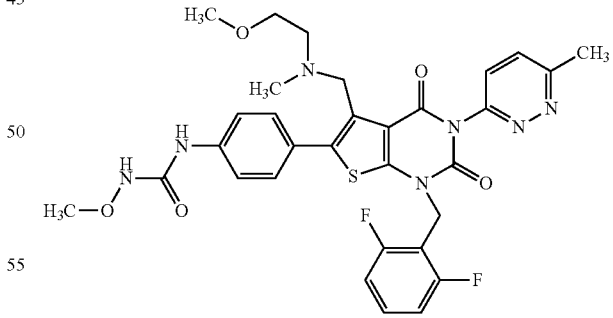

The similar reaction as described in Example 5 by using the compound (303 mg, 0.5 mmol) obtained in Reference Example 7 and 3-amino-6-methylpyridazine (136 mg, 1.25 mmol) gave the title compound (48.3 mg, 15%) as colorless crystals.

$^1$H-NMR (CDCl$_3$) δ: 2.13 (3H, s), 2.61 (2H, t, J=5.8 Hz), 2.79 (3H, s), 3.26 (3H, s), 3.41 (2H, t, J=5.8 Hz), 3.75-3.85 (2H, m), 3.82 (3H, s), 5.25-5.45 (2H, brm), 6.92 (2H, t, J=8.2 Hz), 7.18 (1H, s), 7.2-7.7 (8H, m).

Example 72

Production of N-(4-(5-((benzyl(methyl)amino)methyl)-1-(2,6-difluorobenzyl)-3-(2-hydroxypropyl)-2,4-dioxo-1,2,3,4-tetrahydrothieno[2,3-d]pyrimidin-6-yl)phenyl)-N'-methoxyurea

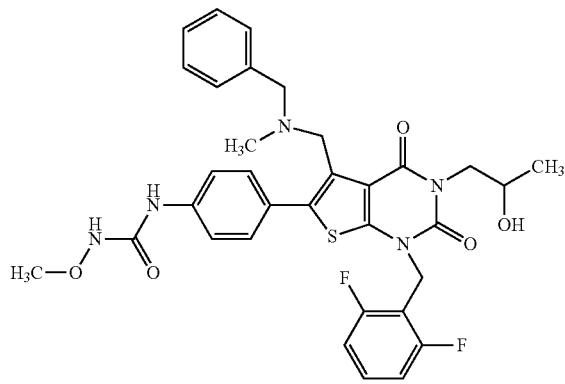 [SMILES: CONC(=O)Nc1ccc(-c2sc3c(c2CN(C)Cc2ccccc2)c(=O)n(CC(C)O)c(=O)n3Cc2c(F)cccc2F)cc1]

The similar reaction as described in Example 5 by using 4-(N-benzyl-N-methylaminomethyl)-2-[N-(2,6-difluorobenzyl)-N-ethoxycarbonylamino]-5-[4-(3-methoxyureido)phenyl]thiophene-3-carboxylic acid (639 mg, 1 mmol) and 1-amino-2-propanol (0.19 g, 2.5 mmol) gave the title compound (409.7 mg, 63%) as colorless crystals.

$^1$H-NMR (CDCl$_3$) δ: 1.30 (3H, d, J=6.0 Hz), 2.06 (3H, s), 2.90 (1H, d, J=5.2 Hz), 3.57 (2H, s), 3.82 (3H, s), 3.91 (2H, s), 4.1-4.25 (1H, m), 4.20 (2H, s), 5.34 (2H, s), 6.91 (2H, t, J=8.0 Hz), 7.16 (1H, s), 7.2-7.4 (6H, m), 7.54 (2H, d, J=8.8 Hz), 7.62 (1H, s), 7.67 (2H, d, J=8.8 Hz).

Elemental analysis C$_{33}$H$_{33}$F$_2$N$_5$O$_5$S
Calcd.: C, 61.00; H, 5.12; N, 10.78.
Found: C, 60.82; H, 5.21; N, 10.68.

Example 73

Production of N-(4-(5-((benzyl(methyl)amino)methyl)-1-(2,6-difluorobenzyl)-3-(2-hydroxy-2-methylpropyl)-2,4-dioxo-1,2,3,4-tetrahydrothieno[2,3-d]pyrimidin-6-yl)phenyl)-N'-methoxyurea

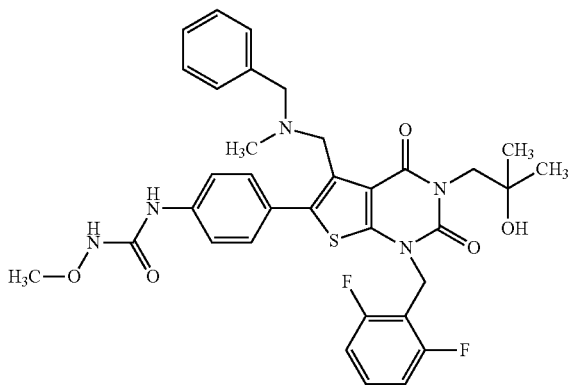 [SMILES: CONC(=O)Nc1ccc(-c2sc3c(c2CN(C)Cc2ccccc2)c(=O)n(CC(C)(C)O)c(=O)n3Cc2c(F)cccc2F)cc1]

The similar reaction as described in Example 5 by using the 4-(N-benzyl-N-methylaminomethyl)-2-[N-(2,6-difluorobenzyl)-N-ethoxycarbonylamino]-5-[4-(3-methoxyureido)phenyl]thiophene-3-carboxylic acid (639 mg, 1 mmol) and compound (0.22 g, 2.5 mmol) obtained in Reference Example 41 gave the title compound (360.9 mg, 54%) as colorless crystals.

$^1$H-NMR (CDCl$_3$) δ: 1.29 (6H, s), 2.06 (3H, s), 3.56 (2H, s), 3.83 (3H, s), 3.91 (2H, s), 3.96 (1H, s), 4.28 (2H, s), 5.36 (2H, s), 6.91 (2H, t, J=8.2 Hz), 7.13 (1H, s), 7.2-7.35 (6H, m), 7.54 (2H, d, J=8.8 Hz), 7.62 (1H, s), 7.67 (2H, d, J=8.8 Hz).

Elemental analysis C$_{34}$H$_{35}$F$_2$N$_5$O$_5$S
Calcd.: C, 61.53; H, 5.32; N, 10.55.
Found: C, 61.30; H, 5.32; N, 10.32.

Example 74

Production of N-(4-(1-(2,6-difluorobenzyl)-3-(2-hydroxypropyl)-5-((methyl(2-(2-pyridinyl)ethyl)amino)methyl)-2,4-dioxo-1,2,3,4-tetrahydrothieno[2,3-d]pyrimidin-6-yl)phenyl)-N'-methoxyurea

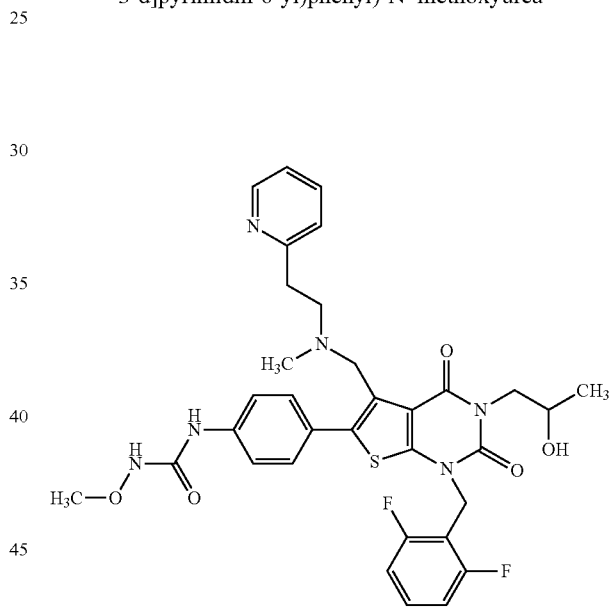

The similar reaction as described in Example 2 by using the compound (260 mg, 0.465 mmol) obtained in Reference Example 52 and 2-(2-hydroxyethyl)pyridine (400 mg, 1.63 mmol) gave the title compound (195.9 mg, 63%) as colorless crystals.

$^1$H-NMR (CDCl$_3$) δ: 1.28 (3H, d, J=5.8 Hz), 2.21 (3H, s), 2.75-2.95 (4H, m), 3.0-3.1 (1H, m), 3.82 (5H, s), 4.1-4.2 (1H, m), 4.17 (2H, s), 5.34 (2H, s), 6.91 (2H, t, J=8.2 Hz), 6.95-7.1 (2H, m), 7.14 (1H, s), 7.2-7.4 (1H, m), 7.4-7.55 (5H, m), 7.59 (1H, s), 8.43 (1H, d, J=5.0 Hz).

Elemental analysis C$_{33}$H$_{34}$F$_2$N$_6$O$_5$S·0.2H$_2$O
Calcd.: C, 59.31; H, 5.19; N, 12.57.
Found: C, 59.24; H, 5.29; N, 12.32.

Example 75

Production of N-(4-(1-(2,6-difluorobenzyl)-3-(2-hydroxy-2-methylpropyl)-5-((methyl(2-(2-pyridinyl)ethyl)amino)methyl)-2,4-dioxo-1,2,3,4-tetrahydrothieno[2,3-d]pyrimidin-6-yl)phenyl)-N'-methoxyurea

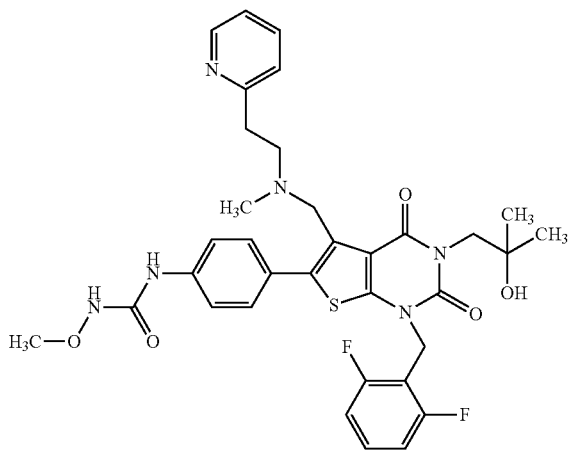 [SMILES: CONC(=O)Nc1ccc(-c2sc3c(c2CN(C)CCc2ccccn2)c(=O)n(CC(C)(C)O)c(=O)n3Cc2c(F)cccc2F)cc1]

The similar reaction as described in Example 2 by using the compound (220 mg, 0.384 mmol) obtained in Reference Example 53 and 2-(2-hydroxyethyl)pyridine (800 mg, 3.25 mmol) gave the title compound (138.2 mg, 53%) as colorless crystals.

$^1$H-NMR (CDCl$_3$) δ: 1.26 (6H, s), 2.21 (3H, s), 2.75-2.95 (4H, m), 3.82 (5H, s), 3.99 (1H, s), 4.24 (2H, s), 5.36 (2H, s), 6.91 (2H, t, J=8.2 Hz), 7.0-7.1 (2H, m), 7.13 (1H, s), 7.2-7.35 (1H, m), 7.45-7.55 (5H, m), 7.59 (1H, s), 8.43 (1H, d, J=4.0 Hz).

Elemental analysis C$_{34}$H$_{36}$F$_2$N$_6$O$_5$S.0.1H$_2$O
Calcd.: C, 59.85; H, 5.38; N, 12.32.
Found: C, 59.81; H, 5.45; N, 12.03.

Example 76

Production of N-(4-(1-(2,6-difluorobenzyl)-5-(((2-methoxyethyl)(methyl)amino)methyl)-2,4-dioxo-3-(2-pyrazinyl)-1,2,3,4-tetrahydrothieno[2,3-d]pyrimidin-6-yl)phenyl)-N'-methoxyurea

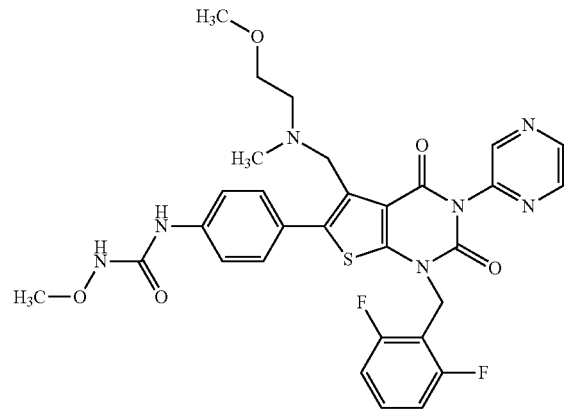 [SMILES: COCCN(C)Cc1c(-c2ccc(NC(=O)NOC)cc2)sc2c1c(=O)n(-c1cnccn1)c(=O)n2Cc1c(F)cccc1F]

The similar reaction as described in Example 5 by using the compound (303 mg, 0.5 mmol) obtained in Reference Example 7 and aminopyrazine (119 mg, 1.25 mmol) gave the title compound (35.2 mg, 11%) as colorless crystals.

$^1$H-NMR (CDCl$_3$) δ: 2.13 (3H, s), 2.62 (2H, t, J=6.0 Hz), 3.26 (3H, s), 3.41 (2H, t, J=6.0 Hz), 3.79 (2H, s), 3.83 (1H, s), 5.36 (2H, s), 6.94 (2H, t, J=8.0 Hz), 7.12 (1H, s), 7.2-7.4 (1H, m), 7.5-7.65 (5H, m), 8.65-8.7 (3H, m).

Elemental analysis C$_{30}$H$_{29}$F$_2$N$_7$O$_5$S.0.1H$_2$O
Calcd.: C, 56.35; H, 4.60; N, 15.33.
Found: C, 56.20; H, 4.52; N, 15.16.

Example 77

Production of N-(4-(5-((benzyl(methyl)amino)methyl)-1-(2,6-difluorobenzyl)-3-(6-methoxy-3-pyridazinyl)-2,4-dioxo-1,2,3,4-tetrahydrothieno[2,3-d]pyrimidin-6-yl)phenyl)-N'-methoxyurea

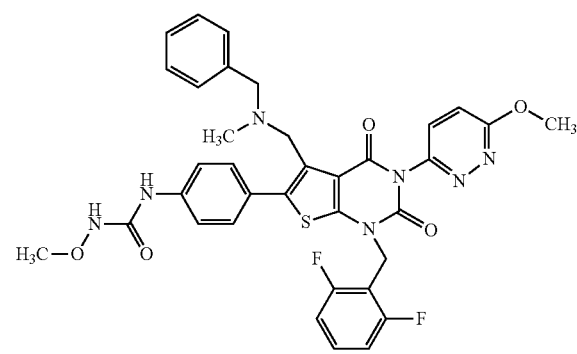

The similar reaction as described in Example 5 by using 4-(N-benzyl-N-methylaminomethyl)-2-[N-(2,6-difluorobenzyl)-N-ethoxycarbonylamino]-5-[4-(3-methoxyureido)phenyl]thiophene-3-carboxylic acid (1.28 g, 2 mmol) and 6-chloro-3-aminopyridazine (648 mg, 5 mmol) gave the title compound (0.36 g, 26%) as colorless crystals.

$^1$H-NMR (CDCl$_3$) δ: 2.06 (3H, s), 3.55 (2H, s), 3.83 (3H, s), 3.87 (2H, s), 4.19 (3H, s), 5.35 (2H, s), 6.92 (2H, t, J=8.2 Hz), 7.1-7.45 (9H, m), 7.55 (2H, d, J=8.4 Hz), 7.63 (1H, s), 7.72 (2H, d, J=8.4 Hz).

Example 78

Production of N-(4-(1-(2,6-difluorobenzyl)-3-(6-methoxy-3-pyridazinyl)-5-((methyl(2-(2-pyridinyl)ethyl)amino)methyl)-2,4-dioxo-1,2,3,4-tetrahydrothieno[2,3-d]pyrimidin-6-yl)phenyl)-N'-methoxyurea

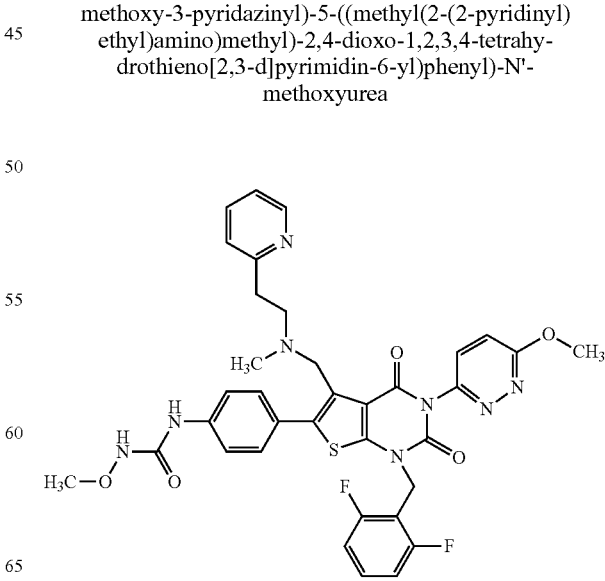

The similar reaction as described in Example 2 by using the compound (135 mg, 0.221 mmol) obtained in Reference Example 54 and 2-(2-hydroxyethyl)pyridine (272 mg, 2.21 mmol) gave the title compound (79.6 mg, 50%) as colorless crystals.

$^1$H-NMR (CDCl$_3$) δ: 2.20 (3H, s), 2.7-2.9 (4H, m), 3.78 (2H, s), 3.82 (3H, s), 4.19 (3H, s), 5.34 (2H, s), 6.85-7.2 (5H, m), 7.25-7.45 (2H, m), 7.45-7.7 (7H, m), 8.42 (1H, d, J=4.0 Hz).

Elemental analysis C$_{35}$H$_{32}$F$_2$N$_8$O$_5$S.1.0H$_2$O
Calcd.: C, 57.37; H, 4.68; N, 15.29.
Found: C, 57.29; H, 4.60; N, 15.15.

Example 79

Production of N-(4-(5-((methyl(2-pyridin-2-ylethyl)amino)methyl)-1-(2,6-difluorobenzyl)-1,2,3,4-tetrahydro-2,4-dioxo-3-(4-methoxyphenyl)thieno[2,3-d]pyrimidin-6-yl)phenyl)-N'-methoxyurea

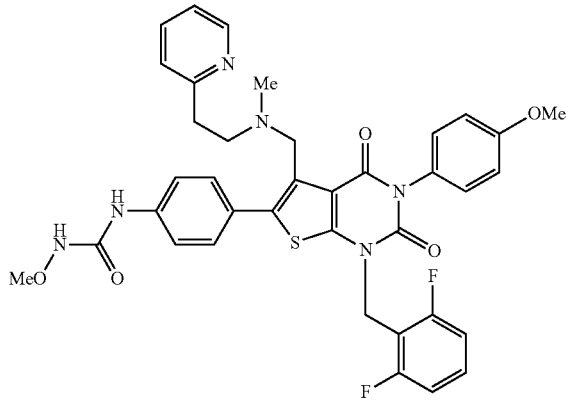 [SMILES: CONC(=O)Nc1ccc(-c2sc3c(c2CN(C)CCc2ccccn2)c(=O)n(-c2ccc(OC)cc2)c(=O)n3Cc2c(F)cccc2F)cc1]

The similar reaction as described in Example 2 by using the compound (800 mg, 1.24 mmol) obtained in Reference Example 25 and 2-(2-hydroxyethyl)pyridine (300 mg, 1.49 mmol) gave the title compound (407 mg, 58%) as white solids.

$^1$H NMR (CDCl$_3$) δ2.20 (3H, s), 2.86 (4H, m), 3.82-3.84 (8H, m), 5.36 (2H, s), 6.92 (2H, t, J=8.3 Hz), 7.00-7.06 (4H, m), 7.14-7.33 (4H, m), 7.46-7.51 (5H, m), 7.61 (1H, s), 8.42 (1H, d, J=5.7 Hz).

Elemental analysis C$_{37}$H$_{34}$F$_2$N$_6$O$_5$S.0.7H$_2$O
Calcd.: C, 61.26; H, 4.92; N, 11.59.
Found: C, 61.06; H, 4.86; N, 11.52.

Example 80

Production of N-[4-(1-(2,6-difluorobenzyl)-3-(6-hydroxypyridazin-3-yl)-5-{[(2-methoxyethyl)(methyl)amino]methyl}-2,4-dioxo-1,2,3,4-tetrahydrothieno[2,3-d]pyrimidin-6-yl)phenyl]-N'-methoxyurea

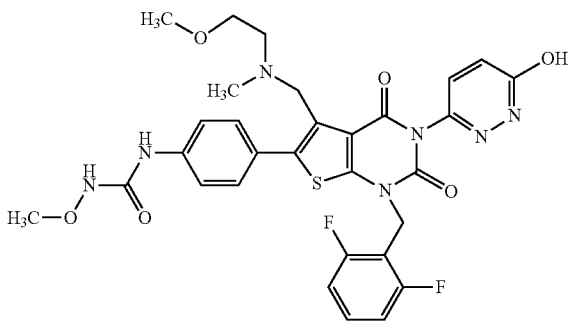 [SMILES: COCCN(C)Cc1c(-c2ccc(NC(=O)NOC)cc2)sc2c1c(=O)n(-c1ccc(O)nn1)c(=O)n2Cc1c(F)cccc1F]

To a solution of the compound (1.34 g, 2 mmol) obtained in Example 57 in THF (30 ml) was added a solution of 4N HCl in acetic acid (2 ml, 8 mmol), and the mixture was stirred at room temperature for 20 hours, at 50° C. for 10 hours and further at 60° C. for 3 hours. The reaction liquid was distributed between aqueous solution of sodium bicarbonate and ethyl acetate, and the organic layer was extracted. The aqueous layer was subjected to salting-out, and extracted with ethyl acetate. The organic layers were collected and combined and the organic layer was dried over anhydrous magnesium sulfate and concentrated under reduced pressure. The residue was purified by NH-silica gel (Produced by Fuji Silysia Chemical Ltd.) column chromatography (eluent; ethyl acetate/methanol=8/1). To the eluate was added diisopropylether to give powders. The powders were collected by filtration, washed with diisopropylether to obtain the title compound (539 mg, 41%) as a pale yellow powder.

$^1$H-NMR (CDCl$_3$) δ: 2.12 (3H, s), 2.63 (2H, t, J=5.8 Hz), 3.28 (3H, s), 3.43 (2H, t, J=5.8 Hz), 3.79 (2H, s), 3.83 (3H, s), 5.35 (2H, s), 6.94 (2H, t, J=8.2 Hz), 7.0-7.1 (1H, m), 7.2-7.4 (3H, m), 7.5-7.65 (4H, m), 7.63 (1H, s), 10.5-10.6 (1H, brs).

Elemental analysis C$_{30}$H$_{29}$F$_2$N$_7$O$_6$S.2.0H$_2$O
Calcd.: C, 52.24; H, 4.82; N, 14.22.
Found: C, 52.24; H, 4.57; N, 14.06.

Example 81

Production of N-{4-[1-(2,6-difluorobenzyl)-5-{[(2-hydroxyethyl)(methyl)amino]methyl}-3-(6-methoxypyridazin-3-yl)-2,4-dioxo-1,2,3,4-tetrahydrothieno[2,3-d]pyrimidin-6-yl]phenyl}-N'-methoxyurea

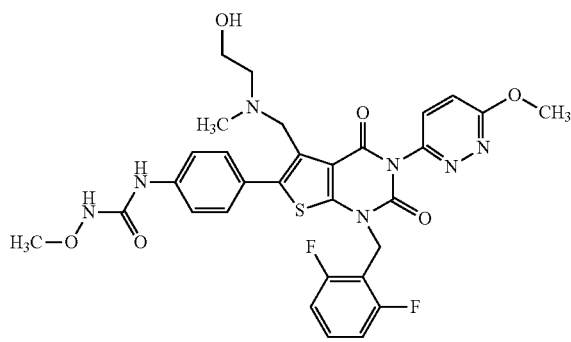

The similar reaction as described in Example 4 by using the compound (305 mg, 0.5 mmol) obtained in Reference Example 54 and 2-bromoethanol (0.62 g, 5 mmol) gave the title compound (145.7 mg, 45%) as colorless crystals.

$^1$H-NMR (CDCl$_3$) δ: 1.98 (3H, s), 2.45-2.5 (2H, m), 2.9-3.2 (1H, m), 3.5-3.55 (2H, m), 3.65-3.85 (2H, brm), 3.82 (3H, s), 4.18 (3H, s), 5.34 (2H, s), 6.93 (2H, t, J=8.0 Hz), 7.11 (1H, d, J=9.0 Hz), 7.18 (1H, s), 7.25-7.35 (1H, m), 7.35-7.45 (3H, m), 7.57 (2H, d, J=8.7 Hz), 7.66 (1H, s).

Elemental analysis C$_{30}$H$_{29}$F$_2$N$_7$O$_6$S.0.6H$_2$O
Calcd.: C, 54.23; H, 4.58; N, 14.76.
Found: C, 53.98; H, 4.61; N, 14.72.

Example 82

Production of N-{4-[1-(2,6-difluorobenzyl)-5-{[(2-hydroxyethyl)(methyl)amino]methyl}-3-(4-methoxyphenyl)-2,4-dioxo-1,2,3,4-tetrahydrothieno[2,3-d]pyrimidin-6-yl]phenyl}-N'-methoxyurea

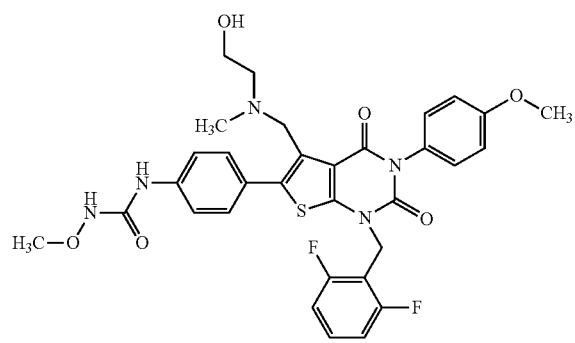

The similar reaction as described in Example 4 by using the compound (123 mg, 0.191 mmol) obtained in Reference Example 25 and 2-bromoethanol (239 mg, 1.91 mmol) gave the title compound (47.1 mg, 39%) as colorless crystals.

$^1$H-NMR (CDCl$_3$) δ: 1.99 (3H, s), 2.45-2.55 (2H, m), 3.5-3.6 (2H, m), 3.79 (2H, s), 3.82 (3H, s), 3.83 (3H, s), 5.36 (2H, s), 6.92 (2H, t, J=8.0 Hz), 6.99 (2H, d, J=8.8 Hz), 7.1-7.3 (4H, m), 7.39 (2H, d, J=8.8 Hz), 7.56 (2H, d, J=8.8 Hz), 7.64 (1H, s).

Example 83

Production of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea

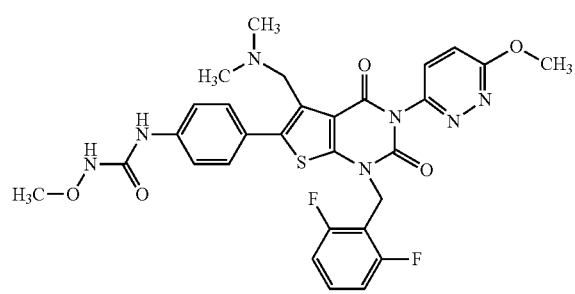

The similar reaction as described in Example 4 by using the compound (100 mg, 0.164 mmol) obtained in Reference Example 54 and methyl iodide (0.010 ml, 0.164 mmol) gave the title compound (17.3 mg, 17%) as colorless crystals.

$^1$H-NMR (CDCl$_3$) δ: 2.15 (6H, s), 3.6-3.8 (2H, m), 3.82 (3H, s), 4.18 (3H, s), 5.35 (2H, s), 6.92 (2H, t, J=8.2 Hz), 7.12 (1H, d, J=8.8 Hz), 7.2-7.65 (7H, m), 7.69 (1H, s).

Example 84

Production of N-{4-[1-(2,6-difluorobenzyl)-5-[(dimethylamino)methyl]-3-(6-methoxypyridin-3-yl)-2,4-dioxo-1,2,3,4-tetrahydrothieno[2,3-d]pyrimidin-6-yl]phenyl}-N'-methoxyurea

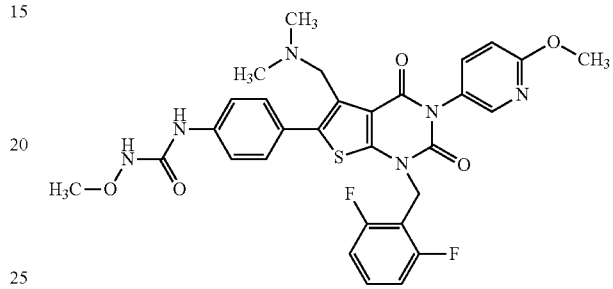

The similar reaction as described in Reference Example 26 by using the compound (41.1 mg, 0.067 mmol) obtained in Reference Example 49 and a solution of dimethylamine in THF (0.67 ml, 1.34 mmol) gave the title compound (18.4 mg, 44%) as white powders.

$^1$H-NMR (CDCl$_3$) δ: 2.13 (6H, s), 3.68 (2H, s), 3.83 (3H, s), 3.96 (3H, s), 5.36 (2H, s), 6.8-7.0 (3H, m), 7.13 (1H, s), 7.2-7.4 (1H, m), 7.45-7.65 (6H, m), 8.10 (1H, d, J=2.6 Hz).

Preparation 1

By a conventional manner, tablet is prepared by using the compound obtained in Example 40 (100 mg), lactose (165 mg), corn starch (25 mg), polyvinyl alcohol (4 mg) and magnesium stearate (1 mg).

Preparation 2

The compound obtained in Example 40 (5 g) was dissolved in distilled water for injection to make the total volume to 100 ml. The solution was subjected to sterile filtration by using membrane filter having a diameter of 0.22 μm (Produced by Sumitomo Electric Industries, Ltd. or Sartorius K.K.), 2 ml each of the solution is poured into a sterilized vial, and is freeze dried in a conventional manner to give freeze-dried injectable preparation.

Preparation 3

By a conventional manner a tablet is prepared by using compound obtained in Example 41 (100 mg), lactose (165 mg), corn starch (25 mg), polyvinyl alcohol (4 mg) and magnesium stearate (1 mg).

Preparation 4

The compound obtained in Example 41 (5 g) was dissolved in distilled water for injection to make the total volume to 100 ml. The solution was subjected to sterile filtration by using membrane filter having a diameter of 0.22 μm (Produced by Sumitomo Electric Industries, Ltd. or Sartorius K.K.), 2 ml each of the solution is poured into a sterilized vial, and is freeze dried in a conventional manner to give freeze-dried injectable preparation.

Preparation 5

| (1) | Compound obtained in Example 40 or Example 41 | 5 g |
|---|---|---|
| (2) | lactose ☐crystalline cellulose (grain) | 330 g |
| (3) | D-mannitol | 29 g |
| (4) | low substituted hydroxypropylcellulose | 20 g |
| (5) | talc | 25 g |
| (6) | hydroxypropylcellulose | 50 g |
| (7) | aspartame | 3 g |
| (8) | dipotassium glycyrrhizinate | 3 g |
| (9) | hydroxypropylmethylcellulose 2910 | 30 g |
| (10) | titanium oxide | 3.5 g |
| (11) | ferric oxide yellow | 0.5 g |
| (12) | light silicic acid anhydride | 1 g |

The above (1), (3), (4), (5), (6), (7) and (8) are suspended or dissolved in purified water, nuclear particles of (2) are coated with the solution to prepare crude fine grains. The crude fine grains are coated with (9) to (11) to prepare coated fine grains. They are mixed with (12) to prepare 1% KM05283 fine grains (500 g). 500 mg each of the fine grains are wrapped, separately.

Experimental Example 1

(1) Preparation of $^{125}$I-Leuprorelin

To a tube containing 10 μl of a $3 \times 10^{-4}$M aqueous solution of leuprorelin and 10 μl of 0.01 mg/ml lactoperoxidase was added 10 μl (37 MBq) of a solution of Na$^{125}$I. After stirring, 10 μl of 0.001% $H_2O_2$ was added, and a reaction was carried out at room temperature for 20 minutes. By adding 700 μl of a 0.05% TFA solution, the reaction was stopped, followed by purification by reversed-phase HPLC. The HPLC conditions used are shown below. $^{125}$I-leuprorelin was eluted at a retention time of 26 to 27 minutes.

Column: TSKgel ODS-80™ (TM indicates a registered trademark; the same applies below) CTR (4.6 mm×10 cm)
Eluents: Solvent A (0.05% TFA)
Solvent B (40% $CH_3CN$–0.05% TFA)
0 minute (100% Solvent A)–3 minutes (100% Solvent A)–7 minutes (50% Solvent A+50% Solvent B)–40 minutes (100% Solvent B)
Eluting temperature: Room temperature
Elution rate: 1 ml/min (2) Preparation of CHO (Chinese Hamster Ovarian) Cell Membrane Fraction Containing Monkey GnRH Receptor Monkey GnRH receptor-expressing CHO cells ($10^9$ cells) were suspended in phosphate-buffered saline supplemented with 5 mM EDTA (PBS-EDTA) and centrifuged at 100×g for 5 minutes. To the cell pellet, 10 ml of a cell homogenate buffer (10 mM NaHCO$_3$, 5 mM EDTA, pH 7.5) was added, followed by homogenization using the Polytron homogenizer. After centrifugation at 400×g for 15 minutes, the supernatant was transferred to an ultracentrifugation tube and centrifuged at 100,000×g for 1 hour to yield a membrane fraction precipitate. This precipitate was suspended in 2 ml of an assay buffer and centrifuged at 100,000×g for 1 hour. The membrane fraction recovered as a precipitate was again suspended in 20 ml of the assay buffer, dispensed, and stored at –80° C. before use upon thawing.

(3) Preparation of CHO (Chinese Hamster Ovarian) Cell Membrane Fraction Containing Human GnRH Receptor Human GnRH receptor-expressing CHO cells ($10^9$ cells) were suspended in phosphate-buffered saline supplemented with 5 mM EDTA (PBS-EDTA) and centrifuged at 100×g for 5 minutes. To the cell pellet, 10 ml of a cell homogenate buffer (10 mM NaHCO$_3$, 5 mM EDTA, pH 7.5) was added, followed by homogenization using the Polytron homogenizer. After centrifugation at 400×g for 15 minutes, the supernatant was transferred to an ultracentrifugation tube and centrifuged at 100,000×g for 1 hour to yield a membrane fraction precipitate. This precipitate was suspended in 2 ml of an assay buffer and centrifuged at 100,000×g for 1 hour. The membrane fraction recovered as a precipitate was again suspended in 20 ml of the assay buffer, dispensed, and stored at –80° C. before use upon thawing.

(4) Determination of $^{125}$I-Leuprorelin Binding Inhibition Rate

The monkey and human membrane fractions prepared in the above (2) and (3) were diluted with the assay buffer to yield a 200 mg/ml dilution, each of which was then dispensed at 188 μl per tube. To a tube containing the cell membrane fraction of the CHO with monkey GnRH receptors expressed were added 2 μl of a solution of 20 mM compound in 60% DMSO and 10 μl of 38 nM $^{125}$I-leuprorelin. To a tube containing the cell membrane fraction of the CHO with human GnRH receptors expressed were added 2 μl of a solution of 2 mM compound in 60% DMSO and 10 ml of 38 nM 125I-leuprorelin. To determine maximum binding quantity, a reaction mixture containing 2 μl of 60% DMSC and 10 μl of 38 nM $^{125}$I-leuprorelin was prepared. To determine non-specific binding amount, a reaction mixture containing 2 μl of a solution of 100 μM leuprorelin in 60% DMSO and 10 μl of 38 nM $^{125}$I-leuprorelin was prepared.

Where the membrane fraction of the CHO with monkey and human GnRH receptors expressed was used, the reaction was carried out at 25° C. for 60 minutes. After each reaction, the reaction mixture was aspirated and filtered through a polyethyleneimine-treated Whatman glass filter (GF-F). After this filtration, the radioactivity of $^{125}$I-leuprorelin remaining on the filter paper was measured with a γ-counter.

The expression (TB–SB)/(TB–NSB)×100 (where SB=radioactivity with the compound added, TB=maximum bound radioactivity, NSB=nonspecifically bound radioactivity) was calculated to find the binding inhibition rate of each test compound. Furthermore, the inhibition rate was determined by varying the concentration of the test substance and the 50% inhibitory concentration (IC$_{50}$ value) of the compound was calculated from Hill plot. The results are shown in below.

TABLE 1

| | IC$_{50}$ value (μM) | |
|---|---|---|
| Test Compound | Monkey | Human |
| Ex. Compd. No. 40 | 0.009 | 0.0002 |
| Ex. Compd. No. 41 | 0.003 | 0.0001 |

The compound of the present invention possesses excellent gonadotropin-releasing hormone antagonizing activity. It is also good in oral absorbability and excellent in stability and pharmacokinetics. With low toxicity, it is also excellent in safety. Therefore, for example, the compound of the present invention can be used as a preventing or treating agent for hormone-dependent diseases. Concretely, for example, it is effective as a preventing or treating agent for sex hormone-dependent cancers (e.g., prostatic cancer, uterine cancer, breast cancer, pituitary tumor, and the like), prostatic hypertrophy, hysteromyoma, endometriosis, metrofibroma, precocious puberty, amenorrhea syndrome, premenstrual syndrome, multilocular ovary syndrome, polycystic ovary syndrome, acne, alopecia, Alzheimer's disease, and the like; as a pregnancy regulator (e.g., contraceptive, etc.), infertility remedy or menstruation regulator, as a preventing or treating agent for irritable bowel syndrome; or as a preventing agent for postoperative recurrence of sex hormone-dependent cancer, as medicament. It is also effective as an animal estrous regulator, food meat quality improving agent or animal growth regulator in the field of animal husbandry, and as a fish spawning promoter in the field of fishery.

The invention claimed is:

1. A method for treating a sex-hormone-dependent prostate cancer comprising a step of administering to a mammalian subject in need thereof an effective amount of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a salt thereof.

2. The method of claim 1, wherein an effective amount of N-(4-(1-(2,6-difluorobenzyl) -5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a salt thereof is 0.1 to 10 mg/kg weight/day.

3. The method of claim 1, wherein the mammalian subject is a human.

\* \* \* \* \*

UNITED STATES PATENT AND TRADEMARK OFFICE
CERTIFICATE OF CORRECTION

PATENT NO. : 8,735,401 B2  
APPLICATION NO. : 13/242541  
DATED : May 27, 2014  
INVENTOR(S) : Nobuo Cho et al.

Page 1 of 1

It is certified that error appears in the above-identified patent and that said Letters Patent is hereby corrected as shown below:

In the claims:

Column 123, lines 15-19 should read,

2. The method of claim 1, wherein an effective amount of <u>N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea</u> ~~N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea~~ or a salt thereof is 0.1 to 10 mg/kg weight/day.

Signed and Sealed this  
Second Day of September, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,735,401 B2
APPLICATION NO. : 13/242541
DATED : May 27, 2014
INVENTOR(S) : Nobuo Cho et al.

It is certified that error appears in the above-identified patent and that said Letters Patent is hereby corrected as shown below:

On the title page:

In the Item "(75) Inventors:", replace "Masami Kusuka" with --Masami Kusaka--.

Signed and Sealed this
Second Day of December, 2014

Michelle K. Lee
*Deputy Director of the United States Patent and Trademark Office*